US005519003A

United States Patent [19]

Mochly-Rosen et al.

[11] Patent Number: 5,519,003

[45] Date of Patent: May 21, 1996

[54] WD-40-DERIVED PEPTIDES AND USES THEREOF

[75] Inventors: Daria Mochly-Rosen, Menlo Park; Dorit Ron, San Francisco, both of Calif.

[73] Assignee: Board of Trustees of the Leland Stanford Junior University, Stanford, Calif.

[21] Appl. No.: 190,802

[22] Filed: Feb. 1, 1994

[51] Int. Cl.[6] .............................. A61K 38/08; C07K 7/06

[52] U.S. Cl. ............................ 514/16; 530/328; 530/329; 435/194

[58] Field of Search ................................ 530/300; 514/2, 514/16

[56] References Cited

PUBLICATIONS

Dalrymple, M. A., et al., "The Product of the PRP4 Gene of S. cerevisiae Shows Homology to β Subunits of G Proteins," *Cell* 58: 811–812 (1989).

Dynlacht, B. D., et al., "The dTAF$_{II}$80 subunit of *Drosophila* TFIID contains β–transducin repeats," *Nature* 363: 176–179 (1993).

Fong, H. K. W., et al., "Repetitive segmental structure of the transducin β subunit: Homology with the CDC4 gene and identification of related mRNAs," *Proc. Natl. Acad. Sci. USA* 83: 2162–2166 (1986).

Guillemot, F., et al., "Physical linkage of a guanine nucleotide–binding protein–related gene to the chicken major histocompatibility complex," *Proc. Natl. Acad. Sci. USA* 86: 4594–4598 (1989).

Keleher, C. A., et al., "Ssn6–Tup1 Is a General Repressor of Transcription in Yeast," *Cell* 68: 709–719 (1992).

Mochly–Rosen, D., et al., "Identification of intracellular receptor proteins for activated protein kinase C," *Proc. Natl. Acad. Sci. USA* 88: 3997–4000 (1991).

Mochly–Rosen, D., et al., "Intracellular Receptors for Activated Protein Kinase C," *J. Biol. Chem.* 266(23): 14866–14868 (1991).

Peitsch, M. C., et al., "Sequence similarity of phospholipase A2 activating protein and the G protein β–subunits: a new concept of effector protein activation in signal transduction?," *TIBS* 18(8): 292–293 (1993).

Smith, B. L., and D. Mochly–Rosen, "Inhibition of Protein Kinase C Function by Injection of Intracellular Receptors for the Enzyme," *Biochem. Biophys. Res. Comm.* 188(3): 1235–1240 (1992).

Takagaki, Y., and J. L. Manley, "A Human Polyadenylation Factor Is a G Protein β–Subunit Homologue," *J. Biol. Chem.* 267(33): 23471–23474 (1992).

van der Voorn, L., and H. L. Ploegh, "The WD–40 repeat," *FEBS Lett.* 307(2): 131–134 (1992).

Williams, F. E., and R. J. Trumbly, "Characterization of *TUP1,* a Mediator of Glucose Repression in *Saccharomyces cerevisiae,*" *Mol. Cell. Biol.* 10(12): 6500–6511 (1990).

Williams, F. E., et al., "The CYC8 and TUP1 Proteins Involved in Glucose Repression in *Saccharomyces cerevisiae* Are Associated in a Protein Complex," *Mol. Cell. Biol.* 11(6): 3307–3316 (1991).

Weinstat–Saslow et al., Genomics 18: 709–711 (1993).

*Primary Examiner*—Robert A. Wax
*Assistant Examiner*—Eric Grimes
*Attorney, Agent, or Firm*—Morrison & Foerster

[57] ABSTRACT

The present invention relates to a polypeptide composition effective to alter the activity of a first protein that interacts with a second protein, where the second protein contains at least one WD-40 region. The polypeptides of the present invention typically have between 4 and 50 amino acids whose sequence is the same as a sequence of the same length in the WD-40 region of the second protein. The invention further includes a method of altering the activity of the above described first protein. In one embodiment of the invention the polypeptide composition is effective to alter the activity of a protein kinase C, where the protein kinase C interacts with a second protein, and the second protein contains at least one WD-40 region (e.g., RACK1).

1 Claim, 54 Drawing Sheets

```
                10         20         30         40         50         60
   1 GGCACGAGGG GTCGCGGTGG CAGCCGTGCG GTGCTTGGCT CCCTAAGCTA TCCGGTGCCA
  61 TCCTTGTCGC TGCGGCGACT CGCAACATCT GCAGCCATGA CCGAGCAAAT GACCCTTCGT
 121 GGGACCCTCA AGGGCCATAA TGGATGGGTT ACACAGATCG CCACCACTCC GCAGTTCCCG
 181 GACATGATCC TGTCGGCGTC TCGAGACAAG ACCATCATCA TGTGGAAGCT GACCAGGGAT
 241 GAGACCAACT ACGGCATACC ACAACGTGCT CTTCGAGGTC ACTCCCACTT TGTTAGCGAT
 301 GTTGTCATCT CCTCTGATGG CCAGTTTGCC CTCTCAGGCT CCTGGGATGG AACCCTACGC
 361 CTCTGGGATC TCACAACGGG CACTACCACG AGACGATTTG TCGGCCACAC CAAGGATGTG
 421 CTGAGCGTGG CTTTCTCCTC TGACAACCGG CAGATTGTCT CTGGGTCCCG AGACAAGACC
 481 ATTAAGTTAT GGAATACTCT GGGTGTCTGC AAGTACACTG TCCAGGATGA GAGTCATTCA
 541 GAATGGGTGT CTTGTGTCCG CTTCTCCCCG AACAGCAGCA ACCCTATCAT CGTCTCCTGC
 601 GGATGGGACA AGCTGGTCAA GGTGTGGAAT CTGGCTAACT GCAAGCTAAA GACCAACCAC
 661 ATTGGCCACA CTGGCTATCT GAACACAGTG ACTGTCTCTC CAGATGGATC CCTCTGTGCT
 721 TCTGGAGGCA AGGATGGCCA GGCTATGCTG TGGGATCTCA ATGAAGGCAA GCACCTTTAC
 781 ACATTAGATG GTGGAGACAT CATCAATGCC TTGTGCTTCA GCCCCAACCG CTACTGGCTC
 841 TGTGCTGCCA CTGGCCCCAG TATCAAGATC TGGGACTTGG AGGGCAAGAT CATGGTAGAT
 901 GAACTGAAGC AAGAAGTTAT CAGCACCAGC AGCAAGGCAG AGCCACCCCA GTGTACCTCT
 961 TTGGCTTGGT CTGCTGATGG CCAGACTCTG TTTGCTGGCT ATACCGACAA CTTGGTGCGT
1021 GTATGGCAGG TGACTATTGG TACCCGCTAA AAGTTTATGA CAGACTCTTA GAAATAAACT
1081 GGCTTTCTGA AAAAAAAAAA AAAAAAAAAA AAAAA
```

Fig. 1A

| | | |
|---|---|---|
| Rat RACK1 | MTEQMTLRGTLKGHNGWVTQ IATTPQFPDMILSASRDKTIIMWKLTRDETN (51) | Repeat I |
| | YGIPQRALRGHSHFVS DVVISSDGQFALSGSWDGTLRLWDLT (93) | Repeat II |
| | TGTTTRRFVGHTKDVL SVAFSSDNRQIVSGSRDKTIKLWNTLG (136) | Repeat III |
| | VCKYTVQDESHSEWVSCVRFSPNSSNPIIVSCGWDKLVKVWNLA (180) | Repeat IV |
| | NCKLKTNHIGHTGYLN TVTVSPDGSLCASGGKDGQAMLWDL (221) | Repeat V |
| | NEGKHLYTLDGGDII NALCFSPNRYWLCAATGPSIKIWDLEGKIIVDE (269) | Repeat VI |
| | LKQEVISTSSKAEPPQCTSLAWSADGQTLFAGYTDNLVRVWQVTIGTR (317) | Repeat VII |

Consensus sequence of repeats:

| | |
|---|---|
| Rat RACK1 | GHS--V----V--SSD---ILSG--D-TIKLW-L |
| Human Gβ2 | GH---I---SVA---DG--LVTGS-D--C-IWDL |

Fig. 1C

| | | | | | | | | | |
|---|---|---|---|---|---|---|---|---|---|
| Arg-C | - | + | + | + | + | + | + | + | + |
| PS(μg) | - | 50 | 50 | 2.5 | 2.5 | 2.5 | 2.5 | 2.5 | 2.5 |
| DG (0.8 μg) | - | + | - | - | - | - | - | - | - |
| Ca (μM) | - | 1000 | 1000 | 50 | 50 | 50 | 50 | 50 | 50 |
| Peptide (10μM) | - | - | - | - | rVI | rVI | rVI | C | I |
| Time of incubation (min) | 30 | 30 | 30 | 30 | 5 | 15 | 30 | 30 | 30 |

| | 1 | 2 | 3 | 4 | 5 | 6 |
|---|---|---|---|---|---|---|
| PS/DG/Ca | + | - | - | - | - | - |
| EGTA | - | + | - | - | - | - |
| Anti-pseudo-substrate antibodies | - | - | + | - | - | - |
| peptides (10μM) | - | - | - | rVI | I | C |

Fig. 11

Human 56 kDa protein (PWP homolog)

1 mnrsrqvtcv awvrcgvake tpdkvelske evkrliaeak eklqeegggs 51 deeetgspse dgmqsartqa rprepledgd peddrtlddd elaeydldky 101 deegdpdaet lgesllgltv ygsndqdpyv tlkdteqyer edflikpsdn 151 livcgraeqd qcnlevhvyn qeedsfyvhh dillsaypls vewlnfdpsp 201 ddstgnyiav gnmtpvievw dldivdslep vftlgsklsk kkkkkgkkss 251 saeghtdavldlswnkl irnvldsasadntvilwdmslgk 291 paaslavhtd kvqtlqfhpf eaqtlisgsy dksvalydcr 331 spdeshrmwr fsgqiervtw 351 nhfspchfla stddgfvynl darsdkpift 381 lnahndeisgldlssqi kgclvtasadkyvkiwdilgdrp 421 slvhsrdmkmgvlfcssccpdlpfiyafggqkegl rvwdi 461 stvssvneaf grrerlvlgs arnssisgpf gsrssdtpme 501 s

AAC-RICH protein

1 pggfqhlqqq qqqqqqqqqq qqqqqqqqtq vqqlhnqlhq qhnqqiqqqa
51 qatqqhlqtq qylqsqihqq sqqsqlsnnl nsnskestni pktntqytnf
101 dsknldlasr yfsecstkdfi 122 gnkkkstsvawnangtkia ssgsdgivrvwnfd 155 plgnsnnnnsnntss nsknnniketi 182 elkghdgsiekiswspknndlla sagtdkvikiwdvkigkcigtvstnsenid 235 vrwspdgdhlalidlptiktlkiykfn geelnqvgwdnngdlilmansmgnieaykf 301 lpksttthvkhlktlyghtas iycmefdptg kylaagsadsivslwdiedm 351 mcvktfikst fpcrsvsfsf dgqfiaassf estieifhie
411 ssqpihtiecgvsslmwhptlpllayapesinennkdpsi rvfgyhs

Fig. 12

BETA TRCP

```
1 megfscslqp ptaseredcn rdepprkiit ekntlrqtklangtssmivp
51 kqrklsanye kekelcvkyf eqwsesdqve fvehlisrmchyqhghinty
101 lkpmlqrdfi talpargldh iaenilsyld akslcsaelv ckewyrvtsd
151 gmlwkklier mvrtdslwrg laerrgwgqy lfknkppdgk tppnsfyral
201 ypkiiqdiet iesnwrcgr
```

```
220      hslqrihcr|se tskgvyclqyddq|kivsglrdntikiwdkn tleckrv
268         lmghtg|svlclqy       de|rviitgsdstvrvwdvntgem
305      lntlihhce|avlhlrfnngmmvtcs|k      drsiavwdmasatditlrrv
351        lvghraa|vnv vdfddkyivs  |     asgdrtikvwntstcefvrt
391        lnghkrg|iaclqyrdrlvvs   |     gssdntirlwdiecga
427 clrv legheel|vrc irfdnkrivs  |     gaydgkikvwdlvaaldprapagt
475 lclrtlvehsgr|vfrl qfdefqi    |vssshddt iliwdflndpgla
```

Fig. 13 beta-prime-cop vks vdlhptepwmlaslyngsvcvwnhetqtlv
51 ktfevcdlpv raakfvarkn wvvtgaddmqirvfnyntle 91 rvhmfeghsdyirciavhptqp filtssddmliklwdwdkkwscsq 137 vfeghthyvmqivinpkdnnqfas asldrtikvwqlgssspnft 181 leghekgvncidyysggdkpyl isgaddrlvkiwdyqnkt 221 cvqtleghaq nvscasfhpe lpiiitgsedgtvriwhsst 262 yrlestlnyg mervwcvasl rgsnnvalgy degsiivklgreepamsmda
318 ngkiiwakhs evqqanlkam gdaeikdger lplavkdmgs
351 ceiypqtiqh npngrfvvvc gdgeyiiyta malrnksfgs aqefawahds
401 seyairesns vvkifknfke kksfkpdfga esiyggfllg vrsvnglafy
451 dwentelirr ieiqpkhifw sdsgelvcia teesffilky lsekvlaaqe
501 thegvtedgi edgfevlgei qeivktglwv gdcfiytssv nrlnyyvgge
551 ivtiahldrt myllgyipkd nrlylgdkel nivsysllvs vleyqtavmr
601 rdfsmadkvl ptipkeqrtr vahflekqgf kqqaltvstd pehrfelalq
651 lgelkiayql aveaeseqkwkqlaelaisk cpfglaqecl hhaqdyggll
701 llatasgnas mvnklaegae rdgknnvafm syflqgklda clellirtgr
751 lpeaaflart ylpsqvsrvv klwrenlskv nqkaaeslad pteyenlfpg
801 lkeafvveew vkethadlwp akqyplvtpn eernvmeeak gfqpsrsaaq
851 qeldgkpasp tpvivtsqta nkeeksllel evdldnleie didttdinld
901 edildd

Fig. 14

CDC4 / CDC20 protein 1 mgsfplaefp lrdipvpysy rvsggiassg svtalvtaag thrnsstakt
51 vetedgeedi deyqrkraag sgestpersd fkrvkhdnhk tlhpvnlqnt
101 gaasvdndgl hnltdisnda ekllmsvddg saapstlsvn mgvashnvaa
151 pttvnaatit gsdvsnnvns atinnpmeeg alplsptass pgtttplakt
201 tktinnnnni adlieskdsi ispeylsdei fsainnnlph ayfknllfrl
251 vanmdrsels dlgtlikdnl krdlitslpf eislkifnyl qfediinslg
301 vsqnwnkiir kstslwkkll isenfvspkg fnslnlklsq kypklsqqdr
351 lrlsflenif ilknwynpkf 371 vpqrttlrgh mtsvitclqf ednyvitgaddkmirvydsi 411 nkkfllqlsghdggvwalkyahg gilvsgstdrtvrvwdi 451 kkgccthvfe ghnstvrcld iveyknikyi vtgsrdntlhvwklpkessvpdhgeehdyp 511 lvfhtpeenp yfvgvlrghmasvrtvsghg nivvsgsydntlivwdvaqm 561 kclyilsghtdriystiydh erkrcisasmdttiriwdleniwnngecsyatnsasp 618 cak ilgamytlqghtalvgllrl sdkflvsaaadgsirgwdan 661 dysrkfsyhh tnlsaittfy vsdnilvsgs enqfniynlr
701 sgklvhanil kdadqiwsvn fkgktlvaav ekdgqsflei ldfskaskin
751 yvsnpvnsss sslesistsl gltrttiip

Fig. 15

GBLP -CHLAMIDOMONAS HOMOLOG

```
1    maetltlratlkghtnwvt aiatpldpssntllsa srdksvlvwelerse
51   snygyarkalrghshfvq dvvi   ssdgqfcltg swdgtlrlwdlntgtttr
101        rfvghtkdvl svafs   vdnrqivsg srdktiklwntlgeck
141     ytigepeghtewvs cvrfspmttnpiivsg gwdkmvkvwnlt
183   ncklknnlvghhgyvn tvtv   spdgslcasg gkdgiamlwdlaegkrly
231     sldagdvihclcfs pnryw lcaatqssik iwdleskslvddl
273    rpefnitskkaqvpy cvslawsadgstlysg ytdgqirvwavghsl
```

Fig. 16 cop-1 protein

1 meeistdpvv pavkpdprts svgeganrhe nddggsggse igapdldkdl
51 lcpicmqiik dafltacghs fcymciithl rnksdcpccs qhltnnqlyp
101 nflldkllkk tsarhvskta spldqfreal qrgcdvsike vdnlltllae
151 rkrkmeqeea ernmqilldf lhclrkqkvd elnevqtdlq yikedinave
201 rhridlyrar drysvklrml gddpstrnaw pheknqigfn snslsirggn
251 fvgnyqnkkv egkaqgsshg lpkkdalsgs dsqslnqstv smarkkriha
301 qfndlqecy qkrrqladqp nskqendksv vrregysngl adfqsvlttf
351 trysrlrvia eirhgdifhs anivssiefd rddelfatagvsrcikvfdf 401 ssvvnepadmqcpivemstrsklscl swnk heknhiassdyegivtvwdv 451 ttrqslmeteenekrawsvdfsrte psmlvsgsddc kvkvwctrqeasvi 501 nidmkanicc vkynpgssny iavgsadhhi 531 hyydlrnisqplhvfsghkkavsymkflsnnelasqst ds tlrlwdv 551 kdn lpvrtfrght neknfvgltvnseylacgse
601 ttryvyhkei trpvtshrfg spdmddaekr qvptllvrfa
651 grvivprc

Fig. 17

CORO PROTEIN

```
                                                                        fgv
1          mskvvrsskyrhvfaaqpkkeecyqnlktk      savwdsnyvaantryiwdaagggsfa
61   veaiphsgkttsvplfnghksavldiafh          pfnenlvgsvsedcniciwgip
111  eggltdsist plqtlsghkr kvgtisfgpv        adnvavtssgdflvktwdve
161         qgknlttveghsdmitscehngsqivtt                ckdkkarvfd

201 prtnsivnev vchqgvknsr aifakdkvit vgfsktsere lhiydpraft
251 tplsaqvvds asgllmpfyd adnsilylag kgdgniryye lvdespyihf
301 lsefksatpq rglcflpkrc lntseceiar glkvtpftve pisfrvprks
351 difqgdiypd tyagepslta eqwvsgtnae pktvslaggf vkkasavefk
401 pvvqvqegpk nekelreeye klkirvayle seivkkdaki keltn
```

Fig. 18

Coronin (p55)

1 mskvvrsskyrhvfaaqpkkeecyqnlkvtksawdsnyvaantryfgviwdaagggsfav 61 ipheasgkttsvplfnghksdvldiafhpfnenlvgsvsedcniciwgipeggltdsist 121 plqtlsghkrkvgtisfgpvadnvavtssgdflvktwdve 161 qgknlttveghsdmitscewn hngsqivttckdkkarvfdprtnsivnev 211 vchqgvknsr aifakdkvit vgfsktsere lhiydpraft 251 tplsaqvvds asgllmpfyd adnsilylag kgdgniryye lvdespyihf 301 lsefksatpq rglcflpkrc lntseceiar glkvtpftve pisfrvprks 351 difqgdiypd tyagepslta eqwvsgtnae pktvslaggf vkkasavefk 401 pvvqvqegpk nekelreeye klkirvayle seivkkdaki keltn

Fig. 19

CSTF 50kDa 1 myrtkvglkd rqqlykliis qllydgyisi anglineikp qsvcapseql 51 lhlıklgmen ddtavqyaig rsdtvapgtg idlefdadvq tmspeaseye 101 tcyvtshkgp crvatysrdg qliatgsada sıкildterm laksampiev 151 mmnetaqqnm 201 enhpvirtlydhvdevtclafhpte qilasgsrdytlklfdyskpsakra 210 fkyiqeaeml rsisfhpsgd filvgtqhpt lrlydintfqcfvsc 256 npqdqhtdaicsvnyns sanmyvtgskdgciklwdgvsnrcittf 3 0 1 ekqhdgaevcsaifsknskyilssgkdsvaklweistgrtlvrytgagls 351 grqvhrtqavfnhte dyvllpdertislccwdsrtaerrn 391 llslghnnivrcivh sptnpgfmtcsddfrarfwyrrstt d

Fig. 20

G-Beta 1 bovine

1 mseldqlrqe aeqlknqird arkacadatl sqitnnidpv griqmrtrrt 51 lrghlakiya mhwgtdsrll vsasqdgkliiwds 85 yttnkvhaiplrsswvmtcayapsgnyvacggldnicsiynlktregnvrvsrela 141 ghtgylsccrfldd nqivtssgdttcalwdietg 174 qqtttftghtgdvmslslap dtrlfvsgacdasaklwdvregmcrq 221 tftghesdin aicffpngna fatgsddatcrlfdlradqe 261 lmtyshdniicgitsvsfsksgrlllagyddfncnvwdal kadrag 307 vlaghdnrvsclg vtddgmavatgswdsflkiwn

Fig. 21

G-Beta- bovine (2)

1 rnqirdarka cgdstltqit agldpvgriq 31 mrtrrtlrghlakiyamhwgtdsr llvsasqdgkliiwds 71 egnvryttnkvhaiplrsswvmtcayapsgnfvacggldnicsiyslktr 121 vsrelpghtgylsccrfldd nqiitssgdttcalwdietg 161 qqtvgfaghsgdvmslslap dgrtfvsgacdasiklwdvr 201 dsmcrqtfighesdinavaffp ngyafttgsddatcrlfdlradq 246 ellmyshdniicgitsvafsrsgrlllagyddfncniwdamkgdr 291 agvlaghdnrvsclgvt ddgmavatgswdsflkiwn

Fig. 22

G- BETA DROSOPH 1 mneldslrqe aeslknaird arkaacdtsllqaatslepigriqmrtrrt 51              lrghl akiyamhwgn    dsrnlv sasqdgkli vwd shttnkv 91 haiplrsswvmtcayapsgsyvacggldnmcsiynlktregnvr 135      vsrelpghg gylsccrfl    ddnqiv tssgdmscg lwdi etglqv
178         tsflght gdvmalsla   pqcktfv sgacdasa klwdi regvckq
221         tfpghe sdinavtf     fpngqafd tgsddatcr lfdi radqe
261       lamyshd niicgitsvafsksgrlll agyddfncn vwdtm
301 kaersgilaghd nrvsclg   vtengmavd tgswdsfl rvwn

Fig. 23

G-BETA HUMAN 1 mteqmtlrgtlkghngwvtqiattp qfpdmilsasrdktiimwkltrdet 51 nygipqralr ghshfvsdvvi ssdgqfalsgswdgtlrlwdlttgtttrr 101 fvghtkdvlsvaf ssdnrqivsgsrdktiklwntlgvcky 141 tvqdeshsewvscvrfsp nssnpiivscgwdklvkvwnla nc 183 klktnhightgylntvtv spdgslcasggkdgqamlwdl 222 negkhlytldggdiinalcfspnrywlcaatgpsikiwdlegkiivdel 271 kqevistsskaeppqctslawsad gqtlfagytdnlvrvwqvtigtr

Fig. 24

G-Beta 2 (Human)

1 mseleqlrqe aeqlrnqird arkacgdstl tqitagldpv griqmrtrrt 51 lrghlakiya mhwgtds rllvsasqdgkliiwdsyt 97 tnkvhaiplrsswvmtcayapsgnfvacggldnicsiyslktre 151 gnvrvsrelpghtgylsccrfl ddnqiitssgdttcalwdietgqqtvgf 201 aghsgdvmslslap dgrtfvsgacdasiklwdvrdsmcrq 241 tfighesdinavaffpn gyafttgsddatcrlfdlradqe 281 llmyshdniicgitsvafsrsgrlllagyddfncniwdam 321 kgdragvlaghdnrvsclgvtddgm avatgswdsflkiwn

Fig. 25

G-Beta 4 (mouse)

1 mseleqlrqeaeqlrnqiqdarkacndatlvqitsnmdsv griqmrtrrt 51 lrghlakiyamhwgydsr llvsasqdgkliiwdsyttnkm 91 haiplrsswvmtcayapsgnyvacggldnicsiynlktregdvrvsrela 141 ghtgylsccrflddg qiitssgdttcalwdietgqqtttf 181 tghsgdvmslslspd lktfvsgacdassklwdirdgmcrq 221 sftghisdinavsffpsg yafatgsddatcrlfdlradqe 261 lllyshdniicgitsvafsksgrlllagyddfncsvwdalkggrs 306 gvlaghdnrvsclgv tddgmavatgswdsflriwn

Fig. 26

GROUCHO PROTEIN DROSOPH 1 mypspvrhpa aggpppqgpi kftiadtler ikeefnflqa hyhsiklece
51 klsnektemq rhyvmyyems yglnvemhkq teiakrlntl inqllpflqa
101 dhqqqvlqav erakqvtmqe lnliigqqih aqqvpggppq pmgalnpfga
151 lgatmglphg pqgllnkppe hhrpdikptg legpaaaeer lrnsvspadr
201 ekyrtrspld iendskrrkd eklqedegek sdqdlvvdva nemeshsprp
251 ngehvsmevr dreslngerl ekpsssgikq erppsrsgss ssrstpslkt
301 kdmekpgtpg akartptpna aapapgvnpk qmmpqgpppa gypgapyqrp
351 adpyqrppsd paygrpppmp ydphahvrtn giphpsaltg gkpaysfhmn
401 gegslqpvpf ppdalvgvgi prharqintl shgevvcavt isnptkyvyt
451 ggkgcvkvwdisqpgnknpv sqldclqrdn yirsvkllpdgrtlivggea
501 snlsiwdlas 511 ptpri kaelt̲s̲aapacyal aspds̲k̲v̲cfsccsd̲gni̲av̲w̲d̲l̲

553 hneilvrqfqg̲h̲tdgascidispdgs̲r̲l̲wt ggld̲ntv̲rsw̲d̲l̲regrql 601 qqhdfssqif slgycptgdwlavgmenshv evlhaskpdk yqlhlhescv
651 lslrfaacgkwfvstgkdnl lnawrtpyga sifqsketss vlscdistdd
701 kyivtgsgdk katvyeviy

Fig. 27

GTP binding protein (squid)

1 mtselealrqeteqlknqirearkaaadttlamatanvepvgriqmrtrr 51 tlrghlakiyamhwasd srnlvsasqdgklivwdgyttnk 91 vhaiplrssw vmtcayapsg nyvacggldn icsiyslktr egnvrvsrel 141 pghtgylsccrfid dnqivtssgdmtcalwnietgnqits 181 fgghtgdvmslslapd mrtfvsgacdasaklfdirdgick 221 qtftghesdinaityfpn gfafatgsddatcrlfdiradq 261 eigmyshdniicgitsvafsksgrlllggyddfncnvwdv 301 lkqeragvlaghdnrvscl gvtedgmavatgswdsflkiw n

Fig. 28

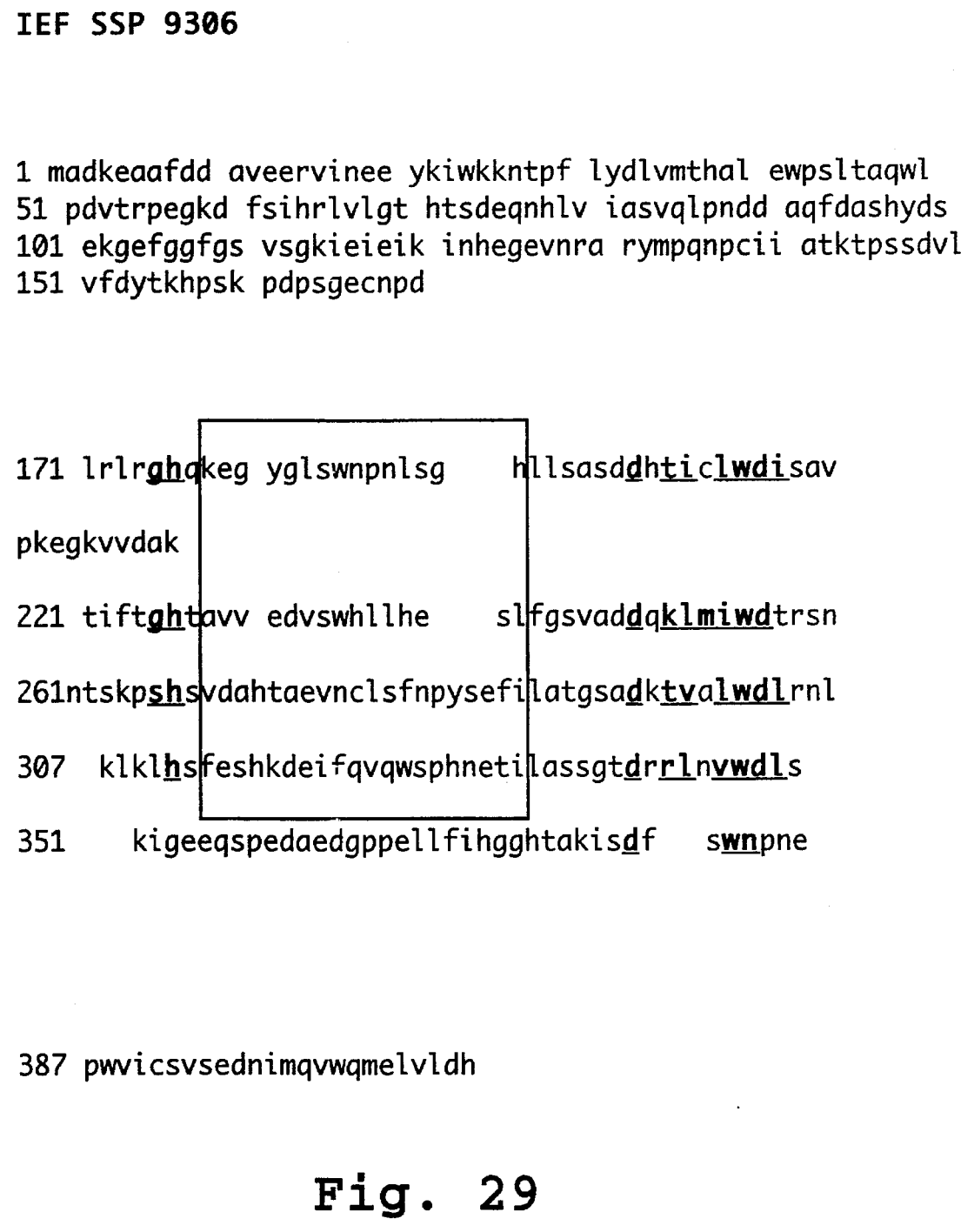

IEF SSP 9306

1 madkeaafdd aveervinee ykiwkkntpf lydlvmthal ewpsltaqwl
51 pdvtrpegkd fsihrlvlgt htsdeqnhlv iasvqlpndd aqfdashyds
101 ekgefggfgs vsgkieieik inhegevnra rympqnpcii atktpssdvl
151 vfdytkhpsk pdpsgecnpd 171 lrlrghqkeg yglswnpnlsg hllsasddhticlwdisav pkegkvvdak 221 tiftghtavv edvswhllhe slfgsvaddqklmiwdtrsn 261ntskpshsvdahtaevnclsfnpysefilatgsadktvalwdlrnl 307 klklhsfeshkdeifqvqwsphnetilassgtdrrlnvwdls 351 kigeeqspedaedgppellfihgghtakisdf swnpne 387 pwvicsvsednimqvwqmelvldh

Fig. 29

HUMAN 12.3

1 mteqmtlrgtlkghngwvtqiattpqfpdm ilsasrdktiimwkltrdet 51 nygipqralrghshfvsdvvissdgq falsgswdgtlrlwdltt 95 gtttrrfvghtk dvlsvafssdn rqivsgsrdktiklwntlg 137 vcky tvqdeshsewvscvrfspn ssnpiivscgwdklvkvwnla 181 ncklktnhighttgylntvtvs pdgslcasggkdgqamlwdln 222 egkhlytldggdii nalcfspnrywlcaatgpsikiwdle 263 gkiivdelkqevistsskaeppqctslawsadgqtlfagytdnlvrvwqvtigtr

Fig. 30

IEF -7442 - human 1 maskemfedt veervineey kiwkkntpfl ydlvmthalq wpsltvqwlp 51 evtkpegkdy alhwlvlgth tsdeqnhlvv arvhipndda qfdashcdsd 101 kgefggfgsv tgkieceiki nhegevnrar ympqnphiia tktpssdvlv 151 fdytkhpakp dpsgecnpdl 171 rlrghqkegyglswnsnlsghllsasddhtvclwdinagpkegkivdaka 221iftghsavvedvawhllheslfgsvaddqklmiwdtrsnt 261 tskpshlvdahtaevnclsfnpysefilatgsadktvalwdlrnlklklh 311 tfeshkdeifqvhwsphneti lassgtdrrlnvwdlskigeeqsaedaed 361 gppellfihgghtakisdfswnpnepwvicsvsednimqiwqmaeniynd 411 eesdvttsel egqgs

Fig. 31 insulin-like growth factor binding protein complex 1 malrkgglal allllswval gprslegadp gtpgeaegpa cpaacvcsyd 51 ddadelsvfc ssrnltrlpd gvpggtqalw ldgnnlssvp paafqnlssl 101 gflnlqggql gslepqallg lenlchlhle rnqlrslalg 141 tfa<u>h</u>tpalaslglsnnrlsrledglf<u>e</u>glgsl<u>wd</u>lnlgwn slavlpdaaf rglgslrelv 201 lagnrlaylq palfsglael reldlsrnal raikanvfvq lprlqklyld 251 rnliaavapg aflglkalrw ldlshnrvag lledtfpgll glrvlrlshn 301 aiaslrprtf kdlhfleelq lghnrirqla ersfeglgql evltldhnql 351 qevkagaflg ltnvavmnls gnclrnlpeq vfrglgklhs lhlegsclgr 401 irphtftgls glrrlflkdn glvgieeqsl wglaelleld ltsnqlthlp 451 hrlfqglgkl eylllsrnrl aelpadalgp lqrafwldvs hnrlealpns 501 llaplgrlry lslrnnslrt ftpqppgler lwlegnpwdc gcplkalrdf 551 alqnpsavpr fvqaicegdd cqppaytynn itcasppevv gldlrdlsea 601 hfapc

Fig. 32 insulin like growth factor binding protein complex - rat 1 malrtggpal vvllafwval gpchlqgtdp gasadaegpq cpvactcshd 51 dytdelsvfc ssknlthlpd dipvstralw ldgnnlssip saafqnlssl 101 dflnlqgswl rslepqallg lqnlyylhle rnrlrnlavg 141 lfthtpslaslslssnllgrleeglfqglshlwdlnlgwn 181 slvvlpdtvf qglgnlhelv 201 lagnkltylq palfcglgel reldlsrnal rsvkanvfvh lprlqklyld 251 rnlitavapg aflgmkalrw ldlshnrvag lmedtfpgll glhvlrlahn 301 aiaslrprtf kdlhfleelq lghnrirqlg ertfeglgql evltlndnqi 351 tevrvgafsg lfnvavmnls gnclrslper vfqgldklhs lhlehsclgh 401 vrlhtfagls glrrlflrdn sissieeqsl aglselleld lttnrlthlp 451 rqlfqglghl eylllsynql ttlsaevlgp lqrafwldis 491 hnhletlaeglfsslgrvrylslrnnslqtfspqpglerlwldanpwdcs 541 cplkalrdfa lqnpgvvprf vqtvcegddc qpvytynnit cagpanvsgl dlrdvsethf 601 vhc

Fig. 33

LIS1 (human)

1 mvlsqrqrde lnraiadylr sngyeeaysv fkkeaeldvn eeldkkyagl 51 lekkwtsvir lqkkvmeles klneakeeft sggplgqkrd pkewiprppe 101 kyalsghrspvtrvifhpvfsvmvsasedatikvwdyetg 151 dfertlkghtdsvqdisfdhsgkllascsadmtiklwdfqgfecir 191 tmhghdhnvssvaimpngdhivsasrdktikmwevqtgycvktf 241 tghrewvrmvrpnqdgtliascsndqtvrvwvvatkecka 291 elrehehvveciswapessy 311 ssiseatgsetkksgkpgp fllsgsrdkt kmwdvstgmc 351 lmtlvghdnwvrgvlfhsggkfilscaddktlrvwdyknk 391 rcmktlnahehfvtsldfhktapyvvtgsvdqtvkvwecr

1 merkdfetwl dnisvtflsl mdlqknetld hlislsgavq lrhlsnnlet
51 llkrdflkll plelsfyllk wldpqtlltc clvskqrnkv isactevwqt
101 acknlgwqid dsvqdslhwk kvylkailrm kqledheafe 141 tssliqhsqrvyalyyk dgllctgsddlsaklwdvstgqc 181 vygiqthtqa avkfde qklvtgsfdntvacwewssgart 220 qhfrghtgavfsvdysdel dilvsgsadfavkvwalsagtc 261 lntltghtewvtkvvlqkckvksllhspgdyillsadkyeikiwpigrei 301 nckclktlsv sedrsiclqp rlhfdgkyiv cssalglyqw
351dfasydilrv iktpevanla llgfgdvfal lfdnhylyim dlrteslisr
401wplpeyrksk rgtsflager pg

Fig. 35

MSL1

1 mnqcakdith eassipidlq eryshwkknt kllydylntn stkwpsltcq 51 ffpdldttsd ehrillssft ssqkpedeti yiskistlgh ikwsslnnfd 101 mdemefkpen strfpskhlv ndisiffpng ecnrarylpq npdiiagass 151 dgaiyifdrt khgstrirqs kishpfetkl fgshgviqdv eamdtssadi 201 neatslawnl qqealllssh sngqvqvwdi kqyshenpii dlplvsinsd 251 gtavndvtwm pthdslfaac tegnavslld lrtkkeklqs 291 nrekhdggvnscrfn yknslilasadsngrlnlwdirnmn 331 kspiatmehgtsvstlewspnfdtvlatagqedgl vklwdtsceetifth 381 gghmlgvndisw dahdpwlmcsvandn svhiwkpagnlvg hs

Fig. 36

MUS MUSCULUS PROTEIN

1 msshesytna aetpenisil sclgetsgal vdtktisdik tmdprvsltp
51 ssdvtgteds svltpqstdv nsvdsyqgye gddddeedde ddkdgdsnlp
101 sledsdnfis clensyipqn vengevveeq slgrrfhpye leagevvegq
151 gggslfypye leagevveaq nvqnlfhrye leegevveaq vvqsmfpyye
201 leagevveae evqgffqrye learevigaq ggqglsrhyg leggevveat
251 avrrliqhhe leegedvddq eessemheet sedsseqydi eddslidewi
301 aletsplprp rwnvlsalrd rqlgssgrfv yeacgarlfv qrfs 351 lehvfeghsgqvntvh fnqhgtllasgsddlkvivwdwlkkrsvln

Fig. 37

391 fdsghknnilqakflpncnd ailamcgrdg qvrvaqlsav
401 agthmtkrlv khggashrlglepdspfrfl tsgedavvfn
451 idlrqahpas kllvikdgdk kvglytvfvn
501 panvyqfavg gqdqfmriyd qrkidenvnn gvlkkfcphh llssdypahi
551 tslmysydgt eilasynded iyifnssdsd gaqyakrykg hrnnstvkgv
601 yfygprsefv 611 msgsdcghifiweksscqiv qfleadeggt incidshpylpvldssgl*dhev*kiwspiae 671 pskklaglkn vikinklkrd nftlrhtslf
701nnsmlcflms hvtqsnygrswrgirinagg gdfsdsssss eetnqes

Fig. 37 (con't)

ORF RB1

1 mnqcakdith eassipidlqeryshwkknt kllydylntn stkwpsltcq
51 ffpdldttsd ehrillssft ssqkpedeti yiskistlghikwsslnnfd
101 mdemefkpen strfpskhlv ndisiffpng ecnrarylpq npdiiagass
151 dgaiyifdrt khgstrirqs kishpfetkl fgshgviqdv eamdtssadi
201 neatslawnl qqealllssh sngqvqvwdi kqyshenpii dlplvsinsd
251 gtavndvtwm pthdslfaac tegnavslld lrtkkeklqs 291 nrekhdggvnscrfnykn slildsadsngrlnlwdirnmn 331 kspiatmehgtsvstlewspnfdtvlatagqedg lvklwdtsceetifth 381 gghmlgvndiswdah dpwlmcsvandn svhiwkpagnlvghs

Fig. 38

Periodic Trp protein 1 misatnwvpr gfssefpeky vlddeeveri nqlaqlnldd akatleeaeg 51 esgveddaat gssnklkdql didddlkeyn leeyddeeia dneggkdvsm 101 fpglsndsdv kfhegekged pyislpnqed sqeekqelqv ypsdnlvlaa 151 rteddvsyld iyvyddgagf hssdipveeg deadpdvarg lvrdpalyvh 201 hdlmlpafpl cvewldykvg snseeaanya aigtfdpqie iwnldcvdka 251 fpdmilgepl dnsmvslksk 271 kkkkksktgh itthhtdavl smahnkyfrsvldstsadhtv klwdlnsgn 321 aarslasihs nkhvsssewhmlngsilltggydsrvaltdvrisdesqmskywsamagee 381 ietvtfasen iilcgtdsgn vysfdirnne nrkpvwtlka 421 hdagistlcs nkfipgmmst gamgektvkl 451 wkfplddatn tkgpsmvlsr dfdvgnvlts sfapdievag tmviggvnkv 501 lklwdvftnr svrksfksel envqarakee aqkigkssri arkytsndnp 551 dtvitiddqg edeeereggd ehddma

Fig. 39

PLAP 1 mhymsghsnf vsyvciipss diyphgliat ggndhnicif sldspmplyi 51 lkghkdtvcslssgkf gtllsgswdttakvwlndkcmmtl 91 qghtaavwavkilpeqglmltgsadktiklwkagrcertf 131 lghedcvrglails eteflscandasirrwqitgeclevy 171 fghtnyiysisvfpnskdfvttaedrslriwkhgecaqti 211 rlpaqsiwcc cvlengdivv gasdgiirvf teseertasa 251 eeikaslsre spliakvltt eppiitpvrr tlpcrvtrsm issclsrlvs 301 tslstsdshl titalhlflt tttte

Fig. 40

RETINOBLASTOMA BINDING PROTEIN - HUMAN 1 madkeaafdd aveervinee ykiwkkntpf lydlvmthal ewpsltaqwl 51 pdvtrpegkd fsihrlvlgt htsdeqnhlv iasvqlpndd aqfdashyds 101 ekgefggfgs vsgkieieik inhegevnra rympqnpcii atktpssdvl 151 vfdytkhpsk pdpsgecnpd 171 lrlrghqkegyglswnpn lsghllsasddhticlwdisavpkegkvvdak 221 tiftghtavvedvswhll heslfgsvaddqklmiwdtrsn 261 ntskpshsvdahtaevnclsfnpysefildtgsadktvalwdlrnlklkl 311 hsfeshkdeifqvqwsph netildssgtdrrlnvwdlskigeeqspedaedgppell 374 fihgghtakisdfswnpnepw vidsvsednimqvwqmaeniyndedpegsvdpegqgs

Fig. 41

S253 PROTEIN 1 mfksktstls ydetpnsneg drnatpvnpk eksqtkhlni pgdrsrhssi
51 adskrsssry dggysadiip aqlrfidnid ygtrlrktlh rnsvvsngyn
101 klsendrwyf dlfdrkyfen yleeptyiki fkkkegleqf drmflaqelk
151 ipdvykstty qgepavanse lfknsiccct fshdgkymvi gckdgslhlw
201 kvinspvkrs emgrseksvs asranslkiq rhlasisshn gsissndlkp
251 sdqfegpskq lhlyapvfys 271 dvfrvfmehaldildanw skngflitasmdktaklwhper 311 kyslktfvhpdfvtsaiffpnddrfiitgcldhrcrlwsi 351 ldnevsyafd ckdlitsltl sppggeytii gtfngyiyvl lthglkfvss
401 fhvsdkstqg ttknsfhpss eygkvqhgpr itglqcffsk vdknlrlivt
451 tndskiqifd lnekkplelf kgfqsgssrh rgqflmmkne pvvftgsddh
501 wfytwkmqsf nlsaemncta phrkkrlsgs mslkgllriv snkstndecl
551 tetsnqsssh tftnssknvl qtqtvgsqai knnhyisfha hnspvtcasi
601 apdvaiknls lsndlifelt sqyfkemgqn ysesketcdn kpnhpvtetg
651 gfssnlsnvv nnvgtilitt dsqglirvfr tdilpeirkk iiekfheynl
701 fhleaagkin nhnndsilen rmderssted nefsttppsn thnsrpshdf
751 celhpnnspv isgmpsrasa ifknsifnks ngsfislksr sestsstvfg
801 phdiprvstt ypklkcdvcn gsnfecaskn piaggdsgft cadcgtilnn
851 fr

Fig. 42

SOF1

1 mkiktikrsa ddyvpvkstq esqmprnlnp elhpferare ytkalnatkl 51 ermfakpfvgqlgyghrdgvy aiaknygslnklatgsadgvikywnmstr 101 eefvsfkahyglvtglcvtqprfhdkkpdlksqnfmlsgsddktvklwsinvddysnkns 161 sdndsvtneeglirtfdgesafqgidshrenstfdtggakihlwdvnrlk 211 pvsdlswgad nitslkfnqn etdilastgs dnsivlydlr tnsptqkivq tmrtnaicwn 271 pmeafnfvta nedhnayyyd mrnlsrslnv fkdhvsavmd vdfsptgdei vtgsydksir 331 iyktnhghsreiyhtkrmqhvf vkysmdskyiisgsddgnvrlwrskaw 381 ersnvkttre knkleydekl kerfrhmpei krisrhrhvp qvikkaqeik 431 nielssikrr eanerrtrkdmpyiserkkq ivgtvhkyed sgrdrkrrke ddkrdtqek

Fig. 43

STE4 - YEAST 1 maahqmdsit ysnnvtqqyi qpqslqdisa vedeiqnkie aarqeskqlh 51 aqinkakhki qdaslfqman kvtsltknki nlkpnivl 89 kghnnkisdfrwsrdsk rilsqsqdgfmliwdsasglkqnai 131 pldsqwvlscaispsstlvasaglnnnctiyrvskenrva 171 qnvasifkghtcyisdieft dnahiltasgdmtcalwdip 211 kakrvreysdhlgdvlalaipeepnlenssntfascgsdgytyiwdsrsp 261 savqsfyvndsdinalrffkdgmsivagsd ngainmydlr 301 sdcsiatfslfrgyeertptptymaanmey ntaqspqtlk 341 stsssyldnqgvvsldfsasgrlmyscytdigcvvwdvlk 381 geivgkleghggrvtgvrsspdglavctgswdstmkiwsp gyq

Fig. 44

TRANSCRIPTION FACTOR TIIF 1 mslevsning gngtqlshdk rellcllkli kkyqlkstee llcqeanvss
51 velseisesd vqqvlgavlg agdanrerkh vqspaqghkq savteanaae
101 elakfiddds fdaqhyeqay kelrtfveds ldiykhelsm vlypilvqiy
151 fkilasglre kakefiekyk cdldgyyieg lfnllllskp eellendlvv
201 ameqdkfvir msrdshslfk rhiqdrrqev vadivskylh fdtyegmarn
251 klqcvatags hlgeakrqdn kmrvyygllk evdfqtlttp apapeeeddd
301 pdapdrpkkk kpkkdpllsk ksksdpnaps idriplpelk dsdkllklka
351 lreaskrlal skdqlpsavfytvln

Fig. 45

```
376                 shqgvtcaeisddstm  lacgfgdssvriwsltpanvrtlkdads
                                                                  ↑
                                                                  lreldkesadi

431 nvrmlddrsgevtrslmghtgpvyrcafapemnlllscsedstirlwsll
481      twscvvtyrghvypvwdvrfaphgyyfvscsydktarlwatdsnqalrvf
531                vghlsdvdcvqfhpnsnyvdtgssdrtvrlwdnmtgqsvr
571               lmtghkgsvsslafsacgryldsgsvdhniiiwdlsngsl
611             vttllrhtstvttitfsrdgtvlaaagldnnltlwdfhkv
651 tedyisnhit vshhqdende dvylmrtfps knspfvslhf trrnllmcvg
701 lfks
```

Fig. 45 (con't)

TUP1

1 mtasvsntqn klnelldair qeflqvsqea ntyrlqnqkd ydfkmnqqla
51 emqqirntvy elelthrkmk dayeaeikhl klgleqrdhq iasltvqqqq
101 qqqqqqqvqq hlqqqqqqla aasasvpvaq qppattsata tpaantttgs
151 psafpvqasr pnlvgsqlpt ttlpvvssna qqqlpqqqlq qqqlqqqqpp
201 pqvsvaplsn taingsptsk etttlpsvka pestlketep ennntskind
251 tgsattattt tateteikpk eedatpaslh qdhylvpynq ranhskpipp
301 flldldsqsv pdalkkqtnd yyilynpalp reidvelhks ldhtsvvccv
351 kfsndgeyla tgcnkttqvy rvsdgslvar lsddsaannh rnsitenntt
401 tstdnntmtt tttttittta mtsaaelakd venlntsssp 441 ssdlyirsvcfspdgkflatgaedrliriwdienrkivmi 481 lqgheqdiysldyfpsgdklvsgsgdrtvriwdlrtgqcs 521 ltlsiedgvttvavspgdgkyiaagsldravrvwdsetgflverldsene 571 sgtghkdsvysvvftrdgqsvvsgsldrsvklwnlqnannksdsktpnsg 621 tcevtyighkdfvlsvattqndeyilsgskdrgvlfwdkk 661 sgnpllmlqg hrnsvisvav angsslgpey nvfatgsgdc
701 kariwkykki apn

Fig. 46

TUP1 HOMOLOG 1 msqkqstnqn qngthqpqpv knqrtnnaag ansgqqpqqq sqgqsqqqgr
51 sngpfsasdl nrivleylnk kgyhrteaml raesgrtltp qnkqspantk
101 tgkfpeqssi ppnpgktakp isnptnlssk rdaeggivss grleglnape
151 nyiraysmlk nwvdssleiy kpelsyimyp ifiylflnlv aknpvyarrf
201 fdrfspdfkd fhgseinrlf svnsidhike nevasafqsh kyritmsktt
251 lnlllyflne nesiggslii svinqhldpn ivesvtarek ladgikvlsd
301 sengngkqnl emnsvpvklg pfpkdeefvk eietelkikd dqekqlnqqt
351 agdnysgann rtllqeykam nnekfkdntg dddkdkikdk iakdeekkes
401 elkvdgekkd snlsspardi lplppktald lkleiqkvke srdaikldnl
451 qlalpsvcmy 461 tfqntnkdmscldfsddcriaaag fqdsyikiwsldgsslnnpnialnnn
511 dkdedptcktlvghsgtvystsf spdnkyllsgsedkt vrlwsmdthtal
561 vsykghnhpvwdvs fsplghyfatashdqt arlwscdhiy
601 plrifaghlndvdcvs fhpngcyvftgssdkt crmwdvst
641 gdsvrlflghtdpvisi avcpdgrwlstgsedgi invwdigtgkr
686 lkqmrghgknaiyslsyskegnvlisggadht vrvwdlkkattep 731 saepdepfig ylgdvtasin qdikeygrrr tviptsdlva
771 sfytkktpvf kvkfsrsnla laggafrp

Fig. 47

YCU7

1 mvrrfrgkel aattfnghrd yvmgaffshd qekiytvskd gavfvweftk
51 rpsddddnes edddkqeevd iskyswritk khffyanqak vkcvtfhpat
101 rllavgftsg efrlydlpdf tliqqlsmgq npvntvsvnq tgewlafgss
151 klgqllvyew 161 qsesyilkqqghfdstnslay spdgsrvvtasedgkikvwd 202 itsgfclatfeehtssvta vqfakrgqvmfsssldgtvrawdli 251 ryrnfrtftgteriqfntlavdpsgevvcagsldnfdih vwsvqt 291 gqlldalsghegpvscl sfsqensvlasaswdktiriwsi 341 fgrsqqvepi evysdvlals mrpdgkevav stlkgqisif niedakqvgn
391 idcrkdiisg rfnqdrftakilndpnfllq yitvlmvwll wlvviitpfv
431 ymmfqmksc

Fig. 48

YCW2 PROTEIN 1 mstlipppsk kqkkeaqlpr evaiipkdlp nvsikfqald tgdnvggalr
51 vpgaisekql eellnqlngt sddpvpytfs ctiqgkkasd pvktiditdn
101 lysslikpgy nstedqitll ytpravfkvk 131 pvtrsssaiaghgstilcsafaph tssrmvtgagdntariwdcdtqtpmh
181 tlkghynwvlcvswsp dgeviatgsmdntirlwdpksgqc
221 lgdalrghskwitslswepihlvkpgskprlasssskdgtikiwdtvsrvc
271 qytmsghtnsvscvkwggqg llysgshdrtvrvwdinsqg 311 rcinilksha hwvnhlslst dyalrigafd ntgkkpstpe 351 eaqkkalenyekickkngnse emmvtasddytmflwnplkstkpiarmtg
401 hqklvnhvafspdgr yivsasfdnsiklwdgr
441 dgkfistfrghiasvyqvawssdc rllvscskdttlkvwdv
481 rtrklsvdlpgiktklyvdw svdgkrvcsggkdkmvrlwth

YKL525

1 mfksktstls ydetpnsneg drnatpvnpk eksqtkhlni pgdrsrhssi
51 adskrsssry dggysadiip aqlrfidnid ygtrlrktlh rnsvvsngyn
101 klsendrwyf dlfdrkyfen yleeptyiki fkkkegleqf drmflaqelk
151 ipdvykstty 161 qgepavanselfknsiccct fshdgkymvi gckdgslhlwk 202 vinspvkrs emgrseksvs asranslkiq rhlasisshn gsissndlkp 251 sdqfegpskqlhlyapvfysdvf rvfmehaldildanwskngflitasmd 301 ktaklwhperkyslktfvhpdfvtsaiffpnddrfiitgcldhrcrlwsi 351 ldnevsyafd ckdlitsltl sppggeytii gtfngyiyvl lthglkfvss
401 fhvsdkstqg ttknsfhpss eygkvqhgpr itglqcffsk vdknlrlivt
451 tndskiqifd lnekkplelf kgfqsgssrh rgqflmmkne pvvftgsddh
501 wfytwkmqsf nlsaemncta phrkkrlsgs mslkgllriv snkstndecl
551 tetsnqsssh tftnssknvl qtqtvgsqai knnhyisfha hnspvtcasi
601 apdvaiknls lsndlifelt sqyfkemgqn ysesketcdn kpnhpvtetg
651 gfssnlsnvv nnvgtilitt dsqglirvfr tdilpeirkk iiekfheynl
701 fhleaagkin nhnndsilen rmdersstedd nefsttppsn thnsrpshdf
751 celhpnnspv isgmpsrasa ifknsifnks ngsfislksr sestsstvfg
801 phdiprvstt ypklkcdvcn gsnfecaskn piaggdsgft cadcgtilnn
851 fr yrb 1410 yeast 1 msqkqstnqn qngthqpqpv knqrtnnaag ansgqqpqqq sqgqsqqqgr 51 sngpfsasdl nrivleylnk kgyhrteaml raesgrtltp qnkqspantk 101 tgkfpeqssi ppnpgktakp isnptnlssk rdaeggivss grleglnape 151 nyiraysmlk nwvdssleiy kpelsyimyp ifiylflnlv aknpvyarrf 201 fdrfspdfkd fhgseinrlf svnsidhike nevasafqsh kyritmsktt 251 lnlllyflne nesiggslii svinqhldpn ivesvtarek ladgikvlsd 301 sengngkqnl emnsvpvklg pfpkdeefvk eietelkikd dqekqlnqqt 351 agdnysgann rtllqeykam nnekfkdntg dddkdkikdk iakdeekkes 401 elkvdgekkd snlsspardi lplppktald lkleiqkvke srdaikldnl 451 qlalpsvcmy tfqntnkdms cldfsddcri aaagfqdsyi kiwsldgssl 501 nnpnialnnn dkdedptckt lvghsgtvys tsfspdnkyl lsgsedktvr

Fig. 51

551 lwsmdthtalvsykghnhpvwdvs fsplghyfatashdqtarlwscdhiy 601 plrifaghlndvdcvs fhpngcyvftgssdktcrmwdvst 641 gdsvrlflghtapvisiav cpdgrwlstgsedgiinvwdigtgkrlkqmr 691 ghgknaiyslsyskegnvlisggadhtvrvwdlkkattep 731 saepdepfig ylgdvtasinqdikeygrrr tviptsdlva sfytkktpvf kvkfsrsnla laggafrp

Fig. 51 (con't)

WD-40-DERIVED PEPTIDES AND USES THEREOF

FIELD OF THE INVENTION

The present invention relates in general to compositions and methods of modulating the function of proteins involved in protein-protein interactions. It relates more specifically to modulating the function of a first protein of a pair of interacting proteins wherein a second protein of the pair contains a "WD-40" or "β-transducin" amino acid repeat motif.

REFERENCES CITED

U.S. Patent Documents

Crea, R., U.S. Pat. No. 4,888,286, issued Dec. 19, 1989.

Eaton, M. A. W., et al., U.S. Pat. No. 4,719,180, issued Jan. 12, 1988.

Yoshio, T., et al., U.S. Pat. No. 4,849,350, issued Jul. 18, 1989.

OTHER REFERENCES

Ausubel, F. M., et al., *Current Protocols in Molecular Biology*, John Wiley and Sons, Inc., Media Pa.

Bohinski, R. C., *Modern Concepts in Biochemistry*, Second Edition, Allyn and Bacon, Inc.

Dayhoff, M. O., in *Atlas of Protein Sequence and Structure* (1972) Vol. 5, National Biomedical Research Foundation, pp. 101–110, and Supplement 2 to this volume, pp. 1–10.

Duronio, R. J., et al., (1992) *Proteins: Structure, Function, and Genetics* 13:41–56.

Escobedo, J. A., et al., *Mol. Cell. Biol.*, 1125–1132 (1991).

Fong, et al., (1986) *Proc Natl Acad Sci USA* 2162–2166.

Hari, et al., *Endocrinology*, 120:829–831 (1987).

Kleuss, C. , et al., *Science* 259:832–834 (1993).

Makowske, O. M. and Rosen, O. M. *J. Biol. Chem.* 4:16155–16159 (1989).

Maniatis, T., et al., *Molecular Cloning: A Laboratory Manual*, Cold Spring Harbor Laboratory (1982).

Miller, J. F. , et al., *Nature* (London) 216:659–63 (1969).

Mochly-Rosen, D., and Koshland, D. E., Jr. *J. Biol. Chem.* 262:2291–2297 (1987).

Mochly-Rosen, et al., *Molec. Biol. Cell.* 1:693–706 (1990).

Mochly-Rosen, D., et al., *Proc. Natl. Acad. Sci. USA* 3997–4000 (1991).

Orr, J. W., et al., *J. Biol. Chem.* 267, 16155–16159 (1992).

Pitcher, J., et al., *Science* 257:1264–1267 (1992).

Reiner, et al., *Nature* 364:717–721 (1993).

Schulz, G. E. and R. H. Schirmer., *Principles of Protein Structure*, Springer-Verlag.

Smith, B. L. and Mochly-Rosen, D. *Biochem. Biophys. Res. Commun.* 188:1235–1240 (1992).

Smith, D. B., et al., *Gene* 67:31 (1988).

Stith, B. J. and J. L. Maller. *Exp. Cell. Res.* 169:514–523 (1987).

Wolf, M. and N. Sahyoun, *J. Biol. Chem.*, 261:13327–13332 (1986).

BACKGROUND OF THE INVENTION

Many intracellular processes are carried out or regulated by multi-subunit protein complexes that become active or repressed by the association or dissociation of individual polypeptide subunits.

One such group or family of proteins is related to the B subunit of transducin. Members of this group are all at least somewhat homologous to the β-subunit of transducin at the amino acid level, and contain a varying number of repeats of a particular motif identified in β-transducin. The repeats have been termed "β-transducin", or "WD-40" repeats (Fong, et al.).

Among the members of this protein family (Duronio, et al.) are the Gβ subunits that couple many receptors to their intracellular effector molecules, Gβ/γ subunits that anchor another protein kinase (the β-adrenergic receptor kinase, βARK), DNA binding proteins and yeast cell cycle proteins. All of these require a transient protein-protein interaction for their function. However, the sequences at the interface of these proteins and their partners have not been identified.

SUMMARY OF THE INVENTION

The invention includes, in one aspect, a polypeptide composition effective to alter the activity of a first protein, such as protein kinase C, or β-adrenergic receptor kinase (βARK). The polypeptide blocks or inhibits an interaction, such as a binding interaction, between the first protein and a second protein containing a WD-40 region.

The polypeptide contains between 4 and 50 amino acids whose sequence is the same as a sequence of the same length in the WD-40 region of the second protein.

The polypeptide may block the binding of the first to the second protein, or may be an agonist, or antagonist of the first protein. The WD-40 region preferably has an amino acid sequence homologous or identical to the sequences defined by SEQ ID NO:76-261.

In a second embodiment, the invention includes a method of altering the activity of the first protein of the type defined above. The method includes selecting a polypeptide having between 4 and 50 amino acids whose sequence is the same as a sequence of the same length in the WD-40 region of the second protein, and contacting the polypeptide with the first protein under conditions which allow the formation of a complex between the polypeptide and the first protein, where this interaction alters the activity of the first protein.

In one embodiment, the contacting is effective to inhibit the interaction between the first and second proteins. In another embodiment, the contacting is effective to stimulate the activity of the first protein. In still another embodiment, the contacting is effective to inhibit the activity of the first protein. The polypeptide preferably has an amino acid sequence homologous or identical to the sequences defined by SEQ ID NO:76-261.

In a more specific aspect of the invention, the invention includes a polypeptide composition effective to alter the activity of protein kinase C, where the protein kinase C interacts with a second protein, and the second protein contains at least one WD-40 region. The polypeptide has between 4 and 50 amino acids whose sequence is the same as a sequence of the same length in the WD-40 region of the second protein.

In a preferred embodiment, the second protein is a receptor for activated protein kinase C, and has the sequence represented by SEQ ID NO:27.

In other specific embodiments, the polypeptide is (i) an agonist of protein kinase C, and the polypeptide has the sequence represented by SEQ ID NO:7; (ii) an antagonist of the activity of protein kinase C; and/or (iii) an inhibitor of the interaction between protein kinase C and the second protein. In the latter embodiment, the polypeptide has sequence corresponding to SEQ ID NO:4 or SEQ ID NO:7.

The WD-40 region preferably has an amino acid sequence homologous or identical to SEQ ID NO:69–75.

In a related embodiment, the invention includes a method of altering the activity of a protein kinase C that interacts with a second protein, where said second protein contains at least one WD-40 region. The method includes selecting a polypeptide having between 4 and 50 amino acids whose sequence is the same as a sequence of the same length in the WD-40 region of the second protein, and contacting the polypeptide with the protein kinase C under conditions which allow the formation of a complex between the polypeptide and the protein kinase C, where said interaction alters the activity of said protein kinase C.

These and other objects and features of the invention will become more fully apparent when the following detailed description of the invention is read in conjunction with the accompanying drawings.

BRIEF DESCRIPTION OF THE FIGURES

FIG. 1A shows the cDNA sequence of rat brain RACK1.

FIG. 1C shows the amino acid sequence of RACK1, aligned to show the seven WD-40 repeats represented in the molecule.

FIG. 11 shows the amino acid sequence of the 56 kDa human protein with the WD-40 repeats aligned and putative binding peptide regions delineated by a box. FIG. 12 shows the amino acid sequence of the AAC-rich protein with the WD-40 repeats aligned and putative binding peptide regions delineated by a box. FIG. 13 shows the amino acid sequence of the B-TRCP protein with the WD-40 repeats aligned and putative binding peptide regions delineated by a box. FIG. 14 shows the amino acid sequence of the Beta-prime-COP protein with the WD-40 repeats aligned and putative binding peptide regions delineated by a box. FIG. 15 shows the amino acid sequence of the CDC4 protein with the WD-40 repeats aligned and putative binding peptide regions delineated by a box. FIG. 16 shows the amino acid sequence of the Chlam-3 protein with the WD-40 repeats aligned and putative binding peptide regions delineated by a box.

FIG. 17 shows the amino acid sequence of the COP-1 protein with the WD-40 repeats aligned and putative binding peptide regions delineated by a box.

FIG. 18 shows the amino acid sequence of the CORO protein with the WD-40 repeats aligned and putative binding peptide regions delineated by a box.

FIG. 19 shows the amino acid sequence of the Coronin p55 protein with the WD-40 repeats aligned and putative binding peptide regions delineated by a box.

FIG. 20 shows the amino acid sequence of the Cstf 50 kDa protein with the WD-40 repeats aligned and putative binding peptide regions delineated by a box.

FIG. 21 shows the amino acid sequence of the bovine G-beta-1 protein with the WD-40 repeats aligned and putative binding peptide regions delineated by a box.

FIG. 22 shows the amino acid sequence of the bovine G-beta-2 protein with the WD-40 repeats aligned and putative binding peptide regions delineated by a box.

FIG. 23 shows the amino acid sequence of the drosophila G-beta protein with the WD-40 repeats aligned and putative binding peptide regions delineated by a box.

FIG. 24 shows the amino acid sequence of the human G-beta-1 protein with the WD-40 repeats aligned and putative binding peptide regions delineated by a box.

FIG. 25 shows the amino acid sequence of the human G-beta-2 protein with the WD-40 repeats aligned and putative binding peptide regions delineated by a box.

FIG. 26 shows the amino acid sequence of the mouse G-beta protein with the WD-40 repeats aligned and putative binding peptide regions delineated by a box.

FIG. 27 shows the amino acid sequence of the drosophila groucho protein with the WD-40 repeats aligned and putative binding peptide regions delineated by a box.

FIG. 28 shows the amino acid sequence of the squid GTP-binding protein with the WD-40 repeats aligned and putative binding peptide regions delineated by a box.

FIG. 29 shows the amino acid sequence of the HSIEF 930 protein with the WD-40 repeats aligned and putative binding peptide regions delineated by a box.

FIG. 30 shows the amino acid sequence of the human 12.3 protein with the WD-40 repeats aligned and putative binding peptide regions delineated by a box.

FIG. 31 shows the amino acid sequence of the human IEF-7442 protein with the WD-40 repeats aligned and putative binding peptide regions delineated by a box.

FIG. 32 shows the amino acid sequence of the insulin-like growth factor binding protein complex with the WD-40 repeats aligned and putative binding peptide regions delineated by a box.

Figure 1B:
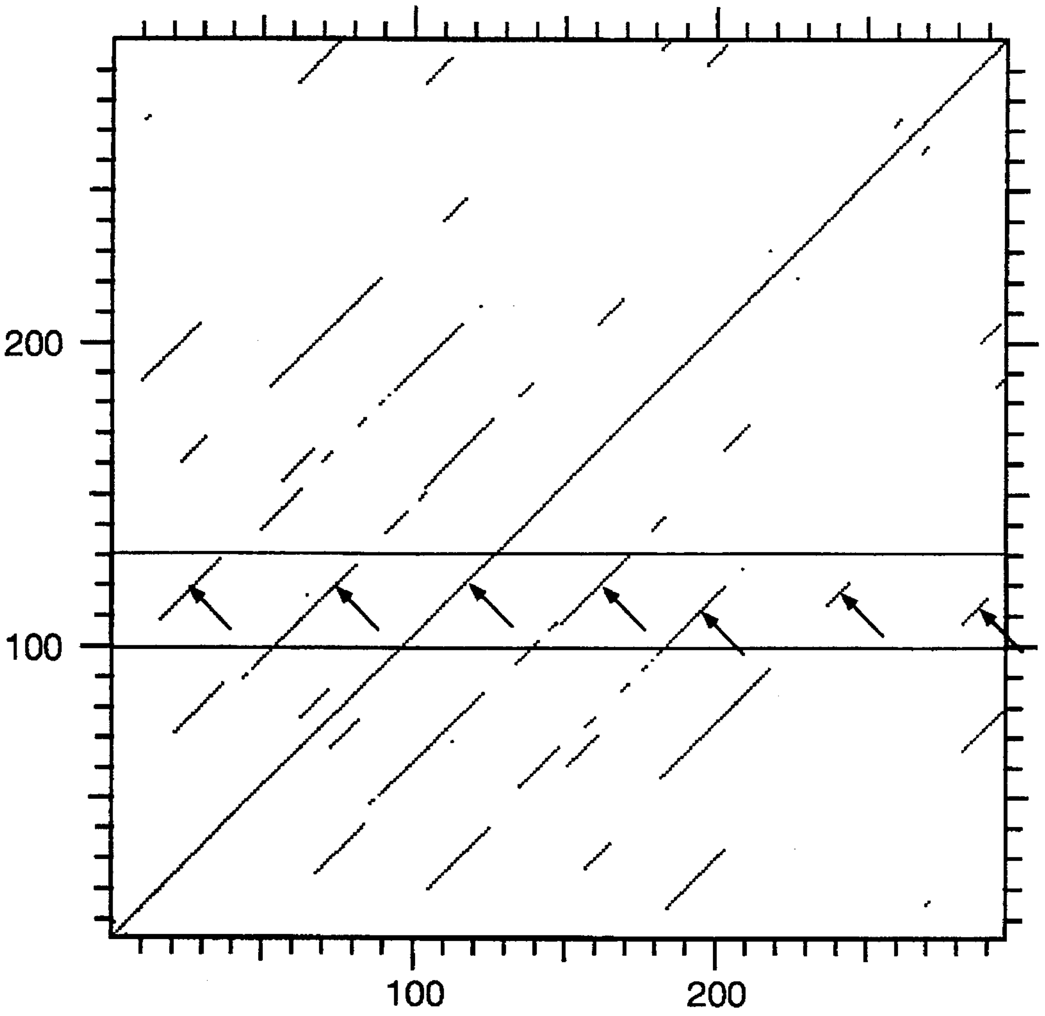
FIG. 1B shows an amino acid self-homology matrix analysis of RACK1.

FIG. 33 shows the amino acid sequence of the rat insulin-like growth factor binding protein with the WD-40 repeats aligned and putative binding peptide regions delineated by a box.

FIG. 34 shows the amino acid sequence of the human LIS1 protein with the WD-40 repeats aligned and putative binding peptide regions delineated by a box.

FIG. 35 shows the amino acid sequence of the MD6 protein with the WD-40 repeats aligned and putative binding peptide regions delineated by a box.

FIG. 36 shows the amino acid sequence of the yeast MSI1 protein with the WD-40 repeats aligned and putative binding peptide regions delineated by a box.

FIG. 37 shows the amino acid sequence of the mouse pc326 MUS protein with the WD-40 repeats aligned and putative binding peptide regions delineated by a box.

FIG. 38 shows the amino acid sequence of the ORD RB1 protein with the WD-40 repeats aligned and putative binding peptide regions delineated by a box.

FIG. 39 shows the amino acid sequence of the periodic trp protein with the WD-40 repeats aligned and putative binding peptide regions delineated by a box.

FIG. 40 shows the amino acid sequence of the PLAP protein with the WD-40 repeats aligned and putative binding peptide regions delineated by a box.

FIG. 41 shows the amino acid sequence of the retinoblastoma binding protein with the WD-40 repeats aligned and putative binding peptide regions delineated by a box.

FIG. 42 shows the amino acid sequence of the S253 protein with the WD-40 repeats aligned and putative binding peptide regions delineated by a box.

FIG. 43 shows the amino acid sequence of the SOF1 protein with the WD-40 repeats aligned and putative binding peptide regions delineated by a box.

FIG. 44 shows the amino acid sequence of the STE4 yeast protein with the WD-40 repeats aligned and putative binding peptide regions delineated by a box.

FIG. 45 shows the amino acid sequence of the TF1 transcription factor protein with the WD-40 repeats aligned and putative binding peptide regions delineated by a box.

FIG. 46 shows the amino acid sequence of the TUP1 protein with the WD-40 repeats aligned and putative binding peptide regions delineated by a box.

FIG. 47 shows the amino acid sequence of the TUP1 homolog protein with the WD-40 repeats aligned and putative binding peptide regions delineated by a box.

FIG. 48 shows the amino acid sequence of the YCU7 protein with the WD-40 repeats aligned and putative binding peptide regions delineated by a box.

FIG. 49 shows the amino acid sequence of the YCW2 protein with the WD-40 repeats aligned and putative binding peptide regions delineated by a box.

FIG. 50 shows the amino acid sequence of the YKL25 protein with the WD-40 repeats aligned and putative binding peptide regions delineated by a box.

FIG. 51 shows the amino acid sequence of the YRB140 protein with the WD-40 repeats aligned and putative binding peptide regions delineated by a box.

DETAILED DESCRIPTION OF THE INVENTION

I. Definitions

Unless otherwise indicated, all terms used herein have the same meaning as they would to one skilled in the art of the present invention. Practitioners are particularly directed to Current Protocols in Molecular Biology (Ausubel) for definitions and terms of the art.

Abbreviations for amino acid residues are the standard 3-letter and/or 1-letter codes used in the art to refer to one of the 20 common L-amino acids. Likewise, abbreviations for nucleic acids are the standard codes used in the art.

An "amino acid group" refers to a group of amino acids where the group is based on common properties, such as hydrophobicity, charge, or size.

A "conserved set" of amino acids refers to a contiguous sequence of amino acids that is conserved between members of a group of proteins. A conserved set may be anywhere from two to over 50 amino acid residues in length. Typically, a conserved set is between two and ten contiguous residues in length. The individual positions within a conserved set each typically comprise one of several amino acids, selected from an amino acid group(s). In cases where a residue is 100% conserved at a particular position, the conserved set sequence will contain only that residue at that position. For example, for the two peptides WRTAA (SEQ ID NO: 263) and WRTAV (SEQ ID NO: 264), there are 4 identical positions (WRTA; SEQ ID NO: 265) and one position where the residue is an "A" or a "V".

Proteins are typically long chains of amino acid based polyamides (polypeptides) capable of creating secondary and tertiary structure. Proteins may be composed of one, two or more polypeptide chains and may further contain some other type of substance in association with the polypeptide chain(s), such as metal ions or carbohydrates. The size of proteins covers a rather wide range from ~5,000 to several hundred thousand g/mole. The 5,000 figure corresponds to the presence of roughly 40–45 amino acids.

Unless otherwise indicated, the sequence for proteins and peptides is given in the order from the amino terminus to the carboxyl terminus. Similarly, the sequence for nucleic acids is given in the order from the 5' end to the 3' end.

The term "interacting proteins" refers to a pair of polypeptides that can form a stably-associated complex due to, for example, electrostatic, hydrophobic, ionic and/or hydrogen-bond interactions under physiological conditions.

Proteins smaller than about 5,000 g/mole are typically referred to as polypeptides or simply peptides (Bohinski).

Two amino acid sequences or two nucleotide sequences are considered homologous (as this term is preferably used in this specification) if they have an alignment score of >5 (in standard deviation units) using the program ALIGN with the mutation gap matrix and a gap penalty of 6 or greater (Dayhoff). The two sequences (or parts thereof) are more preferably homologous if their amino acids are greater than or equal to 50% identical when optimally aligned using the ALIGN program mentioned above.

A peptide or peptide fragment is "derived from" a parent peptide or polypeptide if it has an amino acid sequence that is identical or homologous to at least a portion of the amino acid sequence of the parent peptide or polypeptide. Exemplary derived peptides are peptide rIII (SEQ ID NO:4) and peptide rVI (SEQ ID NO:7), which are derived from the third and seventh WD-40 repeats of RACK1 (SEQ ID NO:27), "respectively".

The term "expression vector" refers to vectors that have the ability to incorporate and express heterologous DNA fragments in a foreign cell. Many prokaryotic and eukaryotic expression vectors are commercially available. Selection of appropriate expression vectors is within the knowledge of those having skill in the art.

The term "PKC" refers to protein kinase C, or C-kinase.

The term "RACK" refers to receptor for activated C-kinase.

The term "PS" refers to phosphatidylserine.

The term "DG" refers to diacylglycerol.

The term "PL" refers to phospholipids.

Phospholipids include both phosphatidylserine and diacylglycerol.

The term "GVBD" refers to germinal vesicle breakdown, a measure of insulin-induced maturation in *Xenopus oocytes.*

The term "PCR" refers to polymerase chain reaction.

The term "NMR" refers to nuclear magnetic resonance.

The term "βARK" refers to β-adrenergic receptor kinase.

II. General Overview Of Invention.

The invention relates to interacting proteins, at least one of which contains an amino acid sequence with one or more of the characteristic repeats termed WD-40 (Fong, et al.,).

According to one aspect of the invention, the function of a first protein of a pair of interacting proteins may be modulated, altered or disrupted by the addition, to a solution or medium containing the protein, of a peptide having a sequence that is identical or homologous to a part of the sequence of a WD-40 motif-containing repeat present in a second protein of the pair of interacting proteins.

The modulation or disruption of function of the first protein is due to the binding or association of the WD-40-derived peptide, termed "binding peptide", with the first protein. The consequences of the binding or association of the binding peptide with the first protein depend on the sequence of the peptide.

Typically, the presence of the binding peptide will inhibit the binding of the first protein to the second protein. This binding may be assayed in vitro by, for example, an overlay assay, whereby the degree of binding of one protein to another may be assessed. Several adaptations of overlay assays applied to embodiments of the present invention are described herein.

Regardless of whether or not the WD-40-derived peptide affects the association of the first protein with the second protein, the peptide may alter or modulate defined activities of the first protein. These activities may be assayed by a variety of methods in vivo and/or in vitro. The method(s) employed depend on the protein whose activity is being measured.

An exemplary first protein of a pair of interacting proteins is protein kinase C (PKC). Upon activation, PKC interacts with receptors for activated C kinase (RACKs), at least one of which (RACK1) contains WD-40 repeats. Several assays for determining the activity of PKC in the presence and in the absence of peptides derived from the WD-40 region of RACK1 are detailed herein.

Certain "interacting proteins" interact only after one or more of them has been stimulated by an exogenous or endogenous factor(s). For instance, PKC, as shown herein, does not bind to RACK proteins until it has been activated by, for example, phosphatydilserine (PS), diacylglycerol (DG) and calcium. However, peptides derived from WD-40 repeats of a second protein of such a pair may be able to associate with or bind to the first protein even in the absence of activators of the first protein, and in so doing, affect the function of the first protein (e.g. activate, inactivate, potentiate, sensitize, desensitize, alter the specificity, etc.).

Binding peptides derived from WD-40 repeats of a second protein of a pair of interacting proteins, may be useful as specific agonists, antagonists, potentiators of function, and the like, of the first protein of the pair. These properties may make the peptides useful in a number of applications, for example, direct use in therapeutic applications or as lead compounds for the development of other therapeutic agents, e.g., small organic molecules.

III. Advantages of the Invention for the Inhibition of Activated PKC Binding to RACK1.

Protein kinase C (PKC) is a family of at least 10 isozymes that share common structures and biochemical characteristics. It has been demonstrated that several isozymes are present within a single cell type, and it has been assumed that individual PKC isozymes are involved in different cellular functions. However, so far, the available activators and inhibitors of PKC do not appear to be isozyme-specific. Therefore, it is currently impossible to determine the role of individual PKC isozymes in normal cellular functions as well as in disease.

PKC activation by, for example, diacylglycerol and calcium, induces the translocation of PKC from a soluble (cytosolic) to a cell particulate (membrane-associated) fraction, as shown in experiments herein (Example 8). Activated PKC is stabilized in the cell particulate fraction by binding to membrane-associated receptors (receptors for activated C-Kinase, or RACKs).

In experiments done in support of the present invention and described herein, a clone (pRACK1) encoding a RACK has been isolated (Example 1). RACK1 belongs to a growing family of proteins that are homologous to the β-subunit of transducin and contain the WD-40 motif (Fong, et al.). It was demonstrated that peptide I (SEQ ID NO:1) binds to purified PKC (see Example 6 and FIG. 4), inhibits the binding of PKC to purified recombinant RACK1 protein (see Example 4 and FIG. 3), and inhibits PKC activity in several in vivo and in vitro assays (see Examples 7–11 and FIGS. 5–9).

Peptide I (SEQ ID NO:1) is homologous to a sequence identified in the sixth WD-40 repeats of RACK1 (see FIG. 1C). A synthetic peptide was prepared based on this sequence (peptide rVI; SEQ ID NO:7; underlined amino acids in repeat VI of FIG. 1C). Six more peptides were also prepared based on the corresponding regions in repeats I–V and VII (peptides rI–rV, rVII; SEQ ID NO:2–6, 8; underlined regions in corresponding repeats, FIG. 1C). Some of the peptides were also found to inhibit the binding of PKC to RACK1 (see Example 4 and FIG. 3). In addition, some of the peptides were found to bind to purified PKC (see Example 6, FIG. 4), partially activate PKC in the absence of other activators (peptide rVI; see Examples 7, 10, 11 and FIGS. 5, 8 and 9), and potentiate the effects of known PKC activators on the enzyme (see Examples 7–9 and FIGS. 5–7).

In *Xenopus oocyte* maturation studies (see, for instance, Example 7), peptide rVI (SEQ ID NO:7) is an agonist of βPKC. Peptide rIII, while less potent, is also an agonist of PKC; it enhances insulin-induced *oocyte* maturation at 50 and 500 μM.

In cardiac myocytes, norepinephrine (NE, 2 μM) causes translocation of δ and εPKC isozymes from the cytosolic to the particulate fraction. Introduction into cardiac myocytes of peptide rIII, and to a lesser extent peptide rVI, caused an immediate translocation of δ and εPKC isozymes in the absence of hormone stimulation. This peptide-induced translocation was followed by degradation of δ and εPKC isozymes. Moreover, NE-induced translocation is further enhanced in cells containing peptide rIII.

In contrast, introduction of peptide I to these cells does not affect PKC distribution in the absence of hormone stimulation, nor does it induce PKC degradation. Furthermore, NE-induced translocation is inhibited by peptide I. Similar concentrations of a number of control peptides did not affect PKC distribution or degradation in control or NE-treated cells.

In studies on rat cardiac myocytes, peptide rIII induced δPKC and εPKC activation that was followed by degradation of these activated isozymes.

Figure 6:
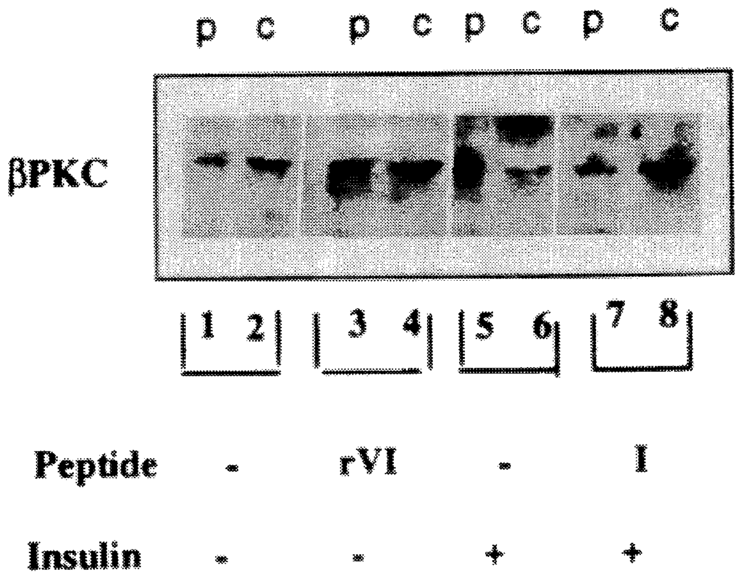
FIG. 6 shows the distribution of βPKC in *Xenopus oocytes* between the cytosolic and membrane-associated fractions following microinjection of either injection solution, peptide I (SEQ ID NO:1) or peptide rVI (SEQ ID NO:7) with or without insulin stimulation.

Peptide rVI also augments hormone-induced translocation of PKC isozymes (see, for example, Example 8 and FIG. 6). In contrast, peptide I (SEQ ID NO:1) inhibited hormone-induced translocation of PKC isozymes (Example 8, FIG. 6) and did not cause degradation.

The data summarized above demonstrate that peptides derived from WD-40 repeats of RACK1 can serve as PKC agonists and antagonists in vivo, and suggest that peptides derived from WD-40 regions of RACK1 contain at least part of the protein-protein interface between PKC and RACK1.

Furthermore, the results suggest that (i) WD-40 repeats present in other proteins, such as Gβ subunit, may also be located at or near a surface involved in protein-protein interactions, (ii) peptides derived from these repeats may be effective in disrupting the interactions of the proteins with their partners (e.g. β-adrenergic receptor kinase (βARK), (iii) the peptides may modulate or alter the activity of the proteins with which the WD-40 repeat-containing proteins interact, and (iv) the peptides may therefore have specific biological effects when administered in vivo.

IV. Identification of Pairs of Interacting Proteins.

A. Biochemical Approaches.

Novel interacting proteins may be identified and isolated by a number of methods known to those skilled in the art. For example, monoclonal antibodies raised to a mixture of antigens, such as a particular tissue homogenate, may be characterized and used to immunoprecipitate a single class of antigen molecules present in that tissue. The precipitated proteins may then be characterized further, and used to co-precipitate other proteins with which they normally interact (Hari, et al., Escobedo, et al.).

An alternate method to identify unknown polypeptides that interact with a known, isolated protein is by the use of, for example, an overlay assay (Wolf, et al., Mochly-Rosen, et al., 1991). A mixture (such as a fraction of a tissue homogenate, for example, a Triton-insoluble protein fraction) potentially containing proteins that bind to a known, isolated protein can be resolved using PAGE, blotted onto a nitrocellulose or nylon membrane, and contacted with a solution containing the known protein and any necessary co-factors or small molecules. After washing, the membrane can be contacted with a probe for the known protein, for example an antibody or a mixture of antibodies, and the signal visualized.

B. Molecular approaches.

Putative binding proteins of a known proteins may be isolated from tissue homogenates, as described above. Alternatively, DNA clones encoding putative binding proteins may be identified by screening, for example, an appropriate cDNA expression library. Expression libraries made from a wide variety of tissues are commercially available (for example, from Clonetech, Palo Alto, Calif.). Expression libraries may also be made de novo from organisms and tissues of choice by practitioners skilled in the art.

The screening of expression libraries for clones expressing a protein or protein fragment of interest may be readily accomplished using techniques known in the art, for example, an overlay assay.

An overlay-assay screening method may be used to identify clones expressing a (known or unknown) protein or protein fragment that binds to a probe in hand. The probe may be a protein postulated to be involved in protein-protein interactions with a protein expected to be present in a cDNA library selected for screening (as was the case for the cloning of RACK1, detailed in Example 1).

Actual screening of a selected cDNA library may be accomplished by inducing plated clones to express cloned exogenous sequences, transferring replicas of the induced plaques or colonies to filter membranes, and screening the membranes with an appropriate probe. According to this method, lifts of filters (for example, nylon or nitrocellulose) from an appropriately-induced cDNA library plates (induced by, for example, IPTG) are washed, blocked, and incubated with a selected probe for a period of time sufficient to allow the selected probe(s) to bind specifically to polypeptide fragments present on the filters. The filters may then be washed and reacted with a reagent (for example, antibodies such as alkaline phosphatase-conjugated goat anti-rabbit or anti-mouse antibodies, available from Boehringer Mannheim Biochemicals, Indianapolis, Ind.). Additional reactions may be carried out as required to detect the presence of bound probe.

One such overlay assay, described in Example 1, was used to screen a rat brain cDNA expression library for proteins that bind purified PKC in the presence of PKC activators (phosphatydilserine, diacylglycerol and calcium). The filters were screened with a mixture of rat brain PKC isozymes (α, β, γ, δ, ε and ζ). Following a series of washes, bound PKC isozymes were detected with a mixture of anti-α, β, γ PKC mouse monoclonal antibodies, and anti-δ, ε and ζ PKC rabbit polyclonal antibodies. Bound antibodies were detected using alkaline phosphatase-conjugated goat anti-rabbit or anti-mouse antibodies and 5-bromo-4-chloro-3-indoyl phosphate p-toluidine salt as a substrate.

Once a clone is identified in a screen such as the one described above, it can be isolated or plaque purified and sequenced. The insert may then be used in other cloning reactions, for example, cloning into an expression vector that enables efficient production of recombinant fusion protein. Examples of appropriate expression vectors are pGEX (Smith, et al., 1988) and pMAL-c2 (New England BioLabs, Beverly, Mass.). An expression vector containing an insert of interest may be used to transform appropriate host cells, such as *E. coli*, and the transformed host cells can be used to produce the recombinant protein in large amounts.

Typically, a recombinant protein is expressed in tandem with a bacterial or viral gene product (endogenous polypeptide) as part of a fusion protein. The junction between the endogenous polypeptide and the recombinant protein typically includes a recognition site for a rare-cutting protease. The endogenous peptide may be designed to incorporate a unique affinity tag (a short peptide sequence) to facilitate the purification of the fusion protein with an affinity reagent, such an antibody directed against the affinity tag. The recombinant protein may then be purified from the fusion protein using the appropriate protease.

Purified recombinant protein may be used in a number of ways, including in an overlay binding assay to screen for peptides or substances that inhibit binding between the recombinant protein and an interacting protein.

An example of the use of a cDNA clone to express protein is detailed in Example 2. RACK1 cDNA, isolated as described above and in Example 1, was subcloned into an expression vector (pMAL-c2, New England BioLabs, Beverly, Mass.) capable of expressing a cloned insert in tandem with maltose-binding protein (MBP). The vector containing the RACK1 insert was used to transform TB1 *E. coli*, which were then induced with IPTG. The cells produced a 78 kDa fusion protein comprised of RACK1 fused to the MBP. The overexpressed fusion protein was purified on an amylose affinity column according to the manufacture's protocol (New England BioLabs, Beverly, Mass.) and incubated with protease Xa to separate the expressed insert from the MBP. Following the incubation, a 36 kDa RACK1 protein was obtained.

V. Identification of WD-40 Repeats.

According to a method of the present invention, protein-protein interactions can be disrupted and/or the activity of an interacting protein can be altered, given at least one of the interacting proteins contains a WD-40 motif, or region, with a peptide(s) derived from a WD-40 repeat(s) of one of the proteins.

WD-40 repeats are typically found in a family of proteins having at least a limited homology with the β subunit of transducin. WD-40 repeats present in a selected member of this family can be identified by (A) performing a self-homology analysis on a selected protein using a homology matrix (performed by, for example, the computer program DNA Strider 1.2, available from Christian Marck, Service de Biochemie et de Genetique Moleculaire, Department de Biologie Cellulaire et Moleculaire, Direction des Sciences de la Vie—CEA—FRANCE), (B) aligning sequences comprising the repeating elements revealed by the homology matrix analysis, and (C) identifying conserved amino acid residues that typically serve to define a WD-40 repeat. The steps are discussed individually, below.

A. Homology matrix analysis.

Determining whether a particular amino acid sequence contains repeated motifs may be accomplished by a number of methods known to those skilled in the art. They range from a simple visual inspection of the sequence to the use of computer programs which can identify repeated motifs. One widely-implemented computer-assisted method is to generate a self-homology matrix. A self-homology matrix computes the homology of each amino acid residue in a particular sequence with every other residue in that sequence. The homology scores are stored in a 2-dimensional matrix. Values higher than a selected criterion level are flagged and displayed as points on an x-y coordinate. The x- and y-axes correspond to consecutive amino acid positions in the sequence.

An example of a self-homology matrix analysis is shown in FIG. 1B. The matrix was generated using the computer program DNA Strider 1.2 (Christian Marck, Service de Biochemie et de Genetique Moleculaire, Department de Biologie Cellulaire et Moleculaire, Direction des Sciences de la Vie—CEA—FRANCE) with the amino acid sequence of RACK1 (SEQ ID NO:27) with a window setting of 21 and a stringency of 6. Some typical features of a self-homology matrix are evident in the figure. The graph shows a "primary" diagonal line extending from the origin with a slope of unity, corresponding to the fact that the sequence is identical to itself. If the sequence contains repeating elements, as RACK1 does, there will be other, shorter sets of contiguous points arranged in diagonal lines substantially parallel to the primary diagonal and offset from the primary diagonal in the x- or y-directions. These shorter lines identify the locations of repeating elements with the sequence. Each repeating element will result in two sets of displayed points, symmetrically distributed about the primary diagonal.

The data displayed in a homology matrix analysis can be used to locate and roughly align the sequences of repeating elements for a more detailed analysis. The horizontal band delineating the region between ~100 and ~130 on the y-axis in FIG. 1B highlights the fact that portions of that region of RACK1, that is, the amino acids between about amino acid 100 and amino acid 130, are repeated a total of seven times in the sequence of RACK1. Arrows point to the repeats in the homology matrix. For purposes of rough alignment, the short diagonal lines pointed out by the arrows can be extended to the horizontal line at amino acid ~100 on the y-axis, and the x-axis location corresponding to the intersection be noted. For example, the intersection corresponding to the second repeat (second arrow from the left) is at x=~50).

Values determined in this manner may then be used to align the amino acid sequence of the repeats with each consecutive repeat beneath the preceding one, the start of each repeat corresponding approximately to the amino acid position determined by the analysis in the preceding paragraph. The amino acid sequence of RACK1, aligned in this manner, is shown in FIG. 1C.

Most commercially-available DNA and protein sequence analysis programs have the capability to perform a self-homology matrix analysis. One example is the program DNA Strider 1.2 (Christian Marck, Service de Biochemie et de Genetique Moleculaire, Department de Biologie Cellulaire et Moleculaire, Direction des Sciences de la Vie—CEA—FRANCE).

Once the repeating elements are identified and the sequences corresponding to repeating elements are roughly aligned, one may proceed to define the degree of homology among the individual repeats at the specific positions within the repeats, as is described below.

B. Aligning amino acid sequences.

If a self-homology matrix was used to obtain a crude alignment, the sequences may aligned by eye on a personal computer or the like using, for example, a text editor, a drawing program or a sequence-analysis program. Examples of programs effective to accomplish an alignment include "MACDRAW PRO" (Claris Corp., Santa Clara, Calif.) and "WORD" (Microsoft Corp., Redmond, Wash.), both of which are available for "MACINTOSH" series computers (Apple Computer Corporation, Cupertino, Calif.), as well as IBM-compatible computers running "WINDOWS" (Microsoft Corp.).

Amino acid sequences corresponding to internal repeats can also be aligned automatically using a protein sequence analysis program, such as "MACVECTOR" (Eastman Kodak Co., New Haven, Conn.).

According to a method of the invention, aligned sequences are examined further to determine if they fulfil criteria to be defined as WD-40 repeats. These criteria are detailed in part C, below.

C. Amino acid residues that define a WD-40 repeat.

Upon completion of steps outlined in parts A and B above, that is, determining whether a particular protein contains internal repeats, and if so, aligning those repeats, it is necessary to determine whether the aligned repeats contain WD-40 regions.

A WD-40 motif is roughly defined as a contiguous sequence of about 25 to 50 amino acids with relatively-well conserved sets of amino acids at the two ends (amino- and carboxyl- terminal) of the sequence. Conserved sets of at least one WD-40 repeat of a WD-40 repeat-containing protein typically contain conserved amino acids at certain positions. The amino-terminal set, comprised of two contiguous amino acids, often contains a Gly followed by a His. The carboxyl-terminal set, comprised of six to eight contiguous amino acids, typically contains an Asp at its first position, and a Trp followed by an Asp at its last two positions.

A more accurate definition of a WD-40 motif incorporates the observation that while specific residues, such as those identified above, are not always conserved within a WD-40 motif, conserved positions within the motif are typically occupied by residues selected from a restricted class of amino acids.

In order to better define the class of conserved residues at selected positions, it is necessary to group amino acids on the basis of certain common properties. A functional way to define common properties between individual amino acids is to analyze the normalized frequencies of amino acid changes between corresponding proteins of homologous organisms (Schulz). According to such analyses, groups of amino acids may be defined where amino acids within a group exchange preferentially with each other, and therefore resemble each other most in their impact on the overall protein structure (Schulz). Examples of amino acid groups defined in this manner, some of which are used in the definition of a WD-40 motif herein, include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

A "WD-40" motif is defined herein as a contiguous set of amino acids between (inclusive) two sets of relatively well conserved residues, termed herein as an "amino-terminal set" and a "carboxyl-terminal set". The amino-terminal set contains two adjacent amino acids. The residue at the first position is typically selected from groups ii, vi or viii, while the residue at the second position is typically selected from groups i, x or Ile. The first and second positions will often consist of Gly and His, respectively. The Gly and His residues are typically present in at least one of the aligned repeats of a WD-40-containing protein.

The carboxyl-terminal conserved set typically includes eight residues, but may contain as few as six residues. The most well-conserved residue in WD-40 motifs identified thus far is an Asp residue, comprising the first amino acid of the carboxyl-terminal conserved set. It is present in virtually all WD-40 repeats illustrated herein. In those repeats where it is not present, the position is occupied by a residue from groups iii or Gly.

The last two amino acids in the carboxyl-terminal conserved set are typically selected from groups iv or Ile, and groups i or viii, respectively. The most commonly used residue at the first of these positions is Trp. It is typically present in at least one of the WD-40 repeats of any given protein. The second position is occupied less consistently by a single residue, but is often occupied by Asp. The Trp-Asp (WD) combination is part of the namesake of WD-40 repeats.

The amino acids present in the internal portion of the carboxyl-terminal conserved set are less well-conserved than the terminal residues, and their total number may differ by up to two residues in different WD-40 repeats. The third position in from the carboxyl-terminal end of the carboxyl-terminal conserved set is typically selected from groups viii or ix, more typically ix. The fifth position in from the carboxyl-terminal end of the carboxyl-terminal conserved set is also typically selected from groups viii or ix, more typically ix.

The length of a WD-40 repeat, including the amino-terminal and carboxyl-terminal conserved sets is typically between about 25 and about 50 residues, more typically between about 29 and 34 residues. The distribution arises primarily from differences in the number of residues present between the amino-terminal and carboxyl-terminal conserved sets.

The number of WD-40 repeats in a particular protein can range from two to more than eight. The average number is about 5.

A determination of whether or not a set of aligned internal repeats are WD-40 repeats can be facilitated by an examination of all of the repeats as a whole, rather than an examination of each repeat individually. This is in part because not all of the aligned repeats will necessarily contain all of the conserved sequences that serve to identify WD-40 repeats, although the conserved residues will typically appear in at least one of the repeats.

For example, FIG. 1C shows the RACK1 amino acid sequence aligned to illustrate the internal repeats present in the sequence. All of the repeats are WD-40 repeats, even though the amino-terminal conserved set of repeat VI, for instance, contains an "LD" as opposed to the more usual "GH", and the carboxyl-terminal conserved set contains a "G" at its first position, as opposed to the highly-conserved "D". Similarly, the carboxyl-conserved set of, for example, repeat I, contains a "WK" at the last to positions, as opposed to the more usual "WD".

It will be appreciated that certain residues or sets of residues will be well-conserved in the WD-40 repeats of a selected protein, even though they may not be conserved in WD-40 repeats in general. Such residues or sets of residues may be useful in several ways. For example, they may be used in performing an alignment of internal repeats in a selected protein, as described in part B, above. The residues may also be useful for identifying regions based on which effective binding peptides may be designed (see section VI., below).

D. Identification of WD-40 repeats in RACK1.

In experiments done in support of the present invention, a protein that binds to activated PKC was cloned and sequenced (see Example 1). Sequence analysis of the deduced amino acid sequence revealed the presence of repeats, which were aligned and are shown in FIG. 1C.

The aligned repeats were identified as WD-40 repeats by application of the criteria identified in parts A, B and C above. For example, the conserved amino-terminal set in repeats I, II, III and V consists of the typical "GH" whereas in repeats IV, VI and VII, the set consists of other residues. These other residues, however, are contained in at least one of the amino acid groups identified above as conserved at the appropriate position. The conserved carboxyl-terminal set contains the highly-conserved "D" at its first position in all repeats except repeat VI. The second-to-last position of this set contains the relatively-well conserved "W" in each repeat, while the last position contains the typical "D" in repeats II, V and VI, and other residues in the other repeats.

Taken together, these data indicate that the repeats contained in RACK1 are WD-40 repeats. The data also illustrate that not all repeats contain all of the elements typical of a WD-40 motif, but that when the repeats are aligned and viewed together as a whole, a WD-40 motif is apparent in all repeats.

E. Identification of WD-40 repeats in sequenced proteins.

Data were compiled in support of the present invention to illustrate how WD-40 repeats in various proteins may be identified, and to illustrate the diversity of amino acid sequences that may be properly identified as WD-40 repeats by those skilled in the art following the guidance set forth herein. Two methods that were used to identify WD-40-containing protein sequences are detailed in Example 7.

In the first method, proteins identified in their description as having a homology to β-transducin were examined as detailed in parts B–D, above, for WD-40 repeats. 30 proteins were identified in this manner. The amino acid sequences of these proteins, with the WD40 regions aligned and delineated, are shown in FIGS. 12–18, 20–27, 29–30, 34–35, 37–38, 40 and 42–50. The sequences are represented in the Sequence Listing as SEQ ID NO:29–35, 37–44, 46–47, 51–52, 54–55, 57 and 59–67.

In the second method, proteins whose sequences were homologous to a consensus WD-40 motif (SEQ ID NO:262), were identified and examined for WD-40 repeats. Ten additional proteins containing WD-40 repeats were identified with this strategy. The amino acid sequences of those proteins, with the WD-40 repeats aligned and delineated, are shown in FIGS. 11, 19, 28, 31–33, 36, 39, 41 and 51. The sequences are represented in the Sequence Listing as SEQ ID NO:28, 36, 45, 48–50, 53, 56, 58 and 68.

Other types of searches may be equally effective at identifying proteins which may contain WD-40 repeats. For example, on-line databases such as GenBank or SwissProt can be searched, either with an entire sequence of a WD-40-containing protein, or with a consensus WD-40 repeat sequence. Various search algorithms and/or programs may be used, including FASTA, BLAST or ENTREZ. FASTA and BLAST are available as a part of the GCG sequence analysis package (University of Wisconsin, Madison, Wis.). ENTREZ is available through the National Center for Biotechnology Information, National Library of Medicine, National Institutes of Health, Bethesda, Md.

Sequences identified with a protein homology search are then analyzed as described in parts A, B and C, above, to identify potential WD-40 motifs. Once located, the motifs can be aligned, and effective binding peptides may be designed.

F. Identification of WD-40 regions in novel polypeptides.

WD-40 repeats may be identified in a novel polypeptide by, for example, the methods described in parts A–D above. It will be appreciated, however, that step A above (homology matrix) is not required in the identification of WD-40 repeats. Following the guidance of the present invention, one skilled in the art may, for instance, identify a WD-40 motif while scanning the sequence of some, perhaps novel, polypeptide merely through a recognition of one or more of the features characteristic of WD-40 repeats.

The precise methods by which one skilled in the art arrives at the conclusion that a particular motif is a WD-40 repeat is less relevant to the present invention than is the use of sequences derived from WD-40 motifs, regardless of how they are identified, to design peptides effective to alter or modulate the activity of one member of a pair of interacting proteins and/or to disrupt protein-protein interactions.

VI. Identification of Activity-altering Peptides.

Upon the alignment and recognition of WD-40 repeats in a particular protein, one may proceed to design a peptide or a set of peptides that may be effective to associate with or bind to the protein with which the WD40-containing protein normally associates. Such a binding or association may be expected to alter or modulate the activity of the protein and/or disrupt the association of the pair of interacting proteins.

The sequence of such a peptide will typically be homologous, if not identical to, a contiguous amino acid sequence contained within at least one of the WD-40 repeats. Examples of the selection of WD-40-derived peptides effective to disrupt protein-protein interactions are detailed in parts C and D below, for RACK-PKC and Gβ/γ-βARK interactions, respectively.

A. Choosing an appropriate region within a WD-40 repeat.

Putative binding peptides may be selected from any portion of a WD-40 repeat. If it is desired to obtain a degree of discrimination between the various WD-40-containing proteins, peptides should be chosen from the region between, and not including, the amino-terminal and carboxyl-terminal conserved sets. This "central region" typically shows greater sequence diversity between different WD-40-containing proteins than the terminal regions, and is roughly outlined by boxes in FIGS. 11–51, which show the amino acid sequences and aligned WD-40 repeats of various WD-40 repeat-containing proteins. Within the central region, peptides should be selected from sequences that have little or no homology to any other known sequences, save the sequence(s) of the protein(s) targeted for disruption.

For example, peptides rIII (SEQ ID NO:4, seven amino acids) and rVI (SEQ ID NO:7, eight amino acids), are identical to segments of RACK1 WD-40 repeats (III and VI, respectively) beginning five amino acids in from the amino termini of the WD-40 repeats from which they are derived (see FIG. 1C, underlined segments). The WD-40 repeat segments corresponding to the binding peptides comprise the left portion of the central region of the respective WD-40 repeats, and are not well-conserved in RACK1.

If it is desired to inhibit the interactions of, for example, all of the isoforms of a particular WD-40-containing protein family, a sequences is selected that includes a significant number of residues that are shared or highly homologous among at least one WD-40 repeat of each of the targeted isoforms.

If, on the other hand, an isoform-specific reagent is desired, a sequence is selected from a WD-40 repeat(s) of a specific isoform, where that sequence does not include a significant number of residues that are identical or highly homologous to residues in WD-40 sequences from related isoforms.

B. Choosing an appropriate length for a peptide.

Effective binding peptides may be designed that range in length from as few as about four residues to 40 or more residues. Preferably, binding peptides will have a length of at least about six residues, and less than about 20 residues. The length will be determined in part by the degree of desired homology to other WD-40 repeats, as described in part A above, and by the level of discrimination between proteins that is required.

For example, binding peptides selected from RACK1 sequences to inhibit RACK1/PKC interactions were seven and eight amino acids in length. The peptides are long enough to bind specifically to the targeted sequences, but short enough to not cross-react with other WD-40 repeat binding proteins. These properties enable the peptides to have very selective and specific effects, as is shown below in Examples 6–11.

C. Design of RACK1 WD-40-derived peptides to inhibit RACK1-PKC interactions.

Peptides rIII (SEQ ID NO:4, seven amino acids) and rVI (SEQ ID NO:7, eight amino acids) were designed in part following the guidance presented in parts A and B above. The peptides are identical to segments of RACK1 WD-40 repeat sequences beginning five amino acids in from the amino termini of the WD-40 repeats from which they are derived. The WD-40 repeat segments corresponding to the binding peptides comprise the left portion of the central region of the WD-40 repeats. The peptides were tested for their ability to disrupt protein-protein interactions in vitro and in vivo, as described in section VII and Examples 6–11 below.

D. Peptides derived from WD-40 repeats of Human G-Beta inhibit interactions of G-Beta subunits with βARK.

Methods described in section V part E were used to identify WD-40 repeats (SEQ ID NO:128–134) in Human G-Beta (SEQ ID NO:41). Segments from the first six WD-40 repeats were selected for the design of G-beta binding peptides (SEQ ID NO:13–18). The segments were selected based on criteria detailed in parts A and B, above.

The G-beta binding peptides are used to disrupt the interactions of G-beta subunits with βARK. The disruption is assayed using a modification of the overlay assay described in Example 4.

VII. Testing of Putative Binding peptides.

Detailed below are several assays by which the efficacy of WD-40-derived peptides at binding to a target protein, inhibiting protein-protein interactions, and altering or modulating the activity of a target protein may be determined.

One class of assays, widely-used to assess the binding of two proteins to each other, are overlay assays. Overlay assays are generally applicable to most proteins. They can be used to, for example, assess the binding of WD-40-derived peptides to their targets, as shown in Example 6 and described in part B below. Overlay assays can also be used to assess the ability of WD-40-derived peptides to inhibit the binding of two interacting proteins, one of which contains a WD-40 motif from which the peptides were derived (see, for instance, Example 4 and part C below).

Other assays may be used to assess effects of WD-40-derived peptides on the activity of the target protein. These assays may be in vivo assays, in vitro assays, or a combination of in vivo and in vitro assays. The assay used will depend on the proteins involved and on the system(s) and/or process(es) that involve the interacting proteins against which the peptide was targeted. For instance, the assays described in parts D–I below are appropriate for characterizing PKC activity in vivo and in vitro.

While many of the assays below are particular useful for characterizing the activity of PKC, they also illustrate a general framework of experiments by which the effects of WD-40 derived peptides on other proteins may be assessed.

A. Overlay assays to evaluate efficacy of putative binding peptides derived from WD-40 regions.

An overlay assay can be used to assess the disruption of the ability of a pair of proteins to associate. Methods for conducting overlay assays are well-known in the art (see, for example, Mochly-Rosen, et al., 1991).

Applications of overlay assays to evaluate putative binding peptides for PKC/RACK1 interactions are presented in Examples 4 and 5 herein. The assays can be generally described as follows.

One protein of a pair of interacting proteins ("immobilized" protein) can be resolved on an SDS/PAGE gel and blotted onto an appropriate membrane (for example, nitrocellulose or nylon) by methods known to those skilled in the art. The blots may then be contacted with a solution containing the other protein of the pair of interacting proteins ("overlay" protein) in the presence, and in the absence of putative binding peptides. Following appropriate wash steps, bound overlay protein can be detected by the use of an appropriate probe, such as an antibody directed against the overlay protein.

A variation on the above protocol may be performed to minimize a possible interference between unbound binding peptide and antibodies used to detect the presence of bound overlay protein. The modification consists of performing another SDS/PAGE electrophoresis between the steps of binding the overlay protein, and detecting the overlay protein with antibody or other probe. It is accomplished by cutting the blot into pieces sized to just encompass the area occupied by the blotted immobilized protein, after the overlay protein had been contacted (in the presence or in the absence of binding peptides) and allowed to bind to the blot. The pieces of membrane are then incubated in a sample buffer, placed in the wells of a second SDS polyacrylamide gel and subjected to electrophoresis.

Following electrophoresis, the gel is blotted as above, and contacted with a probe, for example antibodies, to detect bound overlay protein.

B. Binding of βPKC to peptides homologous to a WD-40 region of RACK1.

The binding of βPKC to peptide I (SEQ ID NO:1), peptide rVI (SEQ ID NO:7) and control peptide (SEQ ID NO:9) was assessed in Example 6 using a PKC overlay assay similar to that described in Example 3. Increasing amounts of peptides were applied onto nitrocellulose using a slot-blot apparatus. The membranes were incubated with PKC in the presence and absence of PS, DG, and calcium.

Figure 4:
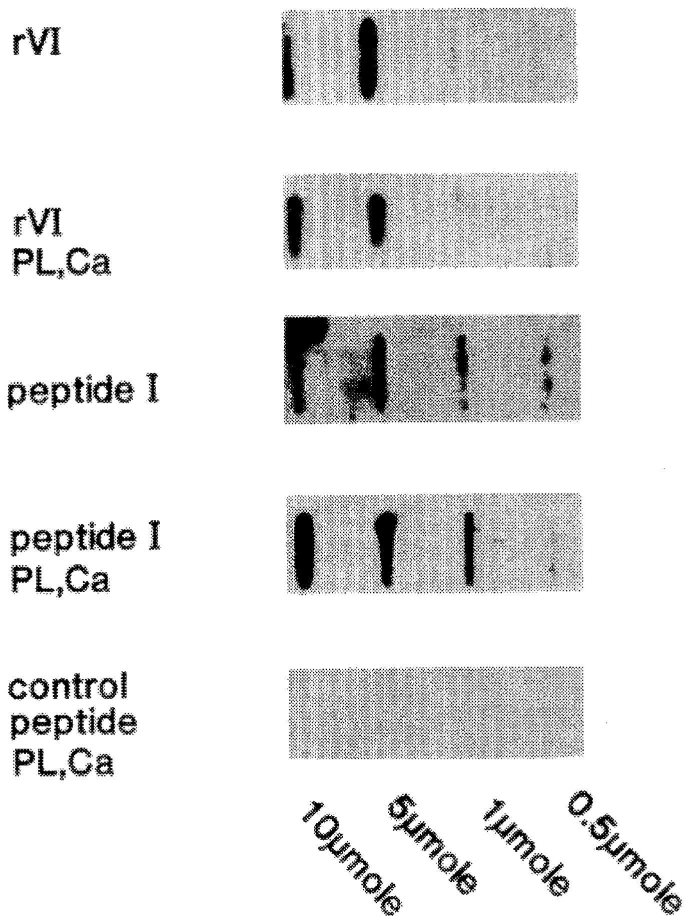
FIG. 4 shows the results of an overlay assay to detect binding of βPKC to either peptide I (SEQ ID NO:1) or peptide rVI (SEQ ID NO:7) immobilized on nitrocellulose membranes under various conditions.

The data are shown in FIG. 4, and show that activated PKC bound to both peptides I and rVI at peptide amounts as low as 5 μmoles, but not to the control peptide. Unactivated PKC did not bind to peptide I, but did bind to peptide rVI at similar concentrations.

The results indicate that while the peptides were homologous to one another and were capable of binding to the same protein, they behaved differently. Peptide rVI (SEQ ID NO:7; 8 residues) was able to bind to both activated as well as unactivated forms of PKC, whereas peptide I (SEQ ID NO:1; 15 residues) could bind only to activated PKC. The differences between the binding properties may be due, for example, to charge differences and/or length differences between the two peptides.

C. Effects of peptides homologous to WD-40 region of RACK1 on PKC binding to RACK1

Figure 3:
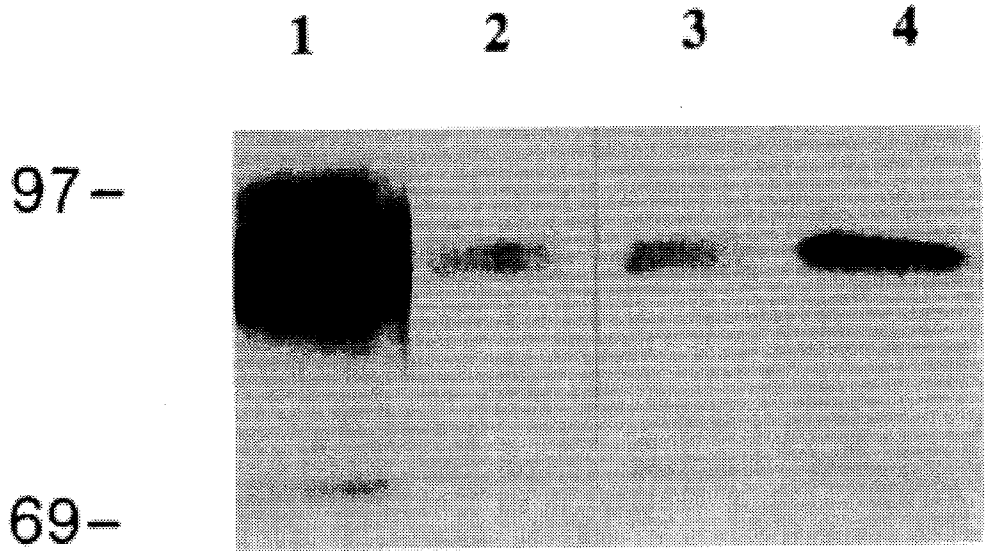
FIG. 3 shows the results of an overlay assay to detect PKC binding to immobilized RACK1 in the presence and absence of WD-40-derived peptides.

Two peptides (peptide rIII; SEQ ID NO:4 and peptide rVI; SEQ ID NO:7) identical to regions of RACK1 WD-40 repeats (underlined, FIG. 1C) were tested for their ability to inhibit PKC binding to recombinant RACK1 using a modification of the overlay procedure referred to above. The experiment is detailed in Example 4 and the results are shown in FIG. 3.

Peptide I caused an 81±6% inhibition of PKC binding to recombinant RACK1 as compared with binding in the absence of added peptide. Both peptides rIII and rVI inhibited the binding of PKC to RACK1. In addition, peptides rI and rII were also effective inhibitors of the interaction of PKC to RACK1. A lesser inhibitory effect was obtained with peptides rIV and rV and no inhibition was obtained with peptide rVII.

The difference in the peptide's ability to inhibit binding may reflect differences in the roles played by the corresponding WD-40 repeats in the protein-protein interactions between PKC and RACK1. The peptide's ability or inability to inhibit protein-protein interactions as assayed by an overlay assay, however, is not necessarily correlated with the effects those peptides may have on the activity of the targeted proteins, as measured by both in vivo and in vitro assays and described in parts D–I below.

D. Effects of peptides homologous to WD-40 regions of RACK1 on PKC-mediated *oocyte* maturation.

Figure 5B:
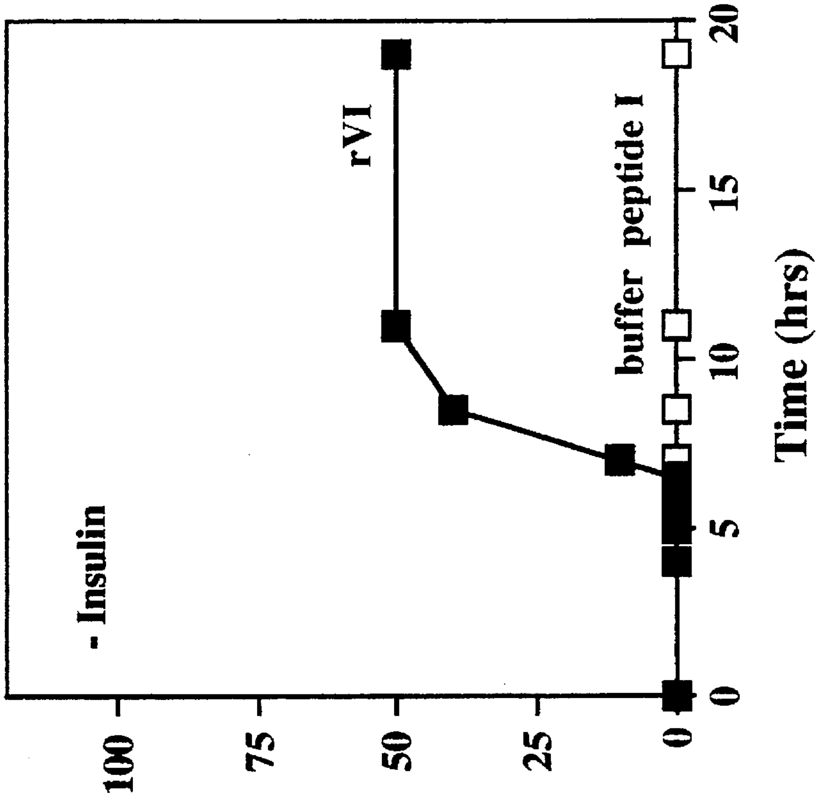
FIG. 5B shows the effects of injecting peptides I (SEQ ID NO:1) and rVI (SEQ ID NO:7) on PKC-mediated germinal vesicle breakdown (GVBD) in the absence of insulin induction.
Figure 5A:
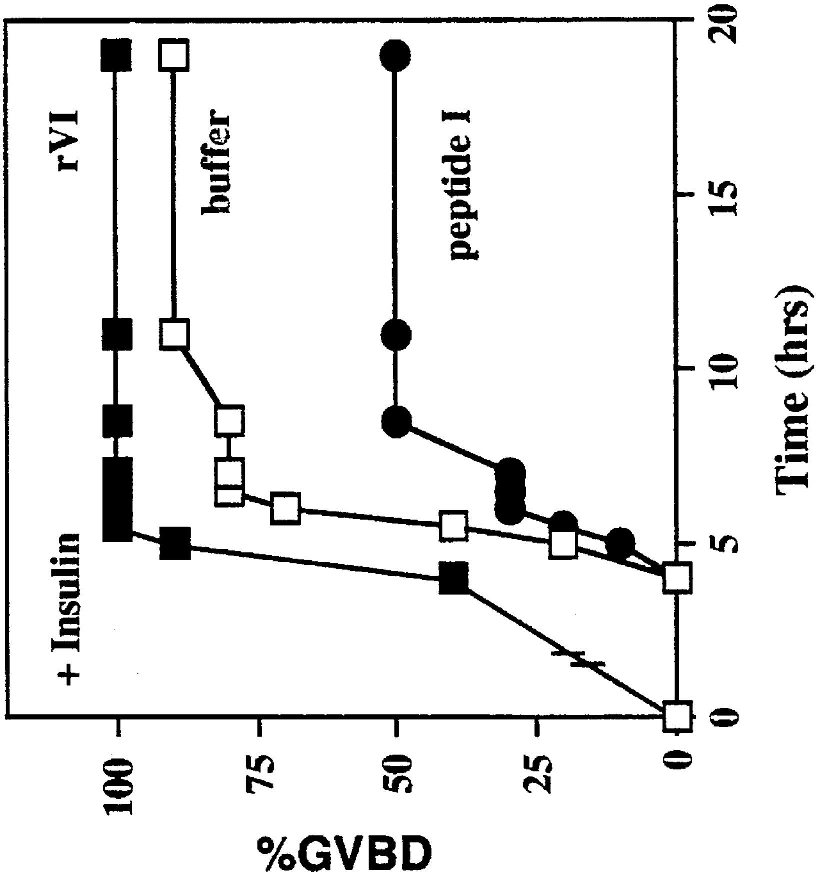
FIG. 5A shows the effects of injecting peptides I (SEQ ID NO:1) and rVI (SEQ ID NO:7) on PKC-mediated germinal vesicle breakdown (GVBD), a measure of insulin-induced *oocyte* maturation.
Figure 5C:
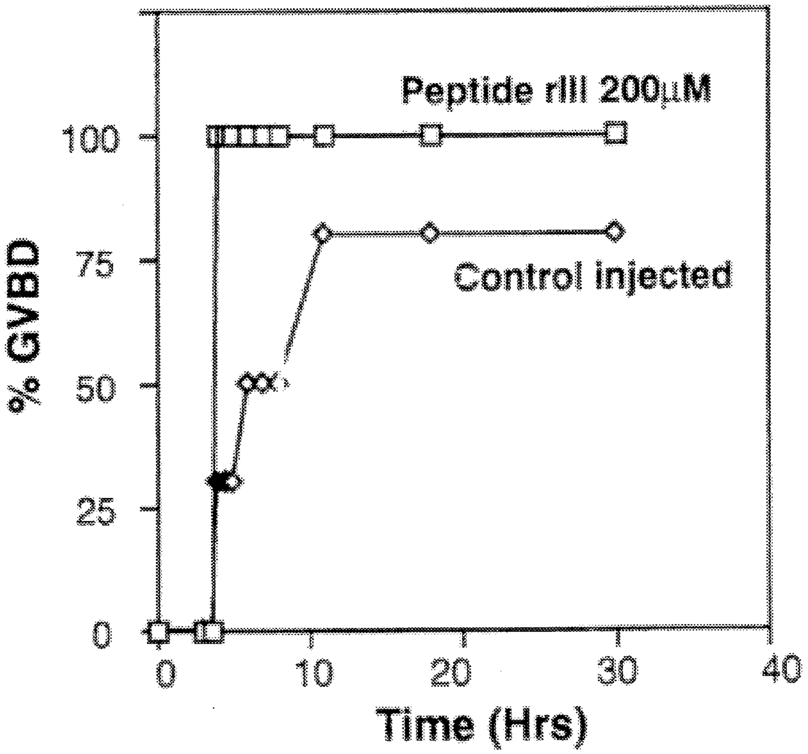
FIG. 5C shows the effects of injecting peptide rIII (SEQ ID NO:4) on PKC-mediated germinal vesicle breakdown (GVBD) in the absence of insulin induction.
Figure 6:
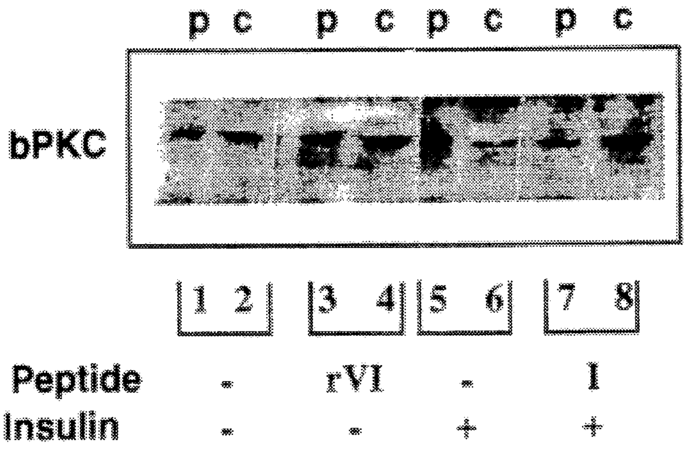

Peptides I (SEQ ID NO:1), rIII (SEQ ID NO:4) and rVI (SEQ ID NO:7) were also tested for their ability to affect insulin-induced, PKC-mediated maturation in *Xenopus oocytes*, as detailed in Example 7 and shown in FIGS. 5A and 5C.

PKC is involved in the maturation of *Xenopus oocytes*. Phorbol esters, which activate PKC, or microinjection of a constitutively active mutant of PKC induce the first stage of *oocyte* maturation in the absence of hormones. Exposure to insulin causes an increase in diacylglycerol levels and microinjection of activated PKC enhances insulin-induced maturation (Stith, et al.). Microinjection of purified RACK proteins causes a significant decrease in the rate of *oocyte* maturation (Smith, et al., 1992). The insulin-induced *oocyte* maturation assay therefore provides an effective in vivo assay for compounds that interfere with the function of PKC.

The maturation response was quantified by monitoring the appearance of a white spot in the animal hemisphere of the *oocyte*, indicating germinal vesicle breakdown (GVBD) and maturation. The indicated peptides were microinjected into *Xenopus oocytes* and the percent of *oocytes* with GVBD following insulin exposure was plotted as a function of time in FIGS. 5A and C.

Approximately 80–85% of sham-injected (control) *oocytes* exposed to insulin reach maturation, as compared with 45–50% of *oocytes* injected with peptide I. The rate of maturation of those *oocytes* that did mature was similar in the two cases. In contrast the effects of peptide I, both peptides rIII and rVI potentiated the effects of insulin on *oocyte* maturation, both in terms of the rate of maturation, and in the total fraction of *oocytes* that mature during the experiment. Injection of peptides rIII or rVI increases the fraction of maturing *oocytes* to essentially 100%. Furthermore, peptide rVI induced *oocyte* maturation in the absence of insulin stimulation (FIG. 5B).

Together, the data above indicate that peptides homologous to the WD-40 region of RACK1 can modulate the function of a protein with which RACK1 interacts (e.g. PKC), that the modulation can occur in vivo, and that it can have clear and profound physiological consequences. Furthermore, the results with peptide rVI suggest that under appropriate circumstances, the peptide alone may act to activate PKC, in the absence of other activating substances.

E. Effects of peptides homologous to WD-40 regions of RACK1 on PKC translocation in *Xenopus oocytes*.

Insulin causes the redistribution of βPKC, but not other PKC isozymes, from a cytosolic form to a membrane-associated form, as evidenced by the relative levels of PKC in the soluble vs. the particulate fraction of *oocyte* homogenate. To assess the effects of RACK1 WD-40-derived peptides on insulin-induced PKC translocation, 50 nl of a 20 mM NaCl solution containing the indicated peptides were microinjected into *Xenopus oocytes*. The *oocytes* were then homogenized, and the relative amount of PKC in the soluble and particulate fractions was assayed. The protocol followed was a modification of a method described by Smith, et al (1992). The results are shown in FIG. 6.

Peptide I (50 μM) did not affect βPKC distribution in untreated *oocytes*, but inhibited insulin-induced βPKC translocation (FIG. 3, lanes 7,8). In contrast, peptide rVI (50 μM) induced βPKC translocation in the absence of insulin treatment (FIG. 3, lanes 3,4). These results suggest that peptide I is an antagonist of hormone-induced PKC translocation, whereas peptide rVI is an agonist and an activator of PKC translocation. In light of the results presented in Example 7, the data also suggest that the inhibition of insulin-induced GVBD following microinjection of peptide I was due to an inhibition of βPKC translocation.

F. Effects of peptides homologous to WD-40 regions of RACK1 on sensitivity of βPKC to Arg-C endopeptidase.

Upon activation of PKC, a pseudosubstrate autoinhibitory sequence at the N-terminus of PKC dissociates from the catalytic site and renders the molecule sensitive to endopeptidase Arg-C (Orr, et al.). Exposure of activated βPKC to Arg-C results in a limited proteolysis, or "nicking" of the enzyme. The nicking typically generates a 78 kDa fragment and several small fragments. Continued exposure to Arg-C typically results in the disappearance of βPKC (Orr, et al.).

Since peptides rIII (SEQ ID NO:4) and rVI (SEQ ID NO:7) exhibited PKC agonist activities in other assays (see, for instance Examples 7 and 8), experiments were performed to determine whether the peptides were capable of activating PKC in a manner to make it susceptible to endopeptidase Arg-C. The experiments are detailed in Example 9 and the results are shown in FIG. 7.

Figure 7:
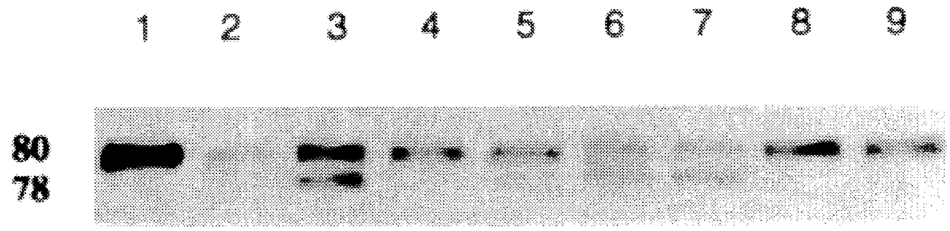
FIG. 7 shows the effects of peptides I and rVI on the sensitivity of βPKC to Arg-C endopeptidase.

In the presence of effective concentrations of PKC activators (0.8 μg/ml DG, 50 μg/ml PS and 1 mM $CaCl_2$), exposure of βPKC to Arg-C resulted in nicking, generating the 78 kDa fragment (FIG. 7, lane 2). In the absence of PKC activators, exposure of βPKC (80 kDa) to endopeptidase Arg-C had no effect on the enzyme (FIG. 7, lane 1).

Incubation of βPKC with Arg-C at low concentrations of activators (2.5 μg/ml PS and 50 μM $CaCl_2$) in the absence of added peptide, in the presence of control peptide (SEQ ID NO:9) and in the presence of peptide I (SEQ ID NO:1) did not result in appreciable nicking activity (FIG. 7, lanes 4, 8 and 9, respectively). However, incubation of βPKC with the same low concentration of activators in the presence of peptides rIII or rVI resulted in the appearance of the 78 kDa nicked PKC fragment (effects of peptide rVI in FIG. 4, lanes 5–7). Concentrations as low as 10 nM of peptide rVI were sufficient to result in nicking activity, indicative of βPKC activation.

The results indicate that peptides rIII and rVI, but not peptide I, are effective to stabilize PKC in an activated conformation that renders it susceptible to Arg-C under conditions of low PKC activators that would otherwise not render the enzyme susceptible to Arg-C.

G. Effects of peptides homologous to WD-40 regions of RACK1 on βPKC autophosphorylation.

Figure 8:
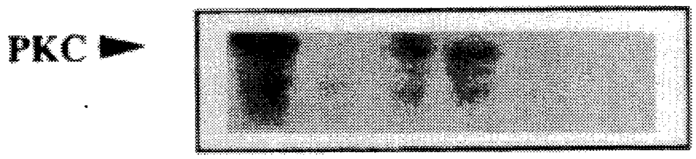
FIG. 8 shows the effects of peptides I and rVI on PKC autophosphorylation in the absence of PKC activators.

Activated PKC is capable of autophosphorylation, which can be assayed by incubation with [7-3-2P]ATP and visualized on an autoradiograph of a gel. Anti-pseudosubstrate antibodies were shown previously to induce autophosphorylation in the absence of PKC activators (Makowske, et al.). Since peptide rVI (SEQ ID NO:7) was effective to induce PKC translocation and GVBD in the absence of PKC activators, experiments were performed to determine if the peptide was also capable of inducing PKC autophosphorylation. The experiments are detailed in Example 10 and the data are shown in FIG. 8.

PKC activated with PS (50 μg/ml), DG (0.8 μg/ml) and $CaCl_2$ (1 mM) shows normal levels of autophoshorylation (lane 1). No autophosphorylation was seen in the absence of PKC activators (lane 2), or in the absence of PKC activators with peptide I (SEQ ID NO:1; lane 5) or control peptide (SEQ ID NO:9; lane 6). In contrast, peptide rVI in the absence of PKC activators induced PKC autophosphorylation to over 80% of the levels obtained for PKC alone in the presence of optimal concentration of PS, DG, and calcium (compare FIG. 8 lane 1 (control) with lane 4 (peptide rVI)).

H. Effects of peptides homologous to WD-40 regions of RACK1 on histone phosphorylation by βPKC.

Another measure of PKC activity is the ability of activated PKC enzyme to phosphorylate histones. PKC phosphorylation of histone was carried out using a modification of the protocol described by Mochly-Rosen, et al., (1987). Phosphorylation was carried out in the presence or absence of PKC activators (PS, DG and calcium) and RACK1-derived peptides. Phosphorylated histone was detected by autoradiography, following SDS-PAGE on a 10% gel.

Figure 9:
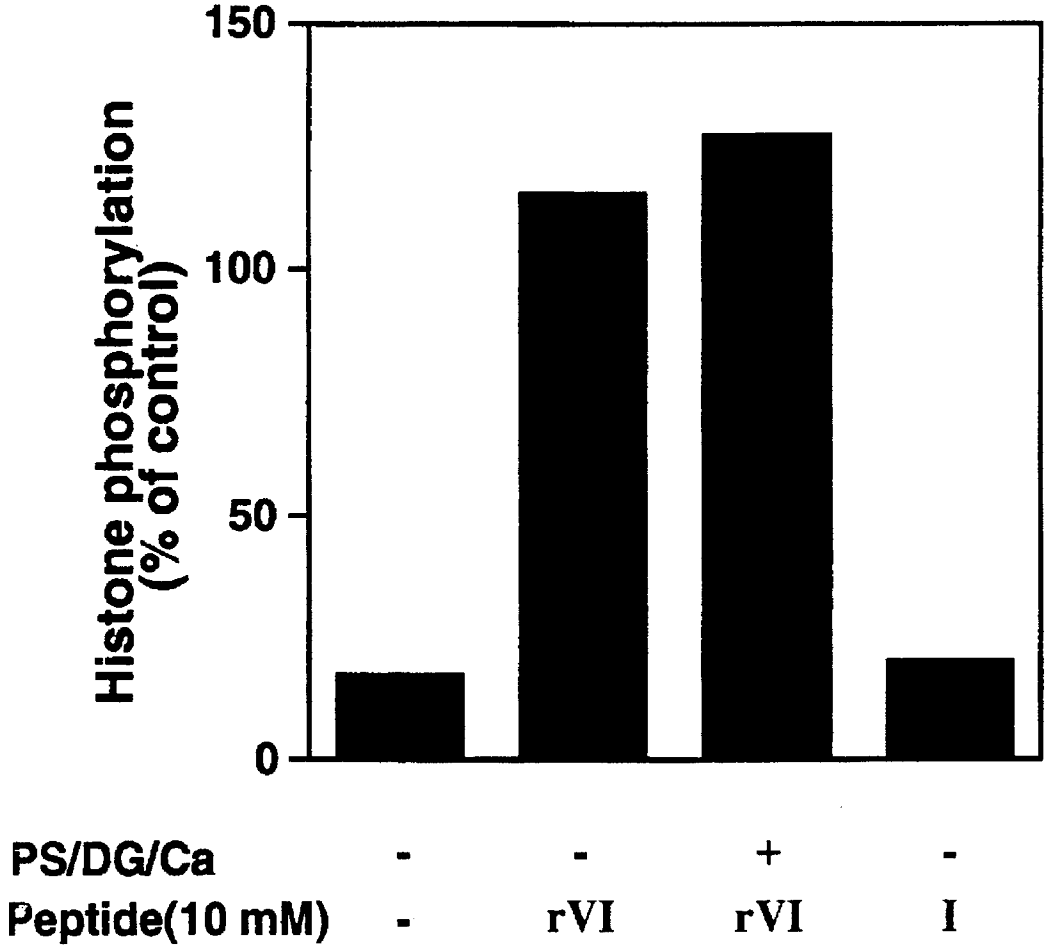
FIG. 9 shows the effects of peptides I and rVI on PKC phosphorylation of histones in the absence of PKC activators.
Figure 10:
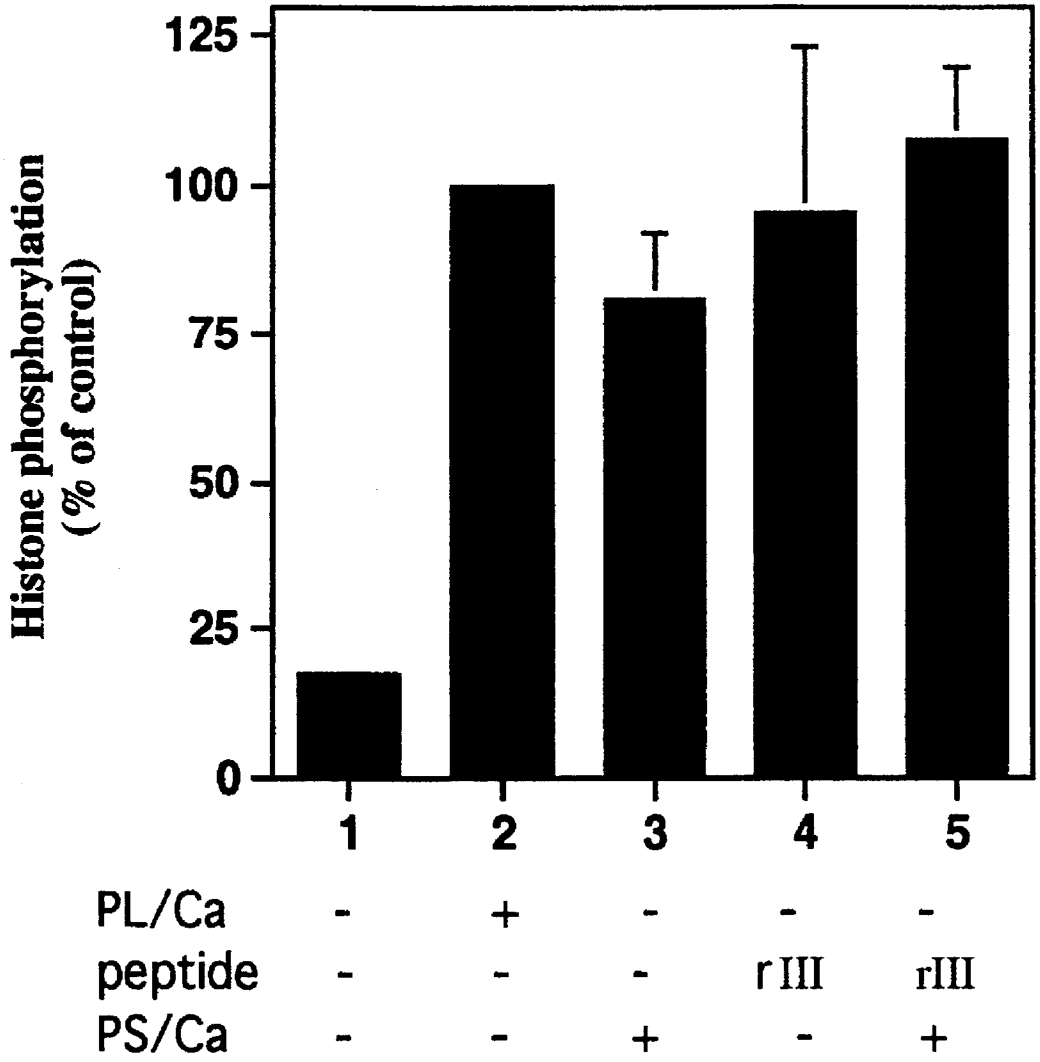
FIG. 10 shows the effects of peptide rIII on PKC phosphorylation of histones in the absence of PKC activators.

Since peptide rVI (SEQ ID NO:7) was effective to induce the autophosphorylation of PKC in the absence of PKC activators, and both peptides rIII (SEQ ID NO:4) and rVI rendered PKC susceptible to proteolysis by Arg-C, experiments were performed to characterize the effect of the peptides on histone type III phosphorylation by PKC. The experiments are detailed in Example 11 and the results are shown in FIGS. 9 and 10.

The results are similar to those obtained for the effects of peptide rVI on autophosphorylation of PKC, that is, peptide rVI was effective to induce PKC-mediated histone phosphorylation in the absence of the PKC activators PS, DG, and calcium, once again supporting that peptide rVI is an agonist of PKC activation. Peptide rIII similarly induced histone phosphorylation (FIG. 10).

VIII. Utility.

A. Peptides as probes for the identification of target proteins.

WD-40 derived peptides may be used, for example, to isolate clones encoding target proteins from an expression library. Variations on the cloning methods described herein can be used to identify clones expressing sequences capable of binding the peptides. For example, WD-40 derived peptides may be used to detect a target protein on a membrane using a standard binding assay. Positive clones may be detected, for example, by radiolabeling the peptides and exposing the membrane to film.

Target proteins isolated in this manner may be completely novel, or they may be partially characterized (in terms of a biological activity in a homogenate, or a band on a protein gel, for example).

Upon isolation of a cDNA encoding a binding protein, the cDNA may be expressed, for example, as detailed herein, and the protein may be characterized. Purified protein thus isolated may be used for a number of applications, including the production of antibodies.

Peptides designed according a method of the present invention may also be used, for example, as probes in a Western blot of a tissue homogenate to identify and determine the molecular weight of known or putative target proteins.

Screens such as those described above may be facilitated by the modification of peptides used for screening to incorporate any of a variety of reporter moieties. For example, the peptides can be radiolabeled with $^{125}I$. Alternatively, the peptides can be modified with a sequence-tag or a ligand for an affinity column by methods known to those skilled in the art.

The peptides may also be modified to covalently cross-link to their targets after binding, for example with any of various affinity reagent for cross linking known to those skilled in the art. This enables the isolation of target proteins that bind the peptides relatively weakly.

B. Peptides as substitutes for defective WD-40 containing proteins.

In cases where a WD-40 containing protein is implicated in a disease (see, for example Reiner, et al.), peptides derived from WD-40 regions of the defective protein may be used as substitutes, for example, to activate a target enzyme. Such an approach may be more feasible than attempting therapy with intact proteins. The approach has an additional advantage in that it does not require knowledge of the chromosomal location of the affected gene.

The peptides can be introduced into affected cells by any of several methods known to those skilled in the art, including through the use of an appropriate expression vector or through in vitro synthesis and administration by an effective, expedient route. In vitro studies can be carried out using skinning or microinjection techniques.

C. Peptides as pharmaceutical agents.

WD-40 derived peptides of the present invention may be used therapeutically, as described above. Such peptides may be designed so as to interact with endogenous target molecules to augment or correct their function. Alternatively, peptides may be designed to specifically interact with target molecules unique to a pathogenic organism.

D. Peptides as modulators of enzyme activity of proteins involved in protein-protein interactions.

Peptides synthesized according to a method of the invention may be effective to modulate the function of a target molecule (e.g. serve as agonists or antagonists). As shown herein, for example, peptides rVIII and rVI can serve to activate or enhance the activation of PKC, whereas peptide I can inhibit PKC.

These activities may be used in screens to identify other compounds which may affect the function of target molecules such as PKC. In particular, because WD-40 derived peptides may interact with PKC in a manner that is more similar to in vivo interactions (i.e. protein binding), they may be useful for identifying molecules or compounds that may interfere with PKC function in vivo, but might not necessarily interfere with PKC in vitro.

For example, peptide rVI can be used to stimulate PKC in the absence of traditional PKC activators, and the rVI-stimulated enzyme may be used in a screen to identify, for example, novel PKC-inhibiting or PKC-potentiating compounds.

If constitutive activation or inactivation of a target enzyme is desired, peptides may be designed with integrated or derivatized cross-linking moieties. The peptides can be cross-linked to their targets upon binding such that the target molecule assumes the desired state of activity for the lifetime of the target molecule.

Conversely, as described herein for PKC, peptides may also be designed so as to accelerate the degradation of the target molecule. For example, peptide rIII accelerated the degradation of PKC in cardiac myocytes.

E. WD-40 derived peptides as specific modulators of isozymes.

Peptides designed according to a method of the present invention can also be used to provide target isozyme-specific modulator molecules. For example, most cells have several PKC isozymes, all of which are activated by the same cellular stimuli. Determining the function of the individual isozymes is therefore difficult.

WD-40 derived peptides that selectively stimulate or inhibit specific target isozymes or groups of isozymes may be useful, both in terms of therapeutic value, and in terms of determining the roles of different isozymes in cellular function and disease. Such information can be useful for the identification of new molecular targets for drug development, as is described in part F, below.

F. Compounds designed based on the predicted structure of binding peptides as pharmaceutical agents.

Peptides derived from WD-40 repeats may be useful for identifying lead compounds for drug development. Peptides as small as 7 residues have been shown herein to possess specific bioactivities upon interaction with their targets in vivo. The structure of such small peptides can be readily determined by a number of methods, such as NMR and X-ray crystallography. A comparison of the structures of peptides similar in sequence, but differing in the biological activities they elicit in the target molecules, can provide information about the structure-activity relationship (SAR) of the target enzyme.

For example, peptide I and RACK1-derived peptides rIII (SEQ ID NO:4) and rVI (SEQ ID NO:7) had opposite effect in vivo, although they are homologous in sequence.

Information gleaned from the examination of structure-activity relationships can be used to design either modified peptides, or other small molecules or lead compounds which can be tested for predicted properties (e.g. agonist or antagonist), as related to the target enzyme. The activity of the lead compounds can be evaluated using assays similar to those used in the evaluation of peptide-binding effects.

Information relating to a SAR of a target enzyme may also be obtained from co-crystallization studies. In such studies, a peptide with a desired activity is crystallized in association with a target protein, and the X-ray structure of the complex is determined. The structure can then be compared, for example, to the structure of the target protein in its native state, and information from such a comparison may be used to design compounds expected to possess specific activities. The compounds can be evaluated using assays similar to those used in the evaluation of peptide-binding effects.

G. PCR of cDNA corresponding to WD-40 repeats to identify mutations in WD-40 containing proteins.

Results presented herein suggest that the middle regions of WD-40 motifs are involved in the association of a WD-40 protein with its target protein. Because this association is likely to play a central role in the activity of a polypeptide complex comprised of interacting proteins, some genetic diseases may include mutations at these regions of WD-40 containing proteins.

Therefore, if a WD-40 containing protein is implicated in a genetic disorder, it may be possible to use PCR to amplify DNA from the WD-40 regions to quickly check if a mutation is contained within one of the WD-40 motifs. Primers can be made corresponding to either (i) the flanking regions of each repeat or (ii) the flanking regions of a series of tandem repeats from the affected gene. Standard sequencing techniques can be used to determine whether a mutation is present. This method does not require prior chromosome mapping of the affected gene and can save time by obviating the need to sequence the entire gene encoding a defective WD-40 protein.

The following examples illustrate, but in no way are intended to limit the present invention.

Materials and Methods

Nitrocellulose filters were obtained from Schleicher and Schuell (Keene, N.H.).

Synthetic peptides were prepared using commercially available automated peptide synthesizers. Alternatively, custom designed peptides may be purchased, for example, from Bachem Bioscience (King of Prussia, Pa). Peptides may also be prepared recombinantly by expressing oligonucleotide sequences encoding the peptides. The oligonucleotide sequences may be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio, et al.; Eaton, et al.). Oligonucleotide coding sequences can be expressed by standard recombinant procedures (Maniatis, et al.; Ausubel, et al.).

"Triton" refers to a nonionic detergent comprising a polyoxyethylene ether and other surface-active compounds. An exemplary Triton detergent is "TRITON X-100" available from Sigma Chemical Company, St. Louis, Mo.

"Tween" refers to a nonionic detergent comprising polyoxyethylenesorbitan monolaurate with a fatty acid composition of approximately 55% lauric acid, with a balance composed primarily of myristic, palmitic and stearic acids. An exemplary Tween detergent is "TWEEN 20", available from Sigma Chemical Company, St. Louis, Mo.

"SDS" refers to sodium dodecyl sulfate.

"PAGE" refers to polyacrylamide gel electrophoresis.

"IPTG" refers to isopropyl β-D-thiogalactopyranoside.

EXAMPLE 1

Expression Cloning of a PKC-binding Protein

A. Buffers.

Overlay block buffer: 50 mM Tris-HCl (pH 7.5), 0.2M NaCl,3% bovine serum albumin (BSA) and 0.1% polyethylene glycol.

Overlay buffer: 50 mM Tris-HCl (pH 7.5), 0.2M NaCl, 12 mM 2-mercaptoethanol, 0.1% BSA, 1% polyethylene glycol, 10 μg per ml soybean trypsin inhibitor and 10 μg per ml leupeptin.

B. Isolation of a PKC-binding cDNA clone by an overlay assay.

A rat brain (Sprague Dawley) cDNA expression library, constructed in the lambda phage cloning vector "UNI-ZAP XR" (Stratagene, La Jolla, Calif.), was screened by an overlay assay as follows.

Lifts of nitrocellulose filters from IPTG-induced cDNA library plates were incubated for 2 hours in overlay block buffer. The filters were then transferred to overlay buffer with or without 1 unit of a mixture of rat brain PKC isozymes (α, β, γ, δ, ϵ and ζ, ~10 nM final concentration each) and incubated for 20 minutes at room temperature with PKC activators (60 μg/ml phosphatidylserine (PS), 2 μg/ml diacylglycerol (DG), 1 mM $CaCl_2$).

Following three 15 minute washes in the overlay buffer, the filters were incubated in the overlay block buffer in the presence of a mixture of monoclonal anti-α, β and γ PKC antibodies (1:1000 dilution; Seikagaku Kogyo, Tokyo, Japan) and polyclonal anti-δ, ϵ and ζ PKC antibodies (1:500 dilution; Life Technologies, Gaithersburg, Md.). After a 16 hr incubation at room temperature, the filters were washed three times, 15 minutes per wash, in overlay buffer.

Binding of PKC was determined using alkaline phosphatase-conjugated goat anti-rabbit or goat anti-mouse antibodies (1:2000 dilution, Boehringer Mannheim Biochemicals, Indianapolis, Ind.). The alkaline phosphatase reaction used 5-bromo-4-chloro-3-indoyl phosphate p-toluidine salt as a substrate, and was performed following the manufacturer's protocol.

Library screening of $2.4\times10^6$ recombinant "UNI-ZAP" lambda phage plaques yielded one clone, pRACK1, that reacted with anti-PKC antibodies in the PKC overlay membrane, but not in the control overlay membrane. These results suggest that pRACK1 encodes a PKC binding protein.

C. Cloning and sequencing cDNA from positive plaques.

The clone pRACK1, identified as detailed in part B above, was plaque purified and cDNA inserts were isolated as phagemids by in vivo excision of the cloning vector, according to the manufacture's protocol (Stratagene, La Jolla, Calif.). DNA sequencing of pRACK1 was carried out using standard di-deoxy sequencing techniques (Maniatis, et al.) The DNA sequence of RACK1 is shown in FIG. 1A. The sequence is also contained in the Sequence Listing as SEQ ID NO:19.

EXAMPLE 2

Expression and Purification of Recombinant RACK1 Protein in *E. coli*

A PstI/XhoI DNA fragment containing an open reading frame of 317 amino acids from the putative translation start site of pRACK1 (see underlined ATG in FIG. 1A) and 8 additional nucleotides upstream of the initiating methionine was subcloned into *E. coli* expression vector pMAL-c2 (New England BioLabs, Beverly, Mass.). This vector contains the male gene, which encodes maltose-binding protein (MBP). Induction of *E. coli* containing the vector results in the production of an MBP-fusion protein (Ausubel, et al.). The vector also includes a recognition site for the protease factor Xa, which allows the protein of interest to be cleaved from MBP after purification without adding any vector-derived residues to the protein.

A culture of TB1 *E. coli* transformed with RACK1-containing pMAL-c2 was induced by a 3 hr incubation with 1.8 mM IPTG. A protein fraction containing a 78 kDa fusion protein, comprised of RACK1 fused to MBP was isolated from the cultured *E. coli* by standard methods (Ausubel). The fusion protein was purified on an amylose affinity column according to the manufacture's protocol (New England BioLabs, Beverly, Mass.) and incubated with protease Xa (New England BioLabs) to yield a 36 kDa protein (RACK1) and a 34 kDa protein (possibly a RACK1 degradation product).

EXAMPLE 3

Binding of PKC to Recombinant RACK1

A. Buffers.

PBS/Tween buffer: 140 mM NaCl, 8 mM $Na_2PO_4$, 1.5 mM $KH_2PO_4$, 3 mM KCl and 0.05% Tween at pH 7.0.

Overlay wash buffer: 50 mM Tris-HCl (pH 7.5), 0.2M NaCl, 12 mM 2-mercaptoethanol, 0.1% polyethylene glycol and 0.1 mM $CaCl_2$.

B. Overlay assay.

Purified recombinant RACK1 protein (100–250 μg per lane, produced as detailed in Example 2) was subjected to SDS/PAGE and blotted onto nitrocellulose membranes (Ausubel). The nitrocellulose membranes were cut into strips, which were incubated for 0.5 hr in overlay buffer (Example 1) in the presence or absence of a mixture of PKC isozymes (α, β, γ, δ, ϵ and ζ, ~10 nM each final concentration) and PKC activators (60 μg/ml phosphatidylserine (PS), 2 μg/ml diacylglycerol (DG), and 1 mM $CaCl_2$). Unbound material was removed by five washes, 5-min each, in overlay wash buffer. Where indicated, PKC activators were present during the incubation of PKC with the nitrocellulose strips. The conditions for each sample and corresponding results are presented in part D below.

C. Detection of bound PKC.

PKC bound to RACK1 immobilized on nitrocellulose strips was detected as follows. The strips were incubated for 16 hours at room temperature with a mixture of anti-PKC antibodies as detailed in part B of Example 1, and then washed three times, 15 minutes per wash, with PBS/Tween buffer. The strips were incubated with anti-mouse and anti-rabbit horseradish peroxidase-linked secondary antibodies (Amersham Life Science, Arlington Heights, Ill.) diluted 1:1000 in PBS/Tween buffer supplements with 2% BSA, for 1 hour at room temperature. After washing three times, 15 minutes per wash with PBS/Tween buffer, the strips were subjected to a chemiluminescent reaction with luminol (diacylhydrazide) as detailed in the maufacturer's protocol (Amersham Life Science, Arlington Heights, Ill.), followed by an immediate exposure to autoradiography film (Eastman Kodak, Rochester, N.Y.) for 30 seconds to 5 minutes.

D. Effects of PKC activation on PKC binding to RACK1.

Figure 2:
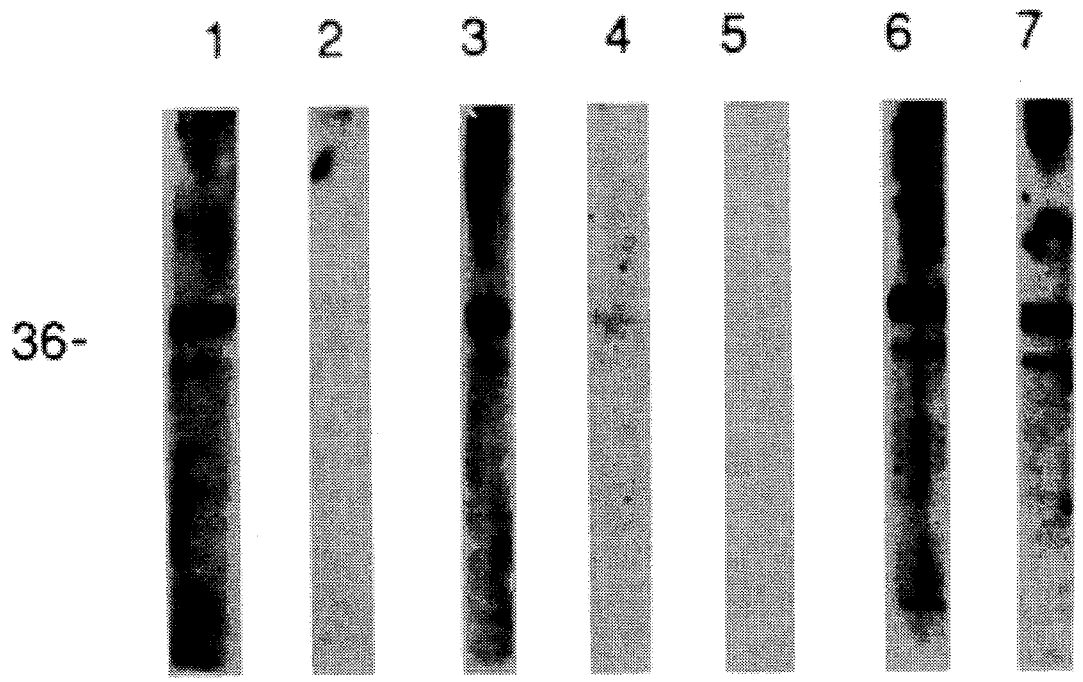
FIG. 2 shows the results of an overlay assay to detect PKC binding to immobilized RACK1 in the presence and absence of PKC activators.

The results presented in FIG. 2 show the influence of PKC activators on the binding of PKC to RACK1 immobilized on nitrocellulose membranes. The overlay assay was carried out as described in part B above. The test reagents contained in each sample and the corresponding lanes on the blot presented in FIG. 2 are as follows. Lane 1: PKC, 60 μg/ml PS, 2 μg/ml DG and 1 mM $CaCl_2$; lane 2: PKC and 1 mM EGTA; lane 3: PKC, 60 μg/ml PS and 2 μg/ml DG; lane 4: PKC and 1 mM $CaCl_2$; lane 5: No PKC added; lanes 6 and 7: PKC, 60 μg/ml PS, 2 μg/ml DG, 1 mM $CaCl_2$, and 10 μM substrate peptide (SEQ ID NO:11; lane 6) or 10 μM pseudosubstrate peptide (SEQ ID NO:12, lane 7). The results are representative of three independent experiments.

It can be appreciated that the binding of PKC as detected by anti-PKC antibodies is minimal in the presence of EGTA or calcium alone (FIG. 2, lanes 2, 4, respectively), is greater in the presence of phosphatidylserine (PS) and diacylglycerol (DG; lane 3), and is maximal in the presence PS, DG and calcium (lane 1). Antibody binding was not observed in the absence of added PKC (lane 5). Furthermore, maltose binding protein alone, or an extract from non-transformed *E. coli* did not bind PKC.

The concentration dependence of PKC binding to RACK1 was characterized with βPKC, since this isozyme is a major component of the PKC mixture used for the overlay assay. The mean half maximal binding was ~0.375 nM, and maximal binding was ~4 nM (n=3; values reflect binding of βPKC isozyme in the presence of other PKC isozymes and was determined by scanning autoradiograms in the linear range of detection, as described in Mochly-Rosen, et al., (1991) .

The results presented above indicate that in order for PKC to bind to RACK1 it must be activated. In vitro, activation may be accomplished, for example, by phosphatidylserine and diacylglycerol, or, more preferably, by phosphatidylserine, diacylglycerol and calcium.

EXAMPLE 4

Inhibition of PKC Binding to RACK1 by RACK1-specific WD-40-homologous Peptides Assays for the inhibition of PKC binding to RACK1 by putative binding peptides were carried out by combining a variation of the overlay protocol described in Example 3 part B above, with an overlay extraction assay described in part B below. The variation in the overlay protocol consisted of incubating the putative binding peptides with a mixture of PKC isozymes for 15 minutes at room temperature before the mixture was used to contact the nitrocellulose strips containing immobilized RACK1.

A. Buffers.

Sample buffer: 0.3M Tris HCl, 5% SDS, 50% glycerol, 0.01% bromophenol blue and 5% β-mercaptoethanol.

B. Overlay extraction protocol.

Nitrocellulose strips containing immobilized RACK1, that had been contacted with a solution containing a mixture of PKC isozymes, were washed and the area corresponding to the 36 kDa (RACK1-containing) band was cut out. The pieces (containing PKC/RACK1 complexes) were incubated with sample buffer for 10 minutes at 80° C. The sample buffer and the nitrocellulose pieces were then placed in wells in the PAGE gel and subjected to SDS-PAGE to elute the bound proteins. The gel was blotted onto nitrocellulose and a Western blot analysis was carried out using the mixture of antibodies (specific for PKC α, β, γ, δ, ε and ζ isozymes) described in Example 1 part B. Bound antibodies were detected by $^{125}$I-protein A.

C. PKC overlay in the presence of binding peptides.

Peptides derived from or homologous to WD-40 repeats of RACK1 were tested for their ability to inhibit PKC binding to recombinant RACK1. Binding of PKC to RACK1 was carried out using a variation of the overlay procedure described in Example 3 part B. In the experimental samples, peptides were incubated with a solution containing a mixture of rat brain PKC isozymes (~10 nM each) for 15 minutes at room temperature.

Following completion of the modified overlay protocol, the samples were subjected to the overlay-extraction protocol detailed in part B, above.

The results in FIG. 3 show the binding of PKC to RACK1, carried out without (lane 1) or with (lanes 2–4) a preincubation of peptides with PKC. Lane 2 shows PKC binding following a preincubation with 10 μM peptide I (SEQ ID NO:1). Peptide I caused an 81±6% inhibition of PKC binding to recombinant RACK1 as compared with binding in the absence of added peptide (n=3). Lanes 3 and 4 show PKC binding following a preincubation with 10 ∞M peptide rIII (SEQ ID NO:4) and 10 μM peptide rVI (SEQ ID NO:7), respectively. Both peptides inhibit the binding of PKC to RACK1. It can be seen that peptide rIII is somewhat more effective than peptide rVI. The results shown are representative of three independent experiments.

The overlay-extraction method (part B above) was used in experiments relating to the peptide inhibition of PKC binding in order to decrease the possibility that some part of the inhibition of PKC binding to RACK1 reflects an interference in the binding of anti-PKC antibodies to the PKC/RACK1 complexes. Free peptides are effectively removed from the PKC/RACK1 complexes during the second round of SDS/PAGE, prior to blotting and detection of immobilized PKC/RACK1 complexes by anti-PKC antibodies.

EXAMPLE 5

Identification of Sequenced Proteins Containing WD-40 Repeats

A search for WD-40 motif-containing proteins was done using the ENTREZ program, release 6.0 (National Center for Biotechnology Information, National Library of Medicine, National Institutes of Health, Bethesda, Md.). The ENTREZ database was searched for protein sequences related to the β subunit of transducin.

Protein sequences homologous to β-transducin were examined for the existence of WD-40 repeats, following the guidance for identification of WD-40 repeats presented in section V of the specification, above.

The proteins were also used to carry out additional searches of the database, in order to identify other proteins which may contain WD-40 repeats, but which might not be homologous to the β subunit of transducin. Sequences identified during the second round of searches were again examined for WD-40 repeats.

This search strategy identified 30 proteins containing WD-40 sequences. The amino acid sequences of these proteins, with the WD-40 regions aligned and delineated, are shown in FIGS. 12–18, 20–27, 29–30, 34–35, 37–38, 40 and 42–50. The sequences are represented in the Sequence Listing as SEQ ID NO:29–35, 37–44, 46–47, 51–52, 54–55, 57 and 59–67. An examination of the sequences in the figures reveals that although there can be divergence between the WD-40 motifs of different proteins, a consistent pattern can be inferred based on the teachings presented in part V of the specification above.

An additional search, using a consensus WD-40 sequence (SEQ ID NO:262), was conducted with the "MACVECTOR" program (Eastman Kodak Co., New Haven, Conn.) to search GenBank (December 1993 release). Default settings (matrix=250) were used for the search. The search identified the 250 proteins with the highest homology to the consensus sequence. These proteins were examined, as detailed in part V above, for WD-40 repeats. Ten additional proteins containing WD-40 repeats were identified with this strategy. The amino acid sequences of those proteins, with the WD-40 repeats aligned and delineated, are shown in FIGS. 11, 19, 28, 31–33, 36, 39, 41 and 51. The sequences are represented in the Sequence Listing as SEQ ID NO:28, 36, 45, 48–50, 53, 56, 58 and 68.

EXAMPLE 6

Binding of βPKC to RACK1 WD-40-derived Peptides

A. Buffers.

Peptide overlay block buffer: 20 mM Tris-HCl (pH 7.5), 0.2M NaCl, 3% bovine serum albumin (BSA) and 0.1% polyethylene glycol.

Overlay wash buffer: 50 mM Tris-HCl (pH 7.5), 0.2M NaCl, 12 mM 2-mercaptoethanol, 0.1% polyethylene glycol and 0.1 mM $CaCl_2$.

B. PKC overlay of immobilized peptides.

The binding of βPKC to peptide I (SEQ ID NO:1), peptide rVI (SEQ ID NO:7) and control peptide (SEQ ID NO:9) was assessed using a PKC overlay assay similar to that described in Example 3. Increasing amounts of peptides (0.5 μmole, 1.0 μmole, 5.0 μmole and 10.0 μmole) suspended in 20 mM NaCl were applied individually onto nitrocellulose using a slot-blot apparatus (Schleicher and Schuell, Keene, N.H.). The nitrocellulose membrane was washed three times, 15 minutes per wash, in peptide overlay buffer and incubated for two hours in peptide overlay block buffer. The membrane was cut into sections and the sections were transferred to different PKC-containing solutions and incubated for 30 minutes at room temperature. All the solutions contained 5 nM rat brain PKC in peptide overlay buffer. Some solutions additionally contained PS, DG, and calcium. The membranes were then washed three times, 15 minutes per wash, in peptide overlay buffer and incubated in peptide overlay block buffer containing anti-βPKC monoclonal antibodies (1:1000 dilution; Seikagaku Kogyo, Tokyo, Japan). After a 16 hr incubation at room temperature, the filters were washed three times, 15 minutes per wash, in peptide overlay buffer.

Binding of PKC was determined using chemiluminescence as described in Example 3, part C. Quantitation of PKC binding was carried out using a "MICRO SCAN" 1000 gel analyzer (Galai Inc., Yokneam, Israel).

The data show that activated PKC bound to both peptides I and rVI, but not to the control peptide, at peptide amounts as low as 5 μmoles. Unactivated PKC did not bind to peptide I, but did bind to peptide rVI at similar concentrations.

The results indicate that peptide rVI is capable of binding both activated as well as unactivated forms of PKC, whereas peptide I binds only to activated PKC.

EXAMPLE 7

Effects of RACK1 WD-40-derived Peptides on PKC-mediated Oocyte Maturation

Exposure to insulin induces maturation in *Xenopus oocytes* via a PKC-dependent pathway (Smith, et al., 1992). The maturation response may be quantified by monitoring the appearance of a white spot in the animal hemisphere of the *oocyte*, indicating germinal vesicle breakdown (GVBD) and maturation. To assess the effects of RACK1 WD-40-derived peptides on insulin-induced PKC-mediated maturation, 50 nl of a 20 mM NaCl solution containing the indicated peptides [peptide I (SEQ ID NO:1; ●), peptide rVI (SEQ ID NO:7; ■), or injection solution ([□)] (peptides at 50 μM) were microinjected into *Xenopus oocytes*. The symbols refer to symbols used in FIG. 5, which shows the data from this example. One hour following the peptide injections, the *oocytes* were exposed to a solution containing insulin (8.25 μg/ml) for 2 minutes (t=0). 10–15 *oocytes* were used for each sample.

The data, representative of three independent experiments, are expressed as the percent of *oocytes* with GVBD following insulin exposure and are plotted as a function of time in FIG. 5.

In *oocytes* injected with buffer or control peptide, onset of maturation was typically 4–5 hours after exposure to insulin. Following this delay, %GVBD followed an approximately exponential time-course, reaching a plateau of about 85–90% GVBD at about 10–12 hours. These data indicate that approximately 80–85% of sham-injected *oocytes* exposed to insulin at t=0 reach maturation, and that maturation is reached relatively quickly (within about 10 hours) relative to the time-course of the experiment (20 hours).

*Oocytes* injected with peptide I (SEQ ID NO:1) responded in a manner similar to control *oocytes*, except the plateau was at about 45–50% GVBD. These data suggest that injection of peptide I blocked maturation in approximately 40–45% of *oocytes* that would normally proceed to maturation, but had little effect on the kinetics or extent of maturation of the remaining (50–55%) *oocytes*.

*Oocytes* injected with peptide rVI (SEQ ID NO:7) responded with a slightly shorter delay (about 3–4 hours), but reached a higher plateau (about 95–100% GVBD) more quickly (within about 5 hours) than control *oocytes*. These data suggest that peptide rVI potentiates the effects of insulin on *oocyte* maturation, both in terms of the rate of maturation, and in the total fraction of *oocytes* that mature during the experiment. Injection of peptide rVI increases the maturing fraction to essentially 100%.

The effects of both peptides I and rVI on GVBD were dose-dependent between 5 μm–500 μM.

Since peptide rVI enhanced insulin-induced GVBD, experiments were performed to determine whether peptide rVI can induce GVBD in the absence of insulin. The data from these experiments are shown in FIG. 5B. Microinjection of peptide rVI (50 μM) alone, but not peptide I, control peptide or buffer, induced GVBD. Maturation initiated with a longer delay (about 6–7 hours) than in the control insulin-induced *oocytes* in FIG. 5A (about 4–5 hours), and reached a plateau of about 50% GVBD.

Together, the data above indicate that peptides homologous to the WD-40 region of RACK1 modulate the function of PKC. Peptide I inhibited PKC-mediated *oocyte* maturation by about 40%, whereas peptide rVI potentiated insulin-induced maturation, and resulted in a limited maturation response even in the absence of insulin. The latter result suggests that peptide rVI, under appropriate circumstances, may act to activate PKC in the absence of other activating substances.

EXAMPLE 8

Effects of RACK1WD-40-derived Peptides on PKC Translocation in *Xenopus Oocytes*

A. Buffers.

Homogenization buffer: 20 mM Tris HCl, pH 7.5, 10 mM EGTA, 2 mM EDTA, 0.25M sucrose, 10 μM phenylmethylsulfonyl fluoride, 20 μg/ml of each leupeptin and soybean trypsin inhibitor.

B. PKC translocation in *oocytes*.

Insulin causes the translocation of μPKC, but not other PKC isozymes, from a cytosolic form to a membrane-associated form, as evidenced by the relative levels of PKC in the soluble vs. the particulate fraction of *oocyte* homogenate. To assess the effects of RACK1 WD-40-derived peptides on insulin-induced PKC translocation, 50 nl of a 20 mM NaCl solution containing the indicated peptides were microinjected into *Xenopus oocytes*. The *oocytes* were then homogenized, and the relative amount of PKC in the soluble and particulate fractions was assayed. The protocol followed was a modification of a method described by Smith, et al. (1992). The results are shown in FIG. 6.

Batches of 50 *oocytes* were microinjected with either peptide rVI (SEQ ID NO:7; 50 μM; lanes 3, 4), peptide I (SEQ ID NO:1; 50 μM, lanes 7, 8) or injection solution (NaCl20 mM, lanes 1,2 and 5,6). Homogenates from each batch were prepared 60 minutes after microinjection (lanes 1–4) or 60 minutes after addition of insulin (lanes 5–8). The homogenates were centrifuged at 10,000 g for 3 minutes, the upper layer (containing fat and yolk) was removed, and the remainder was frozen at −70 ° C. Prior to use, the samples were thawed, 200 μl homogenization buffer was added and the samples were centrifuged at 100,000 g for 30 minutes at 4° C. The supernatants (soluble fraction) were removed and concentrated to 20 μl using "CENTRICON" concentrators (Amicon,Beverly, Mass.). The pellets (particulate fractions) were dissolved in 20 μl of homogenization buffer. The samples were resolved on an 8% SDS/PAGE gel and blotted onto nitrocellulose. The amount of PKC in each fraction was determined by Western blot using anti-βPKC antibodies (1:1000 dilution; Seikagaku Kogyo, Tokyo, Japan). Bound primary antibodies were detected by chemiluminescence as described in Example 3, part C.

The antibodies showed immunoreactivity with an ~80 kDa protein that corresponds to βPKC. Data are representative of three experiments.

The data are shown in FIG. 6. Lanes 1, 3, 5 and 7 contain particulate fractions (p), while lanes 2, 4, 6 and 8 contain soluble (cytosol) fractions (c). Peptide I (50 μM) did not affect βPKC distribution in untreated *oocytes*, but inhibited insulin-induced βPKC translocation (FIG. 3, lanes 7,8). In contrast, peptide rVI (50 μM) induced βPKC translocation in the absence of insulin treatment (FIG. 3, lanes 3,4).

The results above suggest that peptide I is an antagonist of insulin-induced PKC translocation, whereas peptide rVI is an agonist and an activator of PKC translocation. In light of the results presented in Example 7, the data also suggest that the inhibition of insulin-induced GVBD following microinjection of peptide I was due to an inhibition of βPKC translocation.

EXAMPLE 9

Effects of RACK1 WD-40-derived Peptides on Sensitivity of PKC to Arg-C Endopeptidase A. Buffers.

Sample buffer: 0.3M Tris HCl, 5% SDS, 50% glycerol, 0.01% bromophenol blue and 5% β-mercaptoethanol.

B. Nicking of βPKC by Arg-C endopeptidase.

Upon activation of PKC, a pseudosubstrate autoinhibitory sequence at the N-terminus of the molecule dissociates from the catalytic site and becomes sensitive to endopeptidase Arg-C (Orr, et al.). In the absence of PKC activators, exposure of the 80 kDa βPKC to endopeptidase Arg-C has no effect on the enzyme (see FIG. 7, lane 1). In the presence of the PKC activators PS, DG and calcium, however, exposure of βPKC to Arg-C results in a "nicking" of the PKC (i.e. limited proteolysis generating a 78 kDa fragment and several small fragments (see FIG. 7, lane 2)). Continued exposure to Arg-C results in the disappearance of βPKC (Orr, et al.). The present experiment tests whether peptides derived from the WD-40 region of RACK1 alter the sensitivity of βPKC to endopeptidase Arg-C.

The methods used to assay Arg-C sensitivity are a modification of methods described by Orr, et al. Rat brain PKC (~5 nM) was incubated at room temperature in 500 μl of 20 mM Tris-HCl buffer (pH 7.5) alone or with Arg-C (5 units/ml) in the presence or absence of the indicated peptides (final concentration 10 μM or as indicated), PS, DG, and calcium (as indicated). 50 μl aliquots were removed into 20 μl of sample buffer during the reaction as indicated (samples in all the lanes were incubated for 30 minutes , except lanes 5, and 6, which were incubated for 5 and 15 minutes, respectively). The samples were boiled for 10 minutes at 80° C. and loaded onto 8% SDS-PAGE. βPKC was detected by Western blot analysis using anti-βPKC antibodies as described in Examples 6 and 8.

The results are shown in FIG. 7. PKC was incubated for the indicated time alone (lane 1) or in the presence of Arg-C (lanes 2–9), with DG (0.8 μg/ml), PS (50 μg/ml) and $CaCl_2$ (1 mM; lane 2), with PS (50 μg/ml) and $CaCl_2$ (1 mM; lane 3), with PS (2.5 μg/ml) and $CaCl_2$ (50 μM; lane 4); with PS (2.5 μg/ml), $CaCl_2$ (50 μM) and with either peptide rVI (SEQ ID NO:7; 10 μM; lanes 5–7), control peptide (SEQ ID NO:9; lane 8) or with peptide I (SEQ ID NO:1; lane 9).

Incubation of βPKC with Arg-C at low concentrations of activators (2.5 μg/ml PS and 50 μM $CaCl_2$) in the absence of added peptide did not result in appreciable nicking activity (FIG. 7, lane 4). Similarly, nicking of βPKC did not occur in the presence of this concentration of activators with peptide I (lane 9) or with control peptide (lane 8). However, incubation of βPKC with the same concentration of activators in the presence of peptide rVI resulted in a time-dependent appearance of the 78 kDa nicked PKC fragment (FIG. 4, lanes 5–7). Concentrations as low as 10 nM of peptide rVI were sufficient to result in nicking activity, indicative of βPKC activation. The results indicate that peptide rVI, but not peptide I, is effective to stabilize PKC in an activated conformation that renders it susceptible to Arg-C under conditions of low PKC activators that would otherwise not render the enzyme susceptible to Arg-C.

EXAMPLE 10

Effects of RACK1 WD-40-derived Peptides on PKC Autophosphorylation

Activated PKC is capable of autophosphorylation. Since peptide rVI (SEQ ID NO:7) was effective to induce PKC translocation and GVBD in the absence of an activator such as insulin, the ability of the peptide to induce PKC autophosphorylation in the absence of PKC activators was assessed.

PKC autophosphorylation in the presence of βPKC pseudosubstrate antibodies or the indicated peptides was carried out using a modification of the method described by Makowske, et al. Anti-pseudosubstrate antibodies, which were shown previously to induce autophosphorylation in the absence of PKC activators (Makowske, et al.) were used as a positive control. The results are shown in FIG. 8.

Rat brain PKC (~10 nM) was incubated with mild agitation in a final volume of 250 μl of overlay buffer, as in Example 1 either with anti-βPKC pseudosubstrate antibodies (1:10 dilution, Life Technologies, Gaithersburg, Md.) or with the indicated peptide (10 μM). Where indicated, PS (50 μg/ml), DG (0.8 μg/ml) and $CaCl_2$ (1 mM) were also added. The amount of autophosphorylation was determined after 2 hours for the reaction with the anti-pseudosubstrate antibodies, or after 15 minutes for the other samples. 50 μl of a buffer comprised of 20 mM Tris-HCl (pH 7.5), 20 mM $MgCl_2$, 20 μM ATP and 5 μci/ml [$\gamma$-$^{32}$P] ATP. The mixture was incubated for 15 minutes at room temperature and the reaction was stopped by adding 60 μl sample buffer (see Example 9). The samples were then boiled for 10 minutes, loaded onto a 10% SDS-PAGE mini gel and electrophoresed. The gel was fixed with 50% methanol and 10% acetic acid for 1 hour, and the autophosphorylation of PKC was determined by autoradiography.

The results in FIG. 8 show PKC autophosphorylation in the presence of DG, PS, and calcium (lane 1), in the presence of EGTA (lane 2), in the presence of anti-βPKC pseudosubstrate antibodies (diluted 1:10 in 20 mM Tris-HCl; lane 3), in the presence of peptide rVI (SEQ ID NO:7; 10 μM; lane 4), in the presence of peptide I (SEQ ID NO:1; 10 μM; lane 5), or in the presence of control peptide (SEQ ID NO:9; 10 μM; lane 6).

Peptide rVI in the absence of PKC activators induced PKC autophosphorylation to over 80% of the autophosphorylation obtained in the presence of optimal concentration of PS, DG, and calcium (compare FIG. 8 lane 1 (control) with lane 4 (peptide rVI). Neither peptide I nor control peptide induced PKC autophosphorylation in the absence of PKC activators (FIG. 8 lanes 5 and 6, respectively).

EXAMPLE 11

Effects of RACK1 WD-40-derived Peptides on Histone Phosporylation by PKC

Incubation of PKC with peptide rVI (SEQ ID NO:7) induced histone phosphorylation by PKC. The method used was a modification of the protocol described by Mochly-Rosen, et al., (1987). The results are shown in FIG. 9.

Histone type IIIs (Sigma Chemical Company, St. Louis, Mo.) was phosphorylated by PKC (~10 nM) in the absence (lane 1) and presence of peptide rVI (10 μM) (lanes 2 and 3) and in the presence and absence of DG (0.8 μg/ml), PS (50 μg/ml) and $CaCl_2$ (1 mM) (lane 3). The results are expressed as percentage of control that is the amount of Histone phosphorylation by PKC in the presence of DG (0.8 μg/ml), PS (50 μg/ml) and $CaCl_2$ (1 mM). The results are the average±SEM of two independent experiments. PKC was first incubated with the peptide rVI (10 μM) for 15 minutes in overlay buffer as described above. Histone type IIIs (40 μg/ml) was added in Tris-HCl (20 mM), $MgCl_2$ (20 mM), ATP (20 μM) and [$\gamma$-$^{32}$P]ATP (5 μci/ml) with or without PS (50 μg/ml), DG (0.8 μg/ml) and $CaCl_2$ (1 mM). Histone phosphorylation was determined by autoradiography as above.

PKC activators PS, DG, and calcium were not required for either peptide rVI-induced autophosphorylation or histone phosphorylation, suggesting that peptide rVI is an agonist of PKC activation.

In a related experiment, phosphorylation of histone type IIIs (25 μM) by PKC (10 nM) was not inhibited by RACK1; rather, a 4.5±0.1 fold increase of histone phosphorylation occurred when co-incubated with ~100 nM RACK1 (n=2).

It is claimed:

1. A method of altering the activity of a protein kinase C that interacts with a second protein, where the second protein contains at least one WD-40 region, comprising contacting a polypeptide which has an amino acid sequence represented by SEQ ID NO:4 or SEQ ID NO:7 with said protein kinase C under conditions which allow the formation of a complex between the polypeptide and the protein kinase C, where the formation of said complex inhibits the interaction between said protein kinase C and said second protein; or contacting a polypeptide which has the amino acid sequence represented by SEQ ID NO:7 with said protein kinase C under conditions which allow the formation of a complex between the polypeptide and the protein kinase C, where the formation of said complex stimulates the activity of said protein kinase C.

* * * * *

SEQUENCE LISTING ( 1 ) GENERAL INFORMATION:

( i i i ) NUMBER OF SEQUENCES: 265

( 2 ) INFORMATION FOR SEQ ID NO:1:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide I ( x i ) SEQUENCE DESCRIPTION: SEQ ID NO:1:

```
Lys Gly Asp Tyr Glu Lys Ile Leu Val Ala Leu Cys Gly Gly Asn
1               5                   10                  15
```

( 2 ) INFORMATION FOR SEQ ID NO:2:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide, rI, Fig. 1C ( x i ) SEQUENCE DESCRIPTION: SEQ ID NO:2:

```
Val Thr Gln Ile Ala Thr Thr
1               5
```

( 2 ) INFORMATION FOR SEQ ID NO:3:

( i ) SEQUENCE CHARACTERISTICS:
( A ) LENGTH: 7 amino acids ( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide rII, Fig. 1C ( x i ) SEQUENCE DESCRIPTION: SEQ ID NO:3:

Phe Val Ser Asp Val Val Ile
1 5

( 2 ) INFORMATION FOR SEQ ID NO:4:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide rIII, Fig. 1C ( x i ) SEQUENCE DESCRIPTION: SEQ ID NO:4:

Asp Val Leu Ser Val Ala Phe
1 5

( 2 ) INFORMATION FOR SEQ ID NO:5:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: peptide rIV, Fig. 1C ( x i ) SEQUENCE DESCRIPTION: SEQ ID NO:5:

Val Ser Cys Val Arg Phe Ser
1 5

( 2 ) INFORMATION FOR SEQ ID NO:6:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide rV, Fig. 1C ( x i ) SEQUENCE DESCRIPTION: SEQ ID NO:6:

-continued

Gly Tyr Leu Asn Thr Val Thr
1 5

( 2 ) INFORMATION FOR SEQ ID NO:7:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide rVI, Fig. 1C ( x i ) SEQUENCE DESCRIPTION: SEQ ID NO:7:

Asp Ile Ile Asn Ala Leu Cys Phe
1 5

( 2 ) INFORMATION FOR SEQ ID NO:8:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Peptide rVII, Fig. 1C ( x i ) SEQUENCE DESCRIPTION: SEQ ID NO:8:

Pro Gln Cys Thr Ser Leu Ala
1 5

( 2 ) INFORMATION FOR SEQ ID NO:9:

( i ) SEQUENCE CHARACTERISTICS:
( A ) LENGTH: 6 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: control peptide 1, homol. to RACK1 261-266, LKGKIL ( x i ) SEQUENCE DESCRIPTION: SEQ ID NO:9:

Leu Lys Gly Lys Ile Leu
1 5

( 2 ) INFORMATION FOR SEQ ID NO:10:

( i ) SEQUENCE CHARACTERISTICS:
( A ) LENGTH: 6 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: control peptide 2, iden. to RACK1, 265 to 270 IIVDEL ( x i ) SEQUENCE DESCRIPTION: SEQ ID NO:10:

Ile Ile Val Asp Glu Leu
1 5

( 2 ) INFORMATION FOR SEQ ID NO:11:

( i ) SEQUENCE CHARACTERISTICS:
( A ) LENGTH: 18 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: PKC substrate peptide, (Ser25) PKC(19- 36)

( x i ) SEQUENCE DESCRIPTION: SEQ ID NO:11:

Arg Phe Ala Arg Lys Gly Ser Leu Arg Gln Lys Asn Val His Glu Val
1 5 10 15

Lys Asn ( 2 ) INFORMATION FOR SEQ ID NO:12:

( i ) SEQUENCE CHARACTERISTICS:
( A ) LENGTH: 18 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: PKC Pseudosubstrate Inhibitor ( P C K ( 19- 36))

( x i ) SEQUENCE DESCRIPTION: SEQ ID NO:12:

Arg Phe Ala Arg Lys Gly Ala Leu Arg Gln Lys Asn Val His Glu Val
1 5 10 15

Lys Asn ( 2 ) INFORMATION FOR SEQ ID NO:13:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBH Peptide, rI, Fig. 24

-continued ( x i ) SEQUENCE DESCRIPTION: SEQ ID NO:13:

Trp Val Thr Gln Ile Ala Thr Thr Pro Gln Phe Pro Asp Met Ile
1 5 10 15

( 2 ) INFORMATION FOR SEQ ID NO:14:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBH Peptide rII, Fig. 24

( x i ) SEQUENCE DESCRIPTION: SEQ ID NO:14:

Phe Val Ser Asp Val Val Ile Ser Ser Asp Gly Gln Phe Ala Leu
1 5 10 15

( 2 ) INFORMATION FOR SEQ ID NO:15:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBH Peptide rIII, Fig. 24

( x i ) SEQUENCE DESCRIPTION: SEQ ID NO:15:

Asp Val Leu Ser Val Ala Phe Ser Ser Asp Asn Arg Gln Ile Val
1 5 10 15

( 2 ) INFORMATION FOR SEQ ID NO:16:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBH Peptide rIV, Fig. 24

( x i ) SEQUENCE DESCRIPTION: SEQ ID NO:16:

Trp Val Ser Cys Val Arg Phe Ser Pro Asn Ser Ser Asn Pro Ile
1 5 10 15

( 2 ) INFORMATION FOR SEQ ID NO:17:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBH Peptide rV, Fig. 24

( x i ) SEQUENCE DESCRIPTION: SEQ ID NO:17:

Tyr Leu Asn Thr Val Thr Val Ser Pro Asp Gly Ser Leu Cys Ala
1 5 10 15

( 2 ) INFORMATION FOR SEQ ID NO:18:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBH Peptide rVI, Fig. 24

( x i ) SEQUENCE DESCRIPTION: SEQ ID NO:18:

Thr Leu Asp Gly Gly Asp Ile Ile Asn Ala Leu Cys Phe Ser Pro
1 5 10 15

( 2 ) INFORMATION FOR SEQ ID NO:19:

( i ) SEQUENCE CHARACTERISTICS:
( A ) LENGTH: 1115 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 DNA Sequence, Fig. 1A ( x i ) SEQUENCE DESCRIPTION: SEQ ID NO:19:

GGCACGAGGG GTCGCGGTGG CAGCCGTGCG GTGCTTGGCT CCCTAAGCTA TCCGGTGCCA 60

TCCTTGTCGC TGCGGCGACT CGCAACATCT GCAGCCATGA CCGAGCAAAT GACCCTTCGT 120

GGGACCCTCA AGGGCCATAA TGGATGGGTT ACACAGATCG CCACCACTCC GCAGTTCCCG 180

GACATGATCC TGTCGGCGTC TCGAGACAAG ACCATCATCA TGTGGAAGCT GACCAGGGAT 240

GAGACCAACT ACGGCATACC ACAACGTGCT CTTCGAGGTC ACTCCCACTT TGTTAGCGAT 300

GTTGTCATCT CCTCTGATGG CCAGTTTGCC CTCTCAGGCT CCTGGGATGG AACCCTACGC 360

CTCTGGGATC TCACAACGGG CACTACCACG AGACGATTTG TCGGCCACAC CAAGGATGTG 420

CTGAGCGTGG CTTTCTCCTC TGACAACCGG CAGATTGTCT CTGGGTCCCG AGACAAGACC 480

ATTAAGTTAT GGAATACTCT GGGTGTCTGC AAGTACACTG TCCAGGATGA GAGTCATTCA 540

GAATGGGTGT CTTGTGTCCG CTTCTCCCCG AACAGCAGCA ACCCTATCAT CGTCTCCTGC 600

GGATGGGACA AGCTGGTCAA GGTGTGGAAT CTGGCTAACT GCAAGCTAAA GACCAACCAC 660

ATTGGCCACA CTGGCTATCT GAACACAGTG ACTGTCTCTC CAGATGGATC CCTCTGTGCT 720

TCTGGAGGCA AGGATGGCCA GGCTATGCTG TGGGATCTCA ATGAAGGCAA GCACCTTTAC 780

-continued

```
ACATTAGATG GTGGAGACAT CATCAATGCC TTGTGCTTCA GCCCCAACCG CTACTGGCTC    840
TGTGCTGCCA CTGGCCCCAG TATCAAGATC TGGGACTTGG AGGGCAAGAT CATGGTAGAT    900
GAACTGAAGC AAGAAGTTAT CAGCACCAGC AGCAAGGCAG AGCCACCCCA GTGTACCTCT    960
TTGGCTTGGT CTGCTGATGG CCAGACTCTG TTTGCTGGCT ATACCGACAA CTTGGTGCGT   1020
GTATGGCAGG TGACTATTGG TACCCGCTAA AAGTTTATGA CAGACTCTTA GAAATAAACT   1080
GGCTTTCTGA AAAAAAAAAA AAAAAAAAAA AAAAA                              1115
```

( 2 ) INFORMATION FOR SEQ ID NO:20:

( i ) SEQUENCE CHARACTERISTICS:
( A ) LENGTH: 96 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rI DNA Sequence, Fig. 1A ( x i ) SEQUENCE DESCRIPTION: SEQ ID NO:20:

```
GGCCATAATG GATGGGTTAC ACAGATCGCC ACCACTCCGC AGTTCCCGGA CATGATCCTG    60
TCGGCGTCTC GAGACAAGAC CATCATCATG TGGAAG                              96
```

( 2 ) INFORMATION FOR SEQ ID NO:21:

( i ) SEQUENCE CHARACTERISTICS:
( A ) LENGTH: 94 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rII DNA Sequence ( x i ) SEQUENCE DESCRIPTION: SEQ ID NO:21:

```
GGTCACTCCC ACTTTGTTAG CGATGTTGTC ATCTCCTCTG ATGGCCAGTT TGCCCTCTCA    60
GGCTCCTGGG ATGGAACCCT ACGCCTCTGG GATC                                94
```

( 2 ) INFORMATION FOR SEQ ID NO:22:

( i ) SEQUENCE CHARACTERISTICS:
( A ) LENGTH: 93 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rIII DNA Sequence, Fig. 1A ( x i ) SEQUENCE DESCRIPTION: SEQ ID NO:22:

GGCCACACCA AGGATGTGCT GAGCGTGGCT TTCTCCTCTG ACAACCGGCA GATTGTCTCT 60

GGGTCCCGAG ACAAGACCAT TAAGTTATGG AAT 93

( 2 ) INFORMATION FOR SEQ ID NO:23:

( i ) SEQUENCE CHARACTERISTICS:
( A ) LENGTH: 99 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rIV DNA Sequence, Fig. 1A ( x i ) SEQUENCE DESCRIPTION: SEQ ID NO:23:

AGTCATTCAG AATGGGTGTC TTGTGTCCGC TTCTCCCCGA ACAGCAGCAA CCCTATCATC 60

GTCTCCTGCG GATGGGACAA GCTGGTCAAG GTGTGGAAT 99

( 2 ) INFORMATION FOR SEQ ID NO:24:

( i ) SEQUENCE CHARACTERISTICS:
( A ) LENGTH: 93 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rV DNA Sequence, Fig. 1A ( x i ) SEQUENCE DESCRIPTION: SEQ ID NO:24:

GGCCACACTG GCTATCTGAA CACAGTGACT GTCTCTCCAG ATGGATCCCT CTGTGCTTCT 60

GGAGGCAAGG ATGGCCAGGC TATGCTGTGG GAT 93

( 2 ) INFORMATION FOR SEQ ID NO:25:

( i ) SEQUENCE CHARACTERISTICS:
( A ) LENGTH: 93 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rVI DNA Sequence, Fig. 1A ( x i ) SEQUENCE DESCRIPTION: SEQ ID NO:25:

TTAGATGGTG GAGACATCAT CAATGCCTTG TGCTTCAGCC CCAACCGCTA CTGGCTCTGT 60

GCTGCCACTG GCCCCAGTAT CAAGATCTGG GAC 93

( 2 ) INFORMATION FOR SEQ ID NO:26:

-continued ( i ) SEQUENCE CHARACTERISTICS:
( A ) LENGTH: 99 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: RACK1 rVII DNA Sequence, Fig. 1A ( x i ) SEQUENCE DESCRIPTION: SEQ ID NO:26:

AGCAAGGCAG AGCCACCCCA GTGTACCTCT TTGGCTTGGT CTGCTGATGG CCAGACTCTG 60

TTTGCTGGCT ATACCGACAA CTTGGTGCGT GTATGGCAG 99

( 2 ) INFORMATION FOR SEQ ID NO:27:

( i ) SEQUENCE CHARACTERISTICS:
( A ) LENGTH: 317 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: RACK1 Amino Acid Sequence, Fig. 1C ( x i ) SEQUENCE DESCRIPTION: SEQ ID NO:27:

```
Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
            20                  25                  30

Ser Ala Ser Arg Asp Lys Thr Ile Ile Met Trp Lys Leu Thr Arg Asp
        35                  40                  45

Glu Thr Asn Tyr Gly Ile Pro Gln Arg Ala Leu Arg Gly His Ser His
    50                  55                  60

Phe Val Ser Asp Val Val Ile Ser Ser Asp Gly Gln Phe Ala Leu Ser
65                  70                  75                  80

Gly Ser Trp Asp Gly Thr Leu Arg Leu Trp Asp Leu Thr Thr Gly Thr
                85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
        115                 120                 125

Ile Lys Leu Trp Asn Thr Leu Gly Val Cys Lys Tyr Thr Val Gln Asp
    130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
        195                 200                 205

Ser Gly Gly Lys Asp Gly Gln Ala Met Leu Trp Asp Leu Asn Glu Gly
```

-continued 210 215 220

Lys His Leu Tyr Thr Leu Asp Gly Gly Asp Ile Ile Asn Ala Leu Cys
225 230 235 240

Phe Ser Pro Asn Arg Tyr Trp Leu Cys Ala Ala Thr Gly Pro Ser Ile
245 250 255

Lys Ile Trp Asp Leu Glu Gly Lys Ile Ile Val Asp Glu Leu Lys Gln
260 265 270

Glu Val Ile Ser Thr Ser Ser Lys Ala Glu Pro Pro Gln Cys Thr Ser
275 280 285

Leu Ala Trp Ser Ala Asp Gly Gln Thr Leu Phe Ala Gly Tyr Thr Asp
290 295 300

Asn Leu Val Arg Val Trp Gln Val Thr Ile Gly Thr Arg
305 310 315

( 2 ) INFORMATION FOR SEQ ID NO:28:

( i ) SEQUENCE CHARACTERISTICS:
( A ) LENGTH: 501 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: Human 55 kDa protein (PWP homolog), Fig. 11

( x i ) SEQUENCE DESCRIPTION: SEQ ID NO:28:

Met Asn Arg Ser Arg Gln Val Thr Cys Val Ala Trp Val Arg Cys Gly
1 5 10 15

Val Ala Lys Glu Thr Pro Asp Lys Val Glu Leu Ser Lys Glu Glu Val
20 25 30

Lys Arg Leu Ile Ala Glu Ala Lys Glu Lys Leu Gln Glu Glu Gly Gly
35 40 45

Gly Ser Asp Glu Glu Glu Thr Gly Ser Pro Ser Glu Asp Gly Met Gln
50 55 60

Ser Ala Arg Thr Gln Ala Arg Pro Arg Glu Pro Leu Glu Asp Gly Asp
65 70 75 80

Pro Glu Asp Asp Arg Thr Leu Asp Asp Asp Glu Leu Ala Glu Tyr Asp
85 90 95

Leu Asp Lys Tyr Asp Glu Glu Gly Asp Pro Asp Ala Glu Thr Leu Gly
100 105 110

Glu Ser Leu Leu Gly Leu Thr Val Tyr Gly Ser Asn Asp Gln Asp Pro
115 120 125

Tyr Val Thr Leu Lys Asp Thr Glu Gln Tyr Glu Arg Glu Asp Phe Leu
130 135 140

Ile Lys Pro Ser Asp Asn Leu Ile Val Cys Gly Arg Ala Glu Gln Asp
145 150 155 160

Gln Cys Asn Leu Glu Val His Val Tyr Asn Gln Glu Glu Asp Ser Phe
165 170 175

Tyr Val His His Asp Ile Leu Leu Ser Ala Tyr Pro Leu Ser Val Glu
180 185 190

Trp Leu Asn Phe Asp Pro Ser Pro Asp Asp Ser Thr Gly Asn Tyr Ile
195 200 205

Ala Val Gly Asn Met Thr Pro Val Ile Glu Val Trp Asp Leu Asp Ile

-continued

| | | | | | | | | | | | | | | | |
|---|---|---|---|---|---|---|---|---|---|---|---|---|---|---|---|
| | 210 | | | | | 215 | | | | | 220 | | | | |
| Val | Asp | Ser | Leu | Glu | Pro | Val | Phe | Thr | Leu | Gly | Ser | Lys | Leu | Ser | Lys |
| 225 | | | | | 230 | | | | | 235 | | | | | 240 |
| Lys | Lys | Lys | Lys | Lys | Gly | Lys | Lys | Ser | Ser | Ser | Ala | Glu | Gly | His | Thr |
| | | | | 245 | | | | | 250 | | | | | 255 | |
| Asp | Ala | Val | Leu | Asp | Leu | Ser | Trp | Asn | Lys | Leu | Ile | Arg | Asn | Val | Leu |
| | | | 260 | | | | | 265 | | | | | 270 | | |
| Ala | Ser | Ala | Ser | Ala | Asp | Asn | Thr | Val | Ile | Leu | Trp | Asp | Met | Ser | Leu |
| | | 275 | | | | | 280 | | | | | 285 | | | |
| Gly | Lys | Pro | Ala | Ala | Ser | Leu | Ala | Val | His | Thr | Asp | Lys | Val | Gln | Thr |
| | 290 | | | | | 295 | | | | | 300 | | | | |
| Leu | Gln | Phe | His | Pro | Phe | Glu | Ala | Gln | Thr | Leu | Ile | Ser | Gly | Ser | Tyr |
| 305 | | | | | 310 | | | | | 315 | | | | | 320 |
| Asp | Lys | Ser | Val | Ala | Leu | Tyr | Asp | Cys | Arg | Ser | Pro | Asp | Glu | Ser | His |
| | | | | 325 | | | | | 330 | | | | | 335 | |
| Arg | Met | Trp | Arg | Phe | Ser | Gly | Gln | Ile | Glu | Arg | Val | Thr | Trp | Asn | His |
| | | | 340 | | | | | 345 | | | | | 350 | | |
| Phe | Ser | Pro | Cys | His | Phe | Leu | Ala | Ser | Thr | Asp | Asp | Gly | Phe | Val | Tyr |
| | | 355 | | | | | 360 | | | | | 365 | | | |
| Asn | Leu | Asp | Ala | Arg | Ser | Asp | Lys | Pro | Ile | Phe | Thr | Leu | Asn | Ala | His |
| | 370 | | | | | 375 | | | | | 380 | | | | |
| Asn | Asp | Glu | Ile | Ser | Gly | Leu | Asp | Leu | Ser | Ser | Gln | Ile | Lys | Gly | Cys |
| 385 | | | | | 390 | | | | | 395 | | | | | 400 |
| Leu | Val | Thr | Ala | Ser | Ala | Asp | Lys | Tyr | Val | Lys | Ile | Trp | Asp | Ile | Leu |
| | | | | 405 | | | | | 410 | | | | | 415 | |
| Gly | Asp | Arg | Pro | Ser | Leu | Val | His | Ser | Arg | Asp | Met | Lys | Met | Gly | Val |
| | | | 420 | | | | | 425 | | | | | 430 | | |
| Leu | Phe | Cys | Ser | Ser | Cys | Cys | Pro | Asp | Leu | Pro | Phe | Ile | Tyr | Ala | Phe |
| | | 435 | | | | | 440 | | | | | 445 | | | |
| Gly | Gly | Gln | Lys | Glu | Gly | Leu | Arg | Val | Trp | Asp | Ile | Ser | Thr | Val | Ser |
| | 450 | | | | | 455 | | | | | 460 | | | | |
| Ser | Val | Asn | Glu | Ala | Phe | Gly | Arg | Arg | Glu | Arg | Leu | Val | Leu | Gly | Ser |
| 465 | | | | | 470 | | | | | 475 | | | | | 480 |
| Ala | Arg | Asn | Ser | Ser | Ile | Ser | Gly | Pro | Phe | Gly | Ser | Arg | Ser | Ser | Asp |
| | | | | 485 | | | | | 490 | | | | | 495 | |
| Thr | Pro | Met | Glu | Ser | | | | | | | | | | | |
| | | | 500 | | | | | | | | | | | | |

( 2 ) INFORMATION FOR SEQ ID NO:29:

( i ) SEQUENCE CHARACTERISTICS:
( A ) LENGTH: 428 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: AAC-RICH protein, Fig. 12

( x i ) SEQUENCE DESCRIPTION: SEQ ID NO:29:

| | | | | | | | | | | | | | | | |
|---|---|---|---|---|---|---|---|---|---|---|---|---|---|---|---|
| Pro | Gly | Gly | Phe | Gln | His | Leu | Gln | Gln | Gln | Gln | Gln | Gln | Gln | Gln | Gln |
| 1 | | | | 5 | | | | | 10 | | | | | 15 | |
| Gln | Gln | Gln | Gln | Gln | Gln | Gln | Gln | Gln | Gln | Gln | Gln | Thr | Gln | Val | Gln |
| | | | 20 | | | | | 25 | | | | | 30 | | |

-continued

| | | | | | | | | | | | | | | | |
|---|---|---|---|---|---|---|---|---|---|---|---|---|---|---|---|
| Gln | Leu | His | Asn | Gln | Leu | His | Gln | Gln | His | Asn | Gln | Gln | Ile | Gln | Gln |
| | | 35 | | | | | 40 | | | | | 45 | | | |
| Gln | Ala | Gln | Ala | Thr | Gln | Gln | His | Leu | Gln | Thr | Gln | Gln | Tyr | Leu | Gln |
| | 50 | | | | | 55 | | | | | 60 | | | | |
| Ser | Gln | Ile | His | Gln | Gln | Ser | Gln | Gln | Ser | Gln | Leu | Ser | Asn | Asn | Leu |
| 65 | | | | | 70 | | | | | 75 | | | | | 80 |
| Asn | Ser | Asn | Ser | Lys | Glu | Ser | Thr | Asn | Ile | Pro | Lys | Thr | Asn | Thr | Gln |
| | | | | 85 | | | | | 90 | | | | | 95 | |
| Tyr | Thr | Asn | Phe | Asp | Ser | Lys | Asn | Leu | Asp | Leu | Ala | Ser | Arg | Tyr | Phe |
| | | | 100 | | | | | 105 | | | | | 110 | | |
| Ser | Glu | Cys | Ser | Thr | Lys | Asp | Phe | Ile | Gly | Asn | Lys | Lys | Lys | Ser | Thr |
| | | 115 | | | | | 120 | | | | | 125 | | | |
| Ser | Val | Ala | Trp | Asn | Ala | Asn | Gly | Thr | Lys | Ile | Ala | Ser | Ser | Gly | Ser |
| | 130 | | | | | 135 | | | | | 140 | | | | |
| Asp | Gly | Ile | Val | Arg | Val | Trp | Asn | Phe | Asp | Pro | Leu | Gly | Asn | Ser | Asn |
| 145 | | | | | 150 | | | | | 155 | | | | | 160 |
| Asn | Asn | Asn | Asn | Ser | Asn | Asn | Thr | Ser | Ser | Asn | Ser | Lys | Asn | Asn | Asn |
| | | | | 165 | | | | | 170 | | | | | 175 | |
| Ile | Lys | Glu | Thr | Ile | Glu | Leu | Lys | Gly | His | Asp | Gly | Ser | Ile | Glu | Lys |
| | | | 180 | | | | | 185 | | | | | 190 | | |
| Ile | Ser | Trp | Ser | Pro | Lys | Asn | Asn | Asp | Leu | Leu | Ala | Ser | Ala | Gly | Thr |
| | | 195 | | | | | 200 | | | | | 205 | | | |
| Asp | Lys | Val | Ile | Lys | Ile | Trp | Asp | Val | Lys | Ile | Gly | Lys | Cys | Ile | Gly |
| | 210 | | | | | 215 | | | | | 220 | | | | |
| Thr | Val | Ser | Thr | Asn | Ser | Glu | Asn | Ile | Asp | Val | Arg | Trp | Ser | Pro | Asp |
| 225 | | | | | 230 | | | | | 235 | | | | | 240 |
| Gly | Asp | His | Leu | Ala | Leu | Ile | Asp | Leu | Pro | Thr | Ile | Lys | Thr | Leu | Lys |
| | | | | 245 | | | | | 250 | | | | | 255 | |
| Ile | Tyr | Lys | Phe | Asn | Gly | Glu | Glu | Leu | Asn | Gln | Val | Gly | Trp | Asp | Asn |
| | | | 260 | | | | | 265 | | | | | 270 | | |
| Asn | Gly | Asp | Leu | Ile | Leu | Met | Ala | Asn | Ser | Met | Gly | Asn | Ile | Glu | Ala |
| | | 275 | | | | | 280 | | | | | 285 | | | |
| Tyr | Lys | Phe | Leu | Pro | Lys | Ser | Thr | Thr | His | Val | Lys | His | Leu | Lys | Thr |
| | 290 | | | | | 295 | | | | | 300 | | | | |
| Leu | Tyr | Gly | His | Thr | Ala | Ser | Ile | Tyr | Cys | Met | Glu | Phe | Asp | Pro | Thr |
| 305 | | | | | 310 | | | | | 315 | | | | | 320 |
| Gly | Lys | Tyr | Leu | Ala | Ala | Gly | Ser | Ala | Asp | Ser | Ile | Val | Ser | Leu | Trp |
| | | | | 325 | | | | | 330 | | | | | 335 | |
| Asp | Ile | Glu | Asp | Met | Met | Cys | Val | Lys | Thr | Phe | Ile | Lys | Ser | Thr | Phe |
| | | | 340 | | | | | 345 | | | | | 350 | | |
| Pro | Cys | Arg | Ser | Val | Ser | Phe | Ser | Phe | Asp | Gly | Gln | Phe | Ile | Ala | Ala |
| | | 355 | | | | | 360 | | | | | 365 | | | |
| Ser | Ser | Phe | Glu | Ser | Thr | Ile | Glu | Ile | Phe | His | Ile | Glu | Ser | Ser | Gln |
| | 370 | | | | | 375 | | | | | 380 | | | | |
| Pro | Ile | His | Thr | Ile | Glu | Cys | Gly | Val | Ser | Ser | Leu | Met | Trp | His | Pro |
| 385 | | | | | 390 | | | | | 395 | | | | | 400 |
| Thr | Leu | Pro | Leu | Leu | Ala | Tyr | Ala | Pro | Glu | Ser | Ile | Asn | Glu | Asn | Asn |
| | | | | 405 | | | | | 410 | | | | | 415 | |
| Lys | Asp | Pro | Ser | Ile | Arg | Val | Phe | Gly | Tyr | His | Ser | | | | |
| | | | 420 | | | | | 425 | | | | | | | |

( 2 ) INFORMATION FOR SEQ ID NO:30:

( i ) SEQUENCE CHARACTERISTICS:

-continued (A) LENGTH: 517 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: BETA TRCP, Fig. 13

(xi) SEQUENCE DESCRIPTION: SEQ ID NO:30:

| | | | | | | | | | | | | | | | |
|---|---|---|---|---|---|---|---|---|---|---|---|---|---|---|---|
| Met | Glu | Gly | Phe | Ser | Cys | Ser | Leu | Gln | Pro | Pro | Thr | Ala | Ser | Glu | Arg |
| 1 | | | | 5 | | | | | 10 | | | | | 15 | |
| Glu | Asp | Cys | Asn | Arg | Asp | Glu | Pro | Pro | Arg | Lys | Ile | Ile | Thr | Glu | Lys |
| | | | 20 | | | | | 25 | | | | | 30 | | |
| Asn | Thr | Leu | Arg | Gln | Thr | Lys | Leu | Ala | Asn | Gly | Thr | Ser | Ser | Met | Ile |
| | | 35 | | | | | 40 | | | | | 45 | | | |
| Val | Pro | Lys | Gln | Arg | Lys | Leu | Ser | Ala | Asn | Tyr | Glu | Lys | Glu | Lys | Glu |
| | 50 | | | | | 55 | | | | | 60 | | | | |
| Leu | Cys | Val | Lys | Tyr | Phe | Glu | Gln | Trp | Ser | Glu | Cys | Asp | Gln | Val | Glu |
| 65 | | | | | 70 | | | | | 75 | | | | | 80 |
| Phe | Val | Glu | His | Leu | Ile | Ser | Arg | Met | Cys | His | Tyr | Gln | His | Gly | His |
| | | | | 85 | | | | | 90 | | | | | 95 | |
| Ile | Asn | Thr | Tyr | Leu | Lys | Pro | Met | Leu | Gln | Arg | Asp | Phe | Ile | Thr | Ala |
| | | | 100 | | | | | 105 | | | | | 110 | | |
| Leu | Pro | Ala | Arg | Gly | Leu | Asp | His | Ile | Ala | Glu | Asn | Ile | Leu | Ser | Tyr |
| | | 115 | | | | | 120 | | | | | 125 | | | |
| Leu | Asp | Ala | Lys | Ser | Leu | Cys | Ser | Ala | Glu | Leu | Val | Cys | Lys | Glu | Trp |
| | 130 | | | | | 135 | | | | | 140 | | | | |
| Tyr | Arg | Val | Thr | Ser | Asp | Gly | Met | Leu | Trp | Lys | Lys | Leu | Ile | Glu | Arg |
| 145 | | | | | 150 | | | | | 155 | | | | | 160 |
| Met | Val | Arg | Thr | Asp | Ser | Leu | Trp | Arg | Gly | Leu | Ala | Glu | Arg | Arg | Gly |
| | | | | 165 | | | | | 170 | | | | | 175 | |
| Trp | Gly | Gln | Tyr | Leu | Phe | Lys | Asn | Lys | Pro | Pro | Asp | Gly | Lys | Thr | Pro |
| | | | 180 | | | | | 185 | | | | | 190 | | |
| Pro | Asn | Ser | Phe | Tyr | Arg | Ala | Leu | Tyr | Pro | Lys | Ile | Ile | Gln | Asp | Ile |
| | | 195 | | | | | 200 | | | | | 205 | | | |
| Glu | Thr | Ile | Glu | Ser | Asn | Trp | Arg | Cys | Gly | Arg | His | Ser | Leu | Gln | Arg |
| | 210 | | | | | 215 | | | | | 220 | | | | |
| Ile | His | Cys | Arg | Ser | Glu | Thr | Ser | Lys | Gly | Val | Tyr | Cys | Leu | Gln | Tyr |
| 225 | | | | | 230 | | | | | 235 | | | | | 240 |
| Asp | Asp | Gln | Lys | Ile | Val | Ser | Gly | Leu | Arg | Asp | Asn | Thr | Ile | Lys | Ile |
| | | | | 245 | | | | | 250 | | | | | 255 | |
| Trp | Asp | Lys | Asn | Thr | Leu | Glu | Cys | Lys | Arg | Val | Leu | Met | Gly | His | Thr |
| | | | 260 | | | | | 265 | | | | | 270 | | |
| Gly | Ser | Val | Leu | Cys | Leu | Gln | Tyr | Asp | Glu | Arg | Val | Ile | Ile | Thr | Gly |
| | | 275 | | | | | 280 | | | | | 285 | | | |
| Ser | Asp | Ser | Thr | Val | Arg | Val | Trp | Asp | Val | Asn | Thr | Gly | Glu | Met | Leu |
| | 290 | | | | | 295 | | | | | 300 | | | | |
| Asn | Thr | Leu | Ile | His | His | Cys | Glu | Ala | Val | Leu | His | Leu | Arg | Phe | Asn |
| 305 | | | | | 310 | | | | | 315 | | | | | 320 |
| Asn | Gly | Met | Met | Val | Thr | Cys | Ser | Lys | Asp | Arg | Ser | Ile | Ala | Val | Trp |
| | | | | 325 | | | | | 330 | | | | | 335 | |
| Asp | Met | Ala | Ser | Ala | Thr | Asp | Ile | Thr | Leu | Arg | Arg | Val | Leu | Val | Gly |
| | | | 340 | | | | | 345 | | | | | 350 | | |

-continued

| | | | | | | | | | | | | | | | |
|---|---|---|---|---|---|---|---|---|---|---|---|---|---|---|---|
| His | Arg | Ala | Ala | Val | Asn | Val | Val | Asp | Phe | Asp | Asp | Lys | Tyr | Ile | Val |
| | | 355 | | | | | 360 | | | | | 365 | | | |
| Ser | Ala | Ser | Gly | Asp | Arg | Thr | Ile | Lys | Val | Trp | Asn | Thr | Ser | Thr | Cys |
| | 370 | | | | | 375 | | | | | 380 | | | | |
| Glu | Phe | Val | Arg | Thr | Leu | Asn | Gly | His | Lys | Arg | Gly | Ile | Ala | Cys | Leu |
| 385 | | | | | 390 | | | | | 395 | | | | | 400 |
| Gln | Tyr | Arg | Asp | Arg | Leu | Val | Val | Ser | Gly | Ser | Ser | Asp | Asn | Thr | Ile |
| | | | | 405 | | | | | 410 | | | | | 415 | |
| Arg | Leu | Trp | Asp | Ile | Glu | Cys | Gly | Ala | Cys | Leu | Arg | Val | Leu | Glu | Gly |
| | | | 420 | | | | | 425 | | | | | 430 | | |
| His | Glu | Glu | Leu | Val | Arg | Cys | Ile | Arg | Phe | Asp | Asn | Lys | Arg | Ile | Val |
| | | 435 | | | | | 440 | | | | | 445 | | | |
| Ser | Gly | Ala | Tyr | Asp | Gly | Lys | Ile | Lys | Val | Trp | Asp | Leu | Val | Ala | Ala |
| | 450 | | | | | 455 | | | | | 460 | | | | |
| Leu | Asp | Pro | Arg | Ala | Pro | Ala | Gly | Thr | Leu | Cys | Leu | Arg | Thr | Leu | Val |
| 465 | | | | | 470 | | | | | 475 | | | | | 480 |
| Glu | His | Ser | Gly | Arg | Val | Phe | Arg | Leu | Gln | Phe | Asp | Glu | Phe | Gln | Ile |
| | | | | 485 | | | | | 490 | | | | | 495 | |
| Val | Ser | Ser | Ser | His | Asp | Asp | Thr | Ile | Leu | Ile | Trp | Asp | Phe | Leu | Asn |
| | | | 500 | | | | | 505 | | | | | 510 | | |
| Asp | Pro | Gly | Leu | Ala | | | | | | | | | | | |
| | | 515 | | | | | | | | | | | | | |

( 2 ) INFORMATION FOR SEQ ID NO:31:

( i ) SEQUENCE CHARACTERISTICS:
( A ) LENGTH: 906 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: beta-prime- cop, Fig. 14

( x i ) SEQUENCE DESCRIPTION: SEQ ID NO:31:

| | | | | | | | | | | | | | | | |
|---|---|---|---|---|---|---|---|---|---|---|---|---|---|---|---|
| Met | Pro | Leu | Arg | Leu | Asp | Ile | Lys | Arg | Lys | Leu | Thr | Ala | Arg | Ser | Asp |
| 1 | | | | 5 | | | | | 10 | | | | | 15 | |
| Arg | Val | Lys | Ser | Val | Asp | Leu | His | Pro | Thr | Glu | Pro | Trp | Met | Leu | Ala |
| | | | 20 | | | | | 25 | | | | | 30 | | |
| Ser | Leu | Tyr | Asn | Gly | Ser | Val | Cys | Val | Trp | Asn | His | Glu | Thr | Gln | Thr |
| | | 35 | | | | | 40 | | | | | 45 | | | |
| Leu | Val | Lys | Thr | Phe | Glu | Val | Cys | Asp | Leu | Pro | Val | Arg | Ala | Ala | Lys |
| | 50 | | | | | 55 | | | | | 60 | | | | |
| Phe | Val | Ala | Arg | Lys | Asn | Trp | Val | Val | Thr | Gly | Ala | Asp | Asp | Met | Gln |
| 65 | | | | | 70 | | | | | 75 | | | | | 80 |
| Ile | Arg | Val | Phe | Asn | Tyr | Asn | Thr | Leu | Glu | Arg | Val | His | Met | Phe | Glu |
| | | | | 85 | | | | | 90 | | | | | 95 | |
| Ala | His | Ser | Asp | Tyr | Ile | Arg | Cys | Ile | Ala | Val | His | Pro | Thr | Gln | Pro |
| | | | 100 | | | | | 105 | | | | | 110 | | |
| Phe | Ile | Leu | Thr | Ser | Ser | Asp | Asp | Met | Leu | Ile | Lys | Leu | Trp | Asp | Trp |
| | | 115 | | | | | 120 | | | | | 125 | | | |
| Asp | Lys | Lys | Trp | Ser | Cys | Ser | Gln | Val | Phe | Glu | Gly | His | Thr | His | Tyr |
| | 130 | | | | | 135 | | | | | 140 | | | | |

-continued

Val Met Gln Ile Val Ile Asn Pro Lys Asp Asn Asn Gln Phe Ala Ser
145 150 155 160

Ala Ser Leu Asp Arg Thr Ile Lys Val Trp Gln Leu Gly Ser Ser Ser
165 170 175

Pro Asn Phe Thr Leu Glu Gly His Glu Lys Gly Val Asn Cys Ile Asp
180 185 190

Tyr Tyr Ser Gly Gly Asp Lys Pro Tyr Leu Ile Ser Gly Ala Asp Asp
195 200 205

Arg Leu Val Lys Ile Trp Asp Tyr Gln Asn Lys Thr Cys Val Gln Thr
210 215 220

Leu Glu Gly His Ala Gln Asn Val Ser Cys Ala Ser Phe His Pro Glu
225 230 235 240

Leu Pro Ile Ile Ile Thr Gly Ser Glu Asp Gly Thr Val Arg Ile Trp
245 250 255

His Ser Ser Thr Tyr Arg Leu Glu Ser Thr Leu Asn Tyr Gly Met Glu
260 265 270

Arg Val Trp Cys Val Ala Ser Leu Arg Gly Ser Asn Asn Val Ala Leu
275 280 285

Gly Tyr Asp Glu Gly Ser Ile Ile Val Lys Leu Gly Arg Glu Glu Pro
290 295 300

Ala Met Ser Met Asp Ala Asn Gly Lys Ile Ile Trp Ala Lys His Ser
305 310 315 320

Glu Val Gln Gln Ala Asn Leu Lys Ala Met Gly Asp Ala Glu Ile Lys
325 330 335

Asp Gly Glu Arg Leu Pro Leu Ala Val Lys Asp Met Gly Ser Cys Glu
340 345 350

Ile Tyr Pro Gln Thr Ile Gln His Asn Pro Asn Gly Arg Phe Val Val
355 360 365

Val Cys Gly Asp Gly Glu Tyr Ile Ile Tyr Thr Ala Met Ala Leu Arg
370 375 380

Asn Lys Ser Phe Gly Ser Ala Gln Glu Phe Ala Trp Ala His Asp Ser
385 390 395 400

Ser Glu Tyr Ala Ile Arg Glu Ser Asn Ser Val Val Lys Ile Phe Lys
405 410 415

Asn Phe Lys Glu Lys Lys Ser Phe Lys Pro Asp Phe Gly Ala Glu Ser
420 425 430

Ile Tyr Gly Gly Phe Leu Leu Gly Val Arg Ser Val Asn Gly Leu Ala
435 440 445

Phe Tyr Asp Trp Glu Asn Thr Glu Leu Ile Arg Arg Ile Glu Ile Gln
450 455 460

Pro Lys His Ile Phe Trp Ser Asp Ser Gly Glu Leu Val Cys Ile Ala
465 470 475 480

Thr Glu Glu Ser Phe Phe Ile Leu Lys Tyr Leu Ser Glu Lys Val Leu
485 490 495

Ala Ala Gln Glu Thr His Glu Gly Val Thr Glu Asp Gly Ile Glu Asp
500 505 510

Gly Phe Glu Val Leu Gly Glu Ile Gln Glu Ile Val Lys Thr Gly Leu
515 520 525

Trp Val Gly Asp Cys Phe Ile Tyr Thr Ser Ser Val Asn Arg Leu Asn
530 535 540

Tyr Tyr Val Gly Gly Glu Ile Val Thr Ile Ala His Leu Asp Arg Thr
545 550 555 560

Met Tyr Leu Leu Gly Tyr Ile Pro Lys Asp Asn Arg Leu Tyr Leu Gly
565 570 575

-continued

Asp Lys Glu Leu Asn Ile Val Ser Tyr Ser Leu Leu Val Ser Val Leu
580 585 590

Glu Tyr Gln Thr Ala Val Met Arg Arg Asp Phe Ser Met Ala Asp Lys
595 600 605

Val Leu Pro Thr Ile Pro Lys Glu Gln Arg Thr Arg Val Ala His Phe
610 615 620

Leu Glu Lys Gln Gly Phe Lys Gln Gln Ala Leu Thr Val Ser Thr Asp
625 630 635 640

Pro Glu His Arg Phe Glu Leu Ala Leu Gln Leu Gly Glu Leu Lys Ile
645 650 655

Ala Tyr Gln Leu Ala Val Glu Ala Glu Ser Glu Gln Lys Trp Lys Gln
660 665 670

Leu Ala Glu Leu Ala Ile Ser Lys Cys Pro Phe Gly Leu Ala Gln Glu
675 680 685

Cys Leu His His Ala Gln Asp Tyr Gly Gly Leu Leu Leu Leu Ala Thr
690 695 700

Ala Ser Gly Asn Ala Ser Met Val Asn Lys Leu Ala Glu Gly Ala Glu
705 710 715 720

Arg Asp Gly Lys Asn Asn Val Ala Phe Met Ser Tyr Phe Leu Gln Gly
725 730 735

Lys Leu Asp Ala Cys Leu Glu Leu Leu Ile Arg Thr Gly Arg Leu Pro
740 745 750

Glu Ala Ala Phe Leu Ala Arg Thr Tyr Leu Pro Ser Gln Val Ser Arg
755 760 765

Val Val Lys Leu Trp Arg Glu Asn Leu Ser Lys Val Asn Gln Lys Ala
770 775 780

Ala Glu Ser Leu Ala Asp Pro Thr Glu Tyr Glu Asn Leu Phe Pro Gly
785 790 795 800

Leu Lys Glu Ala Phe Val Val Glu Glu Trp Val Lys Glu Thr His Ala
805 810 815

Asp Leu Trp Pro Ala Lys Gln Tyr Pro Leu Val Thr Pro Asn Glu Glu
820 825 830

Arg Asn Val Met Glu Glu Ala Lys Gly Phe Gln Pro Ser Arg Ser Ala
835 840 845

Ala Gln Gln Glu Leu Asp Gly Lys Pro Ala Ser Pro Thr Pro Val Ile
850 855 860

Val Thr Ser Gln Thr Ala Asn Lys Glu Glu Lys Ser Leu Leu Glu Leu
865 870 875 880

Glu Val Asp Leu Asp Asn Leu Glu Ile Glu Asp Ile Asp Thr Thr Asp
885 890 895

Ile Asn Leu Asp Glu Asp Ile Leu Asp Asp
900 905

( 2 ) INFORMATION FOR SEQ ID NO:32:

( i ) SEQUENCE CHARACTERISTICS:
( A ) LENGTH: 779 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein, Fig. 15

-continued ( x i ) SEQUENCE DESCRIPTION: SEQ ID NO:32:

| | | | | | | | | | | | | | | | |
|---|---|---|---|---|---|---|---|---|---|---|---|---|---|---|---|
| Met | Gly | Ser | Phe | Pro | Leu | Ala | Glu | Phe | Pro | Leu | Arg | Asp | Ile | Pro | Val |
| 1 | | | | 5 | | | | | 10 | | | | | 15 | |
| Pro | Tyr | Ser | Tyr | Arg | Val | Ser | Gly | Gly | Ile | Ala | Ser | Ser | Gly | Ser | Val |
| | | | 20 | | | | | 25 | | | | | 30 | | |
| Thr | Ala | Leu | Val | Thr | Ala | Ala | Gly | Thr | His | Arg | Asn | Ser | Ser | Thr | Ala |
| | | 35 | | | | | 40 | | | | | 45 | | | |
| Lys | Thr | Val | Glu | Thr | Glu | Asp | Gly | Glu | Glu | Asp | Ile | Asp | Glu | Tyr | Gln |
| | 50 | | | | | 55 | | | | | 60 | | | | |
| Arg | Lys | Arg | Ala | Ala | Gly | Ser | Gly | Glu | Ser | Thr | Pro | Glu | Arg | Ser | Asp |
| 65 | | | | | 70 | | | | | 75 | | | | | 80 |
| Phe | Lys | Arg | Val | Lys | His | Asp | Asn | His | Lys | Thr | Leu | His | Pro | Val | Asn |
| | | | | 85 | | | | | 90 | | | | | 95 | |
| Leu | Gln | Asn | Thr | Gly | Ala | Ala | Ser | Val | Asp | Asn | Asp | Gly | Leu | His | Asn |
| | | | 100 | | | | | 105 | | | | | 110 | | |
| Leu | Thr | Asp | Ile | Ser | Asn | Asp | Ala | Glu | Lys | Leu | Leu | Met | Ser | Val | Asp |
| | | 115 | | | | | 120 | | | | | 125 | | | |
| Asp | Gly | Ser | Ala | Ala | Pro | Ser | Thr | Leu | Ser | Val | Asn | Met | Gly | Val | Ala |
| | 130 | | | | | 135 | | | | | 140 | | | | |
| Ser | His | Asn | Val | Ala | Ala | Pro | Thr | Thr | Val | Asn | Ala | Ala | Thr | Ile | Thr |
| 145 | | | | | 150 | | | | | 155 | | | | | 160 |
| Gly | Ser | Asp | Val | Ser | Asn | Asn | Val | Asn | Ser | Ala | Thr | Ile | Asn | Asn | Pro |
| | | | | 165 | | | | | 170 | | | | | 175 | |
| Met | Glu | Glu | Gly | Ala | Leu | Pro | Leu | Ser | Pro | Thr | Ala | Ser | Ser | Pro | Gly |
| | | | 180 | | | | | 185 | | | | | 190 | | |
| Thr | Thr | Thr | Pro | Leu | Ala | Lys | Thr | Thr | Lys | Thr | Ile | Asn | Asn | Asn | Asn |
| | | 195 | | | | | 200 | | | | | 205 | | | |
| Asn | Ile | Ala | Asp | Leu | Ile | Glu | Ser | Lys | Asp | Ser | Ile | Ile | Ser | Pro | Glu |
| | 210 | | | | | 215 | | | | | 220 | | | | |
| Tyr | Leu | Ser | Asp | Glu | Ile | Phe | Ser | Ala | Ile | Asn | Asn | Asn | Leu | Pro | His |
| 225 | | | | | 230 | | | | | 235 | | | | | 240 |
| Ala | Tyr | Phe | Lys | Asn | Leu | Leu | Phe | Arg | Leu | Val | Ala | Asn | Met | Asp | Arg |
| | | | | 245 | | | | | 250 | | | | | 255 | |
| Ser | Glu | Leu | Ser | Asp | Leu | Gly | Thr | Leu | Ile | Lys | Asp | Asn | Leu | Lys | Arg |
| | | | 260 | | | | | 265 | | | | | 270 | | |
| Asp | Leu | Ile | Thr | Ser | Leu | Pro | Phe | Glu | Ile | Ser | Leu | Lys | Ile | Phe | Asn |
| | | 275 | | | | | 280 | | | | | 285 | | | |
| Tyr | Leu | Gln | Phe | Glu | Asp | Ile | Ile | Asn | Ser | Leu | Gly | Val | Ser | Gln | Asn |
| | 290 | | | | | 295 | | | | | 300 | | | | |
| Trp | Asn | Lys | Ile | Ile | Arg | Lys | Ser | Thr | Ser | Leu | Trp | Lys | Lys | Leu | Leu |
| 305 | | | | | 310 | | | | | 315 | | | | | 320 |
| Ile | Ser | Glu | Asn | Phe | Val | Ser | Pro | Lys | Gly | Phe | Asn | Ser | Leu | Asn | Leu |
| | | | | 325 | | | | | 330 | | | | | 335 | |
| Lys | Leu | Ser | Gln | Lys | Tyr | Pro | Lys | Leu | Ser | Gln | Gln | Asp | Arg | Leu | Arg |
| | | | 340 | | | | | 345 | | | | | 350 | | |
| Leu | Ser | Phe | Leu | Glu | Asn | Ile | Phe | Ile | Leu | Lys | Asn | Trp | Tyr | Asn | Pro |
| | | 355 | | | | | 360 | | | | | 365 | | | |
| Lys | Phe | Val | Pro | Gln | Arg | Thr | Thr | Leu | Arg | Gly | His | Met | Thr | Ser | Val |
| | 370 | | | | | 375 | | | | | 380 | | | | |
| Ile | Thr | Cys | Leu | Gln | Phe | Glu | Asp | Asn | Tyr | Val | Ile | Thr | Gly | Ala | Asp |
| 385 | | | | | 390 | | | | | 395 | | | | | 400 |
| Asp | Lys | Met | Ile | Arg | Val | Tyr | Asp | Ser | Ile | Asn | Lys | Lys | Phe | Leu | Leu |
| | | | | 405 | | | | | 410 | | | | | 415 | |

-continued

Gln Leu Ser Gly His Asp Gly Gly Val Trp Ala Leu Lys Tyr Ala His
420 425 430

Gly Gly Ile Leu Val Ser Gly Ser Thr Asp Arg Thr Val Arg Val Trp
435 440 445

Asp Ile Lys Lys Gly Cys Cys Thr His Val Phe Glu Gly His Asn Ser
450 455 460

Thr Val Arg Cys Leu Asp Ile Val Glu Tyr Lys Asn Ile Lys Tyr Ile
465 470 475 480

Val Thr Gly Ser Arg Asp Asn Thr Leu His Val Trp Lys Leu Pro Lys
485 490 495

Glu Ser Ser Val Pro Asp His Gly Glu Glu His Asp Tyr Pro Leu Val
500 505 510

Phe His Thr Pro Glu Glu Asn Pro Tyr Phe Val Gly Val Leu Arg Gly
515 520 525

His Met Ala Ser Val Arg Thr Val Ser Gly His Gly Asn Ile Val Val
530 535 540

Ser Gly Ser Tyr Asp Asn Thr Leu Ile Val Trp Asp Val Ala Gln Met
545 550 555 560

Lys Cys Leu Tyr Ile Leu Ser Gly His Thr Asp Arg Ile Tyr Ser Thr
565 570 575

Ile Tyr Asp His Glu Arg Lys Arg Cys Ile Ser Ala Ser Met Asp Thr
580 585 590

Thr Ile Arg Ile Trp Asp Leu Glu Asn Ile Trp Asn Asn Gly Glu Cys
595 600 605

Ser Tyr Ala Thr Asn Ser Ala Ser Pro Cys Ala Lys Ile Leu Gly Ala
610 615 620

Met Tyr Thr Leu Gln Gly His Thr Ala Leu Val Gly Leu Leu Arg Leu
625 630 635 640

Ser Asp Lys Phe Leu Val Ser Ala Ala Ala Asp Gly Ser Ile Arg Gly
645 650 655

Trp Asp Ala Asn Asp Tyr Ser Arg Lys Phe Ser Tyr His His Thr Asn
660 665 670

Leu Ser Ala Ile Thr Thr Phe Tyr Val Ser Asp Asn Ile Leu Val Ser
675 680 685

Gly Ser Glu Asn Gln Phe Asn Ile Tyr Asn Leu Arg Ser Gly Lys Leu
690 695 700

Val His Ala Asn Ile Leu Lys Asp Ala Asp Gln Ile Trp Ser Val Asn
705 710 715 720

Phe Lys Gly Lys Thr Leu Val Ala Ala Val Glu Lys Asp Gly Gln Ser
725 730 735

Phe Leu Glu Ile Leu Asp Phe Ser Lys Ala Ser Lys Ile Asn Tyr Val
740 745 750

Ser Asn Pro Val Asn Ser Ser Ser Ser Ser Leu Glu Ser Ile Ser Thr
755 760 765

Ser Leu Gly Leu Thr Arg Thr Thr Ile Ile Pro
770 775

( 2 ) INFORMATION FOR SEQ ID NO:33:

( i ) SEQUENCE CHARACTERISTICS:
( A ) LENGTH: 318 amino acids
( B ) TYPE: amino acid
( D ) TOPOLOGY: unknown ( i i ) MOLECULE TYPE: protein -continued ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG, Fig. 16

( x i ) SEQUENCE DESCRIPTION: SEQ ID NO:33:

| | | | | | | | | | | | | | | | |
|---|---|---|---|---|---|---|---|---|---|---|---|---|---|---|---|
| Met | Ala | Glu | Thr | Leu | Thr | Leu | Arg | Ala | Thr | Leu | Lys | Gly | His | Thr | Asn |
| 1 | | | | 5 | | | | | 10 | | | | | 15 | |
| Trp | Val | Thr | Ala | Ile | Ala | Thr | Pro | Leu | Asp | Pro | Ser | Ser | Asn | Thr | Leu |
| | | | 20 | | | | | 25 | | | | | 30 | | |
| Leu | Ser | Ala | Ser | Arg | Asp | Lys | Ser | Val | Leu | Val | Trp | Glu | Leu | Glu | Arg |
| | | 35 | | | | | 40 | | | | | 45 | | | |
| Ser | Glu | Ser | Asn | Tyr | Gly | Tyr | Ala | Arg | Lys | Ala | Leu | Arg | Gly | His | Ser |
| | 50 | | | | | 55 | | | | | 60 | | | | |
| His | Phe | Val | Gln | Asp | Val | Val | Ile | Ser | Ser | Asp | Gly | Gln | Phe | Cys | Leu |
| 65 | | | | | 70 | | | | | 75 | | | | | 80 |
| Thr | Gly | Ser | Trp | Asp | Gly | Thr | Leu | Arg | Leu | Trp | Asp | Leu | Asn | Thr | Gly |
| | | | | 85 | | | | | 90 | | | | | 95 | |
| Thr | Thr | Thr | Arg | Arg | Phe | Val | Gly | His | Thr | Lys | Asp | Val | Leu | Ser | Val |
| | | | 100 | | | | | 105 | | | | | 110 | | |
| Ala | Phe | Ser | Val | Asp | Asn | Arg | Gln | Ile | Val | Ser | Gly | Ser | Arg | Asp | Lys |
| | | 115 | | | | | 120 | | | | | 125 | | | |
| Thr | Ile | Lys | Leu | Trp | Asn | Thr | Leu | Gly | Glu | Cys | Lys | Tyr | Thr | Ile | Gly |
| | 130 | | | | | 135 | | | | | 140 | | | | |
| Glu | Pro | Glu | Gly | His | Thr | Glu | Trp | Val | Ser | Cys | Val | Arg | Phe | Ser | Pro |
| 145 | | | | | 150 | | | | | 155 | | | | | 160 |
| Met | Thr | Thr | Asn | Pro | Ile | Ile | Val | Ser | Gly | Gly | Trp | Asp | Lys | Met | Val |
| | | | | 165 | | | | | 170 | | | | | 175 | |
| Lys | Val | Trp | Asn | Leu | Thr | Asn | Cys | Lys | Leu | Lys | Asn | Asn | Leu | Val | Gly |
| | | | 180 | | | | | 185 | | | | | 190 | | |
| His | His | Gly | Tyr | Val | Asn | Thr | Val | Thr | Val | Ser | Pro | Asp | Gly | Ser | Leu |
| | | 195 | | | | | 200 | | | | | 205 | | | |
| Cys | Ala | Ser | Gly | Gly | Lys | Asp | Gly | Ile | Ala | Met | Leu | Trp | Asp | Leu | Ala |
| | 210 | | | | | 215 | | | | | 220 | | | | |
| Glu | Gly | Lys | Arg | Leu | Tyr | Ser | Leu | Asp | Ala | Gly | Asp | Val | Ile | His | Cys |
| 225 | | | | | 230 | | | | | 235 | | | | | 240 |
| Leu | Cys | Phe | Ser | Pro | Asn | Arg | Tyr | Trp | Leu | Cys | Ala | Ala | Thr | Gln | Ser |
| | | | | 245 | | | | | 250 | | | | | 255 | |
| Ser | Ile | Lys | Ile | Trp | Asp | Leu | Glu | Ser | Lys | Ser | Ile | Val | Asp | Asp | Leu |
| | | | 260 | | | | | 265 | | | | | 270 | | |
| Arg | Pro | Glu | Phe | Asn | Ile | Thr | Ser | Lys | Lys | Ala | Gln | Val | Pro | Tyr | Cys |
| | | 275 | | | | | 280 | | | | | 285 | | | |
| Val | Ser | Leu | Ala | Trp | Ser | Ala | Asp | Gly | Ser | Thr | Leu | Tyr | Ser | Gly | Tyr |
| | 290 | | | | | 295 | | | | | 300 | | | | |
| Thr | Asp | Gly | Gln | Ile | Arg | Val | Trp | Ala | Val | Gly | His | Ser | Leu | | |
| 305 | | | | | 310 | | | | | 315 | | | | | |

( 2 ) INFORMATION FOR SEQ ID NO:34:

( i ) SEQUENCE CHARACTERISTICS:
( A ) LENGTH: 658 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: cop-1 protein, Fig. 17

( x i ) SEQUENCE DESCRIPTION: SEQ ID NO:34:

| | | | | | | | | | | | | | | | |
|---|---|---|---|---|---|---|---|---|---|---|---|---|---|---|---|
| Met | Glu | Glu | Ile | Ser | Thr | Asp | Pro | Val | Val | Pro | Ala | Val | Lys | Pro | Asp |
| 1 | | | | 5 | | | | | 10 | | | | | 15 | |
| Pro | Arg | Thr | Ser | Ser | Val | Gly | Glu | Gly | Ala | Asn | Arg | His | Glu | Asn | Asp |
| | | | 20 | | | | | 25 | | | | | 30 | | |
| Asp | Gly | Gly | Ser | Gly | Gly | Ser | Glu | Ile | Gly | Ala | Pro | Asp | Leu | Asp | Lys |
| | | 35 | | | | | 40 | | | | | 45 | | | |
| Asp | Leu | Leu | Cys | Pro | Ile | Cys | Met | Gln | Ile | Ile | Lys | Asp | Ala | Phe | Leu |
| | 50 | | | | | 55 | | | | | 60 | | | | |
| Thr | Ala | Cys | Gly | His | Ser | Phe | Cys | Tyr | Met | Cys | Ile | Ile | Thr | His | Leu |
| 65 | | | | | 70 | | | | | 75 | | | | | 80 |
| Arg | Asn | Lys | Ser | Asp | Cys | Pro | Cys | Cys | Ser | Gln | His | Leu | Thr | Asn | Asn |
| | | | | 85 | | | | | 90 | | | | | 95 | |
| Gln | Leu | Tyr | Pro | Asn | Phe | Leu | Leu | Asp | Lys | Leu | Leu | Lys | Lys | Thr | Ser |
| | | | 100 | | | | | 105 | | | | | 110 | | |
| Ala | Arg | His | Val | Ser | Lys | Thr | Ala | Ser | Pro | Leu | Asp | Gln | Phe | Arg | Glu |
| | | 115 | | | | | 120 | | | | | 125 | | | |
| Ala | Leu | Gln | Arg | Gly | Cys | Asp | Val | Ser | Ile | Lys | Glu | Val | Asp | Asn | Leu |
| | 130 | | | | | 135 | | | | | 140 | | | | |
| Leu | Thr | Leu | Leu | Ala | Glu | Arg | Lys | Arg | Lys | Met | Glu | Gln | Glu | Glu | Ala |
| 145 | | | | | 150 | | | | | 155 | | | | | 160 |
| Glu | Arg | Asn | Met | Gln | Ile | Leu | Leu | Asp | Phe | Leu | His | Cys | Leu | Arg | Lys |
| | | | | 165 | | | | | 170 | | | | | 175 | |
| Gln | Lys | Val | Asp | Glu | Leu | Asn | Glu | Val | Gln | Thr | Asp | Leu | Gln | Tyr | Ile |
| | | | 180 | | | | | 185 | | | | | 190 | | |
| Lys | Glu | Asp | Ile | Asn | Ala | Val | Glu | Arg | His | Arg | Ile | Asp | Leu | Tyr | Arg |
| | | 195 | | | | | 200 | | | | | 205 | | | |
| Ala | Arg | Asp | Arg | Tyr | Ser | Val | Lys | Leu | Arg | Met | Leu | Gly | Asp | Asp | Pro |
| | 210 | | | | | 215 | | | | | 220 | | | | |
| Ser | Thr | Arg | Asn | Ala | Trp | Pro | His | Glu | Lys | Asn | Gln | Ile | Gly | Phe | Asn |
| 225 | | | | | 230 | | | | | 235 | | | | | 240 |
| Ser | Asn | Ser | Leu | Ser | Ile | Arg | Gly | Gly | Asn | Phe | Val | Gly | Asn | Tyr | Gln |
| | | | | 245 | | | | | 250 | | | | | 255 | |
| Asn | Lys | Lys | Val | Glu | Gly | Lys | Ala | Gln | Gly | Ser | Ser | His | Gly | Leu | Pro |
| | | | 260 | | | | | 265 | | | | | 270 | | |
| Lys | Lys | Asp | Ala | Leu | Ser | Gly | Ser | Asp | Ser | Gln | Ser | Leu | Asn | Gln | Ser |
| | | 275 | | | | | 280 | | | | | 285 | | | |
| Thr | Val | Ser | Met | Ala | Arg | Lys | Lys | Arg | Ile | His | Ala | Gln | Phe | Asn | Asp |
| | 290 | | | | | 295 | | | | | 300 | | | | |
| Leu | Gln | Glu | Cys | Tyr | Leu | Gln | Lys | Arg | Arg | Gln | Leu | Ala | Asp | Gln | Pro |
| 305 | | | | | 310 | | | | | 315 | | | | | 320 |
| Asn | Ser | Lys | Gln | Glu | Asn | Asp | Lys | Ser | Val | Val | Arg | Arg | Glu | Gly | Tyr |
| | | | | 325 | | | | | 330 | | | | | 335 | |
| Ser | Asn | Gly | Leu | Ala | Asp | Phe | Gln | Ser | Val | Leu | Thr | Thr | Phe | Thr | Arg |
| | | | 340 | | | | | 345 | | | | | 350 | | |
| Tyr | Ser | Arg | Leu | Arg | Val | Ile | Ala | Glu | Ile | Arg | His | Gly | Asp | Ile | Phe |
| | | 355 | | | | | 360 | | | | | 365 | | | |
| His | Ser | Ala | Asn | Ile | Val | Ser | Ser | Ile | Glu | Phe | Asp | Arg | Asp | Asp | Glu |
| | 370 | | | | | 375 | | | | | 380 | | | | |

Leu Phe Ala Thr Ala Gly Val Ser Arg Cys Ile Lys Val Phe Asp Phe
385 390 395 400

Ser Ser Val Val Asn Glu Pro Ala Asp Met Gln Cys Pro Ile Val Glu
405 410 415

Met Ser Thr Arg Ser Lys Leu Ser Cys Leu Ser Trp Asn Lys His Glu
420 425 430

Lys Asn His Ile Ala Ser Ser Asp Tyr Glu Gly Ile Val Thr Val Trp
435 440 445

Asp Val Thr Thr Arg Gln Ser Leu Met Glu Thr Glu Glu Asn Glu Lys
450 455 460

Arg Ala Trp Ser Val Asp Phe Ser Arg Thr Glu Pro Ser Met Leu Val
465 470 475 480

Ser Gly Ser Asp Asp Cys Lys Val Lys Val Trp Cys Thr Arg Gln Glu
485 490 495

Ala Ser Val Ile Asn Ile Asp Met Lys Ala Asn Ile Cys Cys Val Lys
500 505 510

Tyr Asn Pro Gly Ser Ser Asn Tyr Ile Ala Val Gly Ser Ala Asp His
515 520 525

His Ile His Tyr Tyr Asp Leu Arg Asn Ile Ser Gln Pro Leu His Val
530 535 540

Phe Ser Gly His Lys Lys Ala Val Ser Tyr Met Lys Phe Leu Ser Asn
545 550 555 560

Asn Glu Leu Ala Ser Ala Ser Thr Asp Ser Thr Leu Arg Leu Trp Asp
565 570 575

Val Lys Asp Asn Leu Pro Val Arg Thr Phe Arg Gly His Thr Asn Glu
580 585 590

Lys Asn Phe Val Gly Leu Thr Val Asn Ser Glu Tyr Leu Ala Cys Gly
595 600 605

Ser Glu Thr Thr Arg Tyr Val Tyr His Lys Glu Ile Thr Arg Pro Val
610 615 620

Thr Ser His Arg Phe Gly Ser Pro Asp Met Asp Asp Ala Glu Lys Arg
625 630 635 640

Gln Val Pro Thr Leu Leu Val Arg Phe Ala Gly Arg Val Ile Val Pro
645 650 655

Arg Cys ( 2 ) INFORMATION FOR SEQ ID NO:35:

( i ) SEQUENCE CHARACTERISTICS:
( A ) LENGTH: 440 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: CORO PROTEIN, Fig. 18

( x i ) SEQUENCE DESCRIPTION: SEQ ID NO:35:

Met Ser Lys Val Val Arg Ser Ser Lys Tyr Arg His Val Phe Ala Ala
1 5 10 15

Gln Pro Lys Lys Glu Glu Cys Tyr Gln Asn Leu Lys Thr Lys Ser Ala
20 25 30

Val Trp Asp Ser Asn Tyr Val Ala Ala Asn Thr Arg Tyr Ile Trp Asp
35 40 45

| | | | | | | | | | | | | | | | |
|---|---|---|---|---|---|---|---|---|---|---|---|---|---|---|---|
| Ala | Ala | Gly | Gly | Gly | Ser | Phe | Ala | Val | Glu | Ala | Ile | Pro | His | Ser | Gly |
| | 50 | | | | | 55 | | | | | 60 | | | | |
| Lys | Thr | Thr | Ser | Val | Pro | Leu | Phe | Asn | Gly | His | Lys | Ser | Ala | Val | Leu |
| 65 | | | | | 70 | | | | | 75 | | | | | 80 |
| Asp | Ile | Ala | Phe | His | Pro | Phe | Asn | Glu | Asn | Leu | Val | Gly | Ser | Val | Ser |
| | | | | 85 | | | | | 90 | | | | | 95 | |
| Glu | Asp | Cys | Asn | Ile | Cys | Ile | Trp | Gly | Ile | Pro | Glu | Gly | Gly | Leu | Thr |
| | | | 100 | | | | | 105 | | | | | 110 | | |
| Asp | Ser | Ile | Ser | Thr | Pro | Leu | Gln | Thr | Leu | Ser | Gly | His | Lys | Arg | Lys |
| | | 115 | | | | | 120 | | | | | 125 | | | |
| Val | Gly | Thr | Ile | Ser | Phe | Gly | Pro | Val | Ala | Asp | Asn | Val | Ala | Val | Thr |
| | 130 | | | | | 135 | | | | | 140 | | | | |
| Ser | Ser | Gly | Asp | Phe | Leu | Val | Lys | Thr | Trp | Asp | Val | Glu | Gln | Gly | Lys |
| 145 | | | | | 150 | | | | | 155 | | | | | 160 |
| Asn | Leu | Thr | Thr | Val | Glu | Gly | His | Ser | Asp | Met | Ile | Thr | Ser | Cys | Glu |
| | | | | 165 | | | | | 170 | | | | | 175 | |
| His | Asn | Gly | Ser | Gln | Ile | Val | Thr | Thr | Cys | Lys | Asp | Lys | Lys | Ala | Arg |
| | | | 180 | | | | | 185 | | | | | 190 | | |
| Val | Phe | Asp | Pro | Arg | Thr | Asn | Ser | Ile | Val | Asn | Glu | Val | Val | Cys | His |
| | | 195 | | | | | 200 | | | | | 205 | | | |
| Gln | Gly | Val | Lys | Asn | Ser | Arg | Ala | Ile | Phe | Ala | Lys | Asp | Lys | Val | Ile |
| | 210 | | | | | 215 | | | | | 220 | | | | |
| Thr | Val | Gly | Phe | Ser | Lys | Thr | Ser | Glu | Arg | Glu | Leu | His | Ile | Tyr | Asp |
| 225 | | | | | 230 | | | | | 235 | | | | | 240 |
| Pro | Arg | Ala | Phe | Thr | Thr | Pro | Leu | Ser | Ala | Gln | Val | Val | Asp | Ser | Ala |
| | | | | 245 | | | | | 250 | | | | | 255 | |
| Ser | Gly | Leu | Leu | Met | Pro | Phe | Tyr | Asp | Ala | Asp | Asn | Ser | Ile | Leu | Tyr |
| | | | 260 | | | | | 265 | | | | | 270 | | |
| Leu | Ala | Gly | Lys | Gly | Asp | Gly | Asn | Ile | Arg | Tyr | Tyr | Glu | Leu | Val | Asp |
| | | 275 | | | | | 280 | | | | | 285 | | | |
| Glu | Ser | Pro | Tyr | Ile | His | Phe | Leu | Ser | Glu | Phe | Lys | Ser | Ala | Thr | Pro |
| | 290 | | | | | 295 | | | | | 300 | | | | |
| Gln | Arg | Gly | Leu | Cys | Phe | Leu | Pro | Lys | Arg | Cys | Leu | Asn | Thr | Ser | Glu |
| 305 | | | | | 310 | | | | | 315 | | | | | 320 |
| Cys | Glu | Ile | Ala | Arg | Gly | Leu | Lys | Val | Thr | Pro | Phe | Thr | Val | Glu | Pro |
| | | | | 325 | | | | | 330 | | | | | 335 | |
| Ile | Ser | Phe | Arg | Val | Pro | Arg | Lys | Ser | Asp | Ile | Phe | Gln | Gly | Asp | Ile |
| | | | 340 | | | | | 345 | | | | | 350 | | |
| Tyr | Pro | Asp | Thr | Tyr | Ala | Gly | Glu | Pro | Ser | Leu | Thr | Ala | Glu | Gln | Trp |
| | | 355 | | | | | 360 | | | | | 365 | | | |
| Val | Ser | Gly | Thr | Asn | Ala | Glu | Pro | Lys | Thr | Val | Ser | Leu | Ala | Gly | Gly |
| | 370 | | | | | 375 | | | | | 380 | | | | |
| Phe | Val | Lys | Lys | Ala | Ser | Ala | Val | Glu | Phe | Lys | Pro | Val | Val | Gln | Val |
| 385 | | | | | 390 | | | | | 395 | | | | | 400 |
| Gln | Glu | Gly | Pro | Lys | Asn | Glu | Lys | Glu | Leu | Arg | Glu | Glu | Tyr | Glu | Lys |
| | | | | 405 | | | | | 410 | | | | | 415 | |
| Leu | Lys | Ile | Arg | Val | Ala | Tyr | Leu | Glu | Ser | Glu | Ile | Val | Lys | Lys | Asp |
| | | | 420 | | | | | 425 | | | | | 430 | | |
| Ala | Lys | Ile | Lys | Glu | Leu | Thr | Asn | | | | | | | | |
| | | 435 | | | | | 440 | | | | | | | | |

( 2 ) INFORMATION FOR SEQ ID NO:36:

( i ) SEQUENCE CHARACTERISTICS:

-continued ( A ) LENGTH: 445 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: Coronin (p55), Fig. 19

( x i ) SEQUENCE DESCRIPTION: SEQ ID NO:36:

| | | | | | | | | | | | | | | | |
|---|---|---|---|---|---|---|---|---|---|---|---|---|---|---|---|
| Met | Ser | Lys | Val | Val | Arg | Ser | Ser | Lys | Tyr | Arg | His | Val | Phe | Ala | Ala |
| 1 | | | | 5 | | | | | 10 | | | | | 15 | |
| Gln | Pro | Lys | Lys | Glu | Glu | Cys | Tyr | Gln | Asn | Leu | Lys | Val | Thr | Lys | Ser |
| | | | 20 | | | | | 25 | | | | | 30 | | |
| Ala | Trp | Asp | Ser | Asn | Tyr | Val | Ala | Ala | Asn | Thr | Arg | Tyr | Phe | Gly | Val |
| | | 35 | | | | | 40 | | | | | 45 | | | |
| Ile | Trp | Asp | Ala | Ala | Gly | Gly | Gly | Ser | Phe | Ala | Val | Ile | Pro | His | Glu |
| | 50 | | | | | 55 | | | | | 60 | | | | |
| Ala | Ser | Gly | Lys | Thr | Thr | Ser | Val | Pro | Leu | Phe | Asn | Gly | His | Lys | Ser |
| 65 | | | | | 70 | | | | | 75 | | | | | 80 |
| Ala | Val | Leu | Asp | Ile | Ala | Phe | His | Pro | Phe | Asn | Glu | Asn | Leu | Val | Gly |
| | | | | 85 | | | | | 90 | | | | | 95 | |
| Ser | Val | Ser | Glu | Asp | Cys | Asn | Ile | Cys | Ile | Trp | Gly | Ile | Pro | Glu | Gly |
| | | | 100 | | | | | 105 | | | | | 110 | | |
| Gly | Leu | Thr | Asp | Ser | Ile | Ser | Thr | Pro | Leu | Gln | Thr | Leu | Ser | Gly | His |
| | | 115 | | | | | 120 | | | | | 125 | | | |
| Lys | Arg | Lys | Val | Gly | Thr | Ile | Ser | Phe | Gly | Pro | Val | Ala | Asp | Asn | Val |
| | 130 | | | | | 135 | | | | | 140 | | | | |
| Ala | Val | Thr | Ser | Ser | Gly | Asp | Phe | Leu | Val | Lys | Thr | Trp | Asp | Val | Glu |
| 145 | | | | | 150 | | | | | 155 | | | | | 160 |
| Gln | Gly | Lys | Asn | Leu | Thr | Thr | Val | Glu | Gly | His | Ser | Asp | Met | Ile | Thr |
| | | | | 165 | | | | | 170 | | | | | 175 | |
| Ser | Cys | Glu | Trp | Asn | His | Asn | Gly | Ser | Gln | Ile | Val | Thr | Thr | Cys | Lys |
| | | | 180 | | | | | 185 | | | | | 190 | | |
| Asp | Lys | Lys | Ala | Arg | Val | Phe | Asp | Pro | Arg | Thr | Asn | Ser | Ile | Val | Asn |
| | | 195 | | | | | 200 | | | | | 205 | | | |
| Glu | Val | Val | Cys | His | Gln | Gly | Val | Lys | Asn | Ser | Arg | Ala | Ile | Phe | Ala |
| | 210 | | | | | 215 | | | | | 220 | | | | |
| Lys | Asp | Lys | Val | Ile | Thr | Val | Gly | Phe | Ser | Lys | Thr | Ser | Glu | Arg | Glu |
| 225 | | | | | 230 | | | | | 235 | | | | | 240 |
| Leu | His | Ile | Tyr | Asp | Pro | Arg | Ala | Phe | Thr | Thr | Pro | Leu | Ser | Ala | Gln |
| | | | | 245 | | | | | 250 | | | | | 255 | |
| Val | Val | Asp | Ser | Ala | Ser | Gly | Leu | Leu | Met | Pro | Phe | Tyr | Asp | Ala | Asp |
| | | | 260 | | | | | 265 | | | | | 270 | | |
| Asn | Ser | Ile | Leu | Tyr | Leu | Ala | Gly | Lys | Gly | Asp | Gly | Asn | Ile | Arg | Tyr |
| | | 275 | | | | | 280 | | | | | 285 | | | |
| Tyr | Glu | Leu | Val | Asp | Glu | Ser | Pro | Tyr | Ile | His | Phe | Leu | Ser | Glu | Phe |
| | 290 | | | | | 295 | | | | | 300 | | | | |
| Lys | Ser | Ala | Thr | Pro | Gln | Arg | Gly | Leu | Cys | Phe | Leu | Pro | Lys | Arg | Cys |
| 305 | | | | | 310 | | | | | 315 | | | | | 320 |
| Leu | Asn | Thr | Ser | Glu | Cys | Glu | Ile | Ala | Arg | Gly | Leu | Lys | Val | Thr | Pro |
| | | | | 325 | | | | | 330 | | | | | 335 | |
| Phe | Thr | Val | Glu | Pro | Ile | Ser | Phe | Arg | Val | Pro | Arg | Lys | Ser | Asp | Ile |
| | | | 340 | | | | | 345 | | | | | 350 | | |

-continued

Phe Gln Gly Asp Ile Tyr Pro Asp Thr Tyr Ala Gly Glu Pro Ser Leu
355 360 365

Thr Ala Glu Gln Trp Val Ser Gly Thr Asn Ala Glu Pro Lys Thr Val
370 375 380

Ser Leu Ala Gly Gly Phe Val Lys Lys Ala Ser Ala Val Glu Phe Lys
385 390 395 400

Pro Val Val Gln Val Gln Glu Gly Pro Lys Asn Glu Lys Glu Leu Arg
405 410 415

Glu Glu Tyr Glu Lys Leu Lys Ile Arg Val Ala Tyr Leu Glu Ser Glu
420 425 430

Ile Val Lys Lys Asp Ala Lys Ile Lys Glu Leu Thr Asn
435 440 445

( 2 ) INFORMATION FOR SEQ ID NO:37:

( i ) SEQUENCE CHARACTERISTICS:
( A ) LENGTH: 431 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: CSTF 50kDa, Fig. 20

( x i ) SEQUENCE DESCRIPTION: SEQ ID NO:37:

Met Tyr Arg Thr Lys Val Gly Leu Lys Asp Arg Gln Gln Leu Tyr Lys
1 5 10 15

Leu Ile Ile Ser Gln Leu Leu Tyr Asp Gly Tyr Ile Ser Ile Ala Asn
20 25 30

Gly Leu Ile Asn Glu Ile Lys Pro Gln Ser Val Cys Ala Pro Ser Glu
35 40 45

Gln Leu Leu His Leu Ile Lys Leu Gly Met Glu Asn Asp Asp Thr Ala
50 55 60

Val Gln Tyr Ala Ile Gly Arg Ser Asp Thr Val Ala Pro Gly Thr Gly
65 70 75 80

Ile Asp Leu Glu Phe Asp Ala Asp Val Gln Thr Met Ser Pro Glu Ala
85 90 95

Ser Glu Tyr Glu Thr Cys Tyr Val Thr Ser His Lys Gly Pro Cys Arg
100 105 110

Val Ala Thr Tyr Ser Arg Asp Gly Gln Leu Ile Ala Thr Gly Ser Ala
115 120 125

Asp Ala Ser Ile Lys Ile Leu Asp Thr Glu Arg Met Leu Ala Lys Ser
130 135 140

Ala Met Pro Ile Glu Val Met Met Asn Glu Thr Ala Gln Gln Asn Met
145 150 155 160

Glu Asn His Pro Val Ile Arg Thr Leu Tyr Asp His Val Asp Glu Val
165 170 175

Thr Cys Leu Ala Phe His Pro Thr Glu Gln Ile Leu Ala Ser Gly Ser
180 185 190

Arg Asp Tyr Thr Leu Lys Leu Phe Asp Tyr Ser Lys Pro Ser Ala Lys
195 200 205

Arg Ala Phe Lys Tyr Ile Gln Glu Ala Glu Met Leu Arg Ser Ile Ser
210 215 220

-continued

| | | | | | | | | | | | | | | | |
|---|---|---|---|---|---|---|---|---|---|---|---|---|---|---|---|
| Phe | His | Pro | Ser | Gly | Asp | Phe | Ile | Leu | Val | Gly | Thr | Gln | His | Pro | Thr |
| 225 | | | | | 230 | | | | | 235 | | | | | 240 |
| Leu | Arg | Leu | Tyr | Asp | Ile | Asn | Thr | Phe | Gln | Cys | Phe | Val | Ser | Cys | Asn |
| | | | | 245 | | | | | 250 | | | | | 255 | |
| Pro | Gln | Asp | Gln | His | Thr | Asp | Ala | Ile | Cys | Ser | Val | Asn | Tyr | Asn | Ser |
| | | | 260 | | | | | 265 | | | | | 270 | | |
| Ser | Ala | Asn | Met | Tyr | Val | Thr | Gly | Ser | Lys | Asp | Gly | Cys | Ile | Lys | Leu |
| | | 275 | | | | | 280 | | | | | 285 | | | |
| Trp | Asp | Gly | Val | Ser | Asn | Arg | Cys | Ile | Thr | Thr | Phe | Glu | Lys | Ala | His |
| | 290 | | | | | 295 | | | | | 300 | | | | |
| Asp | Gly | Ala | Glu | Val | Cys | Ser | Ala | Ile | Phe | Ser | Lys | Asn | Ser | Lys | Tyr |
| 305 | | | | | 310 | | | | | 315 | | | | | 320 |
| Ile | Leu | Ser | Ser | Gly | Lys | Asp | Ser | Val | Ala | Lys | Leu | Trp | Glu | Ile | Ser |
| | | | | 325 | | | | | 330 | | | | | 335 | |
| Thr | Gly | Arg | Thr | Leu | Val | Arg | Tyr | Thr | Gly | Ala | Gly | Leu | Ser | Gly | Arg |
| | | | 340 | | | | | 345 | | | | | 350 | | |
| Gln | Val | His | Arg | Thr | Gln | Ala | Val | Phe | Asn | His | Thr | Glu | Asp | Tyr | Val |
| | | 355 | | | | | 360 | | | | | 365 | | | |
| Leu | Leu | Pro | Asp | Glu | Arg | Thr | Ile | Ser | Leu | Cys | Cys | Trp | Asp | Ser | Arg |
| | 370 | | | | | 375 | | | | | 380 | | | | |
| Thr | Ala | Glu | Arg | Arg | Asn | Leu | Leu | Ser | Leu | Gly | His | Asn | Asn | Ile | Val |
| 385 | | | | | 390 | | | | | 395 | | | | | 400 |
| Arg | Cys | Ile | Val | His | Ser | Pro | Thr | Asn | Pro | Gly | Phe | Met | Thr | Cys | Ser |
| | | | | 405 | | | | | 410 | | | | | 415 | |
| Asp | Asp | Phe | Arg | Ala | Arg | Phe | Trp | Tyr | Arg | Arg | Ser | Thr | Thr | Asp | |
| | | | 420 | | | | | 425 | | | | | 430 | | |

( 2 ) INFORMATION FOR SEQ ID NO:38:

( i ) SEQUENCE CHARACTERISTICS:
( A ) LENGTH: 340 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: G-Beta 1 bovine, Fig. 21

( x i ) SEQUENCE DESCRIPTION: SEQ ID NO:38:

| | | | | | | | | | | | | | | | |
|---|---|---|---|---|---|---|---|---|---|---|---|---|---|---|---|
| Met | Ser | Glu | Leu | Asp | Gln | Leu | Arg | Gln | Glu | Ala | Glu | Gln | Leu | Lys | Asn |
| 1 | | | | 5 | | | | | 10 | | | | | 15 | |
| Gln | Ile | Arg | Asp | Ala | Arg | Lys | Ala | Cys | Ala | Asp | Ala | Thr | Leu | Ser | Gln |
| | | | 20 | | | | | 25 | | | | | 30 | | |
| Ile | Thr | Asn | Asn | Ile | Asp | Pro | Val | Gly | Arg | Ile | Gln | Met | Arg | Thr | Arg |
| | | 35 | | | | | 40 | | | | | 45 | | | |
| Arg | Thr | Leu | Arg | Gly | His | Leu | Ala | Lys | Ile | Tyr | Ala | Met | His | Trp | Gly |
| | 50 | | | | | 55 | | | | | 60 | | | | |
| Thr | Asp | Ser | Arg | Leu | Leu | Val | Ser | Ala | Ser | Gln | Asp | Gly | Lys | Leu | Ile |
| 65 | | | | | 70 | | | | | 75 | | | | | 80 |
| Ile | Trp | Asp | Ser | Tyr | Thr | Thr | Asn | Lys | Val | His | Ala | Ile | Pro | Leu | Arg |
| | | | | 85 | | | | | 90 | | | | | 95 | |
| Ser | Ser | Trp | Val | Met | Thr | Cys | Ala | Tyr | Ala | Pro | Ser | Gly | Asn | Tyr | Val |
| | | | 100 | | | | | 105 | | | | | 110 | | |
| Ala | Cys | Gly | Gly | Leu | Asp | Asn | Ile | Cys | Ser | Ile | Tyr | Asn | Leu | Lys | Thr |

-continued 115 120 125

Arg Glu Gly Asn Val Arg Val Ser Arg Glu Leu Ala Gly His Thr Gly
130 135 140

Tyr Leu Ser Cys Cys Arg Phe Leu Asp Asp Asn Gln Ile Val Thr Ser
145 150 155 160

Ser Gly Asp Thr Thr Cys Ala Leu Trp Asp Ile Glu Thr Gly Gln Gln
165 170 175

Thr Thr Thr Phe Thr Gly His Thr Gly Asp Val Met Ser Leu Ser Leu
180 185 190

Ala Pro Asp Thr Arg Leu Phe Val Ser Gly Ala Cys Asp Ala Ser Ala
195 200 205

Lys Leu Trp Asp Val Arg Glu Gly Met Cys Arg Gln Thr Phe Thr Gly
210 215 220

His Glu Ser Asp Ile Asn Ala Ile Cys Phe Phe Pro Asn Gly Asn Ala
225 230 235 240

Phe Ala Thr Gly Ser Asp Asp Ala Thr Cys Arg Leu Phe Asp Leu Arg
245 250 255

Ala Asp Gln Glu Leu Met Thr Tyr Ser His Asp Asn Ile Ile Cys Gly
260 265 270

Ile Thr Ser Val Ser Phe Ser Lys Ser Gly Arg Leu Leu Leu Ala Gly
275 280 285

Tyr Asp Asp Phe Asn Cys Asn Val Trp Asp Ala Leu Lys Ala Asp Arg
290 295 300

Ala Gly Val Leu Ala Gly His Asp Asn Arg Val Ser Cys Leu Gly Val
305 310 315 320

Thr Asp Asp Gly Met Ala Val Ala Thr Gly Ser Trp Asp Ser Phe Leu
325 330 335

Lys Ile Trp Asn
340

( 2 ) INFORMATION FOR SEQ ID NO:39:

( i ) SEQUENCE CHARACTERISTICS:
( A ) LENGTH: 326 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: G-Beta- bovine (2), Fig. 22

( x i ) SEQUENCE DESCRIPTION: SEQ ID NO:39:

Arg Asn Gln Ile Arg Asp Ala Arg Lys Ala Cys Gly Asp Ser Thr Leu
1 5 10 15

Thr Gln Ile Thr Ala Gly Leu Asp Pro Val Gly Arg Ile Gln Met Arg
20 25 30

Thr Arg Arg Thr Leu Arg Gly His Leu Ala Lys Ile Tyr Ala Met His
35 40 45

Trp Gly Thr Asp Ser Arg Leu Leu Val Ser Ala Ser Gln Asp Gly Lys
50 55 60

Leu Ile Ile Trp Asp Ser Glu Gly Asn Val Arg Tyr Thr Thr Asn Lys
65 70 75 80

Val His Ala Ile Pro Leu Arg Ser Ser Trp Val Met Thr Cys Ala Tyr
85 90 95

Ala Pro Ser Gly Asn Phe Val Ala Cys Gly Gly Leu Asp Asn Ile Cys
100 105 110

Ser Ile Tyr Ser Leu Lys Thr Arg Val Ser Arg Glu Leu Pro Gly His
115 120 125

Thr Gly Tyr Leu Ser Cys Cys Arg Phe Leu Asp Asp Asn Gln Ile Ile
130 135 140

Thr Ser Ser Gly Asp Thr Thr Cys Ala Leu Trp Asp Ile Glu Thr Gly
145 150 155 160

Gln Gln Thr Val Gly Phe Ala Gly His Ser Gly Asp Val Met Ser Leu
165 170 175

Ser Leu Ala Pro Asp Gly Arg Thr Phe Val Ser Gly Ala Cys Asp Ala
180 185 190

Ser Ile Lys Leu Trp Asp Val Arg Asp Ser Met Cys Arg Gln Thr Phe
195 200 205

Ile Gly His Glu Ser Asp Ile Asn Ala Val Ala Phe Phe Pro Asn Gly
210 215 220

Tyr Ala Phe Thr Thr Gly Ser Asp Asp Ala Thr Cys Arg Leu Phe Asp
225 230 235 240

Leu Arg Ala Asp Gln Glu Leu Leu Met Tyr Ser His Asp Asn Ile Ile
245 250 255

Cys Gly Ile Thr Ser Val Ala Phe Ser Arg Ser Gly Arg Leu Leu Leu
260 265 270

Ala Gly Tyr Asp Asp Phe Asn Cys Asn Ile Trp Asp Ala Met Lys Gly
275 280 285

Asp Arg Ala Gly Val Leu Ala Gly His Asp Asn Arg Val Ser Cys Leu
290 295 300

Gly Val Thr Asp Asp Gly Met Ala Val Ala Thr Gly Ser Trp Asp Ser
305 310 315 320

Phe Leu Lys Ile Trp Asn
325

( 2 ) INFORMATION FOR SEQ ID NO:40:

( i ) SEQUENCE CHARACTERISTICS:
( A ) LENGTH: 340 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: G- BETA DROSOPH, Fig. 23

( x i ) SEQUENCE DESCRIPTION: SEQ ID NO:40:

Met Asn Glu Leu Asp Ser Leu Arg Gln Glu Ala Glu Ser Leu Lys Asn
1 5 10 15

Ala Ile Arg Asp Ala Arg Lys Ala Ala Cys Asp Thr Ser Leu Leu Gln
20 25 30

Ala Ala Thr Ser Leu Glu Pro Ile Gly Arg Ile Gln Met Arg Thr Arg
35 40 45

Arg Thr Leu Arg Gly His Leu Ala Lys Ile Tyr Ala Met His Trp Gly
50 55 60

Asn Asp Ser Arg Asn Leu Val Ser Ala Ser Gln Asp Gly Lys Leu Ile
65 70 75 80

-continued

Val Trp Asp Ser His Thr Thr Asn Lys Val His Ala Ile Pro Leu Arg
85 90 95

Ser Ser Trp Val Met Thr Cys Ala Tyr Ala Pro Ser Gly Ser Tyr Val
100 105 110

Ala Cys Gly Gly Leu Asp Asn Met Cys Ser Ile Tyr Asn Leu Lys Thr
115 120 125

Arg Glu Gly Asn Val Arg Val Ser Arg Glu Leu Pro Gly His Gly Gly
130 135 140

Tyr Leu Ser Cys Cys Arg Phe Leu Asp Asp Asn Gln Ile Val Thr Ser
145 150 155 160

Ser Gly Asp Met Ser Cys Gly Leu Trp Asp Ile Glu Thr Gly Leu Gln
165 170 175

Val Thr Ser Phe Leu Gly His Thr Gly Asp Val Met Ala Leu Ser Leu
180 185 190

Ala Pro Gln Cys Lys Thr Phe Val Ser Gly Ala Cys Asp Ala Ser Ala
195 200 205

Lys Leu Trp Asp Ile Arg Glu Gly Val Cys Lys Gln Thr Phe Pro Gly
210 215 220

His Glu Ser Asp Ile Asn Ala Val Thr Phe Phe Pro Asn Gly Gln Ala
225 230 235 240

Phe Ala Thr Gly Ser Asp Asp Ala Thr Cys Arg Leu Phe Asp Ile Arg
245 250 255

Ala Asp Gln Glu Leu Ala Met Tyr Ser His Asp Asn Ile Ile Cys Gly
260 265 270

Ile Thr Ser Val Ala Phe Ser Lys Ser Gly Arg Leu Leu Leu Ala Gly
275 280 285

Tyr Asp Asp Phe Asn Cys Asn Val Trp Asp Thr Met Lys Ala Glu Arg
290 295 300

Ser Gly Ile Leu Ala Gly His Asp Asn Arg Val Ser Cys Leu Gly Val
305 310 315 320

Thr Glu Asn Gly Met Ala Val Ala Thr Gly Ser Trp Asp Ser Phe Leu
325 330 335

Arg Val Trp Asn
340

( 2 ) INFORMATION FOR SEQ ID NO:41:

( i ) SEQUENCE CHARACTERISTICS:
( A ) LENGTH: 317 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: G-BETA HUMAN, Fig. 24

( x i ) SEQUENCE DESCRIPTION: SEQ ID NO:41:

Met Thr Glu Gln Met Thr Leu Arg Gly Thr Leu Lys Gly His Asn Gly
1 5 10 15

Trp Val Thr Gln Ile Ala Thr Thr Pro Gln Phe Pro Asp Met Ile Leu
20 25 30

Ser Ala Ser Arg Asp Lys Thr Ile Ile Met Trp Lys Leu Thr Arg Asp
35 40 45

Glu Thr Asn Tyr Gly Ile Pro Gln Arg Ala Leu Arg Gly His Ser His

-continued 50 55 60

Phe Val Ser Asp Val Val Ile Ser Ser Asp Gly Gln Phe Ala Leu Ser
65 70 75 80

Gly Ser Trp Asp Gly Thr Leu Arg Leu Trp Asp Leu Thr Thr Gly Thr
85 90 95

Thr Thr Arg Arg Phe Val Gly His Thr Lys Asp Val Leu Ser Val Ala
100 105 110

Phe Ser Ser Asp Asn Arg Gln Ile Val Ser Gly Ser Arg Asp Lys Thr
115 120 125

Ile Lys Leu Trp Asn Thr Leu Gly Val Cys Lys Tyr Thr Val Gln Asp
130 135 140

Glu Ser His Ser Glu Trp Val Ser Cys Val Arg Phe Ser Pro Asn Ser
145 150 155 160

Ser Asn Pro Ile Ile Val Ser Cys Gly Trp Asp Lys Leu Val Lys Val
165 170 175

Trp Asn Leu Ala Asn Cys Lys Leu Lys Thr Asn His Ile Gly His Thr
180 185 190

Gly Tyr Leu Asn Thr Val Thr Val Ser Pro Asp Gly Ser Leu Cys Ala
195 200 205

Ser Gly Gly Lys Asp Gly Gln Ala Met Leu Trp Asp Leu Asn Glu Gly
210 215 220

Lys His Leu Tyr Thr Leu Asp Gly Gly Asp Ile Ile Asn Ala Leu Cys
225 230 235 240

Phe Ser Pro Asn Arg Tyr Trp Leu Cys Ala Ala Thr Gly Pro Ser Ile
245 250 255

Lys Ile Trp Asp Leu Glu Gly Lys Ile Ile Val Asp Glu Leu Lys Gln
260 265 270

Glu Val Ile Ser Thr Ser Ser Lys Ala Glu Pro Pro Gln Cys Thr Ser
275 280 285

Leu Ala Trp Ser Ala Asp Gly Gln Thr Leu Phe Ala Gly Tyr Thr Asp
290 295 300

Asn Leu Val Arg Val Trp Gln Val Thr Ile Gly Thr Arg
305 310 315

( 2 ) INFORMATION FOR SEQ ID NO:42:

( i ) SEQUENCE CHARACTERISTICS:
( A ) LENGTH: 340 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: G-Beta 2 (Human), Fig. 25

( x i ) SEQUENCE DESCRIPTION: SEQ ID NO:42:

Met Ser Glu Leu Glu Gln Leu Arg Gln Glu Ala Glu Gln Leu Arg Asn
1 5 10 15

Gln Ile Arg Asp Ala Arg Lys Ala Cys Gly Asp Ser Thr Leu Thr Gln
20 25 30

Ile Thr Ala Gly Leu Asp Pro Val Gly Arg Ile Gln Met Arg Thr Arg
35 40 45

Arg Thr Leu Arg Gly His Leu Ala Lys Ile Tyr Ala Met His Trp Gly
50 55 60

-continued

Thr Asp Ser Arg Leu Leu Val Ser Ala Ser Gln Asp Gly Lys Leu Ile
65 70 75 80

Ile Trp Asp Ser Tyr Thr Thr Asn Lys Val His Ala Ile Pro Leu Arg
85 90 95

Ser Ser Trp Val Met Thr Cys Ala Tyr Ala Pro Ser Gly Asn Phe Val
100 105 110

Ala Cys Gly Gly Leu Asp Asn Ile Cys Ser Ile Tyr Ser Leu Lys Thr
115 120 125

Arg Glu Gly Asn Val Arg Val Ser Arg Glu Leu Pro Gly His Thr Gly
130 135 140

Tyr Leu Ser Cys Cys Arg Phe Leu Asp Asp Asn Gln Ile Ile Thr Ser
145 150 155 160

Ser Gly Asp Thr Thr Cys Ala Leu Trp Asp Ile Glu Thr Gly Gln Gln
165 170 175

Thr Val Gly Phe Ala Gly His Ser Gly Asp Val Met Ser Leu Ser Leu
180 185 190

Ala Pro Asp Gly Arg Thr Phe Val Ser Gly Ala Cys Asp Ala Ser Ile
195 200 205

Lys Leu Trp Asp Val Arg Asp Ser Met Cys Arg Gln Thr Phe Ile Gly
210 215 220

His Glu Ser Asp Ile Asn Ala Val Ala Phe Phe Pro Asn Gly Tyr Ala
225 230 235 240

Phe Thr Thr Gly Ser Asp Asp Ala Thr Cys Arg Leu Phe Asp Leu Arg
245 250 255

Ala Asp Gln Glu Leu Leu Met Tyr Ser His Asp Asn Ile Ile Cys Gly
260 265 270

Ile Thr Ser Val Ala Phe Ser Arg Ser Gly Arg Leu Leu Leu Ala Gly
275 280 285

Tyr Asp Asp Phe Asn Cys Asn Ile Trp Asp Ala Met Lys Gly Asp Arg
290 295 300

Ala Gly Val Leu Ala Gly His Asp Asn Arg Val Ser Cys Leu Gly Val
305 310 315 320

Thr Asp Asp Gly Met Ala Val Ala Thr Gly Ser Trp Asp Ser Phe Leu
325 330 335

Lys Ile Trp Asn
340

( 2 ) INFORMATION FOR SEQ ID NO:43:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: G-Beta 4 (mouse), Fig. 26

( x i ) SEQUENCE DESCRIPTION: SEQ ID NO:43:

Lys Lys Asx Glu Thr Asx Val Asn Met Gly Arg Tyr Thr Pro Arg Ile
1 5 10 15

Lys His Ile Lys Arg Pro Arg Arg Thr Asp Xaa Xaa Gly
20 25

( 2 ) INFORMATION FOR SEQ ID NO:44:

( i ) SEQUENCE CHARACTERISTICS:
( A ) LENGTH: 718 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: GROUCHO PROTEIN DROSOPH, Fig. 27

( x i ) SEQUENCE DESCRIPTION: SEQ ID NO:44:

| | | | | | | | | | | | | | | | |
|---|---|---|---|---|---|---|---|---|---|---|---|---|---|---|---|
| Met | Tyr | Pro | Ser | Pro | Val | Arg | His | Pro | Ala | Ala | Gly | Gly | Pro | Pro | Pro |
| 1 | | | | 5 | | | | | 10 | | | | | 15 | |
| Gln | Gly | Pro | Ile | Lys | Phe | Thr | Ile | Ala | Asp | Thr | Leu | Glu | Arg | Ile | Lys |
| | | | 20 | | | | | 25 | | | | | 30 | | |
| Glu | Glu | Phe | Asn | Phe | Leu | Gln | Ala | His | Tyr | His | Ser | Ile | Lys | Leu | Glu |
| | | 35 | | | | | 40 | | | | | 45 | | | |
| Cys | Glu | Lys | Leu | Ser | Asn | Glu | Lys | Thr | Glu | Met | Gln | Arg | His | Tyr | Val |
| | 50 | | | | | 55 | | | | | 60 | | | | |
| Met | Tyr | Tyr | Glu | Met | Ser | Tyr | Gly | Leu | Asn | Val | Glu | Met | His | Lys | Gln |
| 65 | | | | | 70 | | | | | 75 | | | | | 80 |
| Thr | Glu | Ile | Ala | Lys | Arg | Leu | Asn | Thr | Leu | Ile | Asn | Gln | Leu | Leu | Pro |
| | | | | 85 | | | | | 90 | | | | | 95 | |
| Phe | Leu | Gln | Ala | Asp | His | Gln | Gln | Gln | Val | Leu | Gln | Ala | Val | Glu | Arg |
| | | | 100 | | | | | 105 | | | | | 110 | | |
| Ala | Lys | Gln | Val | Thr | Met | Gln | Glu | Leu | Asn | Leu | Ile | Ile | Gly | Gln | Gln |
| | | 115 | | | | | 120 | | | | | 125 | | | |
| Ile | His | Ala | Gln | Gln | Val | Pro | Gly | Gly | Pro | Pro | Gln | Pro | Met | Gly | Ala |
| | 130 | | | | | 135 | | | | | 140 | | | | |
| Leu | Asn | Pro | Phe | Gly | Ala | Leu | Gly | Ala | Thr | Met | Gly | Leu | Pro | His | Gly |
| 145 | | | | | 150 | | | | | 155 | | | | | 160 |
| Pro | Gln | Gly | Leu | Leu | Asn | Lys | Pro | Pro | Glu | His | His | Arg | Pro | Asp | Ile |
| | | | | 165 | | | | | 170 | | | | | 175 | |
| Lys | Pro | Thr | Gly | Leu | Glu | Gly | Pro | Ala | Ala | Ala | Glu | Glu | Arg | Leu | Arg |
| | | | 180 | | | | | 185 | | | | | 190 | | |
| Asn | Ser | Val | Ser | Pro | Ala | Asp | Arg | Glu | Lys | Tyr | Arg | Thr | Arg | Ser | Pro |
| | | 195 | | | | | 200 | | | | | 205 | | | |
| Leu | Asp | Ile | Glu | Asn | Asp | Ser | Lys | Arg | Arg | Lys | Asp | Glu | Lys | Leu | Gln |
| | 210 | | | | | 215 | | | | | 220 | | | | |
| Glu | Asp | Glu | Gly | Glu | Lys | Ser | Asp | Gln | Asp | Leu | Val | Val | Asp | Val | Ala |
| 225 | | | | | 230 | | | | | 235 | | | | | 240 |
| Asn | Glu | Met | Glu | Ser | His | Ser | Pro | Arg | Pro | Asn | Gly | Glu | His | Val | Ser |
| | | | | 245 | | | | | 250 | | | | | 255 | |
| Met | Glu | Val | Arg | Asp | Arg | Glu | Ser | Leu | Asn | Gly | Glu | Arg | Leu | Glu | Lys |
| | | | 260 | | | | | 265 | | | | | 270 | | |
| Pro | Ser | Ser | Ser | Gly | Ile | Lys | Gln | Glu | Arg | Pro | Pro | Ser | Arg | Ser | Gly |
| | | 275 | | | | | 280 | | | | | 285 | | | |
| Ser | Ser | Ser | Ser | Arg | Ser | Thr | Pro | Ser | Leu | Lys | Thr | Lys | Asp | Met | Glu |
| | 290 | | | | | 295 | | | | | 300 | | | | |
| Lys | Pro | Gly | Thr | Pro | Gly | Ala | Lys | Ala | Arg | Thr | Pro | Thr | Pro | Asn | Ala |
| 305 | | | | | 310 | | | | | 315 | | | | | 320 |
| Ala | Ala | Pro | Ala | Pro | Gly | Val | Asn | Pro | Lys | Gln | Met | Met | Pro | Gln | Gly |

-continued 325                 330                 335

Pro Pro Pro Ala Gly Tyr Pro Gly Ala Pro Tyr Gln Arg Pro Ala Asp
            340                 345                 350

Pro Tyr Gln Arg Pro Pro Ser Asp Pro Ala Tyr Gly Arg Pro Pro Pro
        355                 360                 365

Met Pro Tyr Asp Pro His Ala His Val Arg Thr Asn Gly Ile Pro His
    370                 375                 380

Pro Ser Ala Leu Thr Gly Gly Lys Pro Ala Tyr Ser Phe His Met Asn
385                 390                 395                 400

Gly Glu Gly Ser Leu Gln Pro Val Pro Phe Pro Pro Asp Ala Leu Val
                405                 410                 415

Gly Val Gly Ile Pro Arg His Ala Arg Gln Ile Asn Thr Leu Ser His
            420                 425                 430

Gly Glu Val Val Cys Ala Val Thr Ile Ser Asn Pro Thr Lys Tyr Val
        435                 440                 445

Tyr Thr Gly Gly Lys Gly Cys Val Lys Val Trp Asp Ile Ser Gln Pro
    450                 455                 460

Gly Asn Lys Asn Pro Val Ser Gln Leu Asp Cys Leu Gln Arg Asp Asn
465                 470                 475                 480

Tyr Ile Arg Ser Val Lys Leu Leu Pro Asp Gly Arg Thr Leu Ile Val
                485                 490                 495

Gly Gly Glu Ala Ser Asn Leu Ser Ile Trp Asp Leu Ala Ser Pro Thr
            500                 505                 510

Pro Arg Ile Lys Ala Glu Leu Thr Ser Ala Ala Pro Ala Cys Tyr Ala
        515                 520                 525

Leu Ala Ser Pro Asp Ser Lys Val Cys Phe Ser Cys Cys Ser Asp Gly
    530                 535                 540

Asn Ile Ala Val Trp Asp Leu His Asn Glu Ile Leu Val Arg Gln Phe
545                 550                 555                 560

Gln Gly His Thr Asp Gly Ala Ser Cys Ile Asp Ile Ser Pro Asp Gly
                565                 570                 575

Ser Arg Leu Trp Thr Gly Gly Leu Asp Asn Thr Val Arg Ser Trp Asp
            580                 585                 590

Leu Arg Glu Gly Arg Gln Leu Gln Gln His Asp Phe Ser Ser Gln Ile
        595                 600                 605

Phe Ser Leu Gly Tyr Cys Pro Thr Gly Asp Trp Leu Ala Val Gly Met
    610                 615                 620

Glu Asn Ser His Val Glu Val Leu His Ala Ser Lys Pro Asp Lys Tyr
625                 630                 635                 640

Gln Leu His Leu His Glu Ser Cys Val Leu Ser Leu Arg Phe Ala Ala
                645                 650                 655

Cys Gly Lys Trp Phe Val Ser Thr Gly Lys Asp Asn Leu Leu Asn Ala
            660                 665                 670

Trp Arg Thr Pro Tyr Gly Ala Ser Ile Phe Gln Ser Lys Glu Thr Ser
        675                 680                 685

Ser Val Leu Ser Cys Asp Ile Ser Thr Asp Asp Lys Tyr Ile Val Thr
    690                 695                 700

Gly Ser Gly Asp Lys Lys Ala Thr Val Tyr Glu Val Ile Tyr
705                 710                 715

( 2 ) INFORMATION FOR SEQ ID NO:45:

( i ) SEQUENCE CHARACTERISTICS:
( A ) LENGTH: 341 amino acids
( B ) TYPE: amino acid -continued ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: GTP binding protein (squid), Fig. 28

( x i ) SEQUENCE DESCRIPTION: SEQ ID NO:45:

| | | | | | | | | | | | | | | | |
|---|---|---|---|---|---|---|---|---|---|---|---|---|---|---|---|
| Met | Thr | Ser | Glu | Leu | Glu | Ala | Leu | Arg | Gln | Glu | Thr | Glu | Gln | Leu | Lys |
| 1 | | | | 5 | | | | | 10 | | | | | 15 | |
| Asn | Gln | Ile | Arg | Glu | Ala | Arg | Lys | Ala | Ala | Ala | Asp | Thr | Thr | Leu | Ala |
| | | | 20 | | | | | 25 | | | | | 30 | | |
| Met | Ala | Thr | Ala | Asn | Val | Glu | Pro | Val | Gly | Arg | Ile | Gln | Met | Arg | Thr |
| | | 35 | | | | | 40 | | | | | 45 | | | |
| Arg | Arg | Thr | Leu | Arg | Gly | His | Leu | Ala | Lys | Ile | Tyr | Ala | Met | His | Trp |
| | 50 | | | | | 55 | | | | | 60 | | | | |
| Ala | Ser | Asp | Ser | Arg | Asn | Leu | Val | Ser | Ala | Ser | Gln | Asp | Gly | Lys | Leu |
| 65 | | | | | 70 | | | | | 75 | | | | | 80 |
| Ile | Val | Trp | Asp | Gly | Tyr | Thr | Thr | Asn | Lys | Val | His | Ala | Ile | Pro | Leu |
| | | | | 85 | | | | | 90 | | | | | 95 | |
| Arg | Ser | Ser | Trp | Val | Met | Thr | Cys | Ala | Tyr | Ala | Pro | Ser | Gly | Asn | Tyr |
| | | | 100 | | | | | 105 | | | | | 110 | | |
| Val | Ala | Cys | Gly | Gly | Leu | Asp | Asn | Ile | Cys | Ser | Ile | Tyr | Ser | Leu | Lys |
| | | 115 | | | | | 120 | | | | | 125 | | | |
| Thr | Arg | Glu | Gly | Asn | Val | Arg | Val | Ser | Arg | Glu | Leu | Pro | Gly | His | Thr |
| | 130 | | | | | 135 | | | | | 140 | | | | |
| Gly | Tyr | Leu | Ser | Cys | Cys | Arg | Phe | Ile | Asp | Asp | Asn | Gln | Ile | Val | Thr |
| 145 | | | | | 150 | | | | | 155 | | | | | 160 |
| Ser | Ser | Gly | Asp | Met | Thr | Cys | Ala | Leu | Trp | Asn | Ile | Glu | Thr | Gly | Asn |
| | | | | 165 | | | | | 170 | | | | | 175 | |
| Gln | Ile | Thr | Ser | Phe | Gly | Gly | His | Thr | Gly | Asp | Val | Met | Ser | Leu | Ser |
| | | | 180 | | | | | 185 | | | | | 190 | | |
| Leu | Ala | Pro | Asp | Met | Arg | Thr | Phe | Val | Ser | Gly | Ala | Cys | Asp | Ala | Ser |
| | | 195 | | | | | 200 | | | | | 205 | | | |
| Ala | Lys | Leu | Phe | Asp | Ile | Arg | Asp | Gly | Ile | Cys | Lys | Gln | Thr | Phe | Thr |
| | 210 | | | | | 215 | | | | | 220 | | | | |
| Gly | His | Glu | Ser | Asp | Ile | Asn | Ala | Ile | Thr | Tyr | Phe | Pro | Asn | Gly | Phe |
| 225 | | | | | 230 | | | | | 235 | | | | | 240 |
| Ala | Phe | Ala | Thr | Gly | Ser | Asp | Asp | Ala | Thr | Cys | Arg | Leu | Phe | Asp | Ile |
| | | | | 245 | | | | | 250 | | | | | 255 | |
| Arg | Ala | Asp | Gln | Glu | Ile | Gly | Met | Tyr | Ser | His | Asp | Asn | Ile | Ile | Cys |
| | | | 260 | | | | | 265 | | | | | 270 | | |
| Gly | Ile | Thr | Ser | Val | Ala | Phe | Ser | Lys | Ser | Gly | Arg | Leu | Leu | Leu | Gly |
| | | 275 | | | | | 280 | | | | | 285 | | | |
| Gly | Tyr | Asp | Asp | Phe | Asn | Cys | Asn | Val | Trp | Asp | Val | Leu | Lys | Gln | Glu |
| | 290 | | | | | 295 | | | | | 300 | | | | |
| Arg | Ala | Gly | Val | Leu | Ala | Gly | His | Asp | Asn | Arg | Val | Ser | Cys | Leu | Gly |
| 305 | | | | | 310 | | | | | 315 | | | | | 320 |
| Val | Thr | Glu | Asp | Gly | Met | Ala | Val | Ala | Thr | Gly | Ser | Trp | Asp | Ser | Phe |
| | | | | 325 | | | | | 330 | | | | | 335 | |
| Leu | Lys | Ile | Trp | Asn | | | | | | | | | | | |
| | | | 340 | | | | | | | | | | | | |

( 2 ) INFORMATION FOR SEQ ID NO:46:

( i ) SEQUENCE CHARACTERISTICS:
( A ) LENGTH: 410 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: IEF SSP 9306, Fig. 29

( x i ) SEQUENCE DESCRIPTION: SEQ ID NO:46:

| | | | | | | | | | | | | | | | |
|---|---|---|---|---|---|---|---|---|---|---|---|---|---|---|---|
| Met | Ala | Asp | Lys | Glu | Ala | Ala | Phe | Asp | Asp | Ala | Val | Glu | Glu | Arg | Val |
| 1 | | | | 5 | | | | | 10 | | | | | 15 | |
| Ile | Asn | Glu | Glu | Tyr | Lys | Ile | Trp | Lys | Lys | Asn | Thr | Pro | Phe | Leu | Tyr |
| | | | 20 | | | | | 25 | | | | | 30 | | |
| Asp | Leu | Val | Met | Thr | His | Ala | Leu | Glu | Trp | Pro | Ser | Leu | Thr | Ala | Gln |
| | | 35 | | | | | 40 | | | | | 45 | | | |
| Trp | Leu | Pro | Asp | Val | Thr | Arg | Pro | Glu | Gly | Lys | Asp | Phe | Ser | Ile | His |
| | 50 | | | | | 55 | | | | | 60 | | | | |
| Arg | Leu | Val | Leu | Gly | Thr | His | Thr | Ser | Asp | Glu | Gln | Asn | His | Leu | Val |
| 65 | | | | | 70 | | | | | 75 | | | | | 80 |
| Ile | Ala | Ser | Val | Gln | Leu | Pro | Asn | Asp | Asp | Ala | Gln | Phe | Asp | Ala | Ser |
| | | | | 85 | | | | | 90 | | | | | 95 | |
| His | Tyr | Asp | Ser | Glu | Lys | Gly | Glu | Phe | Gly | Gly | Phe | Gly | Ser | Val | Ser |
| | | | 100 | | | | | 105 | | | | | 110 | | |
| Gly | Lys | Ile | Glu | Ile | Glu | Ile | Lys | Ile | Asn | His | Glu | Gly | Glu | Val | Asn |
| | | 115 | | | | | 120 | | | | | 125 | | | |
| Arg | Ala | Arg | Tyr | Met | Pro | Gln | Asn | Pro | Cys | Ile | Ile | Ala | Thr | Lys | Thr |
| | 130 | | | | | 135 | | | | | 140 | | | | |
| Pro | Ser | Ser | Asp | Val | Leu | Val | Phe | Asp | Tyr | Thr | Lys | His | Pro | Ser | Lys |
| 145 | | | | | 150 | | | | | 155 | | | | | 160 |
| Pro | Asp | Pro | Ser | Gly | Glu | Cys | Asn | Pro | Asp | Leu | Arg | Leu | Arg | Gly | His |
| | | | | 165 | | | | | 170 | | | | | 175 | |
| Gln | Lys | Glu | Gly | Tyr | Gly | Leu | Ser | Trp | Asn | Pro | Asn | Leu | Ser | Gly | His |
| | | | 180 | | | | | 185 | | | | | 190 | | |
| Leu | Leu | Ser | Ala | Ser | Asp | Asp | His | Thr | Ile | Cys | Leu | Trp | Asp | Ile | Ser |
| | | 195 | | | | | 200 | | | | | 205 | | | |
| Ala | Val | Pro | Lys | Glu | Gly | Lys | Val | Val | Asp | Ala | Lys | Thr | Ile | Phe | Thr |
| | 210 | | | | | 215 | | | | | 220 | | | | |
| Gly | His | Thr | Ala | Val | Val | Glu | Asp | Val | Ser | Trp | His | Leu | Leu | His | Glu |
| 225 | | | | | 230 | | | | | 235 | | | | | 240 |
| Ser | Leu | Phe | Gly | Ser | Val | Ala | Asp | Asp | Gln | Lys | Leu | Met | Ile | Trp | Asp |
| | | | | 245 | | | | | 250 | | | | | 255 | |
| Thr | Arg | Ser | Asn | Asn | Thr | Ser | Lys | Pro | Ser | His | Ser | Val | Asp | Ala | His |
| | | | 260 | | | | | 265 | | | | | 270 | | |
| Thr | Ala | Glu | Val | Asn | Cys | Leu | Ser | Phe | Asn | Pro | Tyr | Ser | Glu | Phe | Ile |
| | | 275 | | | | | 280 | | | | | 285 | | | |
| Leu | Ala | Thr | Gly | Ser | Ala | Asp | Lys | Thr | Val | Ala | Leu | Trp | Asp | Leu | Arg |
| | 290 | | | | | 295 | | | | | 300 | | | | |
| Asn | Leu | Lys | Leu | Lys | Leu | His | Ser | Phe | Glu | Ser | His | Lys | Asp | Glu | Ile |
| 305 | | | | | 310 | | | | | 315 | | | | | 320 |
| Phe | Gln | Val | Gln | Trp | Ser | Pro | His | Asn | Glu | Thr | Ile | Leu | Ala | Ser | Ser |
| | | | | 325 | | | | | 330 | | | | | 335 | |

Gly Thr Asp Arg Arg Leu Asn Val Trp Asp Leu Ser Lys Ile Gly Glu
340 345 350

Glu Gln Ser Pro Glu Asp Ala Glu Asp Gly Pro Pro Glu Leu Leu Phe
355 360 365

Ile His Gly Gly His Thr Ala Lys Ile Ser Asp Phe Ser Trp Asn Pro
370 375 380

Asn Glu Pro Trp Val Ile Cys Ser Val Ser Glu Asp Asn Ile Met Gln
385 390 395 400

Val Trp Gln Met Glu Leu Val Leu Asp His
405 410

( 2 ) INFORMATION FOR SEQ ID NO:47:

( i ) SEQUENCE CHARACTERISTICS:
( A ) LENGTH: 317 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: HUMAN 12.3, Fig. 30

( x i ) SEQUENCE DESCRIPTION: SEQ ID NO:47:

Met Thr Glu Gln Met Thr Leu Arg Gly Thr Leu Lys Gly His Asn Gly
1 5 10 15

Trp Val Thr Gln Ile Ala Thr Thr Pro Gln Phe Pro Asp Met Ile Leu
20 25 30

Ser Ala Ser Arg Asp Lys Thr Ile Ile Met Trp Lys Leu Thr Arg Asp
35 40 45

Glu Thr Asn Tyr Gly Ile Pro Gln Arg Ala Leu Arg Gly His Ser His
50 55 60

Phe Val Ser Asp Val Val Ile Ser Ser Asp Gly Gln Phe Ala Leu Ser
65 70 75 80

Gly Ser Trp Asp Gly Thr Leu Arg Leu Trp Asp Leu Thr Thr Gly Thr
85 90 95

Thr Thr Arg Arg Phe Val Gly His Thr Lys Asp Val Leu Ser Val Ala
100 105 110

Phe Ser Ser Asp Asn Arg Gln Ile Val Ser Gly Ser Arg Asp Lys Thr
115 120 125

Ile Lys Leu Trp Asn Thr Leu Gly Val Cys Lys Tyr Thr Val Gln Asp
130 135 140

Glu Ser His Ser Glu Trp Val Ser Cys Val Arg Phe Ser Pro Asn Ser
145 150 155 160

Ser Asn Pro Ile Ile Val Ser Cys Gly Trp Asp Lys Leu Val Lys Val
165 170 175

Trp Asn Leu Ala Asn Cys Lys Leu Lys Thr Asn His Ile Gly His Thr
180 185 190

Gly Tyr Leu Asn Thr Val Thr Val Ser Pro Asp Gly Ser Leu Cys Ala
195 200 205

Ser Gly Gly Lys Asp Gly Gln Ala Met Leu Trp Asp Leu Asn Glu Gly
210 215 220

Lys His Leu Tyr Thr Leu Asp Gly Gly Asp Ile Ile Asn Ala Leu Cys
225 230 235 240

-continued

Phe Ser Pro Asn Arg Tyr Trp Leu Cys Ala Ala Thr Gly Pro Ser Ile
245 250 255

Lys Ile Trp Asp Leu Glu Gly Lys Ile Ile Val Asp Glu Leu Lys Gln
260 265 270

Glu Val Ile Ser Thr Ser Ser Lys Ala Glu Pro Pro Gln Cys Thr Ser
275 280 285

Leu Ala Trp Ser Ala Asp Gly Gln Thr Leu Phe Ala Gly Tyr Thr Asp
290 295 300

Asn Leu Val Arg Val Trp Gln Val Thr Ile Gly Thr Arg
305 310 315

( 2 ) INFORMATION FOR SEQ ID NO:48:

( i ) SEQUENCE CHARACTERISTICS:
( A ) LENGTH: 425 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: IEF -7442 - human, Fig. 31

( x i ) SEQUENCE DESCRIPTION: SEQ ID NO:48:

Met Ala Ser Lys Glu Met Phe Glu Asp Thr Val Glu Glu Arg Val Ile
1 5 10 15

Asn Glu Glu Tyr Lys Ile Trp Lys Lys Asn Thr Pro Phe Leu Tyr Asp
20 25 30

Leu Val Met Thr His Ala Leu Gln Trp Pro Ser Leu Thr Val Gln Trp
35 40 45

Leu Pro Glu Val Thr Lys Pro Glu Gly Lys Asp Tyr Ala Leu His Trp
50 55 60

Leu Val Leu Gly Thr His Thr Ser Asp Glu Gln Asn His Leu Val Val
65 70 75 80

Ala Arg Val His Ile Pro Asn Asp Asp Ala Gln Phe Asp Ala Ser His
85 90 95

Cys Asp Ser Asp Lys Gly Glu Phe Gly Gly Phe Gly Ser Val Thr Gly
100 105 110

Lys Ile Glu Cys Glu Ile Lys Ile Asn His Glu Gly Glu Val Asn Arg
115 120 125

Ala Arg Tyr Met Pro Gln Asn Pro His Ile Ile Ala Thr Lys Thr Pro
130 135 140

Ser Ser Asp Val Leu Val Phe Asp Tyr Thr Lys His Pro Ala Lys Pro
145 150 155 160

Asp Pro Ser Gly Glu Cys Asn Pro Asp Leu Arg Leu Arg Gly His Gln
165 170 175

Lys Glu Gly Tyr Gly Leu Ser Trp Asn Ser Asn Leu Ser Gly His Leu
180 185 190

Leu Ser Ala Ser Asp Asp His Thr Val Cys Leu Trp Asp Ile Asn Ala
195 200 205

Gly Pro Lys Glu Gly Lys Ile Val Asp Ala Lys Ala Ile Phe Thr Gly
210 215 220

His Ser Ala Val Val Glu Asp Val Ala Trp His Leu Leu His Glu Ser
225 230 235 240

Leu Phe Gly Ser Val Ala Asp Asp Gln Lys Leu Met Ile Trp Asp Thr

-continued 245 250 255

Arg Ser Asn Thr Thr Ser Lys Pro Ser His Leu Val Asp Ala His Thr
260 265 270

Ala Glu Val Asn Cys Leu Ser Phe Asn Pro Tyr Ser Glu Phe Ile Leu
275 280 285

Ala Thr Gly Ser Ala Asp Lys Thr Val Ala Leu Trp Asp Leu Arg Asn
290 295 300

Leu Lys Leu Lys Leu His Thr Phe Glu Ser His Lys Asp Glu Ile Phe
305 310 315 320

Gln Val His Trp Ser Pro His Asn Glu Thr Ile Leu Ala Ser Ser Gly
325 330 335

Thr Asp Arg Arg Leu Asn Val Trp Asp Leu Ser Lys Ile Gly Glu Glu
340 345 350

Gln Ser Ala Glu Asp Ala Glu Asp Gly Pro Pro Glu Leu Leu Phe Ile
355 360 365

His Gly Gly His Thr Ala Lys Ile Ser Asp Phe Ser Trp Asn Pro Asn
370 375 380

Glu Pro Trp Val Ile Cys Ser Val Ser Glu Asp Asn Ile Met Gln Ile
385 390 395 400

Trp Gln Met Ala Glu Asn Ile Tyr Asn Asp Glu Glu Ser Asp Val Thr
405 410 415

Thr Ser Glu Leu Glu Gly Gln Gly Ser
420 425

( 2 ) INFORMATION FOR SEQ ID NO:49:

( i ) SEQUENCE CHARACTERISTICS:
( A ) LENGTH: 605 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: Insulin-like growth factor binding protein complex, Fig. 32

( x i ) SEQUENCE DESCRIPTION: SEQ ID NO:49:

Met Ala Leu Arg Lys Gly Gly Leu Ala Leu Ala Leu Leu Leu Leu Ser
1 5 10 15

Trp Val Ala Leu Gly Pro Arg Ser Leu Glu Gly Ala Asp Pro Gly Thr
20 25 30

Pro Gly Glu Ala Glu Gly Pro Ala Cys Pro Ala Ala Cys Val Cys Ser
35 40 45

Tyr Asp Asp Asp Ala Asp Glu Leu Ser Val Phe Cys Ser Ser Arg Asn
50 55 60

Leu Thr Arg Leu Pro Asp Gly Val Pro Gly Gly Thr Gln Ala Leu Trp
65 70 75 80

Leu Asp Gly Asn Asn Leu Ser Ser Val Pro Pro Ala Ala Phe Gln Asn
85 90 95

Leu Ser Ser Leu Gly Phe Leu Asn Leu Gln Gly Gly Gln Leu Gly Ser
100 105 110

Leu Glu Pro Gln Ala Leu Leu Gly Leu Glu Asn Leu Cys His Leu His
115 120 125

Leu Glu Arg Asn Gln Leu Arg Ser Leu Ala Leu Gly Thr Phe Ala His 130 135 140

Thr Pro Ala Leu Ala Ser Leu Gly Leu Ser Asn Asn Arg Leu Ser Arg
145 150 155 160

Leu Glu Asp Gly Leu Phe Glu Gly Leu Gly Ser Leu Trp Asp Leu Asn
165 170 175

Leu Gly Trp Asn Ser Leu Ala Val Leu Pro Asp Ala Ala Phe Arg Gly
180 185 190

Leu Gly Ser Leu Arg Glu Leu Val Leu Ala Gly Asn Arg Leu Ala Tyr
195 200 205

Leu Gln Pro Ala Leu Phe Ser Gly Leu Ala Glu Leu Arg Glu Leu Asp
210 215 220

Leu Ser Arg Asn Ala Leu Arg Ala Ile Lys Ala Asn Val Phe Val Gln
225 230 235 240

Leu Pro Arg Leu Gln Lys Leu Tyr Leu Asp Arg Asn Leu Ile Ala Ala
245 250 255

Val Ala Pro Gly Ala Phe Leu Gly Leu Lys Ala Leu Arg Trp Leu Asp
260 265 270

Leu Ser His Asn Arg Val Ala Gly Leu Leu Glu Asp Thr Phe Pro Gly
275 280 285

Leu Leu Gly Leu Arg Val Leu Arg Leu Ser His Asn Ala Ile Ala Ser
290 295 300

Leu Arg Pro Arg Thr Phe Lys Asp Leu His Phe Leu Glu Glu Leu Gln
305 310 315 320

Leu Gly His Asn Arg Ile Arg Gln Leu Ala Glu Arg Ser Phe Glu Gly
325 330 335

Leu Gly Gln Leu Glu Val Leu Thr Leu Asp His Asn Gln Leu Gln Glu
340 345 350

Val Lys Ala Gly Ala Phe Leu Gly Leu Thr Asn Val Ala Val Met Asn
355 360 365

Leu Ser Gly Asn Cys Leu Arg Asn Leu Pro Glu Gln Val Phe Arg Gly
370 375 380

Leu Gly Lys Leu His Ser Leu His Leu Glu Gly Ser Cys Leu Gly Arg
385 390 395 400

Ile Arg Pro His Thr Phe Thr Gly Leu Ser Gly Leu Arg Arg Leu Phe
405 410 415

Leu Lys Asp Asn Gly Leu Val Gly Ile Glu Glu Gln Ser Leu Trp Gly
420 425 430

Leu Ala Glu Leu Leu Glu Leu Asp Leu Thr Ser Asn Gln Leu Thr His
435 440 445

Leu Pro His Arg Leu Phe Gln Gly Leu Gly Lys Leu Glu Tyr Leu Leu
450 455 460

Leu Ser Arg Asn Arg Leu Ala Glu Leu Pro Ala Asp Ala Leu Gly Pro
465 470 475 480

Leu Gln Arg Ala Phe Trp Leu Asp Val Ser His Asn Arg Leu Glu Ala
485 490 495

Leu Pro Asn Ser Leu Leu Ala Pro Leu Gly Arg Leu Arg Tyr Leu Ser
500 505 510

Leu Arg Asn Asn Ser Leu Arg Thr Phe Thr Pro Gln Pro Pro Gly Leu
515 520 525

Glu Arg Leu Trp Leu Glu Gly Asn Pro Trp Asp Cys Gly Cys Pro Leu
530 535 540

Lys Ala Leu Arg Asp Phe Ala Leu Gln Asn Pro Ser Ala Val Pro Arg
545 550 555 560

Phe Val Gln Ala Ile Cys Glu Gly Asp Asp Cys Gln Pro Pro Ala Tyr
565 570 575

Thr Tyr Asn Asn Ile Thr Cys Ala Ser Pro Pro Glu Val Val Gly Leu
580 585 590

Asp Leu Arg Asp Leu Ser Glu Ala His Phe Ala Pro Cys
595 600 605

( 2 ) INFORMATION FOR SEQ ID NO:50:

( i ) SEQUENCE CHARACTERISTICS:
( A ) LENGTH: 603 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: Insulin-like growth factor bind. pro. complex- rat, Fig. 33

( x i ) SEQUENCE DESCRIPTION: SEQ ID NO:50:

Met Ala Leu Arg Thr Gly Gly Pro Ala Leu Val Val Leu Leu Ala Phe
1 5 10 15

Trp Val Ala Leu Gly Pro Cys His Leu Gln Gly Thr Asp Pro Gly Ala
20 25 30

Ser Ala Asp Ala Glu Gly Pro Gln Cys Pro Val Ala Cys Thr Cys Ser
35 40 45

His Asp Asp Tyr Thr Asp Glu Leu Ser Val Phe Cys Ser Ser Lys Asn
50 55 60

Leu Thr His Leu Pro Asp Asp Ile Pro Val Ser Thr Arg Ala Leu Trp
65 70 75 80

Leu Asp Gly Asn Asn Leu Ser Ser Ile Pro Ser Ala Ala Phe Gln Asn
85 90 95

Leu Ser Ser Leu Asp Phe Leu Asn Leu Gln Gly Ser Trp Leu Arg Ser
100 105 110

Leu Glu Pro Gln Ala Leu Leu Gly Leu Gln Asn Leu Tyr Tyr Leu His
115 120 125

Leu Glu Arg Asn Arg Leu Arg Asn Leu Ala Val Gly Leu Phe Thr His
130 135 140

Thr Pro Ser Leu Ala Ser Leu Ser Leu Ser Ser Asn Leu Leu Gly Arg
145 150 155 160

Leu Glu Glu Gly Leu Phe Gln Gly Leu Ser His Leu Trp Asp Leu Asn
165 170 175

Leu Gly Trp Asn Ser Leu Val Val Leu Pro Asp Thr Val Phe Gln Gly
180 185 190

Leu Gly Asn Leu His Glu Leu Val Leu Ala Gly Asn Lys Leu Thr Tyr
195 200 205

Leu Gln Pro Ala Leu Phe Cys Gly Leu Gly Glu Leu Arg Glu Leu Asp
210 215 220

Leu Ser Arg Asn Ala Leu Arg Ser Val Lys Ala Asn Val Phe Val His
225 230 235 240

Leu Pro Arg Leu Gln Lys Leu Tyr Leu Asp Arg Asn Leu Ile Thr Ala
245 250 255

Val Ala Pro Gly Ala Phe Leu Gly Met Lys Ala Leu Arg Trp Leu Asp
260 265 270

-continued

| | | | | | | | | | | | | | | | |
|---|---|---|---|---|---|---|---|---|---|---|---|---|---|---|---|
| Leu | Ser | His | Asn | Arg | Val | Ala | Gly | Leu | Met | Glu | Asp | Thr | Phe | Pro | Gly |
| | | 275 | | | | | 280 | | | | | 285 | | | |
| Leu | Leu | Gly | Leu | His | Val | Leu | Arg | Leu | Ala | His | Asn | Ala | Ile | Ala | Ser |
| | 290 | | | | | 295 | | | | | 300 | | | | |
| Leu | Arg | Pro | Arg | Thr | Phe | Lys | Asp | Leu | His | Phe | Leu | Glu | Glu | Leu | Gln |
| 305 | | | | | 310 | | | | | 315 | | | | | 320 |
| Leu | Gly | His | Asn | Arg | Ile | Arg | Gln | Leu | Gly | Glu | Arg | Thr | Phe | Glu | Gly |
| | | | | 325 | | | | | 330 | | | | | 335 | |
| Leu | Gly | Gln | Leu | Glu | Val | Leu | Thr | Leu | Asn | Asp | Asn | Gln | Ile | Thr | Glu |
| | | | 340 | | | | | 345 | | | | | 350 | | |
| Val | Arg | Val | Gly | Ala | Phe | Ser | Gly | Leu | Phe | Asn | Val | Ala | Val | Met | Asn |
| | | 355 | | | | | 360 | | | | | 365 | | | |
| Leu | Ser | Gly | Asn | Cys | Leu | Arg | Ser | Leu | Pro | Glu | Arg | Val | Phe | Gln | Gly |
| | 370 | | | | | 375 | | | | | 380 | | | | |
| Leu | Asp | Lys | Leu | His | Ser | Leu | His | Leu | Glu | His | Ser | Cys | Leu | Gly | His |
| 385 | | | | | 390 | | | | | 395 | | | | | 400 |
| Val | Arg | Leu | His | Thr | Phe | Ala | Gly | Leu | Ser | Gly | Leu | Arg | Arg | Leu | Phe |
| | | | | 405 | | | | | 410 | | | | | 415 | |
| Leu | Arg | Asp | Asn | Ser | Ile | Ser | Ser | Ile | Glu | Glu | Gln | Ser | Leu | Ala | Gly |
| | | | 420 | | | | | 425 | | | | | 430 | | |
| Leu | Ser | Glu | Leu | Leu | Glu | Leu | Asp | Leu | Thr | Thr | Asn | Arg | Leu | Thr | His |
| | | 435 | | | | | 440 | | | | | 445 | | | |
| Leu | Pro | Arg | Gln | Leu | Phe | Gln | Gly | Leu | Gly | His | Leu | Glu | Tyr | Leu | Leu |
| | 450 | | | | | 455 | | | | | 460 | | | | |
| Leu | Ser | Tyr | Asn | Gln | Leu | Thr | Thr | Leu | Ser | Ala | Glu | Val | Leu | Gly | Pro |
| 465 | | | | | 470 | | | | | 475 | | | | | 480 |
| Leu | Gln | Arg | Ala | Phe | Trp | Leu | Asp | Ile | Ser | His | Asn | His | Leu | Glu | Thr |
| | | | | 485 | | | | | 490 | | | | | 495 | |
| Leu | Ala | Glu | Gly | Leu | Phe | Ser | Ser | Leu | Gly | Arg | Val | Arg | Tyr | Leu | Ser |
| | | | 500 | | | | | 505 | | | | | 510 | | |
| Leu | Arg | Asn | Asn | Ser | Leu | Gln | Thr | Phe | Ser | Pro | Gln | Pro | Gly | Leu | Glu |
| | | 515 | | | | | 520 | | | | | 525 | | | |
| Arg | Leu | Trp | Leu | Asp | Ala | Asn | Pro | Trp | Asp | Cys | Ser | Cys | Pro | Leu | Lys |
| | 530 | | | | | 535 | | | | | 540 | | | | |
| Ala | Leu | Arg | Asp | Phe | Ala | Leu | Gln | Asn | Pro | Gly | Val | Val | Pro | Arg | Phe |
| 545 | | | | | 550 | | | | | 555 | | | | | 560 |
| Val | Gln | Thr | Val | Cys | Glu | Gly | Asp | Asp | Cys | Gln | Pro | Val | Tyr | Thr | Tyr |
| | | | | 565 | | | | | 570 | | | | | 575 | |
| Asn | Asn | Ile | Thr | Cys | Ala | Gly | Pro | Ala | Asn | Val | Ser | Gly | Leu | Asp | Leu |
| | | | 580 | | | | | 585 | | | | | 590 | | |
| Arg | Asp | Val | Ser | Glu | Thr | His | Phe | Val | His | Cys | | | | | |
| | | 595 | | | | | 600 | | | | | | | | |

( 2 ) INFORMATION FOR SEQ ID NO:51:

( i ) SEQUENCE CHARACTERISTICS:
( A ) LENGTH: 409 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: LIS1 (human), Fig. 34

-continued ( x i ) SEQUENCE DESCRIPTION: SEQ ID NO:51:

Met Val Leu Ser Gln Arg Gln Arg Asp Glu Leu Asn Arg Ala Ile Ala
1 5 10 15

Asp Tyr Leu Arg Ser Asn Gly Tyr Glu Glu Ala Tyr Ser Val Phe Lys
20 25 30

Lys Glu Ala Glu Leu Asp Val Asn Glu Glu Leu Asp Lys Lys Tyr Ala
35 40 45

Gly Leu Leu Glu Lys Lys Trp Thr Ser Val Ile Arg Leu Gln Lys Lys
50 55 60

Val Met Glu Leu Glu Ser Lys Leu Asn Glu Ala Lys Glu Glu Phe Thr
65 70 75 80

Ser Gly Gly Pro Leu Gly Gln Lys Arg Asp Pro Lys Glu Trp Ile Pro
85 90 95

Arg Pro Pro Glu Lys Tyr Ala Leu Ser Gly His Arg Ser Pro Val Thr
100 105 110

Arg Val Ile Phe His Pro Val Phe Ser Val Met Val Ser Ala Ser Glu
115 120 125

Asp Ala Thr Ile Lys Val Trp Asp Tyr Glu Thr Gly Asp Phe Glu Arg
130 135 140

Thr Leu Lys Gly His Thr Asp Ser Val Gln Asp Ile Ser Phe Asp His
145 150 155 160

Ser Gly Lys Leu Leu Ala Ser Cys Ser Ala Asp Met Thr Ile Lys Leu
165 170 175

Trp Asp Phe Gln Gly Phe Glu Cys Ile Arg Thr Met His Gly His Asp
180 185 190

His Asn Val Ser Ser Val Ala Ile Met Pro Asn Gly Asp His Ile Val
195 200 205

Ser Ala Ser Arg Asp Lys Thr Ile Lys Met Trp Glu Val Gln Thr Gly
210 215 220

Tyr Cys Val Lys Thr Phe Thr Gly His Arg Glu Trp Val Arg Met Val
225 230 235 240

Arg Pro Asn Gln Asp Gly Thr Leu Ile Ala Ser Cys Ser Asn Asp Gln
245 250 255

Thr Val Arg Val Trp Val Val Ala Thr Lys Glu Cys Lys Ala Glu Leu
260 265 270

Arg Glu His Glu His Val Val Glu Cys Ile Ser Trp Ala Pro Glu Ser
275 280 285

Ser Tyr Ser Ser Ile Ser Glu Ala Thr Gly Ser Glu Thr Lys Lys Ser
290 295 300

Gly Lys Pro Gly Pro Phe Leu Leu Ser Gly Ser Arg Asp Lys Thr Lys
305 310 315 320

Met Trp Asp Val Ser Thr Gly Met Cys Leu Met Thr Leu Val Gly His
325 330 335

Asp Asn Trp Val Arg Gly Val Leu Phe His Ser Gly Gly Lys Phe Ile
340 345 350

Leu Ser Cys Ala Asp Asp Lys Thr Leu Arg Val Trp Asp Tyr Lys Asn
355 360 365

Lys Arg Cys Met Lys Thr Leu Asn Ala His Glu His Phe Val Thr Ser
370 375 380

Leu Asp Phe His Lys Thr Ala Pro Tyr Val Val Thr Gly Ser Val Asp
385 390 395 400

Gln Thr Val Lys Val Trp Glu Cys Arg
405

( 2 ) INFORMATION FOR SEQ ID NO:52:

( i ) SEQUENCE CHARACTERISTICS:
( A ) LENGTH: 422 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: MD6, Fig. 35

( x i ) SEQUENCE DESCRIPTION: SEQ ID NO:52:

Met Glu Arg Lys Asp Phe Glu Thr Trp Leu Asp Asn Ile Ser Val Thr
1 5 10 15

Phe Leu Ser Leu Met Asp Leu Gln Lys Asn Glu Thr Leu Asp His Leu
20 25 30

Ile Ser Leu Ser Gly Ala Val Gln Leu Arg His Leu Ser Asn Asn Leu
35 40 45

Glu Thr Leu Leu Lys Arg Asp Phe Leu Lys Leu Leu Pro Leu Glu Leu
50 55 60

Ser Phe Tyr Leu Leu Lys Trp Leu Asp Pro Gln Thr Leu Leu Thr Cys
65 70 75 80

Cys Leu Val Ser Lys Gln Arg Asn Lys Val Ile Ser Ala Cys Thr Glu
85 90 95

Val Trp Gln Thr Ala Cys Lys Asn Leu Gly Trp Gln Ile Asp Asp Ser
100 105 110

Val Gln Asp Ser Leu His Trp Lys Lys Val Tyr Leu Lys Ala Ile Leu
115 120 125

Arg Met Lys Gln Leu Glu Asp His Glu Ala Phe Glu Thr Ser Ser Leu
130 135 140

Ile Gly His Ser Ala Arg Val Tyr Ala Leu Tyr Tyr Lys Asp Gly Leu
145 150 155 160

Leu Cys Thr Gly Ser Asp Asp Leu Ser Ala Lys Leu Trp Asp Val Ser
165 170 175

Thr Gly Gln Cys Val Tyr Gly Ile Gln Thr His Thr Cys Ala Ala Val
180 185 190

Lys Phe Asp Glu Gln Lys Leu Val Thr Gly Ser Phe Asp Asn Thr Val
195 200 205

Ala Cys Trp Glu Trp Ser Ser Gly Ala Arg Thr Gln His Phe Arg Gly
210 215 220

His Thr Gly Ala Val Phe Ser Val Asp Tyr Ser Asp Glu Leu Asp Ile
225 230 235 240

Leu Val Ser Gly Ser Ala Asp Phe Ala Val Lys Val Trp Ala Leu Ser
245 250 255

Ala Gly Thr Cys Leu Asn Thr Leu Thr Gly His Thr Glu Trp Val Thr
260 265 270

Lys Val Val Leu Gln Lys Cys Lys Val Lys Ser Leu Leu His Ser Pro
275 280 285

Gly Asp Tyr Ile Leu Leu Ser Ala Asp Lys Tyr Glu Ile Lys Ile Trp
290 295 300

Pro Ile Gly Arg Glu Ile Asn Cys Lys Cys Leu Lys Thr Leu Ser Val
305 310 315 320

Ser Glu Asp Arg Ser Ile Cys Leu Gln Pro Arg Leu His Phe Asp Gly

-continued 325 330 335

Lys Tyr Ile Val Cys Ser Ser Ala Leu Gly Leu Tyr Gln Trp Asp Phe
340 345 350

Ala Ser Tyr Asp Ile Leu Arg Val Ile Lys Thr Pro Glu Val Ala Asn
355 360 365

Leu Ala Leu Leu Gly Phe Gly Asp Val Phe Ala Leu Leu Phe Asp Asn
370 375 380

His Tyr Leu Tyr Ile Met Asp Leu Arg Thr Glu Ser Leu Ile Ser Arg
385 390 395 400

Trp Pro Leu Pro Glu Tyr Arg Lys Ser Lys Arg Gly Thr Ser Phe Leu
405 410 415

Ala Gly Glu Arg Pro Gly
420

( 2 ) INFORMATION FOR SEQ ID NO:53:

( i ) SEQUENCE CHARACTERISTICS:
( A ) LENGTH: 422 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: MSL1, Fig. 36

( x i ) SEQUENCE DESCRIPTION: SEQ ID NO:53:

Met Asn Gln Cys Ala Lys Asp Ile Thr His Glu Ala Ser Ser Ile Pro
1 5 10 15

Ile Asp Leu Gln Glu Arg Tyr Ser His Trp Lys Lys Asn Thr Lys Leu
20 25 30

Leu Tyr Asp Tyr Leu Asn Thr Asn Ser Thr Lys Trp Pro Ser Leu Thr
35 40 45

Cys Gln Phe Phe Pro Asp Leu Asp Thr Thr Ser Asp Glu His Arg Ile
50 55 60

Leu Leu Ser Ser Phe Thr Ser Ser Gln Lys Pro Glu Asp Glu Thr Ile
65 70 75 80

Tyr Ile Ser Lys Ile Ser Thr Leu Gly His Ile Lys Trp Ser Ser Leu
85 90 95

Asn Asn Phe Asp Met Asp Glu Met Glu Phe Lys Pro Glu Asn Ser Thr
100 105 110

Arg Phe Pro Ser Lys His Leu Val Asn Asp Ile Ser Ile Phe Phe Pro
115 120 125

Asn Gly Glu Cys Asn Arg Ala Arg Tyr Leu Pro Gln Asn Pro Asp Ile
130 135 140

Ile Ala Gly Ala Ser Ser Asp Gly Ala Ile Tyr Ile Phe Asp Arg Thr
145 150 155 160

Lys His Gly Ser Thr Arg Ile Arg Gln Ser Lys Ile Ser His Pro Phe
165 170 175

Glu Thr Lys Leu Phe Gly Ser His Gly Val Ile Gln Asp Val Glu Ala
180 185 190

Met Asp Thr Ser Ser Ala Asp Ile Asn Glu Ala Thr Ser Leu Ala Trp
195 200 205

Asn Leu Gln Gln Glu Ala Leu Leu Leu Ser Ser His Ser Asn Gly Gln
210 215 220

Val Gln Val Trp Asp Ile Lys Gln Tyr Ser His Glu Asn Pro Ile Ile
225 230 235 240

Asp Leu Pro Leu Val Ser Ile Asn Ser Asp Gly Thr Ala Val Asn Asp
245 250 255

Val Thr Trp Met Pro Thr His Asp Ser Leu Phe Ala Ala Cys Thr Glu
260 265 270

Gly Asn Ala Val Ser Leu Leu Asp Leu Arg Thr Lys Lys Glu Lys Leu
275 280 285

Gln Ser Asn Arg Glu Lys His Asp Gly Gly Val Asn Ser Cys Arg Phe
290 295 300

Asn Tyr Lys Asn Ser Leu Ile Leu Ala Ser Ala Asp Ser Asn Gly Arg
305 310 315 320

Leu Asn Leu Trp Asp Ile Arg Asn Met Asn Lys Ser Pro Ile Ala Thr
325 330 335

Met Glu His Gly Thr Ser Val Ser Thr Leu Glu Trp Ser Pro Asn Phe
340 345 350

Asp Thr Val Leu Ala Thr Ala Gly Gln Glu Asp Gly Leu Val Lys Leu
355 360 365

Trp Asp Thr Ser Cys Glu Glu Thr Ile Phe Thr His Gly Gly His Met
370 375 380

Leu Gly Val Asn Asp Ile Ser Trp Asp Ala His Asp Pro Trp Leu Met
385 390 395 400

Cys Ser Val Ala Asn Asp Asn Ser Val His Ile Trp Lys Pro Ala Gly
405 410 415

Asn Leu Val Gly His Ser
420

( 2 ) INFORMATION FOR SEQ ID NO:54:

( i ) SEQUENCE CHARACTERISTICS:
( A ) LENGTH: 816 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: MUS MUSCULUS PROTEIN, Fig. 37

( x i ) SEQUENCE DESCRIPTION: SEQ ID NO:54:

Phe Arg Met Asp Asn Ala Ser Thr Arg Ile Asp Glu Arg Phe Arg Ile
1 5 10 15

Asp Ala Tyr Ala Asn Ala Arg Tyr Pro Met Pro Arg Thr Glu Ile Asn
20 25 30

Ser Glu Gln Glu Asn Cys Glu Asn Thr Ile Thr Leu Glu Asp Ser Glu
35 40 45

Gln Glu Asn Cys Glu Ala Ala Cys Met Pro Leu Glu Thr Glu Ser Glu
50 55 60

Gln Glu Asn Cys Glu Met Ser Ser His Glu Ser Tyr Thr Asn Ala Ala
65 70 75 80

Glu Thr Pro Glu Asn Ile Ser Ile Leu Ser Cys Leu Gly Glu Thr Ser
85 90 95

Gly Ala Leu Val Asp Thr Lys Thr Ile Ser Asp Ile Lys Thr Met Asp
100 105 110

-continued

Pro Arg Val Ser Leu Thr Pro Ser Ser Asp Val Thr Gly Thr Glu Asp
115 120 125

Ser Ser Val Leu Thr Pro Gln Ser Thr Asp Val Asn Ser Val Asp Ser
130 135 140

Tyr Gln Gly Tyr Glu Gly Asp Asp Asp Asp Glu Glu Asp Asp Glu Asp
145 150 155 160

Asp Lys Asp Gly Asp Ser Asn Leu Pro Ser Leu Glu Asp Ser Asp Asn
165 170 175

Phe Ile Ser Cys Leu Glu Asn Ser Tyr Ile Pro Gln Asn Val Glu Asn
180 185 190

Gly Glu Val Val Glu Glu Gln Ser Leu Gly Arg Arg Phe His Pro Tyr
195 200 205

Glu Leu Glu Ala Gly Glu Val Val Glu Gly Gln Gly Gly Gly Ser Leu
210 215 220

Phe Tyr Pro Tyr Glu Leu Glu Ala Gly Glu Val Val Glu Ala Gln Asn
225 230 235 240

Val Gln Asn Leu Phe His Arg Tyr Glu Leu Glu Glu Gly Glu Val Val
245 250 255

Glu Ala Gln Val Val Gln Ser Met Phe Pro Tyr Tyr Glu Leu Glu Ala
260 265 270

Gly Glu Val Val Glu Ala Glu Glu Val Gln Gly Phe Phe Gln Arg Tyr
275 280 285

Glu Leu Glu Ala Arg Glu Val Ile Gly Ala Gln Gly Gly Gln Gly Leu
290 295 300

Ser Arg His Tyr Gly Leu Glu Gly Gly Glu Val Val Glu Ala Thr Ala
305 310 315 320

Val Arg Arg Leu Ile Gln His His Glu Leu Glu Glu Gly Glu Asp Val
325 330 335

Asp Asp Gln Glu Glu Ser Ser Glu Met His Glu Glu Thr Ser Glu Asp
340 345 350

Ser Ser Glu Gln Tyr Asp Ile Glu Asp Asp Ser Leu Ile Asp Glu Trp
355 360 365

Ile Ala Leu Glu Thr Ser Pro Leu Pro Arg Pro Arg Trp Asn Val Leu
370 375 380

Ser Ala Leu Arg Asp Arg Gln Leu Gly Ser Ser Gly Arg Phe Val Tyr
385 390 395 400

Glu Ala Cys Gly Ala Arg Leu Phe Val Gln Arg Phe Ser Leu Glu His
405 410 415

Val Phe Glu Gly His Ser Gly Cys Val Asn Thr Val His Phe Asn Gln
420 425 430

His Gly Thr Leu Leu Ala Ser Gly Ser Asp Asp Leu Lys Val Ile Val
435 440 445

Trp Asp Trp Leu Lys Lys Arg Ser Val Leu Asn Phe Asp Ser Gly His
450 455 460

Lys Asn Asn Ile Leu Gln Ala Lys Phe Leu Pro Asn Cys Asn Asp Ala
465 470 475 480

Ile Leu Ala Met Cys Gly Arg Asp Gly Gln Val Arg Val Ala Gln Leu
485 490 495

Ser Ala Val Ala Gly Thr His Met Thr Lys Arg Leu Val Lys His Gly
500 505 510

Gly Ala Ser His Arg Leu Gly Leu Glu Pro Asp Ser Pro Phe Arg Phe
515 520 525

Leu Thr Ser Gly Glu Asp Ala Val Val Phe Asn Ile Asp Leu Arg Gln
530 535 540

-continued

| | | | | | | | | | | | | | | | |
|---|---|---|---|---|---|---|---|---|---|---|---|---|---|---|---|
| Ala | His | Pro | Ala | Ser | Lys | Leu | Leu | Val | Ile | Lys | Asp | Gly | Asp | Lys | Lys |
| 545 | | | | | 550 | | | | | 555 | | | | | 560 |
| Val | Gly | Leu | Tyr | Thr | Val | Phe | Val | Asn | Pro | Ala | Asn | Val | Tyr | Gln | Phe |
| | | | | 565 | | | | | 570 | | | | | 575 | |
| Ala | Val | Gly | Gly | Gln | Asp | Gln | Phe | Met | Arg | Ile | Tyr | Asp | Gln | Arg | Lys |
| | | | 580 | | | | | 585 | | | | | 590 | | |
| Ile | Asp | Glu | Asn | Val | Asn | Asn | Gly | Val | Leu | Lys | Lys | Phe | Cys | Pro | His |
| | | 595 | | | | | 600 | | | | | 605 | | | |
| His | Leu | Leu | Ser | Ser | Asp | Tyr | Pro | Ala | His | Ile | Thr | Ser | Leu | Met | Tyr |
| | 610 | | | | | 615 | | | | | 620 | | | | |
| Ser | Tyr | Asp | Gly | Thr | Glu | Ile | Leu | Ala | Ser | Tyr | Asn | Asp | Glu | Asp | Ile |
| 625 | | | | | 630 | | | | | 635 | | | | | 640 |
| Tyr | Ile | Phe | Asn | Ser | Ser | Asp | Ser | Asp | Gly | Ala | Gln | Tyr | Ala | Lys | Arg |
| | | | | 645 | | | | | 650 | | | | | 655 | |
| Tyr | Lys | Gly | His | Arg | Asn | Asn | Ser | Thr | Val | Lys | Gly | Val | Tyr | Phe | Tyr |
| | | | 660 | | | | | 665 | | | | | 670 | | |
| Gly | Pro | Arg | Ser | Glu | Phe | Val | Met | Ser | Gly | Ser | Asp | Cys | Gly | His | Ile |
| | | 675 | | | | | 680 | | | | | 685 | | | |
| Phe | Ile | Trp | Glu | Lys | Ser | Ser | Cys | Gln | Ile | Val | Gln | Phe | Leu | Glu | Ala |
| | 690 | | | | | 695 | | | | | 700 | | | | |
| Asp | Glu | Gly | Gly | Thr | Ile | Asn | Cys | Ile | Asp | Ser | His | Pro | Tyr | Leu | Pro |
| 705 | | | | | 710 | | | | | 715 | | | | | 720 |
| Val | Leu | Ala | Ser | Ser | Gly | Leu | Asp | His | Glu | Val | Lys | Ile | Trp | Ser | Pro |
| | | | | 725 | | | | | 730 | | | | | 735 | |
| Ile | Ala | Glu | Pro | Ser | Lys | Lys | Leu | Ala | Gly | Leu | Lys | Asn | Val | Ile | Lys |
| | | | 740 | | | | | 745 | | | | | 750 | | |
| Ile | Asn | Lys | Leu | Lys | Arg | Asp | Asn | Phe | Thr | Leu | Arg | His | Thr | Ser | Leu |
| | | 755 | | | | | 760 | | | | | 765 | | | |
| Phe | Asn | Asn | Ser | Met | Leu | Cys | Phe | Leu | Met | Ser | His | Val | Thr | Gln | Ser |
| | 770 | | | | | 775 | | | | | 780 | | | | |
| Asn | Tyr | Gly | Arg | Ser | Trp | Arg | Gly | Ile | Arg | Ile | Asn | Ala | Gly | Gly | Gly |
| 785 | | | | | 790 | | | | | 795 | | | | | 800 |
| Asp | Phe | Ser | Asp | Ser | Ser | Ser | Ser | Ser | Glu | Glu | Thr | Asn | Gln | Glu | Ser |
| | | | | 805 | | | | | 810 | | | | | 815 | |

( 2 ) INFORMATION FOR SEQ ID NO:55:

( i ) SEQUENCE CHARACTERISTICS:
( A ) LENGTH: 422 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: ORF RB1, Fig. 38

( x i ) SEQUENCE DESCRIPTION: SEQ ID NO:55:

| | | | | | | | | | | | | | | | |
|---|---|---|---|---|---|---|---|---|---|---|---|---|---|---|---|
| Met | Asn | Gln | Cys | Ala | Lys | Asp | Ile | Thr | His | Glu | Ala | Ser | Ser | Ile | Pro |
| 1 | | | | 5 | | | | | 10 | | | | | 15 | |
| Ile | Asp | Leu | Gln | Glu | Arg | Tyr | Ser | His | Trp | Lys | Lys | Asn | Thr | Lys | Leu |
| | | | 20 | | | | | 25 | | | | | 30 | | |
| Leu | Tyr | Asp | Tyr | Leu | Asn | Thr | Asn | Ser | Thr | Lys | Trp | Pro | Ser | Leu | Thr |
| | | 35 | | | | | 40 | | | | | 45 | | | |

-continued

```
Cys Gln Phe Phe Pro Asp Leu Asp Thr Thr Ser Asp Glu His Arg Ile
     50                       55                       60

Leu Leu Ser Ser Phe Thr Ser Ser Gln Lys Pro Glu Asp Glu Thr Ile
65                       70                       75                       80

Tyr Ile Ser Lys Ile Ser Thr Leu Gly His Ile Lys Trp Ser Ser Leu
                    85                       90                       95

Asn Asn Phe Asp Met Asp Glu Met Glu Phe Lys Pro Glu Asn Ser Thr
               100                      105                      110

Arg Phe Pro Ser Lys His Leu Val Asn Asp Ile Ser Ile Phe Phe Pro
          115                      120                      125

Asn Gly Glu Cys Asn Arg Ala Arg Tyr Leu Pro Gln Asn Pro Asp Ile
     130                      135                      140

Ile Ala Gly Ala Ser Ser Asp Gly Ala Ile Tyr Ile Phe Asp Arg Thr
145                      150                      155                      160

Lys His Gly Ser Thr Arg Ile Arg Gln Ser Lys Ile Ser His Pro Phe
                    165                      170                      175

Glu Thr Lys Leu Phe Gly Ser His Gly Val Ile Gln Asp Val Glu Ala
               180                      185                      190

Met Asp Thr Ser Ser Ala Asp Ile Asn Glu Ala Thr Ser Leu Ala Trp
          195                      200                      205

Asn Leu Gln Gln Glu Ala Leu Leu Leu Ser Ser His Ser Asn Gly Gln
     210                      215                      220

Val Gln Val Trp Asp Ile Lys Gln Tyr Ser His Glu Asn Pro Ile Ile
225                      230                      235                      240

Asp Leu Pro Leu Val Ser Ile Asn Ser Asp Gly Thr Ala Val Asn Asp
                    245                      250                      255

Val Thr Trp Met Pro Thr His Asp Ser Leu Phe Ala Ala Cys Thr Glu
               260                      265                      270

Gly Asn Ala Val Ser Leu Leu Asp Leu Arg Thr Lys Lys Glu Lys Leu
          275                      280                      285

Gln Ser Asn Arg Glu Lys His Asp Gly Gly Val Asn Ser Cys Arg Phe
     290                      295                      300

Asn Tyr Lys Asn Ser Leu Ile Leu Ala Ser Ala Asp Ser Asn Gly Arg
305                      310                      315                      320

Leu Asn Leu Trp Asp Ile Arg Asn Met Asn Lys Ser Pro Ile Ala Thr
                    325                      330                      335

Met Glu His Gly Thr Ser Val Ser Thr Leu Glu Trp Ser Pro Asn Phe
               340                      345                      350

Asp Thr Val Leu Ala Thr Ala Gly Gln Glu Asp Gly Leu Val Lys Leu
          355                      360                      365

Trp Asp Thr Ser Cys Glu Glu Thr Ile Phe Thr His Gly Gly His Met
     370                      375                      380

Leu Gly Val Asn Asp Ile Ser Trp Asp Ala His Asp Pro Trp Leu Met
385                      390                      395                      400

Cys Ser Val Ala Asn Asp Asn Ser Val His Ile Trp Lys Pro Ala Gly
                    405                      410                      415

Asn Leu Val Gly His Ser
               420
```

( 2 ) INFORMATION FOR SEQ ID NO:56:

( i ) SEQUENCE CHARACTERISTICS:
( A ) LENGTH: 576 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: Periodic Trp protein, Fig. 39

( x i ) SEQUENCE DESCRIPTION: SEQ ID NO:56:

Met Ile Ser Ala Thr Asn Trp Val Pro Arg Gly Phe Ser Ser Glu Phe
1 5 10 15

Pro Glu Lys Tyr Val Leu Asp Asp Glu Glu Val Glu Arg Ile Asn Gln
20 25 30

Leu Ala Gln Leu Asn Leu Asp Asp Ala Lys Ala Thr Leu Glu Glu Ala
35 40 45

Glu Gly Glu Ser Gly Val Glu Asp Asp Ala Ala Thr Gly Ser Ser Asn
50 55 60

Lys Leu Lys Asp Gln Leu Asp Ile Asp Asp Asp Leu Lys Glu Tyr Asn
65 70 75 80

Leu Glu Glu Tyr Asp Asp Glu Glu Ile Ala Asp Asn Glu Gly Gly Lys
85 90 95

Asp Val Ser Met Phe Pro Gly Leu Ser Asn Asp Ser Asp Val Lys Phe
100 105 110

His Glu Gly Glu Lys Gly Glu Asp Pro Tyr Ile Ser Leu Pro Asn Gln
115 120 125

Glu Asp Ser Gln Glu Glu Lys Gln Glu Leu Gln Val Tyr Pro Ser Asp
130 135 140

Asn Leu Val Leu Ala Ala Arg Thr Glu Asp Asp Val Ser Tyr Leu Asp
145 150 155 160

Ile Tyr Val Tyr Asp Asp Gly Ala Gly Phe His Ser Ser Asp Ile Pro
165 170 175

Val Glu Glu Gly Asp Glu Ala Asp Pro Asp Val Ala Arg Gly Leu Val
180 185 190

Arg Asp Pro Ala Leu Tyr Val His His Asp Leu Met Leu Pro Ala Phe
195 200 205

Pro Leu Cys Val Glu Trp Leu Asp Tyr Lys Val Gly Ser Asn Ser Glu
210 215 220

Glu Ala Ala Asn Tyr Ala Ala Ile Gly Thr Phe Asp Pro Gln Ile Glu
225 230 235 240

Ile Trp Asn Leu Asp Cys Val Asp Lys Ala Phe Pro Asp Met Ile Leu
245 250 255

Gly Glu Pro Leu Asp Asn Ser Met Val Ser Leu Lys Ser Lys Lys Lys
260 265 270

Lys Lys Lys Ser Lys Thr Gly His Ile Thr Thr His His Thr Asp Ala
275 280 285

Val Leu Ser Met Ala His Asn Lys Tyr Phe Arg Ser Val Leu Ala Ser
290 295 300

Thr Ser Ala Asp His Thr Val Lys Leu Trp Asp Leu Asn Ser Gly Asn
305 310 315 320

Ala Ala Arg Ser Leu Ala Ser Ile His Ser Asn Lys Asn Val Ser Ser
325 330 335

Ser Glu Trp His Met Leu Asn Gly Ser Ile Leu Leu Thr Gly Gly Tyr
340 345 350

Asp Ser Arg Val Ala Leu Thr Asp Val Arg Ile Ser Asp Glu Ser Gln
355 360 365

-continued

Met Ser Lys Tyr Trp Ser Ala Met Ala Gly Glu Glu Ile Glu Thr Val
370 375 380

Thr Phe Ala Ser Glu Asn Ile Ile Leu Cys Gly Thr Asp Ser Gly Asn
385 390 395 400

Val Tyr Ser Phe Asp Ile Arg Asn Asn Glu Asn Arg Lys Pro Val Trp
405 410 415

Thr Leu Lys Ala His Asp Ala Gly Ile Ser Thr Leu Cys Ser Asn Lys
420 425 430

Phe Ile Pro Gly Met Met Ser Thr Gly Ala Met Gly Glu Lys Thr Val
435 440 445

Lys Leu Trp Lys Phe Pro Leu Asp Asp Ala Thr Asn Thr Lys Gly Pro
450 455 460

Ser Met Val Leu Ser Arg Asp Phe Asp Val Gly Asn Val Leu Thr Ser
465 470 475 480

Ser Phe Ala Pro Asp Ile Glu Val Ala Gly Thr Met Val Ile Gly Gly
485 490 495

Val Asn Lys Val Leu Lys Leu Trp Asp Val Phe Thr Asn Arg Ser Val
500 505 510

Arg Lys Ser Phe Lys Ser Glu Leu Glu Asn Val Gln Ala Arg Ala Lys
515 520 525

Glu Glu Ala Gln Lys Ile Gly Lys Ser Ser Arg Ile Ala Arg Lys Tyr
530 535 540

Thr Ser Asn Asp Asn Pro Asp Thr Val Ile Thr Ile Asp Asp Gln Gly
545 550 555 560

Glu Asp Glu Glu Glu Arg Glu Gly Gly Asp Glu His Asp Asp Met Ala
565 570 575

( 2 ) INFORMATION FOR SEQ ID NO:57:

( i ) SEQUENCE CHARACTERISTICS:
( A ) LENGTH: 325 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: PLAP, Fig. 40

( x i ) SEQUENCE DESCRIPTION: SEQ ID NO:57:

Met His Tyr Met Ser Gly His Ser Asn Phe Val Ser Tyr Val Cys Ile
1 5 10 15

Ile Pro Ser Ser Asp Ile Tyr Pro His Gly Leu Ile Ala Thr Gly Gly
20 25 30

Asn Asp His Asn Ile Cys Ile Phe Ser Leu Asp Ser Pro Met Pro Leu
35 40 45

Tyr Ile Leu Lys Gly His Lys Asp Thr Val Cys Ser Leu Ser Ser Gly
50 55 60

Lys Phe Gly Thr Leu Leu Ser Gly Ser Trp Asp Thr Thr Ala Lys Val
65 70 75 80

Trp Leu Asn Asp Lys Cys Met Met Thr Leu Gln Gly His Thr Ala Ala
85 90 95

Val Trp Ala Val Lys Ile Leu Pro Glu Gln Gly Leu Met Leu Thr Gly
100 105 110

Ser Ala Asp Lys Thr Ile Lys Leu Trp Lys Ala Gly Arg Cys Glu Arg

-continued 115 120 125

Thr Phe Leu Gly His Glu Asp Cys Val Arg Gly Leu Ala Ile Leu Ser
130 135 140

Glu Thr Glu Phe Leu Ser Cys Ala Asn Asp Ala Ser Ile Arg Arg Trp
145 150 155 160

Gln Ile Thr Gly Glu Cys Leu Glu Val Tyr Phe Gly His Thr Asn Tyr
165 170 175

Ile Tyr Ser Ile Ser Val Phe Pro Asn Ser Lys Asp Phe Val Thr Thr
180 185 190

Ala Glu Asp Arg Ser Leu Arg Ile Trp Lys His Gly Glu Cys Ala Gln
195 200 205

Thr Ile Arg Leu Pro Ala Gln Ser Ile Trp Cys Cys Cys Val Leu Glu
210 215 220

Asn Gly Asp Ile Val Val Gly Ala Ser Asp Gly Ile Ile Arg Val Phe
225 230 235 240

Thr Glu Ser Glu Glu Arg Thr Ala Ser Ala Glu Glu Ile Lys Ala Ser
245 250 255

Leu Ser Arg Glu Ser Pro Leu Ile Ala Lys Val Leu Thr Thr Glu Pro
260 265 270

Pro Ile Ile Thr Pro Val Arg Arg Thr Leu Pro Cys Arg Val Thr Arg
275 280 285

Ser Met Ile Ser Ser Cys Leu Ser Arg Leu Val Ser Thr Ser Leu Ser
290 295 300

Thr Ser Asp Ser His Leu Thr Ile Thr Ala Leu His Leu Phe Leu Thr
305 310 315 320

Thr Thr Thr Thr Glu
325

( 2 ) INFORMATION FOR SEQ ID NO:58:

( i ) SEQUENCE CHARACTERISTICS:
( A ) LENGTH: 425 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: RETINOBLASTOMA BINDING PROTEIN - HUMAN, Fig. 41

( x i ) SEQUENCE DESCRIPTION: SEQ ID NO:58:

Met Ala Asp Lys Glu Ala Ala Phe Asp Asp Ala Val Glu Glu Arg Val
1 5 10 15

Ile Asn Glu Glu Tyr Lys Ile Trp Lys Lys Asn Thr Pro Phe Leu Tyr
20 25 30

Asp Leu Val Met Thr His Ala Leu Glu Trp Pro Ser Leu Thr Ala Gln
35 40 45

Trp Leu Pro Asp Val Thr Arg Pro Glu Gly Lys Asp Phe Ser Ile His
50 55 60

Arg Leu Val Leu Gly Thr His Thr Ser Asp Glu Gln Asn His Leu Val
65 70 75 80

Ile Ala Ser Val Gln Leu Pro Asn Asp Asp Ala Gln Phe Asp Ala Ser
85 90 95

His Tyr Asp Ser Glu Lys Gly Glu Phe Gly Gly Phe Gly Ser Val Ser

-continued

| | | | | | | | | | | | | | | | |
|---|---|---|---|---|---|---|---|---|---|---|---|---|---|---|---|
| | | | 100 | | | | | 105 | | | | | 110 | | |
| Gly | Lys | Ile | Glu | Ile | Glu | Ile | Lys | Ile | Asn | His | Glu | Gly | Glu | Val | Asn |
| | | 115 | | | | | 120 | | | | | 125 | | | |
| Arg | Ala | Arg | Tyr | Met | Pro | Gln | Asn | Pro | Cys | Ile | Ile | Ala | Thr | Lys | Thr |
| | 130 | | | | | 135 | | | | | 140 | | | | |
| Pro | Ser | Ser | Asp | Val | Leu | Val | Phe | Asp | Tyr | Thr | Lys | His | Pro | Ser | Lys |
| 145 | | | | | 150 | | | | | 155 | | | | | 160 |
| Pro | Asp | Pro | Ser | Gly | Glu | Cys | Asn | Pro | Asp | Leu | Arg | Leu | Arg | Gly | His |
| | | | | 165 | | | | | 170 | | | | | 175 | |
| Gln | Lys | Glu | Gly | Tyr | Gly | Leu | Ser | Trp | Asn | Pro | Asn | Leu | Ser | Gly | His |
| | | | 180 | | | | | 185 | | | | | 190 | | |
| Leu | Leu | Ser | Ala | Ser | Asp | Asp | His | Thr | Ile | Cys | Leu | Trp | Asp | Ile | Ser |
| | | 195 | | | | | 200 | | | | | 205 | | | |
| Ala | Val | Pro | Lys | Glu | Gly | Lys | Val | Val | Asp | Ala | Lys | Thr | Ile | Phe | Thr |
| | 210 | | | | | 215 | | | | | 220 | | | | |
| Gly | His | Thr | Ala | Val | Val | Glu | Asp | Val | Ser | Trp | His | Leu | Leu | His | Glu |
| 225 | | | | | 230 | | | | | 235 | | | | | 240 |
| Ser | Leu | Phe | Gly | Ser | Val | Ala | Asp | Asp | Gln | Lys | Leu | Met | Ile | Trp | Asp |
| | | | | 245 | | | | | 250 | | | | | 255 | |
| Thr | Arg | Ser | Asn | Asn | Thr | Ser | Lys | Pro | Ser | His | Ser | Val | Asp | Ala | His |
| | | | 260 | | | | | 265 | | | | | 270 | | |
| Thr | Ala | Glu | Val | Asn | Cys | Leu | Ser | Phe | Asn | Pro | Tyr | Ser | Glu | Phe | Ile |
| | | 275 | | | | | 280 | | | | | 285 | | | |
| Leu | Ala | Thr | Gly | Ser | Ala | Asp | Lys | Thr | Val | Ala | Leu | Trp | Asp | Leu | Arg |
| | 290 | | | | | 295 | | | | | 300 | | | | |
| Asn | Leu | Lys | Leu | Lys | Leu | His | Ser | Phe | Glu | Ser | His | Lys | Asp | Glu | Ile |
| 305 | | | | | 310 | | | | | 315 | | | | | 320 |
| Phe | Gln | Val | Gln | Trp | Ser | Pro | His | Asn | Glu | Thr | Ile | Leu | Ala | Ser | Ser |
| | | | | 325 | | | | | 330 | | | | | 335 | |
| Gly | Thr | Asp | Arg | Arg | Leu | Asn | Val | Trp | Asp | Leu | Ser | Lys | Ile | Gly | Glu |
| | | | 340 | | | | | 345 | | | | | 350 | | |
| Glu | Gln | Ser | Pro | Glu | Asp | Ala | Glu | Asp | Gly | Pro | Pro | Glu | Leu | Leu | Phe |
| | | 355 | | | | | 360 | | | | | 365 | | | |
| Ile | His | Gly | Gly | His | Thr | Ala | Lys | Ile | Ser | Asp | Phe | Ser | Trp | Asn | Pro |
| | 370 | | | | | 375 | | | | | 380 | | | | |
| Asn | Glu | Pro | Trp | Val | Ile | Cys | Ser | Val | Ser | Glu | Asp | Asn | Ile | Met | Gln |
| 385 | | | | | 390 | | | | | 395 | | | | | 400 |
| Val | Trp | Gln | Met | Ala | Glu | Asn | Ile | Tyr | Asn | Asp | Glu | Asp | Pro | Glu | Gly |
| | | | | 405 | | | | | 410 | | | | | 415 | |
| Ser | Val | Asp | Pro | Glu | Gly | Gln | Gly | Ser | | | | | | | |
| | | | 420 | | | | | 425 | | | | | | | |

( 2 ) INFORMATION FOR SEQ ID NO:59:

( i ) SEQUENCE CHARACTERISTICS:
( A ) LENGTH: 852 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: S253 PROTEIN, Fig. 42

( x i ) SEQUENCE DESCRIPTION: SEQ ID NO:59:

-continued

| | | | | | | | | | | | | | | | |
|---|---|---|---|---|---|---|---|---|---|---|---|---|---|---|---|
| Met | Phe | Lys | Ser | Lys | Thr | Ser | Thr | Leu | Ser | Tyr | Asp | Glu | Thr | Pro | Asn |
| 1 | | | | 5 | | | | | 10 | | | | | 15 | |
| Ser | Asn | Glu | Gly | Asp | Arg | Asn | Ala | Thr | Pro | Val | Asn | Pro | Lys | Glu | Lys |
| | | | 20 | | | | | 25 | | | | | 30 | | |
| Ser | Gln | Thr | Lys | His | Leu | Asn | Ile | Pro | Gly | Asp | Arg | Ser | Arg | His | Ser |
| | | 35 | | | | | 40 | | | | | 45 | | | |
| Ser | Ile | Ala | Asp | Ser | Lys | Arg | Ser | Ser | Ser | Arg | Tyr | Asp | Gly | Gly | Tyr |
| | 50 | | | | | 55 | | | | | 60 | | | | |
| Ser | Ala | Asp | Ile | Ile | Pro | Ala | Gln | Leu | Arg | Phe | Ile | Asp | Asn | Ile | Asp |
| 65 | | | | | 70 | | | | | 75 | | | | | 80 |
| Tyr | Gly | Thr | Arg | Leu | Arg | Lys | Thr | Leu | His | Arg | Asn | Ser | Val | Val | Ser |
| | | | | 85 | | | | | 90 | | | | | 95 | |
| Asn | Gly | Tyr | Asn | Lys | Leu | Ser | Glu | Asn | Asp | Arg | Trp | Tyr | Phe | Asp | Leu |
| | | | 100 | | | | | 105 | | | | | 110 | | |
| Phe | Asp | Arg | Lys | Tyr | Phe | Glu | Asn | Tyr | Leu | Glu | Glu | Pro | Thr | Tyr | Ile |
| | | 115 | | | | | 120 | | | | | 125 | | | |
| Lys | Ile | Phe | Lys | Lys | Lys | Glu | Gly | Leu | Glu | Gln | Phe | Asp | Arg | Met | Phe |
| | 130 | | | | | 135 | | | | | 140 | | | | |
| Leu | Ala | Gln | Glu | Leu | Lys | Ile | Pro | Asp | Val | Tyr | Lys | Ser | Thr | Thr | Tyr |
| 145 | | | | | 150 | | | | | 155 | | | | | 160 |
| Gln | Gly | Glu | Pro | Ala | Val | Ala | Asn | Ser | Glu | Leu | Phe | Lys | Asn | Ser | Ile |
| | | | | 165 | | | | | 170 | | | | | 175 | |
| Cys | Cys | Cys | Thr | Phe | Ser | His | Asp | Gly | Lys | Tyr | Met | Val | Ile | Gly | Cys |
| | | | 180 | | | | | 185 | | | | | 190 | | |
| Lys | Asp | Gly | Ser | Leu | His | Leu | Trp | Lys | Val | Ile | Asn | Ser | Pro | Val | Lys |
| | | 195 | | | | | 200 | | | | | 205 | | | |
| Arg | Ser | Glu | Met | Gly | Arg | Ser | Glu | Lys | Ser | Val | Ser | Ala | Ser | Arg | Ala |
| | 210 | | | | | 215 | | | | | 220 | | | | |
| Asn | Ser | Leu | Lys | Ile | Gln | Arg | His | Leu | Ala | Ser | Ile | Ser | Ser | His | Asn |
| 225 | | | | | 230 | | | | | 235 | | | | | 240 |
| Gly | Ser | Ile | Ser | Ser | Asn | Asp | Leu | Lys | Pro | Ser | Asp | Gln | Phe | Glu | Gly |
| | | | | 245 | | | | | 250 | | | | | 255 | |
| Pro | Ser | Lys | Gln | Leu | His | Leu | Tyr | Ala | Pro | Val | Phe | Tyr | Ser | Asp | Val |
| | | | 260 | | | | | 265 | | | | | 270 | | |
| Phe | Arg | Val | Phe | Met | Glu | His | Ala | Leu | Asp | Ile | Leu | Asp | Ala | Asn | Trp |
| | | 275 | | | | | 280 | | | | | 285 | | | |
| Ser | Lys | Asn | Gly | Phe | Leu | Ile | Thr | Ala | Ser | Met | Asp | Lys | Thr | Ala | Lys |
| | 290 | | | | | 295 | | | | | 300 | | | | |
| Leu | Trp | His | Pro | Glu | Arg | Lys | Tyr | Ser | Leu | Lys | Thr | Phe | Val | His | Pro |
| 305 | | | | | 310 | | | | | 315 | | | | | 320 |
| Asp | Phe | Val | Thr | Ser | Ala | Ile | Phe | Phe | Pro | Asn | Asp | Asp | Arg | Phe | Ile |
| | | | | 325 | | | | | 330 | | | | | 335 | |
| Ile | Thr | Gly | Cys | Leu | Asp | His | Arg | Cys | Arg | Leu | Trp | Ser | Ile | Leu | Asp |
| | | | 340 | | | | | 345 | | | | | 350 | | |
| Asn | Glu | Val | Ser | Tyr | Ala | Phe | Asp | Cys | Lys | Asp | Leu | Ile | Thr | Ser | Leu |
| | | 355 | | | | | 360 | | | | | 365 | | | |
| Thr | Leu | Ser | Pro | Pro | Gly | Gly | Glu | Tyr | Thr | Ile | Ile | Gly | Thr | Phe | Asn |
| | 370 | | | | | 375 | | | | | 380 | | | | |
| Gly | Tyr | Ile | Tyr | Val | Leu | Leu | Thr | His | Gly | Leu | Lys | Phe | Val | Ser | Ser |
| 385 | | | | | 390 | | | | | 395 | | | | | 400 |
| Phe | His | Val | Ser | Asp | Lys | Ser | Thr | Gln | Gly | Thr | Thr | Lys | Asn | Ser | Phe |
| | | | | 405 | | | | | 410 | | | | | 415 | |
| His | Pro | Ser | Ser | Glu | Tyr | Gly | Lys | Val | Gln | His | Gly | Pro | Arg | Ile | Thr |

-continued

```
            420                 425                 430

Gly Leu Gln Cys Phe Phe Ser Lys Val Asp Lys Asn Leu Arg Leu Ile
        435                 440                 445

Val Thr Thr Asn Asp Ser Lys Ile Gln Ile Phe Asp Leu Asn Glu Lys
    450                 455                 460

Lys Pro Leu Glu Leu Phe Lys Gly Phe Gln Ser Gly Ser Ser Arg His
465                 470                 475                 480

Arg Gly Gln Phe Leu Met Met Lys Asn Glu Pro Val Val Phe Thr Gly
                485                 490                 495

Ser Asp Asp His Trp Phe Tyr Thr Trp Lys Met Gln Ser Phe Asn Leu
            500                 505                 510

Ser Ala Glu Met Asn Cys Thr Ala Pro His Arg Lys Lys Arg Leu Ser
        515                 520                 525

Gly Ser Met Ser Leu Lys Gly Leu Leu Arg Ile Val Ser Asn Lys Ser
    530                 535                 540

Thr Asn Asp Glu Cys Leu Thr Glu Thr Ser Asn Gln Ser Ser Ser His
545                 550                 555                 560

Thr Phe Thr Asn Ser Ser Lys Asn Val Leu Gln Thr Gln Thr Val Gly
                565                 570                 575

Ser Gln Ala Ile Lys Asn Asn His Tyr Ile Ser Phe His Ala His Asn
            580                 585                 590

Ser Pro Val Thr Cys Ala Ser Ile Ala Pro Asp Val Ala Ile Lys Asn
        595                 600                 605

Leu Ser Leu Ser Asn Asp Leu Ile Phe Glu Leu Thr Ser Gln Tyr Phe
    610                 615                 620

Lys Glu Met Gly Gln Asn Tyr Ser Glu Ser Lys Glu Thr Cys Asp Asn
625                 630                 635                 640

Lys Pro Asn His Pro Val Thr Glu Thr Gly Gly Phe Ser Ser Asn Leu
                645                 650                 655

Ser Asn Val Val Asn Asn Val Gly Thr Ile Leu Ile Thr Thr Asp Ser
            660                 665                 670

Gln Gly Leu Ile Arg Val Phe Arg Thr Asp Ile Leu Pro Glu Ile Arg
        675                 680                 685

Lys Lys Ile Ile Glu Lys Phe His Glu Tyr Asn Leu Phe His Leu Glu
    690                 695                 700

Ala Ala Gly Lys Ile Asn Asn His Asn Asn Asp Ser Ile Leu Glu Asn
705                 710                 715                 720

Arg Met Asp Glu Arg Ser Ser Thr Glu Asp Asn Glu Phe Ser Thr Thr
                725                 730                 735

Pro Pro Ser Asn Thr His Asn Ser Arg Pro Ser His Asp Phe Cys Glu
            740                 745                 750

Leu His Pro Asn Asn Ser Pro Val Ile Ser Gly Met Pro Ser Arg Ala
        755                 760                 765

Ser Ala Ile Phe Lys Asn Ser Ile Phe Asn Lys Ser Asn Gly Ser Phe
    770                 775                 780

Ile Ser Leu Lys Ser Arg Ser Glu Ser Thr Ser Ser Thr Val Phe Gly
785                 790                 795                 800

Pro His Asp Ile Pro Arg Val Ser Thr Thr Tyr Pro Lys Leu Lys Cys
                805                 810                 815

Asp Val Cys Asn Gly Ser Asn Phe Glu Cys Ala Ser Lys Asn Pro Ile
            820                 825                 830

Ala Gly Gly Asp Ser Gly Phe Thr Cys Ala Asp Cys Gly Thr Ile Leu
        835                 840                 845
```

Asn Asn Phe Arg
    850

( 2 ) INFORMATION FOR SEQ ID NO:60:

( i ) SEQUENCE CHARACTERISTICS:
( A ) LENGTH: 488 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: SOF1, Fig. 43

( x i ) SEQUENCE DESCRIPTION: SEQ ID NO:60:

Met Lys Ile Lys Thr Ile Lys Arg Ser Ala Asp Asp Tyr Val Pro Val
1               5                   10                  15

Lys Ser Thr Gln Glu Ser Gln Met Pro Arg Asn Leu Asn Pro Glu Leu
            20                  25                  30

His Pro Phe Glu Arg Ala Arg Glu Tyr Thr Lys Ala Leu Asn Ala Thr
        35                  40                  45

Lys Leu Glu Arg Met Phe Ala Lys Pro Phe Val Gly Gln Leu Gly Tyr
    50                  55                  60

Gly His Arg Asp Gly Val Tyr Ala Ile Ala Lys Asn Tyr Gly Ser Leu
65                  70                  75                  80

Asn Lys Leu Ala Thr Gly Ser Ala Asp Gly Val Ile Lys Tyr Trp Asn
                85                  90                  95

Met Ser Thr Arg Glu Glu Phe Val Ser Phe Lys Ala His Tyr Gly Leu
            100                 105                 110

Val Thr Gly Leu Cys Val Thr Gln Pro Arg Phe His Asp Lys Lys Pro
        115                 120                 125

Asp Leu Lys Ser Gln Asn Phe Met Leu Ser Cys Ser Asp Asp Lys Thr
    130                 135                 140

Val Lys Leu Trp Ser Ile Asn Val Asp Asp Tyr Ser Asn Lys Asn Ser
145                 150                 155                 160

Ser Asp Asn Asp Ser Val Thr Asn Glu Glu Gly Leu Ile Arg Thr Phe
                165                 170                 175

Asp Gly Glu Ser Ala Phe Gln Gly Ile Asp Ser His Arg Glu Asn Ser
            180                 185                 190

Thr Phe Ala Thr Gly Gly Ala Lys Ile His Leu Trp Asp Val Asn Arg
        195                 200                 205

Leu Lys Pro Val Ser Asp Leu Ser Trp Gly Ala Asp Asn Ile Thr Ser
    210                 215                 220

Leu Lys Phe Asn Gln Asn Glu Thr Asp Ile Leu Ala Ser Thr Gly Ser
225                 230                 235                 240

Asp Asn Ser Ile Val Leu Tyr Asp Leu Arg Thr Asn Ser Pro Thr Gln
                245                 250                 255

Lys Ile Val Gln Thr Met Arg Thr Asn Ala Ile Cys Trp Asn Pro Met
            260                 265                 270

Glu Ala Phe Asn Phe Val Thr Ala Asn Glu Asp His Asn Ala Tyr Tyr
        275                 280                 285

Tyr Asp Met Arg Asn Leu Ser Arg Ser Leu Asn Val Phe Lys Asp His
    290                 295                 300

Val Ser Ala Val Met Asp Val Asp Phe Ser Pro Thr Gly Asp Glu Ile

-continued 305 310 315 320

Val Thr Gly Ser Tyr Asp Lys Ser Ile Arg Ile Tyr Lys Thr Asn His
325 330 335

Gly His Ser Arg Glu Ile Tyr His Thr Lys Arg Met Gln His Val Phe
340 345 350

Val Lys Tyr Ser Met Asp Ser Lys Tyr Ile Ile Ser Gly Ser Asp Asp
355 360 365

Gly Asn Val Arg Leu Trp Arg Ser Lys Ala Trp Glu Arg Ser Asn Val
370 375 380

Lys Thr Thr Arg Glu Lys Asn Lys Leu Glu Tyr Asp Glu Lys Leu Lys
385 390 395 400

Glu Arg Phe Arg His Met Pro Glu Ile Lys Arg Ile Ser Arg His Arg
405 410 415

His Val Pro Gln Val Ile Lys Lys Ala Gln Glu Ile Lys Asn Ile Glu
420 425 430

Leu Ser Ser Ile Lys Arg Arg Glu Ala Asn Glu Arg Arg Thr Arg Lys
435 440 445

Asp Met Pro Tyr Ile Ser Glu Arg Lys Lys Gln Ile Val Gly Thr Val
450 455 460

His Lys Tyr Glu Asp Ser Gly Arg Asp Arg Lys Arg Arg Lys Glu Asp
465 470 475 480

Asp Lys Arg Asp Thr Gln Glu Lys
485

( 2 ) INFORMATION FOR SEQ ID NO:61:

( i ) SEQUENCE CHARACTERISTICS:
( A ) LENGTH: 423 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: STE4 - YEAST, Fig. 44

( x i ) SEQUENCE DESCRIPTION: SEQ ID NO:61:

Met Ala Ala His Gln Met Asp Ser Ile Thr Tyr Ser Asn Asn Val Thr
1 5 10 15

Gln Gln Tyr Ile Gln Pro Gln Ser Leu Gln Asp Ile Ser Ala Val Glu
20 25 30

Asp Glu Ile Gln Asn Lys Ile Glu Ala Ala Arg Gln Glu Ser Lys Gln
35 40 45

Leu His Ala Gln Ile Asn Lys Ala Lys His Lys Ile Gln Asp Ala Ser
50 55 60

Leu Phe Gln Met Ala Asn Lys Val Thr Ser Leu Thr Lys Asn Lys Ile
65 70 75 80

Asn Leu Lys Pro Asn Ile Val Leu Lys Gly His Asn Asn Lys Ile Ser
85 90 95

Asp Phe Arg Trp Ser Arg Asp Ser Lys Arg Ile Leu Ser Ala Ser Gln
100 105 110

Asp Gly Phe Met Leu Ile Trp Asp Ser Ala Ser Gly Leu Lys Gln Asn
115 120 125

Ala Ile Pro Leu Asp Ser Gln Trp Val Leu Ser Cys Ala Ile Ser Pro
130 135 140

Ser Ser Thr Leu Val Ala Ser Ala Gly Leu Asn Asn Asn Cys Thr Ile
145 150 155 160

Tyr Arg Val Ser Lys Glu Asn Arg Val Ala Gln Asn Val Ala Ser Ile
165 170 175

Phe Lys Gly His Thr Cys Tyr Ile Ser Asp Ile Glu Phe Thr Asp Asn
180 185 190

Ala His Ile Leu Thr Ala Ser Gly Asp Met Thr Cys Ala Leu Trp Asp
195 200 205

Ile Pro Lys Ala Lys Arg Val Arg Glu Tyr Ser Asp His Leu Gly Asp
210 215 220

Val Leu Ala Leu Ala Ile Pro Glu Glu Pro Asn Leu Glu Asn Ser Ser
225 230 235 240

Asn Thr Phe Ala Ser Cys Gly Ser Asp Gly Tyr Thr Tyr Ile Trp Asp
245 250 255

Ser Arg Ser Pro Ser Ala Val Gln Ser Phe Tyr Val Asn Asp Ser Asp
260 265 270

Ile Asn Ala Leu Arg Phe Phe Lys Asp Gly Met Ser Ile Val Ala Gly
275 280 285

Ser Asp Asn Gly Ala Ile Asn Met Tyr Asp Leu Arg Ser Asp Cys Ser
290 295 300

Ile Ala Thr Phe Ser Leu Phe Arg Gly Tyr Glu Glu Arg Thr Pro Thr
305 310 315 320

Pro Thr Tyr Met Ala Ala Asn Met Glu Tyr Asn Thr Ala Gln Ser Pro
325 330 335

Gln Thr Leu Lys Ser Thr Ser Ser Ser Tyr Leu Asp Asn Gln Gly Val
340 345 350

Val Ser Leu Asp Phe Ser Ala Ser Gly Arg Leu Met Tyr Ser Cys Tyr
355 360 365

Thr Asp Ile Gly Cys Val Val Trp Asp Val Leu Lys Gly Glu Ile Val
370 375 380

Gly Lys Leu Glu Gly His Gly Gly Arg Val Thr Gly Val Arg Ser Ser
385 390 395 400

Pro Asp Gly Leu Ala Val Cys Thr Gly Ser Trp Asp Ser Thr Met Lys
405 410 415

Ile Trp Ser Pro Gly Tyr Gln
420

( 2 ) INFORMATION FOR SEQ ID NO:62:

( i ) SEQUENCE CHARACTERISTICS:
( A ) LENGTH: 704 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: TRANSCRIPTION FACTOR TIIF, Fig. 45

( x i ) SEQUENCE DESCRIPTION: SEQ ID NO:62:

Met Ser Leu Glu Val Ser Asn Ile Asn Gly Gly Asn Gly Thr Gln Leu
1 5 10 15

Ser His Asp Lys Arg Glu Leu Leu Cys Leu Leu Lys Leu Ile Lys Lys
20 25 30

-continued

| | | | | | | | | | | | | | | | |
|---|---|---|---|---|---|---|---|---|---|---|---|---|---|---|---|
| Tyr | Gln | Leu | Lys | Ser | Thr | Glu | Glu | Leu | Leu | Cys | Gln | Glu | Ala | Asn | Val |
| | | 35 | | | | | 40 | | | | | 45 | | | |
| Ser | Ser | Val | Glu | Leu | Ser | Glu | Ile | Ser | Glu | Ser | Asp | Val | Gln | Gln | Val |
| | 50 | | | | | 55 | | | | | 60 | | | | |
| Leu | Gly | Ala | Val | Leu | Gly | Ala | Gly | Asp | Ala | Asn | Arg | Glu | Arg | Lys | His |
| 65 | | | | | 70 | | | | | 75 | | | | | 80 |
| Val | Gln | Ser | Pro | Ala | Gln | Gly | His | Lys | Gln | Ser | Ala | Val | Thr | Glu | Ala |
| | | | | 85 | | | | | 90 | | | | | 95 | |
| Asn | Ala | Ala | Glu | Glu | Leu | Ala | Lys | Phe | Ile | Asp | Asp | Asp | Ser | Phe | Asp |
| | | | 100 | | | | | 105 | | | | | 110 | | |
| Ala | Gln | His | Tyr | Glu | Gln | Ala | Tyr | Lys | Glu | Leu | Arg | Thr | Phe | Val | Glu |
| | | 115 | | | | | 120 | | | | | 125 | | | |
| Asp | Ser | Leu | Asp | Ile | Tyr | Lys | His | Glu | Leu | Ser | Met | Val | Leu | Tyr | Pro |
| | 130 | | | | | 135 | | | | | 140 | | | | |
| Ile | Leu | Val | Gln | Ile | Tyr | Phe | Lys | Ile | Leu | Ala | Ser | Gly | Leu | Arg | Glu |
| 145 | | | | | 150 | | | | | 155 | | | | | 160 |
| Lys | Ala | Lys | Glu | Phe | Ile | Glu | Lys | Tyr | Lys | Cys | Asp | Leu | Asp | Gly | Tyr |
| | | | | 165 | | | | | 170 | | | | | 175 | |
| Tyr | Ile | Glu | Gly | Leu | Phe | Asn | Leu | Leu | Leu | Leu | Ser | Lys | Pro | Glu | Glu |
| | | | 180 | | | | | 185 | | | | | 190 | | |
| Leu | Leu | Glu | Asn | Asp | Leu | Val | Val | Ala | Met | Glu | Gln | Asp | Lys | Phe | Val |
| | | 195 | | | | | 200 | | | | | 205 | | | |
| Ile | Arg | Met | Ser | Arg | Asp | Ser | His | Ser | Leu | Phe | Lys | Arg | His | Ile | Gln |
| | 210 | | | | | 215 | | | | | 220 | | | | |
| Asp | Arg | Arg | Gln | Glu | Val | Val | Ala | Asp | Ile | Val | Ser | Lys | Tyr | Leu | His |
| 225 | | | | | 230 | | | | | 235 | | | | | 240 |
| Phe | Asp | Thr | Tyr | Glu | Gly | Met | Ala | Arg | Asn | Lys | Leu | Gln | Cys | Val | Ala |
| | | | | 245 | | | | | 250 | | | | | 255 | |
| Thr | Ala | Gly | Ser | His | Leu | Gly | Glu | Ala | Lys | Arg | Gln | Asp | Asn | Lys | Met |
| | | | 260 | | | | | 265 | | | | | 270 | | |
| Arg | Val | Tyr | Tyr | Gly | Leu | Leu | Lys | Glu | Val | Asp | Phe | Gln | Thr | Leu | Thr |
| | | 275 | | | | | 280 | | | | | 285 | | | |
| Thr | Pro | Ala | Pro | Ala | Pro | Glu | Glu | Glu | Asp | Asp | Asp | Pro | Asp | Ala | Pro |
| | 290 | | | | | 295 | | | | | 300 | | | | |
| Asp | Arg | Pro | Lys | Lys | Lys | Lys | Pro | Lys | Lys | Asp | Pro | Leu | Leu | Ser | Lys |
| 305 | | | | | 310 | | | | | 315 | | | | | 320 |
| Lys | Ser | Lys | Ser | Asp | Pro | Asn | Ala | Pro | Ser | Ile | Asp | Arg | Ile | Pro | Leu |
| | | | | 325 | | | | | 330 | | | | | 335 | |
| Pro | Glu | Leu | Lys | Asp | Ser | Asp | Lys | Leu | Leu | Lys | Leu | Lys | Ala | Leu | Arg |
| | | | 340 | | | | | 345 | | | | | 350 | | |
| Glu | Ala | Ser | Lys | Arg | Leu | Ala | Leu | Ser | Lys | Asp | Gln | Leu | Pro | Ser | Ala |
| | | 355 | | | | | 360 | | | | | 365 | | | |
| Val | Phe | Tyr | Thr | Val | Leu | Asn | Ser | His | Gln | Gly | Val | Thr | Cys | Ala | Glu |
| | 370 | | | | | 375 | | | | | 380 | | | | |
| Ile | Ser | Asp | Asp | Ser | Thr | Met | Leu | Ala | Cys | Gly | Phe | Gly | Asp | Ser | Ser |
| 385 | | | | | 390 | | | | | 395 | | | | | 400 |
| Val | Arg | Ile | Trp | Ser | Leu | Thr | Pro | Ala | Asn | Val | Arg | Thr | Leu | Lys | Asp |
| | | | | 405 | | | | | 410 | | | | | 415 | |
| Ala | Asp | Ser | Leu | Arg | Glu | Leu | Asp | Lys | Glu | Ser | Ala | Asp | Ile | Asn | Val |
| | | | 420 | | | | | 425 | | | | | 430 | | |
| Arg | Met | Leu | Asp | Asp | Arg | Ser | Gly | Glu | Val | Thr | Arg | Ser | Leu | Met | Gly |
| | | 435 | | | | | 440 | | | | | 445 | | | |
| His | Thr | Gly | Pro | Val | Tyr | Arg | Cys | Ala | Phe | Ala | Pro | Glu | Met | Asn | Leu |
| | 450 | | | | | 455 | | | | | 460 | | | | |

-continued

Leu Leu Ser Cys Ser Glu Asp Ser Thr Ile Arg Leu Trp Ser Leu Leu
465 470 475 480

Thr Trp Ser Cys Val Val Thr Tyr Arg Gly His Val Tyr Pro Val Trp
485 490 495

Asp Val Arg Phe Ala Pro His Gly Tyr Tyr Phe Val Ser Cys Ser Tyr
500 505 510

Asp Lys Thr Ala Arg Leu Trp Ala Thr Asp Ser Asn Gln Ala Leu Arg
515 520 525

Val Phe Val Gly His Leu Ser Asp Val Asp Cys Val Gln Phe His Pro
530 535 540

Asn Ser Asn Tyr Val Ala Thr Gly Ser Ser Asp Arg Thr Val Arg Leu
545 550 555 560

Trp Asp Asn Met Thr Gly Gln Ser Val Arg Leu Met Thr Gly His Lys
565 570 575

Gly Ser Val Ser Ser Leu Ala Phe Ser Ala Cys Gly Arg Tyr Leu Ala
580 585 590

Ser Gly Ser Val Asp His Asn Ile Ile Ile Trp Asp Leu Ser Asn Gly
595 600 605

Ser Leu Val Thr Thr Leu Leu Arg His Thr Ser Thr Val Thr Thr Ile
610 615 620

Thr Phe Ser Arg Asp Gly Thr Val Leu Ala Ala Ala Gly Leu Asp Asn
625 630 635 640

Asn Leu Thr Leu Trp Asp Phe His Lys Val Thr Glu Asp Tyr Ile Ser
645 650 655

Asn His Ile Thr Val Ser His His Gln Asp Glu Asn Asp Glu Asp Val
660 665 670

Tyr Leu Met Arg Thr Phe Pro Ser Lys Asn Ser Pro Phe Val Ser Leu
675 680 685

His Phe Thr Arg Arg Asn Leu Leu Met Cys Val Gly Leu Phe Lys Ser
690 695 700

( 2 ) INFORMATION FOR SEQ ID NO:63:

( i ) SEQUENCE CHARACTERISTICS:
( A ) LENGTH: 713 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: TUP1, Fig. 46

( x i ) SEQUENCE DESCRIPTION: SEQ ID NO:63:

Met Thr Ala Ser Val Ser Asn Thr Gln Asn Lys Leu Asn Glu Leu Leu
1 5 10 15

Asp Ala Ile Arg Gln Glu Phe Leu Gln Val Ser Gln Glu Ala Asn Thr
20 25 30

Tyr Arg Leu Gln Asn Gln Lys Asp Tyr Asp Phe Lys Met Asn Gln Gln
35 40 45

Leu Ala Glu Met Gln Gln Ile Arg Asn Thr Val Tyr Glu Leu Glu Leu
50 55 60

Thr His Arg Lys Met Lys Asp Ala Tyr Glu Ala Glu Ile Lys His Leu
65 70 75 80

-continued

Lys Leu Gly Leu Glu Gln Arg Asp His Gln Ile Ala Ser Leu Thr Val
85 90 95

Gln Gln Gln Gln Gln Gln Gln Gln Gln Gln Gln Val Gln Gln His Leu
100 105 110

Gln Gln Gln Gln Gln Gln Leu Ala Ala Ala Ser Ala Ser Val Pro Val
115 120 125

Ala Gln Gln Pro Pro Ala Thr Thr Ser Ala Thr Ala Thr Pro Ala Ala
130 135 140

Asn Thr Thr Thr Gly Ser Pro Ser Ala Phe Pro Val Gln Ala Ser Arg
145 150 155 160

Pro Asn Leu Val Gly Ser Gln Leu Pro Thr Thr Thr Leu Pro Val Val
165 170 175

Ser Ser Asn Ala Gln Gln Gln Leu Pro Gln Gln Gln Leu Gln Gln Gln
180 185 190

Gln Leu Gln Gln Gln Gln Pro Pro Pro Gln Val Ser Val Ala Pro Leu
195 200 205

Ser Asn Thr Ala Ile Asn Gly Ser Pro Thr Ser Lys Glu Thr Thr Thr
210 215 220

Leu Pro Ser Val Lys Ala Pro Glu Ser Thr Leu Lys Glu Thr Glu Pro
225 230 235 240

Glu Asn Asn Asn Thr Ser Lys Ile Asn Asp Thr Gly Ser Ala Thr Thr
245 250 255

Ala Thr Thr Thr Thr Ala Thr Glu Thr Glu Ile Lys Pro Lys Glu Glu
260 265 270

Asp Ala Thr Pro Ala Ser Leu His Gln Asp His Tyr Leu Val Pro Tyr
275 280 285

Asn Gln Arg Ala Asn His Ser Lys Pro Ile Pro Pro Phe Leu Leu Asp
290 295 300

Leu Asp Ser Gln Ser Val Pro Asp Ala Leu Lys Lys Gln Thr Asn Asp
305 310 315 320

Tyr Tyr Ile Leu Tyr Asn Pro Ala Leu Pro Arg Glu Ile Asp Val Glu
325 330 335

Leu His Lys Ser Leu Asp His Thr Ser Val Val Cys Cys Val Lys Phe
340 345 350

Ser Asn Asp Gly Glu Tyr Leu Ala Thr Gly Cys Asn Lys Thr Thr Gln
355 360 365

Val Tyr Arg Val Ser Asp Gly Ser Leu Val Ala Arg Leu Ser Asp Asp
370 375 380

Ser Ala Ala Asn Asn His Arg Asn Ser Ile Thr Glu Asn Asn Thr Thr
385 390 395 400

Thr Ser Thr Asp Asn Asn Thr Met Thr Thr Thr Thr Thr Thr Thr Ile
405 410 415

Thr Thr Thr Ala Met Thr Ser Ala Ala Glu Leu Ala Lys Asp Val Glu
420 425 430

Asn Leu Asn Thr Ser Ser Ser Pro Ser Ser Asp Leu Tyr Ile Arg Ser
435 440 445

Val Cys Phe Ser Pro Asp Gly Lys Phe Leu Ala Thr Gly Ala Glu Asp
450 455 460

Arg Leu Ile Arg Ile Trp Asp Ile Glu Asn Arg Lys Ile Val Met Ile
465 470 475 480

Leu Gln Gly His Glu Gln Asp Ile Tyr Ser Leu Asp Tyr Phe Pro Ser
485 490 495

Gly Asp Lys Leu Val Ser Gly Ser Gly Asp Arg Thr Val Arg Ile Trp
500 505 510

-continued

Asp Leu Arg Thr Gly Gln Cys Ser Leu Thr Leu Ser Ile Glu Asp Gly
515 520 525

Val Thr Thr Val Ala Val Ser Pro Gly Asp Gly Lys Tyr Ile Ala Ala
530 535 540

Gly Ser Leu Asp Arg Ala Val Arg Val Trp Asp Ser Glu Thr Gly Phe
545 550 555 560

Leu Val Glu Arg Leu Asp Ser Glu Asn Glu Ser Gly Thr Gly His Lys
565 570 575

Asp Ser Val Tyr Ser Val Val Phe Thr Arg Asp Gly Gln Ser Val Val
580 585 590

Ser Gly Ser Leu Asp Arg Ser Val Lys Leu Trp Asn Leu Gln Asn Ala
595 600 605

Asn Asn Lys Ser Asp Ser Lys Thr Pro Asn Ser Gly Thr Cys Glu Val
610 615 620

Thr Tyr Ile Gly His Lys Asp Phe Val Leu Ser Val Ala Thr Thr Gln
625 630 635 640

Asn Asp Glu Tyr Ile Leu Ser Gly Ser Lys Asp Arg Gly Val Leu Phe
645 650 655

Trp Asp Lys Lys Ser Gly Asn Pro Leu Leu Met Leu Gln Gly His Arg
660 665 670

Asn Ser Val Ile Ser Val Ala Val Ala Asn Gly Ser Ser Leu Gly Pro
675 680 685

Glu Tyr Asn Val Phe Ala Thr Gly Ser Gly Asp Cys Lys Ala Arg Ile
690 695 700

Trp Lys Tyr Lys Lys Ile Ala Pro Asn
705 710

( 2 ) INFORMATION FOR SEQ ID NO:64:

( i ) SEQUENCE CHARACTERISTICS:
( A ) LENGTH: 798 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG, Fig. 47

( x i ) SEQUENCE DESCRIPTION: SEQ ID NO:64:

Met Ser Gln Lys Gln Ser Thr Asn Gln Asn Gln Asn Gly Thr His Gln
1 5 10 15

Pro Gln Pro Val Lys Asn Gln Arg Thr Asn Asn Ala Ala Gly Ala Asn
20 25 30

Ser Gly Gln Gln Pro Gln Gln Gln Ser Gln Gly Gln Ser Gln Gln Gln
35 40 45

Gly Arg Ser Asn Gly Pro Phe Ser Ala Ser Asp Leu Asn Arg Ile Val
50 55 60

Leu Glu Tyr Leu Asn Lys Lys Gly Tyr His Arg Thr Glu Ala Met Leu
65 70 75 80

Arg Ala Glu Ser Gly Arg Thr Leu Thr Pro Gln Asn Lys Gln Ser Pro
85 90 95

Ala Asn Thr Lys Thr Gly Lys Phe Pro Glu Gln Ser Ser Ile Pro Pro
100 105 110

-continued

| | | | | | | | | | | | | | | | |
|---|---|---|---|---|---|---|---|---|---|---|---|---|---|---|---|
| Asn | Pro | Gly | Lys | Thr | Ala | Lys | Pro | Ile | Ser | Asn | Pro | Thr | Asn | Leu | Ser |
| | | 115 | | | | | 120 | | | | | 125 | | | |
| Ser | Lys | Arg | Asp | Ala | Glu | Gly | Gly | Ile | Val | Ser | Ser | Gly | Arg | Leu | Glu |
| | 130 | | | | | 135 | | | | | 140 | | | | |
| Gly | Leu | Asn | Ala | Pro | Glu | Asn | Tyr | Ile | Arg | Ala | Tyr | Ser | Met | Leu | Lys |
| 145 | | | | | 150 | | | | | 155 | | | | | 160 |
| Asn | Trp | Val | Asp | Ser | Ser | Leu | Glu | Ile | Tyr | Lys | Pro | Glu | Leu | Ser | Tyr |
| | | | | 165 | | | | | 170 | | | | | 175 | |
| Ile | Met | Tyr | Pro | Ile | Phe | Ile | Tyr | Leu | Phe | Leu | Asn | Leu | Val | Ala | Lys |
| | | | 180 | | | | | 185 | | | | | 190 | | |
| Asn | Pro | Val | Tyr | Ala | Arg | Arg | Phe | Phe | Asp | Arg | Phe | Ser | Pro | Asp | Phe |
| | | 195 | | | | | 200 | | | | | 205 | | | |
| Lys | Asp | Phe | His | Gly | Ser | Glu | Ile | Asn | Arg | Leu | Phe | Ser | Val | Asn | Ser |
| | 210 | | | | | 215 | | | | | 220 | | | | |
| Ile | Asp | His | Ile | Lys | Glu | Asn | Glu | Val | Ala | Ser | Ala | Phe | Gln | Ser | His |
| 225 | | | | | 230 | | | | | 235 | | | | | 240 |
| Lys | Tyr | Arg | Ile | Thr | Met | Ser | Lys | Thr | Thr | Leu | Asn | Leu | Leu | Leu | Tyr |
| | | | | 245 | | | | | 250 | | | | | 255 | |
| Phe | Leu | Asn | Glu | Asn | Glu | Ser | Ile | Gly | Gly | Ser | Leu | Ile | Ile | Ser | Val |
| | | | 260 | | | | | 265 | | | | | 270 | | |
| Ile | Asn | Gln | His | Leu | Asp | Pro | Asn | Ile | Val | Glu | Ser | Val | Thr | Ala | Arg |
| | | 275 | | | | | 280 | | | | | 285 | | | |
| Glu | Lys | Leu | Ala | Asp | Gly | Ile | Lys | Val | Leu | Ser | Asp | Ser | Glu | Asn | Gly |
| | 290 | | | | | 295 | | | | | 300 | | | | |
| Asn | Gly | Lys | Gln | Asn | Leu | Glu | Met | Asn | Ser | Val | Pro | Val | Lys | Leu | Gly |
| 305 | | | | | 310 | | | | | 315 | | | | | 320 |
| Pro | Phe | Pro | Lys | Asp | Glu | Glu | Phe | Val | Lys | Glu | Ile | Glu | Thr | Glu | Leu |
| | | | | 325 | | | | | 330 | | | | | 335 | |
| Lys | Ile | Lys | Asp | Asp | Gln | Glu | Lys | Gln | Leu | Asn | Gln | Gln | Thr | Ala | Gly |
| | | | 340 | | | | | 345 | | | | | 350 | | |
| Asp | Asn | Tyr | Ser | Gly | Ala | Asn | Asn | Arg | Thr | Leu | Leu | Gln | Glu | Tyr | Lys |
| | | 355 | | | | | 360 | | | | | 365 | | | |
| Ala | Met | Asn | Asn | Glu | Lys | Phe | Lys | Asp | Asn | Thr | Gly | Asp | Asp | Asp | Lys |
| | 370 | | | | | 375 | | | | | 380 | | | | |
| Asp | Lys | Ile | Lys | Asp | Lys | Ile | Ala | Lys | Asp | Glu | Glu | Lys | Lys | Glu | Ser |
| 385 | | | | | 390 | | | | | 395 | | | | | 400 |
| Glu | Leu | Lys | Val | Asp | Gly | Glu | Lys | Lys | Asp | Ser | Asn | Leu | Ser | Ser | Pro |
| | | | | 405 | | | | | 410 | | | | | 415 | |
| Ala | Arg | Asp | Ile | Leu | Pro | Leu | Pro | Pro | Lys | Thr | Ala | Leu | Asp | Leu | Lys |
| | | | 420 | | | | | 425 | | | | | 430 | | |
| Leu | Glu | Ile | Gln | Lys | Val | Lys | Glu | Ser | Arg | Asp | Ala | Ile | Lys | Leu | Asp |
| | | 435 | | | | | 440 | | | | | 445 | | | |
| Asn | Leu | Gln | Leu | Ala | Leu | Pro | Ser | Val | Cys | Met | Tyr | Thr | Phe | Gln | Asn |
| | 450 | | | | | 455 | | | | | 460 | | | | |
| Thr | Asn | Lys | Asp | Met | Ser | Cys | Leu | Asp | Phe | Ser | Asp | Asp | Cys | Arg | Ile |
| 465 | | | | | 470 | | | | | 475 | | | | | 480 |
| Ala | Ala | Ala | Gly | Phe | Gln | Asp | Ser | Tyr | Ile | Lys | Ile | Trp | Ser | Leu | Asp |
| | | | | 485 | | | | | 490 | | | | | 495 | |
| Gly | Ser | Ser | Leu | Asn | Asn | Pro | Asn | Ile | Ala | Leu | Asn | Asn | Asn | Asp | Lys |
| | | | 500 | | | | | 505 | | | | | 510 | | |
| Asp | Glu | Asp | Pro | Thr | Cys | Lys | Thr | Leu | Val | Gly | His | Ser | Gly | Thr | Val |
| | | 515 | | | | | 520 | | | | | 525 | | | |
| Tyr | Ser | Thr | Ser | Phe | Ser | Pro | Asp | Asn | Lys | Tyr | Leu | Leu | Ser | Gly | Ser |
| | 530 | | | | | 535 | | | | | 540 | | | | |

-continued

Glu Asp Lys Thr Val Arg Leu Trp Ser Met Asp Thr His Thr Ala Leu
545 550 555 560

Val Ser Tyr Lys Gly His Asn His Pro Val Trp Asp Val Ser Phe Ser
565 570 575

Pro Leu Gly His Tyr Phe Ala Thr Ala Ser His Asp Gln Thr Ala Arg
580 585 590

Leu Trp Ser Cys Asp His Ile Tyr Pro Leu Arg Ile Phe Ala Gly His
595 600 605

Leu Asn Asp Val Asp Cys Val Ser Phe His Pro Asn Gly Cys Tyr Val
610 615 620

Phe Thr Gly Ser Ser Asp Lys Thr Cys Arg Met Trp Asp Val Ser Thr
625 630 635 640

Gly Asp Ser Val Arg Leu Phe Leu Gly His Thr Ala Pro Val Ile Ser
645 650 655

Ile Ala Val Cys Pro Asp Gly Arg Trp Leu Ser Thr Gly Ser Glu Asp
660 665 670

Gly Ile Ile Asn Val Trp Asp Ile Gly Thr Gly Lys Arg Leu Lys Gln
675 680 685

Met Arg Gly His Gly Lys Asn Ala Ile Tyr Ser Leu Ser Tyr Ser Lys
690 695 700

Glu Gly Asn Val Leu Ile Ser Gly Gly Ala Asp His Thr Val Arg Val
705 710 715 720

Trp Asp Leu Lys Lys Ala Thr Thr Glu Pro Ser Ala Glu Pro Asp Glu
725 730 735

Pro Phe Ile Gly Tyr Leu Gly Asp Val Thr Ala Ser Ile Asn Gln Asp
740 745 750

Ile Lys Glu Tyr Gly Arg Arg Arg Thr Val Ile Pro Thr Ser Asp Leu
755 760 765

Val Ala Ser Phe Tyr Thr Lys Lys Thr Pro Val Phe Lys Val Lys Phe
770 775 780

Ser Arg Ser Asn Leu Ala Leu Ala Gly Gly Ala Phe Arg Pro
785 790 795

( 2 ) INFORMATION FOR SEQ ID NO:65:

( i ) SEQUENCE CHARACTERISTICS:
( A ) LENGTH: 439 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: YCU7, Fig. 48

( x i ) SEQUENCE DESCRIPTION: SEQ ID NO:65:

Met Val Arg Arg Phe Arg Gly Lys Glu Leu Ala Ala Thr Thr Phe Asn
1 5 10 15

Gly His Arg Asp Tyr Val Met Gly Ala Phe Phe Ser His Asp Gln Glu
20 25 30

Lys Ile Tyr Thr Val Ser Lys Asp Gly Ala Val Phe Val Trp Glu Phe
35 40 45

Thr Lys Arg Pro Ser Asp Asp Asp Asp Asn Glu Ser Glu Asp Asp Asp
50 55 60

-continued

```
Lys Gln Glu Glu Val Asp Ile Ser Lys Tyr Ser Trp Arg Ile Thr Lys
65                  70                  75                  80

Lys His Phe Phe Tyr Ala Asn Gln Ala Lys Val Lys Cys Val Thr Phe
                85                  90                  95

His Pro Ala Thr Arg Leu Leu Ala Val Gly Phe Thr Ser Gly Glu Phe
            100                 105                 110

Arg Leu Tyr Asp Leu Pro Asp Phe Thr Leu Ile Gln Gln Leu Ser Met
        115                 120                 125

Gly Gln Asn Pro Val Asn Thr Val Ser Val Asn Gln Thr Gly Glu Trp
    130                 135                 140

Leu Ala Phe Gly Ser Ser Lys Leu Gly Gln Leu Leu Val Tyr Glu Trp
145                 150                 155                 160

Gln Ser Glu Ser Tyr Ile Leu Lys Gln Gln Gly His Phe Asp Ser Thr
                165                 170                 175

Asn Ser Leu Ala Tyr Ser Pro Asp Gly Ser Arg Val Val Thr Ala Ser
            180                 185                 190

Glu Asp Gly Lys Ile Lys Val Trp Asp Ile Thr Ser Gly Phe Cys Leu
        195                 200                 205

Ala Thr Phe Glu Glu His Thr Ser Ser Val Thr Ala Val Gln Phe Ala
    210                 215                 220

Lys Arg Gly Gln Val Met Phe Ser Ser Ser Leu Asp Gly Thr Val Arg
225                 230                 235                 240

Ala Trp Asp Leu Ile Arg Tyr Arg Asn Phe Arg Thr Phe Thr Gly Thr
                245                 250                 255

Glu Arg Ile Gln Phe Asn Cys Leu Ala Val Asp Pro Ser Gly Glu Val
            260                 265                 270

Val Cys Ala Gly Ser Leu Asp Asn Phe Asp Ile His Val Trp Ser Val
        275                 280                 285

Gln Thr Gly Gln Leu Leu Asp Ala Leu Ser Gly His Glu Gly Pro Val
    290                 295                 300

Ser Cys Leu Ser Phe Ser Gln Glu Asn Ser Val Leu Ala Ser Ala Ser
305                 310                 315                 320

Trp Asp Lys Thr Ile Arg Ile Trp Ser Ile Phe Gly Arg Ser Gln Gln
                325                 330                 335

Val Glu Pro Ile Glu Val Tyr Ser Asp Val Leu Ala Leu Ser Met Arg
            340                 345                 350

Pro Asp Gly Lys Glu Val Ala Val Ser Thr Leu Lys Gly Gln Ile Ser
        355                 360                 365

Ile Phe Asn Ile Glu Asp Ala Lys Gln Val Gly Asn Ile Asp Cys Arg
    370                 375                 380

Lys Asp Ile Ile Ser Gly Arg Phe Asn Gln Asp Arg Phe Thr Ala Lys
385                 390                 395                 400

Ile Leu Asn Asp Pro Asn Phe Leu Leu Gln Tyr Ile Thr Val Leu Met
                405                 410                 415

Val Trp Leu Leu Trp Leu Val Val Ile Ile Thr Pro Phe Val Tyr Met
            420                 425                 430

Met Phe Gln Met Lys Ser Cys
        435
```

( 2 ) INFORMATION FOR SEQ ID NO:66:

( i ) SEQUENCE CHARACTERISTICS:
( A ) LENGTH: 514 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: YCW2 PROTEIN, Fig. 49

( x i ) SEQUENCE DESCRIPTION: SEQ ID NO:66:

```
Met Ser Thr Leu Ile Pro Pro Pro Ser Lys Lys Gln Lys Lys Glu Ala
1               5                   10                  15

Gln Leu Pro Arg Glu Val Ala Ile Ile Pro Lys Asp Leu Pro Asn Val
            20                  25                  30

Ser Ile Lys Phe Gln Ala Leu Asp Thr Gly Asp Asn Val Gly Gly Ala
        35                  40                  45

Leu Arg Val Pro Gly Ala Ile Ser Glu Lys Gln Leu Glu Glu Leu Leu
    50                  55                  60

Asn Gln Leu Asn Gly Thr Ser Asp Asp Pro Val Pro Tyr Thr Phe Ser
65                  70                  75                  80

Cys Thr Ile Gln Gly Lys Lys Ala Ser Asp Pro Val Lys Thr Ile Asp
                85                  90                  95

Ile Thr Asp Asn Leu Tyr Ser Ser Leu Ile Lys Pro Gly Tyr Asn Ser
            100                 105                 110

Thr Glu Asp Gln Ile Thr Leu Leu Tyr Thr Pro Arg Ala Val Phe Lys
        115                 120                 125

Val Lys Pro Val Thr Arg Ser Ser Ser Ala Ile Ala Gly His Gly Ser
    130                 135                 140

Thr Ile Leu Cys Ser Ala Phe Ala Pro His Thr Ser Ser Arg Met Val
145                 150                 155                 160

Thr Gly Ala Gly Asp Asn Thr Ala Arg Ile Trp Asp Cys Asp Thr Gln
                165                 170                 175

Thr Pro Met His Thr Leu Lys Gly His Tyr Asn Trp Val Leu Cys Val
            180                 185                 190

Ser Trp Ser Pro Asp Gly Glu Val Ile Ala Thr Gly Ser Met Asp Asn
        195                 200                 205

Thr Ile Arg Leu Trp Asp Pro Lys Ser Gly Gln Cys Leu Gly Asp Ala
    210                 215                 220

Leu Arg Gly His Ser Lys Trp Ile Thr Ser Leu Ser Trp Glu Pro Ile
225                 230                 235                 240

His Leu Val Lys Pro Gly Ser Lys Pro Arg Leu Ala Ser Ser Ser Lys
                245                 250                 255

Asp Gly Thr Ile Lys Ile Trp Asp Thr Val Ser Arg Val Cys Gln Tyr
            260                 265                 270

Thr Met Ser Gly His Thr Asn Ser Val Ser Cys Val Lys Trp Gly Gly
        275                 280                 285

Gln Gly Leu Leu Tyr Ser Gly Ser His Asp Arg Thr Val Arg Val Trp
    290                 295                 300

Asp Ile Asn Ser Gln Gly Arg Cys Ile Asn Ile Leu Lys Ser His Ala
305                 310                 315                 320

His Trp Val Asn His Leu Ser Leu Ser Thr Asp Tyr Ala Leu Arg Ile
                325                 330                 335

Gly Ala Phe Asp His Thr Gly Lys Lys Pro Ser Thr Pro Glu Glu Ala
            340                 345                 350

Gln Lys Lys Ala Leu Glu Asn Tyr Glu Lys Ile Cys Lys Lys Asn Gly
        355                 360                 365
```

Asn Ser Glu Glu Met Met Val Thr Ala Ser Asp Asp Tyr Thr Met Phe
370 375 380

Leu Trp Asn Pro Leu Lys Ser Thr Lys Pro Ile Ala Arg Met Thr Gly
385 390 395 400

His Gln Lys Leu Val Asn His Val Ala Phe Ser Pro Asp Gly Arg Tyr
405 410 415

Ile Val Ser Ala Ser Phe Asp Asn Ser Ile Lys Leu Trp Asp Gly Arg
420 425 430

Asp Gly Lys Phe Ile Ser Thr Phe Arg Gly His Ile Ala Ser Val Tyr
435 440 445

Gln Val Ala Trp Ser Ser Asp Cys Arg Leu Leu Val Ser Cys Ser Lys
450 455 460

Asp Thr Thr Leu Lys Val Trp Asp Val Arg Thr Arg Lys Leu Ser Val
465 470 475 480

Asp Leu Pro Gly Ile Lys Thr Lys Leu Tyr Val Asp Trp Ser Val Asp
485 490 495

Gly Lys Arg Val Cys Ser Gly Gly Lys Asp Lys Met Val Arg Leu Trp
500 505 510

Thr His ( 2 ) INFORMATION FOR SEQ ID NO:67:

( i ) SEQUENCE CHARACTERISTICS:
( A ) LENGTH: 852 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: YKL525, Fig. 50

( x i ) SEQUENCE DESCRIPTION: SEQ ID NO:67:

Met Phe Lys Ser Lys Thr Ser Thr Leu Ser Tyr Asp Glu Thr Pro Asn
1 5 10 15

Ser Asn Glu Gly Asp Arg Asn Ala Thr Pro Val Asn Pro Lys Glu Lys
20 25 30

Ser Gln Thr Lys His Leu Asn Ile Pro Gly Asp Arg Ser Arg His Ser
35 40 45

Ser Ile Ala Asp Ser Lys Arg Ser Ser Ser Arg Tyr Asp Gly Gly Tyr
50 55 60

Ser Ala Asp Ile Ile Pro Ala Gln Leu Arg Phe Ile Asp Asn Ile Asp
65 70 75 80

Tyr Gly Thr Arg Leu Arg Lys Thr Leu His Arg Asn Ser Val Val Ser
85 90 95

Asn Gly Tyr Asn Lys Leu Ser Glu Asn Asp Arg Trp Tyr Phe Asp Leu
100 105 110

Phe Asp Arg Lys Tyr Phe Glu Asn Tyr Leu Glu Glu Pro Thr Tyr Ile
115 120 125

Lys Ile Phe Lys Lys Lys Glu Gly Leu Glu Gln Phe Asp Arg Met Phe
130 135 140

Leu Ala Gln Glu Leu Lys Ile Pro Asp Val Tyr Lys Ser Thr Thr Tyr
145 150 155 160

Gln Gly Glu Pro Ala Val Ala Asn Ser Glu Leu Phe Lys Asn Ser Ile
165 170 175

-continued

Cys Cys Cys Thr Phe Ser His Asp Gly Lys Tyr Met Val Ile Gly Cys
180 185 190

Lys Asp Gly Ser Leu His Leu Trp Lys Val Ile Asn Ser Pro Val Lys
195 200 205

Arg Ser Glu Met Gly Arg Ser Glu Lys Ser Val Ser Ala Ser Arg Ala
210 215 220

Asn Ser Leu Lys Ile Gln Arg His Leu Ala Ser Ile Ser Ser His Asn
225 230 235 240

Gly Ser Ile Ser Ser Asn Asp Leu Lys Pro Ser Asp Gln Phe Glu Gly
245 250 255

Pro Ser Lys Gln Leu His Leu Tyr Ala Pro Val Phe Tyr Ser Asp Val
260 265 270

Phe Arg Val Phe Met Glu His Ala Leu Asp Ile Leu Asp Ala Asn Trp
275 280 285

Ser Lys Asn Gly Phe Leu Ile Thr Ala Ser Met Asp Lys Thr Ala Lys
290 295 300

Leu Trp His Pro Glu Arg Lys Tyr Ser Leu Lys Thr Phe Val His Pro
305 310 315 320

Asp Phe Val Thr Ser Ala Ile Phe Phe Pro Asn Asp Asp Arg Phe Ile
325 330 335

Ile Thr Gly Cys Leu Asp His Arg Cys Arg Leu Trp Ser Ile Leu Asp
340 345 350

Asn Glu Val Ser Tyr Ala Phe Asp Cys Lys Asp Leu Ile Thr Ser Leu
355 360 365

Thr Leu Ser Pro Pro Gly Gly Glu Tyr Thr Ile Ile Gly Thr Phe Asn
370 375 380

Gly Tyr Ile Tyr Val Leu Leu Thr His Gly Leu Lys Phe Val Ser Ser
385 390 395 400

Phe His Val Ser Asp Lys Ser Thr Gln Gly Thr Thr Lys Asn Ser Phe
405 410 415

His Pro Ser Ser Glu Tyr Gly Lys Val Gln His Gly Pro Arg Ile Thr
420 425 430

Gly Leu Gln Cys Phe Phe Ser Lys Val Asp Lys Asn Leu Arg Leu Ile
435 440 445

Val Thr Thr Asn Asp Ser Lys Ile Gln Ile Phe Asp Leu Asn Glu Lys
450 455 460

Lys Pro Leu Glu Leu Phe Lys Gly Phe Gln Ser Gly Ser Ser Arg His
465 470 475 480

Arg Gly Gln Phe Leu Met Met Lys Asn Glu Pro Val Val Phe Thr Gly
485 490 495

Ser Asp Asp His Trp Phe Tyr Thr Trp Lys Met Gln Ser Phe Asn Leu
500 505 510

Ser Ala Glu Met Asn Cys Thr Ala Pro His Arg Lys Lys Arg Leu Ser
515 520 525

Gly Ser Met Ser Leu Lys Gly Leu Leu Arg Ile Val Ser Asn Lys Ser
530 535 540

Thr Asn Asp Glu Cys Leu Thr Glu Thr Ser Asn Gln Ser Ser Ser His
545 550 555 560

Thr Phe Thr Asn Ser Ser Lys Asn Val Leu Gln Thr Gln Thr Val Gly
565 570 575

Ser Gln Ala Ile Lys Asn Asn His Tyr Ile Ser Phe His Ala His Asn
580 585 590

Ser Pro Val Thr Cys Ala Ser Ile Ala Pro Asp Val Ala Ile Lys Asn

-continued 595 600 605

Leu Ser Leu Ser Asn Asp Leu Ile Phe Glu Leu Thr Ser Gln Tyr Phe
610 615 620

Lys Glu Met Gly Gln Asn Tyr Ser Glu Ser Lys Glu Thr Cys Asp Asn
625 630 635 640

Lys Pro Asn His Pro Val Thr Glu Thr Gly Gly Phe Ser Ser Asn Leu
645 650 655

Ser Asn Val Val Asn Asn Val Gly Thr Ile Leu Ile Thr Thr Asp Ser
660 665 670

Gln Gly Leu Ile Arg Val Phe Arg Thr Asp Ile Leu Pro Glu Ile Arg
675 680 685

Lys Lys Ile Ile Glu Lys Phe His Glu Tyr Asn Leu Phe His Leu Glu
690 695 700

Ala Ala Gly Lys Ile Asn Asn His Asn Asn Asp Ser Ile Leu Glu Asn
705 710 715 720

Arg Met Asp Glu Arg Ser Ser Thr Glu Asp Asn Glu Phe Ser Thr Thr
725 730 735

Pro Pro Ser Asn Thr His Asn Ser Arg Pro Ser His Asp Phe Cys Glu
740 745 750

Leu His Pro Asn Asn Ser Pro Val Ile Ser Gly Met Pro Ser Arg Ala
755 760 765

Ser Ala Ile Phe Lys Asn Ser Ile Phe Asn Lys Ser Asn Gly Ser Phe
770 775 780

Ile Ser Leu Lys Ser Arg Ser Glu Ser Thr Ser Ser Thr Val Phe Gly
785 790 795 800

Pro His Asp Ile Pro Arg Val Ser Thr Thr Tyr Pro Lys Leu Lys Cys
805 810 815

Asp Val Cys Asn Gly Ser Asn Phe Glu Cys Ala Ser Lys Asn Pro Ile
820 825 830

Ala Gly Gly Asp Ser Gly Phe Thr Cys Ala Asp Cys Gly Thr Ile Leu
835 840 845

Asn Asn Phe Arg
850

( 2 ) INFORMATION FOR SEQ ID NO:68:

( i ) SEQUENCE CHARACTERISTICS:
( A ) LENGTH: 798 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: yrb 1410 yeast, Fig. 51

( x i ) SEQUENCE DESCRIPTION: SEQ ID NO:68:

Met Ser Gln Lys Gln Ser Thr Asn Gln Asn Gln Asn Gly Thr His Gln
1 5 10 15

Pro Gln Pro Val Lys Asn Gln Arg Thr Asn Asn Ala Ala Gly Ala Asn
20 25 30

Ser Gly Gln Gln Pro Gln Gln Gln Ser Gln Gly Gln Ser Gln Gln Gln
35 40 45

Gly Arg Ser Asn Gly Pro Phe Ser Ala Ser Asp Leu Asn Arg Ile Val
50 55 60

-continued

Leu Glu Tyr Leu Asn Lys Lys Gly Tyr His Arg Thr Glu Ala Met Leu
65 70 75 80

Arg Ala Glu Ser Gly Arg Thr Leu Thr Pro Gln Asn Lys Gln Ser Pro
85 90 95

Ala Asn Thr Lys Thr Gly Lys Phe Pro Glu Gln Ser Ser Ile Pro Pro
100 105 110

Asn Pro Gly Lys Thr Ala Lys Pro Ile Ser Asn Pro Thr Asn Leu Ser
115 120 125

Ser Lys Arg Asp Ala Glu Gly Gly Ile Val Ser Ser Gly Arg Leu Glu
130 135 140

Gly Leu Asn Ala Pro Glu Asn Tyr Ile Arg Ala Tyr Ser Met Leu Lys
145 150 155 160

Asn Trp Val Asp Ser Ser Leu Glu Ile Tyr Lys Pro Glu Leu Ser Tyr
165 170 175

Ile Met Tyr Pro Ile Phe Ile Tyr Leu Phe Leu Asn Leu Val Ala Lys
180 185 190

Asn Pro Val Tyr Ala Arg Arg Phe Phe Asp Arg Phe Ser Pro Asp Phe
195 200 205

Lys Asp Phe His Gly Ser Glu Ile Asn Arg Leu Phe Ser Val Asn Ser
210 215 220

Ile Asp His Ile Lys Glu Asn Glu Val Ala Ser Ala Phe Gln Ser His
225 230 235 240

Lys Tyr Arg Ile Thr Met Ser Lys Thr Thr Leu Asn Leu Leu Leu Tyr
245 250 255

Phe Leu Asn Glu Asn Glu Ser Ile Gly Gly Ser Leu Ile Ile Ser Val
260 265 270

Ile Asn Gln His Leu Asp Pro Asn Ile Val Glu Ser Val Thr Ala Arg
275 280 285

Glu Lys Leu Ala Asp Gly Ile Lys Val Leu Ser Asp Ser Glu Asn Gly
290 295 300

Asn Gly Lys Gln Asn Leu Glu Met Asn Ser Val Pro Val Lys Leu Gly
305 310 315 320

Pro Phe Pro Lys Asp Glu Glu Phe Val Lys Glu Ile Glu Thr Glu Leu
325 330 335

Lys Ile Lys Asp Asp Gln Glu Lys Gln Leu Asn Gln Gln Thr Ala Gly
340 345 350

Asp Asn Tyr Ser Gly Ala Asn Asn Arg Thr Leu Leu Gln Glu Tyr Lys
355 360 365

Ala Met Asn Asn Glu Lys Phe Lys Asp Asn Thr Gly Asp Asp Asp Lys
370 375 380

Asp Lys Ile Lys Asp Lys Ile Ala Lys Asp Glu Glu Lys Lys Glu Ser
385 390 395 400

Glu Leu Lys Val Asp Gly Glu Lys Lys Asp Ser Asn Leu Ser Ser Pro
405 410 415

Ala Arg Asp Ile Leu Pro Leu Pro Pro Lys Thr Ala Leu Asp Leu Lys
420 425 430

Leu Glu Ile Gln Lys Val Lys Glu Ser Arg Asp Ala Ile Lys Leu Asp
435 440 445

Asn Leu Gln Leu Ala Leu Pro Ser Val Cys Met Tyr Thr Phe Gln Asn
450 455 460

Thr Asn Lys Asp Met Ser Cys Leu Asp Phe Ser Asp Asp Cys Arg Ile
465 470 475 480

Ala Ala Ala Gly Phe Gln Asp Ser Tyr Ile Lys Ile Trp Ser Leu Asp

-continued 485 490 495

Gly Ser Ser Leu Asn Asn Pro Asn Ile Ala Leu Asn Asn Asn Asp Lys
500 505 510

Asp Glu Asp Pro Thr Cys Lys Thr Leu Val Gly His Ser Gly Thr Val
515 520 525

Tyr Ser Thr Ser Phe Ser Pro Asp Asn Lys Tyr Leu Leu Ser Gly Ser
530 535 540

Glu Asp Lys Thr Val Arg Leu Trp Ser Met Asp Thr His Thr Ala Leu
545 550 555 560

Val Ser Tyr Lys Gly His Asn His Pro Val Trp Asp Val Ser Phe Ser
565 570 575

Pro Leu Gly His Tyr Phe Ala Thr Ala Ser His Asp Gln Thr Ala Arg
580 585 590

Leu Trp Ser Cys Asp His Ile Tyr Pro Leu Arg Ile Phe Ala Gly His
595 600 605

Leu Asn Asp Val Asp Cys Val Ser Phe His Pro Asn Gly Cys Tyr Val
610 615 620

Phe Thr Gly Ser Ser Asp Lys Thr Cys Arg Met Trp Asp Val Ser Thr
625 630 635 640

Gly Asp Ser Val Arg Leu Phe Leu Gly His Thr Ala Pro Val Ile Ser
645 650 655

Ile Ala Val Cys Pro Asp Gly Arg Trp Leu Ser Thr Gly Ser Glu Asp
660 665 670

Gly Ile Ile Asn Val Trp Asp Ile Gly Thr Gly Lys Arg Leu Lys Gln
675 680 685

Met Arg Gly His Gly Lys Asn Ala Ile Tyr Ser Leu Ser Tyr Ser Lys
690 695 700

Glu Gly Asn Val Leu Ile Ser Gly Gly Ala Asp His Thr Val Arg Val
705 710 715 720

Trp Asp Leu Lys Lys Ala Thr Thr Glu Pro Ser Ala Glu Pro Asp Glu
725 730 735

Pro Phe Ile Gly Tyr Leu Gly Asp Val Thr Ala Ser Ile Asn Gln Asp
740 745 750

Ile Lys Glu Tyr Gly Arg Arg Arg Thr Val Ile Pro Thr Ser Asp Leu
755 760 765

Val Ala Ser Phe Tyr Thr Lys Lys Thr Pro Val Phe Lys Val Lys Phe
770 775 780

Ser Arg Ser Asn Leu Ala Leu Ala Gly Gly Ala Phe Arg Pro
785 790 795

( 2 ) INFORMATION FOR SEQ ID NO:69:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rI, Fig. 1C ( x i ) SEQUENCE DESCRIPTION: SEQ ID NO:69:

Gly His Asn Gly Trp Val Thr Gln Ile Ala Thr Thr Pro Gln Phe Pro
1 5 10 15

Asp Met Ile Leu Ser Ala Ser Arg Asp Lys Thr Ile Ile Met Trp Lys
20 25 30

( 2 ) INFORMATION FOR SEQ ID NO:70:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rII, Fig. 1C ( x i ) SEQUENCE DESCRIPTION: SEQ ID NO:70:

Gly His Ser His Phe Val Ser Asp Val Val Ile Ser Ser Asp Gly Gln
1 5 10 15

Phe Ala Leu Ser Gly Ser Trp Asp Gly Thr Leu Arg Leu Trp Asp
20 25 30

( 2 ) INFORMATION FOR SEQ ID NO:71:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rIII, Fig. 1C ( x i ) SEQUENCE DESCRIPTION: SEQ ID NO:71:

Gly His Thr Lys Asp Val Leu Ser Val Ala Phe Ser Ser Asp Asn Arg
1 5 10 15

Gln Ile Val Ser Gly Ser Arg Asp Lys Thr Ile Lys Leu Trp Asn
20 25 30

( 2 ) INFORMATION FOR SEQ ID NO:72:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rIV, Fig. 1C ( x i ) SEQUENCE DESCRIPTION: SEQ ID NO:72:

Ser His Ser Glu Trp Val Ser Cys Val Arg Phe Ser Pro Asn Ser Ser
1 5 10 15

Asn Pro Ile Ile Val Ser Cys Gly Trp Asp Lys Leu Val Lys Val Trp
20 25 30

Asn ( 2 ) INFORMATION FOR SEQ ID NO:73:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rV, Fig. 1C ( x i ) SEQUENCE DESCRIPTION: SEQ ID NO:73:

Gly His Thr Gly Tyr Leu Asn Thr Val Thr Val Ser Pro Asp Gly Ser
1 5 10 15

Leu Cys Ala Ser Gly Gly Lys Asp Gly Gln Ala Met Leu Trp Asp
20 25 30

( 2 ) INFORMATION FOR SEQ ID NO:74:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rVI, Fig. 1C ( x i ) SEQUENCE DESCRIPTION: SEQ ID NO:74:

Leu Asp Gly Gly Asp Ile Ile Asn Ala Leu Cys Phe Ser Pro Asn Arg
1 5 10 15

Tyr Trp Leu Cys Ala Ala Thr Gly Pro Ser Ile Lys Ile Trp Asp
20 25 30

( 2 ) INFORMATION FOR SEQ ID NO:75:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RACK1 protein rVII, Fig. 1C ( x i ) SEQUENCE DESCRIPTION: SEQ ID NO:75:

Ser Lys Ala Glu Pro Pro Gln Cys Thr Ser Leu Ala Trp Ser Ala Asp
1 5 10 15

Gly Gln Thr Leu Phe Ala Gly Tyr Thr Asp Asn Leu Val Arg Val Trp
20 25 30

Gln ( 2 ) INFORMATION FOR SEQ ID NO:76:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Human 55 kDa protein rI, Fig. 11

( x i ) SEQUENCE DESCRIPTION: SEQ ID NO:76:

Gly His Thr Asp Ala Val Leu Asp Leu Ser Trp Asn Lys Leu Ile Arg
1 5 10 15

Asn Val Leu Ala Ser Ala Ser Ala Asp Asn Thr Val Ile Leu Trp Asp
20 25 30

( 2 ) INFORMATION FOR SEQ ID NO:77:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Human 55 kDa protein rII, Fig. 11

( x i ) SEQUENCE DESCRIPTION: SEQ ID NO:77:

Ala His Asn Asp Glu Ile Ser Gly Leu Asp Leu Ser Ser Gln Ile Lys
1 5 10 15

Gly Cys Leu Val Thr Ala Ser Ala Asp Lys Tyr Val Lys Ile Trp Asp
20 25 30

( 2 ) INFORMATION FOR SEQ ID NO:78:

( i ) SEQUENCE CHARACTERISTICS:
( A ) LENGTH: 37 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Human 55 kDa protein rIII, Fig. 11

( x i ) SEQUENCE DESCRIPTION: SEQ ID NO:78:

Val His Ser Arg Asp Met Lys Met Gly Val Leu Phe Cys Ser Ser Cys
1 5 10 15

Cys Pro Asp Leu Pro Phe Ile Tyr Ala Phe Gly Gly Gln Lys Glu Gly
20 25 30

Leu Arg Val Trp Asp
35

( 2 ) INFORMATION FOR SEQ ID NO:79:

( i ) SEQUENCE CHARACTERISTICS:

( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: AAC-RICH protein rI, Fig. 12

( x i ) SEQUENCE DESCRIPTION: SEQ ID NO:79:

Gly Asn Lys Lys Lys Ser Thr Ser Val Ala Trp Asn Ala Asn Gly Thr
1 5 10 15

Lys Ile Ala Ser Ser Gly Ser Asp Gly Ile Val Arg Val Trp Asn
20 25 30

( 2 ) INFORMATION FOR SEQ ID NO:80:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: AAC-RICH protein rII, Fig. 12

( x i ) SEQUENCE DESCRIPTION: SEQ ID NO:80:

Gly His Asp Gly Ser Ile Glu Lys Ile Ser Trp Ser Pro Lys Asn Asn
1 5 10 15

Asp Leu Leu Ala Ser Ala Gly Thr Asp Lys Val Ile Lys Ile Trp Asp
20 25 30

( 2 ) INFORMATION FOR SEQ ID NO:81:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: AAC-RICH protein rIII, Fig. 12

( x i ) SEQUENCE DESCRIPTION: SEQ ID NO:81:

Asp His Leu Ala Leu Ile Asp Leu Pro Thr Ile Lys Thr Leu Lys Ile
1 5 10 15

Tyr Lys Phe Asn Gly Glu Glu Leu Asn Gln Val Gly Trp Asp
20 25 30

( 2 ) INFORMATION FOR SEQ ID NO:82:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: AAC-RICH protein rIV, Fig. 12

( x i ) SEQUENCE DESCRIPTION: SEQ ID NO:82:

Gly His Thr Ala Ser Ile Tyr Cys Met Glu Phe Asp Pro Thr Gly Lys
1 5 10 15

Tyr Leu Ala Ala Gly Ser Ala Asp Ser Ile Val Ser Leu Trp Asp
20 25 30

( 2 ) INFORMATION FOR SEQ ID NO:83:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rI, Fig. 13

( x i ) SEQUENCE DESCRIPTION: SEQ ID NO:83:

Ile His Cys Arg Ser Glu Thr Ser Lys Gly Val Tyr Cys Leu Gln Tyr
1 5 10 15

Asp Asp Gln Lys Ile Val Ser Gly Leu Arg Asp Asn Thr Ile Lys Ile
20 25 30

Trp Asp ( 2 ) INFORMATION FOR SEQ ID NO:84:

( i ) SEQUENCE CHARACTERISTICS:
( A ) LENGTH: 28 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rII, Fig. 13

( x i ) SEQUENCE DESCRIPTION: SEQ ID NO:84:

Gly His Thr Gly Ser Val Leu Cys Leu Gln Tyr Asp Glu Arg Val Ile
1 5 10 15

Ile Thr Gly Ser Asp Ser Thr Val Arg Val Trp Asp
20 25

( 2 ) INFORMATION FOR SEQ ID NO:85:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rIII, Fig. 13

( x i ) SEQUENCE DESCRIPTION: SEQ ID NO:85:

Ile His His Cys Glu Ala Val Leu His Leu Arg Phe Asn Asn Gly Met
1 5 10 15

Met Val Thr Cys Ser Lys Asp Arg Ser Ile Ala Val Trp Asp
20 25 30

( 2 ) INFORMATION FOR SEQ ID NO:86:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rIV, Fig. 13

( x i ) SEQUENCE DESCRIPTION: SEQ ID NO:86:

Gly His Arg Ala Ala Val Asn Val Val Asp Phe Asp Asp Lys Tyr Ile
1 5 10 15

Val Ser Ala Ser Gly Asp Arg Thr Ile Lys Val Trp Asn
20 25

( 2 ) INFORMATION FOR SEQ ID NO:87:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rV, Fig. 13

( x i ) SEQUENCE DESCRIPTION: SEQ ID NO:87:

Gly His Lys Arg Gly Ile Ala Cys Leu Gln Tyr Arg Asp Arg Leu Val
1 5 10 15

Val Ser Gly Ser Ser Asp Asn Thr Ile Arg Leu Trp Asp
20 25

( 2 ) INFORMATION FOR SEQ ID NO:88:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rVI, Fig. 13

( x i ) SEQUENCE DESCRIPTION: SEQ ID NO:88:

Gly His Glu Glu Leu Val Arg Cys Ile Arg Phe Asp Asn Lys Arg Ile
1 5 10 15

Val Ser Gly Ala Tyr Asp Gly Lys Ile Lys Val Trp Asp
20 25

( 2 ) INFORMATION FOR SEQ ID NO:89:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: BETA TRCP rVII, Fig. 13

( x i ) SEQUENCE DESCRIPTION: SEQ ID NO:89:

Glu His Ser Gly Arg Val Phe Arg Leu Gln Phe Asp Glu Phe Gln Ile
1 5 10 15

Val Ser Ser Ser His Asp Asp Thr Ile Leu Ile Trp Asp
20 25

( 2 ) INFORMATION FOR SEQ ID NO:90:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: beta-prime- cop rI, Fig. 14

( x i ) SEQUENCE DESCRIPTION: SEQ ID NO:90:

Ala His Ser Asp Tyr Ile Arg Cys Ile Ala Val His Pro Thr Gln Pro
1 5 10 15

Phe Ile Leu Thr Ser Ser Asp Asp Met Leu Ile Lys Leu Trp Asp
20 25 30

( 2 ) INFORMATION FOR SEQ ID NO:91:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: beta-prime- cop rII, Fig. 14

( x i ) SEQUENCE DESCRIPTION: SEQ ID NO:91:

Gly His Thr His Tyr Val Met Gln Ile Val Ile Asn Pro Lys Asp Asn
1 5 10 15

Asn Gln Phe Ala Ser Ala Ser Leu Asp Arg Thr Ile Lys Val Trp Gln
20 25 30

( 2 ) INFORMATION FOR SEQ ID NO:92:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: beta-prime- cop rIII, Fig. 14

( x i ) SEQUENCE DESCRIPTION: SEQ ID NO:92:

Gly His Glu Lys Gly Val Asn Cys Ile Asp Tyr Tyr Ser Gly Gly Asp
1 5 10 15

Lys Pro Tyr Leu Ile Ser Gly Ala Asp Asp Arg Leu Val Lys Ile Trp
20 25 30

Asp ( 2 ) INFORMATION FOR SEQ ID NO:93:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: beta-prime- cop rIV, Fig. 14

( x i ) SEQUENCE DESCRIPTION: SEQ ID NO:93:

Gly His Ala Gln Asn Val Ser Cys Ala Ser Phe His Pro Glu Leu Pro
1 5 10 15

Ile Ile Ile Thr Gly Ser Glu Asp Gly Thr Val Arg Ile Trp His
20 25 30

( 2 ) INFORMATION FOR SEQ ID NO:94:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein rI, Fig. 15

( x i ) SEQUENCE DESCRIPTION: SEQ ID NO:94:

Gly His Met Thr Ser Val Ile Thr Cys Leu Gln Phe Glu Asp Asn Tyr
1 5 10 15

Val Ile Thr Gly Ala Asp Asp Lys Met Ile Arg Val Tyr Asp
20 25 30

( 2 ) INFORMATION FOR SEQ ID NO:95:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein rII, Fig. 15

( x i ) SEQUENCE DESCRIPTION: SEQ ID NO:95:

Gly His Asp Gly Gly Val Trp Ala Leu Lys Tyr Ala His Gly Gly Ile
1 5 10 15

Leu Val Ser Gly Ser Thr Asp Arg Thr Val Arg Val Trp Asp
20 25 30

( 2 ) INFORMATION FOR SEQ ID NO:96:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein rIII, Fig. 15

( x i ) SEQUENCE DESCRIPTION: SEQ ID NO:96:

Gly His Asn Ser Thr Val Arg Cys Leu Asp Ile Val Glu Tyr Lys Asn
1 5 10 15

Ile Lys Tyr Ile Val Thr Gly Ser Arg Asp Asn Thr Leu His Val Trp
20 25 30

Lys ( 2 ) INFORMATION FOR SEQ ID NO:97:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein rIV, Fig. 15

( x i ) SEQUENCE DESCRIPTION: SEQ ID NO:97:

Gly His Met Ala Ser Val Arg Thr Val Ser Gly His Gly Asn Ile Val
1 5 10 15

Val Ser Gly Ser Tyr Asp Asn Thr Leu Ile Val Trp Asp
20 25

( 2 ) INFORMATION FOR SEQ ID NO:98:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein rV, Fig. 15

( x i ) SEQUENCE DESCRIPTION: SEQ ID NO:98:

Gly His Thr Asp Arg Ile Tyr Ser Thr Ile Tyr Asp His Glu Arg Lys
1 5 10 15

Arg Cys Ile Ser Ala Ser Met Asp Thr Thr Ile Arg Ile Trp Asp
20 25 30

( 2 ) INFORMATION FOR SEQ ID NO:99:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CDC4 / CDC20 protein rVI, Fig. 15

( x i ) SEQUENCE DESCRIPTION: SEQ ID NO:99:

Gly His Thr Ala Leu Val Gly Leu Leu Arg Leu Ser Asp Lys Phe Leu
1 5 10 15

Val Ser Ala Ala Ala Asp Gly Ser Ile Arg Gly Trp Asp
20 25

( 2 ) INFORMATION FOR SEQ ID NO:100:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP- CHLAMIDOMONAS HOMOLOG rI, Fig. 16

( x i ) SEQUENCE DESCRIPTION: SEQ ID NO:100:

Gly His Thr Asn Trp Val Thr Ala Ile Ala Thr Pro Leu Asp Pro Ser
1 5 10 15

Ser Asn Thr Leu Leu Ser Ala Ser Arg Asp Lys Ser Val Leu Val Trp
20 25 30

Glu ( 2 ) INFORMATION FOR SEQ ID NO:101:

( i ) SEQUENCE CHARACTERISTICS:
( A ) LENGTH: 31 amino acids
( B ) TYPE: amino acid ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG rII, Fig.

( x i ) SEQUENCE DESCRIPTION: SEQ ID NO:101:

Gly His Ser His Phe Val Gln Asp Val Val Ile Ser Ser Asp Gly Gln
1 5 10 15

Phe Cys Leu Thr Gly Ser Trp Asp Gly Thr Leu Arg Leu Trp Asp
20 25 30

( 2 ) INFORMATION FOR SEQ ID NO:102:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG rIII, Fig. 16

( x i ) SEQUENCE DESCRIPTION: SEQ ID NO:102:

Gly His Thr Lys Asp Val Leu Ser Val Ala Phe Ser Val Asp Asn Arg
1 5 10 15

Gln Ile Val Ser Gly Ser Arg Asp Lys Thr Ile Lys Leu Trp Asn
20 25 30

( 2 ) INFORMATION FOR SEQ ID NO:103:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG rIV, Fig. 16

( x i ) SEQUENCE DESCRIPTION: SEQ ID NO:103:

Gly His Thr Glu Trp Val Ser Cys Val Arg Phe Ser Pro Met Thr Thr
1 5 10 15

Asn Pro Ile Ile Val Ser Gly Gly Trp Asp Lys Met Val Lys Val Trp
20 25 30

Asn ( 2 ) INFORMATION FOR SEQ ID NO:104:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG rV, Fig. 16

( x i ) SEQUENCE DESCRIPTION: SEQ ID NO:104:

Gly His His Gly Tyr Val Asn Thr Val Thr Val Ser Pro Asp Gly Ser
1 5 10 15

Leu Cys Ala Ser Gly Gly Lys Asp Gly Ile Ala Met Leu Trp Asp
20 25 30

( 2 ) INFORMATION FOR SEQ ID NO:105:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG rVI, Fig. 16

( x i ) SEQUENCE DESCRIPTION: SEQ ID NO:105:

Ile His Cys Leu Cys Phe Ser Pro Asn Arg Tyr Trp Leu Cys Ala Ala
1 5 10 15

Thr Gln Ser Ser Ile Lys Ile Trp Asp Leu Glu Ser Lys Ser Ile Val
20 25 30

( 2 ) INFORMATION FOR SEQ ID NO:106:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GBLP - CHLAMIDOMONAS HOMOLOG rVII, Fig. 16

( x i ) SEQUENCE DESCRIPTION: SEQ ID NO:106:

Lys Lys Ala Gln Val Pro Tyr Cys Val Ser Leu Ala Trp Ser Ala Asp
1 5 10 15

Gly Ser Thr Leu Tyr Ser Gly Tyr Thr Asp Gly Gln Ile Arg Val Trp
20 25 30

Ala ( 2 ) INFORMATION FOR SEQ ID NO:107:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: cop-1 protein rI, Fig. 17

( x i ) SEQUENCE DESCRIPTION: SEQ ID NO:107:

Met Ser Thr Arg Ser Lys Leu Ser Cys Leu Ser Trp Asn Lys His Glu
1 5 10 15

Lys Asn His Ile Ala Ser Ser Asp Tyr Glu Gly Ile Val Thr Val Trp
20 25 30

Asp ( 2 ) INFORMATION FOR SEQ ID NO:108:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: cop-1 protein rII, Fig. 17

( x i ) SEQUENCE DESCRIPTION: SEQ ID NO:108:

Glu Lys Arg Ala Trp Ser Val Asp Phe Ser Arg Thr Glu Pro Ser Met
1 5 10 15

Leu Val Ser Gly Ser Asp Asp Cys Lys Val Lys Val Trp Cys
20 25 30

( 2 ) INFORMATION FOR SEQ ID NO:109:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: cop-1 protein rIII, Fig. 17

( x i ) SEQUENCE DESCRIPTION: SEQ ID NO:109:

Gly His Lys Lys Ala Val Ser Tyr Met Lys Phe Leu Ser Asn Asn Glu
1 5 10 15

Leu Ala Ser Ala Ser Thr Asp Ser Thr Leu Arg Leu Trp Asp
20 25 30

( 2 ) INFORMATION FOR SEQ ID NO:110:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide -continued ( i i i ) HYPOTHETICAL: NO ( i v ) ANTI-SENSE: NO ( v i ) ORIGINAL SOURCE:
( C ) INDIVIDUAL ISOLATE: Coronin (p55) rI, Fig. 19

( x i ) SEQUENCE DESCRIPTION: SEQ ID NO:110:

Gly His Lys Ser Ala Val Leu Asp Ile Ala Phe His Pro Phe Asn Glu
1 5 10 15

Asn Leu Val Gly Ser Val Ser Glu Asp Cys Asn Ile Cys Ile Trp Gly
20 25 30

( 2 ) INFORMATION FOR SEQ ID NO:111:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Coronin (p55) rII, Fig. 19

( x i ) SEQUENCE DESCRIPTION: SEQ ID NO:111:

Gly His Lys Arg Lys Val Gly Thr Ile Ser Phe Gly Pro Val Ala Asp
1 5 10 15

Asn Val Ala Val Thr Ser Ser Gly Asp Phe Leu Val Lys Thr Trp Asp
20 25 30

( 2 ) INFORMATION FOR SEQ ID NO:112:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Coronin (p55) rIII, Fig. 19

( x i ) SEQUENCE DESCRIPTION: SEQ ID NO:112:

Gly His Ser Asp Met Ile Thr Ser Cys Glu Trp Asn His Asn Gly Ser
1 5 10 15

Gln Ile Val Thr Thr Cys Lys Asp Lys Lys Ala Arg Val Phe Asp
20 25 30

( 2 ) INFORMATION FOR SEQ ID NO:113:

( i ) SEQUENCE CHARACTERISTICS:
( A ) LENGTH: 38 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:

( C ) INDIVIDUAL ISOLATE: CORO PROTEIN rI, Fig. 18

( x i ) SEQUENCE DESCRIPTION: SEQ ID NO:113:

Arg His Val Phe Ala Ala Gln Pro Lys Lys Glu Glu Cys Tyr Gln Asn
1 5 10 15

Leu Lys Thr Lys Ser Ala Val Trp Asp Ser Asn Tyr Val Ala Ala Asn
20 25 30

Thr Arg Tyr Ile Trp Asp
35

( 2 ) INFORMATION FOR SEQ ID NO:114:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CORO PROTEIN rII, Fig. 18

( x i ) SEQUENCE DESCRIPTION: SEQ ID NO:114:

Gly His Lys Ser Ala Val Leu Asp Ile Ala Phe His Pro Phe Asn Glu
1 5 10 15

Asn Leu Val Gly Ser Val Ser Glu Asp Cys Asn Ile Cys Ile Trp Gly
20 25 30

( 2 ) INFORMATION FOR SEQ ID NO:115:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CORO PROTEIN rIII, Fig. 18

( x i ) SEQUENCE DESCRIPTION: SEQ ID NO:115:

Gly His Lys Arg Lys Val Gly Thr Ile Ser Phe Gly Pro Val Ala Asp
1 5 10 15

Asn Val Ala Val Thr Ser Ser Gly Asp Phe Leu Val Lys Thr Trp Asp
20 25 30

( 2 ) INFORMATION FOR SEQ ID NO:116:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CORO PROTEIN rIV, Fig. 18

( x i ) SEQUENCE DESCRIPTION: SEQ ID NO:116:

Gly His Ser Asp Met Ile Thr Ser Cys Glu His Asn Gly Ser Gln Ile
1 5 10 15

Val Thr Thr Cys Lys Asp Lys Lys Ala Arg Val Phe Asp
20 25

( 2 ) INFORMATION FOR SEQ ID NO:117:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CSTF 50kDa rI, Fig. 20

( x i ) SEQUENCE DESCRIPTION: SEQ ID NO:117:

Asp His Val Asp Glu Val Thr Cys Leu Ala Phe His Pro Thr Glu Gln
1 5 10 15

Ile Leu Ala Ser Gly Ser Arg Asp Tyr Thr Leu Lys Leu Phe Asp
20 25 30

( 2 ) INFORMATION FOR SEQ ID NO:118:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CSTF 50kDa rII, Fig. 20

( x i ) SEQUENCE DESCRIPTION: SEQ ID NO:118:

Asp His Val Asp Glu Val Thr Cys Leu Ala Phe His Pro Thr Glu Gln
1 5 10 15

Ile Leu Ala Ser Gly Ser Arg Asp Tyr Thr Leu Lys Leu Phe Asp
20 25 30

( 2 ) INFORMATION FOR SEQ ID NO:119:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CSTF 50kDa rIII, Fig. 20

( x i ) SEQUENCE DESCRIPTION: SEQ ID NO:119:

Ala His Asp Gly Ala Glu Val Cys Ser Ala Ile Phe Ser Lys Asn Ser
1 5 10 15

-continued

Lys Tyr Ile Leu Ser Ser Gly Lys Asp Ser Val Ala Lys Leu Trp Glu
20 25 30

( 2 ) INFORMATION FOR SEQ ID NO:120:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CSTF 50kDa rIV, Fig. 20

( x i ) SEQUENCE DESCRIPTION: SEQ ID NO:120:

Val His Arg Thr Gln Ala Val Phe Asn His Thr Glu Asp Tyr Val Leu
1 5 10 15

Leu Pro Asp Glu Arg Thr Ile Ser Leu Cys Cys Trp Asp
20 25

( 2 ) INFORMATION FOR SEQ ID NO:121:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: CSTF 50kDa rV, Fig. 20

( x i ) SEQUENCE DESCRIPTION: SEQ ID NO:121:

Gly His Asn Asn Ile Val Arg Cys Ile Val His Ser Pro Thr Asn Pro
1 5 10 15

Gly Phe Met Thr Cys Ser Asp Asp Phe Arg Ala Arg Phe Trp Tyr
20 25 30

( 2 ) INFORMATION FOR SEQ ID NO:122:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- BETA DROSOPH rI, Fig. 23

( x i ) SEQUENCE DESCRIPTION: SEQ ID NO:122:

Gly His Leu Ala Lys Ile Tyr Ala Met His Trp Gly Asn Asp Ser Arg
1 5 10 15

Asn Leu Val Ser Ala Ser Gln Asp Gly Lys Leu Ile Val Trp Asp
20 25 30

( 2 ) INFORMATION FOR SEQ ID NO:123:

(i) SEQUENCE CHARACTERISTICS:
(A) LENGTH: 30 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G- BETA DROSOPH rII, Fig. 23

(xi) SEQUENCE DESCRIPTION: SEQ ID NO:123:

Gly His Gly Gly Tyr Leu Ser Cys Cys Arg Phe Leu Asp Asp Asn Gln
1 5 10 15

Ile Val Thr Ser Ser Gly Asp Met Ser Cys Gly Leu Trp Asp
20 25 30

(2) INFORMATION FOR SEQ ID NO:124:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G- BETA DROSOPH rIII, Fig. 23

(xi) SEQUENCE DESCRIPTION: SEQ ID NO:124:

Gly His Thr Gly Asp Val Met Ala Leu Ser Leu Ala Pro Gln Cys Lys
1 5 10 15

Thr Phe Val Ser Gly Ala Cys Asp Ala Ser Ala Lys Leu Trp Asp
20 25 30

(2) INFORMATION FOR SEQ ID NO:125:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G- BETA DROSOPH rIV, Fig. 23

(xi) SEQUENCE DESCRIPTION: SEQ ID NO:125:

Gly His Glu Ser Asp Ile Asn Ala Val Thr Phe Phe Pro Asn Gly Gln
1 5 10 15

Ala Phe Ala Thr Gly Ser Asp Asp Ala Thr Cys Arg Leu Phe Asp
20 25 30

(2) INFORMATION FOR SEQ ID NO:126:

(i) SEQUENCE CHARACTERISTICS:
(A) LENGTH: 34 amino acids
(B) TYPE: amino acid
(D) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- BETA DROSOPH rV, Fig. 23

( x i ) SEQUENCE DESCRIPTION: SEQ ID NO:126:

Ser His Asp Asn Ile Ile Cys Gly Ile Thr Ser Val Ala Phe Ser Lys
1 5 10 15

Ser Gly Arg Leu Leu Leu Ala Gly Tyr Asp Asp Phe Asn Cys Asn Val
20 25 30

Trp Asp ( 2 ) INFORMATION FOR SEQ ID NO:127:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- BETA DROSOPH rVI, Fig. 23

( x i ) SEQUENCE DESCRIPTION: SEQ ID NO:127:

Gly His Asp Asn Arg Val Ser Cys Leu Gly Val Thr Glu Asn Gly Met
1 5 10 15

Ala Val Ala Thr Gly Ser Trp Asp Ser Phe Leu Arg Val Trp Asn
20 25 30

( 2 ) INFORMATION FOR SEQ ID NO:128:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G-BETA HUMAN rI, Fig. 24

( x i ) SEQUENCE DESCRIPTION: SEQ ID NO:128:

Gly His Asn Gly Trp Val Thr Gln Ile Ala Thr Thr Pro Gln Phe Pro
1 5 10 15

Asp Met Ile Leu Ser Ala Ser Arg Asp Lys Thr Ile Ile Met Trp Lys
20 25 30

( 2 ) INFORMATION FOR SEQ ID NO:129:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide (iii) HYPOTHETICAL: NO (iv) ANTI-SENSE: NO (vi) ORIGINAL SOURCE:
(C) INDIVIDUAL ISOLATE: G-BETA HUMAN rII, Fig. 24

(xi) SEQUENCE DESCRIPTION: SEQ ID NO:129:

Gly His Ser His Phe Val Ser Asp Val Val Ile Ser Ser Asp Gly Gln
1 5 10 15

Phe Ala Leu Ser Gly Ser Trp Asp Gly Thr Leu Arg Leu Trp Asp
20 25 30

(2) INFORMATION FOR SEQ ID NO:130:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-BETA HUMAN rIII, Fig. 24

(xi) SEQUENCE DESCRIPTION: SEQ ID NO:130:

Gly His Thr Lys Asp Val Leu Ser Val Ala Phe Ser Ser Asp Asn Arg
1 5 10 15

Gln Ile Val Ser Gly Ser Arg Asp Lys Thr Ile Lys Leu Trp Asn
20 25 30

(2) INFORMATION FOR SEQ ID NO:131:

(i) SEQUENCE CHARACTERISTICS:
(A) LENGTH: 33 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-BETA HUMAN rIV, Fig. 24

(xi) SEQUENCE DESCRIPTION: SEQ ID NO:131:

Ser His Ser Glu Trp Val Ser Cys Val Arg Phe Ser Pro Asn Ser Ser
1 5 10 15

Asn Pro Ile Ile Val Ser Cys Gly Trp Asp Lys Leu Val Lys Val Trp
20 25 30

Asn (2) INFORMATION FOR SEQ ID NO:132:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-BETA HUMAN rV, Fig. 24

(xi) SEQUENCE DESCRIPTION: SEQ ID NO:132:

Gly His Thr Gly Tyr Leu Asn Thr Val Thr Val Ser Pro Asp Gly Ser
1 5 10 15

Leu Cys Ala Ser Gly Gly Lys Asp Gly Gln Ala Met Leu Trp Asp
20 25 30

(2) INFORMATION FOR SEQ ID NO:133:

(i) SEQUENCE CHARACTERISTICS:
(A) LENGTH: 36 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-BETA HUMAN rVI, Fig. 24

(xi) SEQUENCE DESCRIPTION: SEQ ID NO:133:

Lys His Leu Tyr Thr Leu Asp Gly Gly Asp Ile Ile Asn Ala Leu Cys
1 5 10 15

Phe Ser Pro Asn Arg Tyr Trp Leu Cys Ala Ala Thr Gly Pro Ser Ile
20 25 30

Lys Ile Trp Asp
35

(2) INFORMATION FOR SEQ ID NO:134:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-BETA HUMAN rVII, Fig. 24

(xi) SEQUENCE DESCRIPTION: SEQ ID NO:134:

Ala Glu Pro Pro Gln Cys Thr Ser Leu Ala Trp Ser Ala Asp Gly Gln
1 5 10 15

Thr Leu Phe Ala Gly Tyr Thr Asp Asn Leu Val Arg Val Trp Gln
20 25 30

(2) INFORMATION FOR SEQ ID NO:135:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:

( C ) INDIVIDUAL ISOLATE: G-Beta 1 bovine rI, Fig. 21

( x i ) SEQUENCE DESCRIPTION: SEQ ID NO:135:

Gly His Leu Ala Lys Ile Tyr Ala Met His Trp Gly Thr Asp Ser Arg
1 5 10 15

Leu Leu Val Ser Ala Ser Gln Asp Gly Lys Leu Ile Ile Trp Asp
20 25 30

( 2 ) INFORMATION FOR SEQ ID NO:136:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G-Beta 1 bovine rII, Fig. 21

( x i ) SEQUENCE DESCRIPTION: SEQ ID NO:136:

Gly His Thr Gly Tyr Leu Ser Cys Cys Arg Phe Leu Asp Asp Asn Gln
1 5 10 15

Ile Val Thr Ser Ser Gly Asp Thr Thr Cys Ala Leu Trp Asp
20 25 30

( 2 ) INFORMATION FOR SEQ ID NO:137:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G-Beta 1 bovine rIII, Fig. 21

( x i ) SEQUENCE DESCRIPTION: SEQ ID NO:137:

Gly His Thr Gly Asp Val Met Ser Leu Ser Leu Ala Pro Asp Thr Arg
1 5 10 15

Leu Phe Val Ser Gly Ala Cys Asp Ala Ser Ala Lys Leu Trp Asp
20 25 30

( 2 ) INFORMATION FOR SEQ ID NO:138:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G-Beta 1 bovine rIV, Fig. 21

( x i ) SEQUENCE DESCRIPTION: SEQ ID NO:138:

Gly His Glu Ser Asp Ile Asn Ala Ile Cys Phe Phe Pro Asn Gly Asn 1 5 10 15

Ala Phe Ala Thr Gly Ser Asp Asp Ala Thr Cys Arg Leu Phe Asp
20 25 30

(2) INFORMATION FOR SEQ ID NO:139:

(i) SEQUENCE CHARACTERISTICS:
(A) LENGTH: 34 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-Beta 1 bovine rV, Fig. 21

(xi) SEQUENCE DESCRIPTION: SEQ ID NO:139:

Ser His Asp Asn Ile Ile Cys Gly Ile Thr Ser Val Ser Phe Ser Lys
1 5 10 15

Ser Gly Arg Leu Leu Leu Ala Gly Tyr Asp Asp Phe Asn Cys Asn Val
20 25 30

Trp Asp (2) INFORMATION FOR SEQ ID NO:140:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-Beta 1 bovine rVI, Fig. 21

(xi) SEQUENCE DESCRIPTION: SEQ ID NO:140:

Gly His Asp Asn Arg Val Ser Cys Leu Gly Val Thr Asp Asp Gly Met
1 5 10 15

Ala Val Ala Thr Gly Ser Trp Asp Ser Phe Leu Lys Ile Trp Asn
20 25 30

(2) INFORMATION FOR SEQ ID NO:141:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-Beta- bovine(2) rI, Fig. 22

(xi) SEQUENCE DESCRIPTION: SEQ ID NO:141:

Gly His Leu Ala Lys Ile Tyr Ala Met His Trp Gly Thr Asp Ser Arg
1 5 10 15

Leu Leu Val Ser Ala Ser Gln Asp Gly Lys Leu Ile Ile Trp Asp 20 25 30

(2) INFORMATION FOR SEQ ID NO:142:

(i) SEQUENCE CHARACTERISTICS:
(A) LENGTH: 30 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-Beta- bovine(2) rII, Fig. 22

(xi) SEQUENCE DESCRIPTION: SEQ ID NO:142:

Gly His Thr Gly Tyr Leu Ser Cys Cys Arg Phe Leu Asp Asp Asn Gln
1 5 10 15

Ile Ile Thr Ser Ser Gly Asp Thr Thr Cys Ala Leu Trp Asp
20 25 30

(2) INFORMATION FOR SEQ ID NO:143:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-Beta- bovine(2) rIII, Fig. 22

(xi) SEQUENCE DESCRIPTION: SEQ ID NO:143:

Gly His Ser Gly Asp Val Met Ser Leu Ser Leu Ala Pro Asp Gly Arg
1 5 10 15

Thr Phe Val Ser Gly Ala Cys Asp Ala Ser Ile Lys Leu Trp Asp
20 25 30

(2) INFORMATION FOR SEQ ID NO:144:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: G-Beta- bovine(2) rIV, Fig. 22

(xi) SEQUENCE DESCRIPTION: SEQ ID NO:144:

Gly His Glu Ser Asp Ile Asn Ala Val Ala Phe Phe Pro Asn Gly Tyr
1 5 10 15

Ala Phe Thr Thr Gly Ser Asp Asp Ala Thr Cys Arg Leu Phe Asp
20 25 30

(2) INFORMATION FOR SEQ ID NO:145:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G-Beta- bovine(2) rV, Fig. 22

( x i ) SEQUENCE DESCRIPTION: SEQ ID NO:145:

Ser His Asp Asn Ile Ile Cys Gly Ile Thr Ser Val Ala Phe Ser Arg
1 5 10 15

Ser Gly Arg Leu Leu Leu Ala Gly Tyr Asp Asp Phe Asn Cys Asn Ile
20 25 30

Trp Asp ( 2 ) INFORMATION FOR SEQ ID NO:146:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G-Beta- bovine(2) rVI, Fig. 22

( x i ) SEQUENCE DESCRIPTION: SEQ ID NO:146:

Gly His Asp Asn Arg Val Ser Cys Leu Gly Val Thr Asp Asp Gly Met
1 5 10 15

Ala Val Ala Thr Gly Ser Trp Asp Ser Phe Leu Lys Ile Trp Asn
20 25 30

( 2 ) INFORMATION FOR SEQ ID NO:147:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta2(Human) rI, Fig. 25

( x i ) SEQUENCE DESCRIPTION: SEQ ID NO:147:

Gly His Leu Ala Lys Ile Tyr Ala Met His Trp Gly Thr Asp Ser Arg
1 5 10 15

Leu Leu Val Ser Ala Ser Gln Asp Gly Lys Leu Ile Ile Trp Asp
20 25 30

( 2 ) INFORMATION FOR SEQ ID NO:148:

( i ) SEQUENCE CHARACTERISTICS:
( A ) LENGTH: 30 amino acids
( B ) TYPE: amino acid ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta2(Human) rII, Fig. 25

( x i ) SEQUENCE DESCRIPTION: SEQ ID NO:148:

```
Gly His Thr Gly Tyr Leu Ser Cys Cys Arg Phe Leu Asp Asp Asn Gln
1               5                   10                  15

Ile Ile Thr Ser Ser Gly Asp Thr Thr Cys Ala Leu Trp Asp
            20                  25                  30
```

( 2 ) INFORMATION FOR SEQ ID NO:149:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta2(Human) rIII, Fig. 25

( x i ) SEQUENCE DESCRIPTION: SEQ ID NO:149:

```
Gly His Ser Gly Asp Val Met Ser Leu Ser Leu Ala Pro Asp Gly Arg
1               5                   10                  15

Thr Phe Val Ser Gly Ala Cys Asp Ala Ser Ile Lys Leu Trp Asp
            20                  25                  30
```

( 2 ) INFORMATION FOR SEQ ID NO:150:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta2(Human) rIV, Fig. 25

( x i ) SEQUENCE DESCRIPTION: SEQ ID NO:150:

```
Gly His Glu Ser Asp Ile Asn Ala Val Ala Phe Phe Pro Asn Gly Tyr
1               5                   10                  15

Ala Phe Thr Thr Gly Ser Asp Asp Ala Thr Cys Arg Leu Phe Asp
            20                  25                  30
```

( 2 ) INFORMATION FOR SEQ ID NO:151:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta2(Human) rV, Fig. 25

( x i ) SEQUENCE DESCRIPTION: SEQ ID NO:151:

Ser His Asp Asn Ile Ile Cys Gly Ile Thr Ser Val Ala Phe Ser Arg
1 5 10 15

Ser Gly Arg Leu Leu Leu Ala Gly Tyr Asp Asp Phe Asn Cys Asn Ile
20 25 30

Trp Asp ( 2 ) INFORMATION FOR SEQ ID NO:152:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta2(Human) rVI, Fig. 25

( x i ) SEQUENCE DESCRIPTION: SEQ ID NO:152:

Gly His Asp Asn Arg Val Ser Cys Leu Gly Val Thr Asp Asp Gly Met
1 5 10 15

Ala Val Ala Thr Gly Ser Trp Asp Ser Phe Leu Lys Ile Trp Asn
20 25 30

( 2 ) INFORMATION FOR SEQ ID NO:153:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta4(mouse) rI, Fig. 26

( x i ) SEQUENCE DESCRIPTION: SEQ ID NO:153:

Gly His Leu Ala Lys Ile Tyr Ala Met His Trp Gly Tyr Asp Ser Arg
1 5 10 15

Leu Leu Val Ser Ala Ser Gln Asp Gly Lys Leu Ile Ile Trp Asp
20 25 30

( 2 ) INFORMATION FOR SEQ ID NO:154:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta4(mouse) rII, Fig. 26

( x i ) SEQUENCE DESCRIPTION: SEQ ID NO:154:

Gly His Thr Gly Tyr Leu Ser Cys Cys Arg Phe Leu Asp Asp Gly Gln
1 5 10 15

Ile Ile Thr Ser Ser Gly Asp Thr Thr Cys Ala Leu Trp Asp
20 25 30

( 2 ) INFORMATION FOR SEQ ID NO:155:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta4(mouse) rIII, Fig. 26

( x i ) SEQUENCE DESCRIPTION: SEQ ID NO:155:

Gly His Ser Gly Asp Val Met Ser Leu Ser Leu Ser Pro Asp Leu Lys
1 5 10 15

Thr Phe Val Ser Gly Ala Cys Asp Ala Ser Ser Lys Leu Trp Asp
20 25 30

( 2 ) INFORMATION FOR SEQ ID NO:156:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta4(mouse) rIV, Fig. 26

( x i ) SEQUENCE DESCRIPTION: SEQ ID NO:156:

Gly His Ile Ser Asp Ile Asn Ala Val Ser Phe Phe Pro Ser Gly Tyr
1 5 10 15

Ala Phe Ala Thr Gly Ser Asp Asp Ala Thr Cys Arg Leu Phe Asp
20 25 30

( 2 ) INFORMATION FOR SEQ ID NO:157:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta4(mouse) rV, Fig. 26

( x i ) SEQUENCE DESCRIPTION: SEQ ID NO:157:

-continued

Ser His Asp Asn Ile Ile Cys Gly Ile Thr Ser Val Ala Phe Ser Lys
1 5 10 15

Ser Gly Arg Leu Leu Leu Ala Gly Tyr Asp Asp Phe Asn Cys Ser Val
20 25 30

Trp Asp ( 2 ) INFORMATION FOR SEQ ID NO:158:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: G- Beta4(mouse) rVI, Fig. 26

( x i ) SEQUENCE DESCRIPTION: SEQ ID NO:158:

Gly His Asp Asn Arg Val Ser Cys Leu Gly Val Thr Asp Asp Gly Met
1 5 10 15

Ala Val Ala Thr Gly Ser Trp Asp Ser Phe Leu Arg Ile Trp Asn
20 25 30

( 2 ) INFORMATION FOR SEQ ID NO:159:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GROUCHO PROT. DRSPH rI, Fig. 27

( x i ) SEQUENCE DESCRIPTION: SEQ ID NO:159:

Thr Ser Ala Ala Pro Ala Cys Tyr Ala Leu Ala Ser Pro Asp Ser Lys
1 5 10 15

Val Cys Phe Ser Cys Cys Ser Asp Gly Asn Ile Ala Val Trp Asp
20 25 30

( 2 ) INFORMATION FOR SEQ ID NO:160:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GROUCHO PROT. DRSPH rII, Fig. 27

( x i ) SEQUENCE DESCRIPTION: SEQ ID NO:160:

Gly His Thr Asp Gly Ala Ser Cys Ile Asp Ile Ser Pro Asp Gly Ser
1 5 10 15

Arg Leu Trp Thr Gly Gly Leu Asp Asn Thr Val Arg Ser Trp Asp
20 25 30

( 2 ) INFORMATION FOR SEQ ID NO:161:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GTP binding prt squid rI, Fig. 28

( x i ) SEQUENCE DESCRIPTION: SEQ ID NO:161:

Gly His Leu Ala Lys Ile Tyr Ala Met His Trp Ala Ser Asp Ser Arg
1 5 10 15

Asn Leu Val Ser Ala Ser Gln Asp Gly Lys Leu Ile Val Trp Asp
20 25 30

( 2 ) INFORMATION FOR SEQ ID NO:162:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GTP binding prt squid rII, Fig. 28

( x i ) SEQUENCE DESCRIPTION: SEQ ID NO:162:

Gly His Thr Gly Tyr Leu Ser Cys Cys Arg Phe Ile Asp Asp Asn Gln
1 5 10 15

Ile Val Thr Ser Ser Gly Asp Met Thr Cys Ala Leu Trp Asn
20 25 30

( 2 ) INFORMATION FOR SEQ ID NO:163:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GTP binding prt squid rIII, Fig. 28

( x i ) SEQUENCE DESCRIPTION: SEQ ID NO:163:

Gly His Thr Gly Asp Val Met Ser Leu Ser Leu Ala Pro Asp Met Arg
1 5 10 15

Thr Phe Val Ser Gly Ala Cys Asp Ala Ser Ala Lys Leu Phe Asp
20 25 30

( 2 ) INFORMATION FOR SEQ ID NO:164:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GTP binding prt squid rIV, Fig. 28

( x i ) SEQUENCE DESCRIPTION: SEQ ID NO:164:

Gly His Glu Ser Asp Ile Asn Ala Ile Thr Tyr Phe Pro Asn Gly Phe
1 5 10 15

Ala Phe Ala Thr Gly Ser Asp Asp Ala Thr Cys Arg Leu Phe Asp
20 25 30

( 2 ) INFORMATION FOR SEQ ID NO:165:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GTP binding prt squid rV, Fig. 28

( x i ) SEQUENCE DESCRIPTION: SEQ ID NO:165:

Ser His Asp Asn Ile Ile Cys Gly Ile Thr Ser Val Ala Phe Ser Lys
1 5 10 15

Ser Gly Arg Leu Leu Leu Gly Gly Tyr Asp Asp Phe Asn Cys Asn Val
20 25 30

Trp Asp ( 2 ) INFORMATION FOR SEQ ID NO:166:

( i ) SEQUENCE CHARACTERISTICS:
( A ) LENGTH: 24 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: GTP binding prt squid rVI, Fig. 28

( x i ) SEQUENCE DESCRIPTION: SEQ ID NO:166:

Gly His Asp Asn Arg Val Ser Cys Leu Gly Val Thr Glu Asp Gly Met
1 5 10 15

Ala Val Ala Thr Gly Ser Trp Asp
20

( 2 ) INFORMATION FOR SEQ ID NO:167:

( i ) SEQUENCE CHARACTERISTICS:
( A ) LENGTH: 32 amino acids (B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: IEF SSP 9306 rI, Fig. 29

(xi) SEQUENCE DESCRIPTION: SEQ ID NO:167:

Gly His Gln Lys Glu Gly Tyr Gly Leu Ser Trp Asn Pro Asn Leu Ser
1 5 10 15

Gly His Leu Leu Ser Ala Ser Asp Asp His Thr Ile Cys Leu Trp Asp
20 25 30

(2) INFORMATION FOR SEQ ID NO:168:

(i) SEQUENCE CHARACTERISTICS:
(A) LENGTH: 32 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: IEF SSP 9306 rII, Fig. 29

(xi) SEQUENCE DESCRIPTION: SEQ ID NO:168:

Gly His Thr Ala Val Val Glu Asp Val Ser Trp His Leu Leu His Glu
1 5 10 15

Ser Leu Phe Gly Ser Val Ala Asp Asp Gln Lys Leu Met Ile Trp Asp
20 25 30

(2) INFORMATION FOR SEQ ID NO:169:

(i) SEQUENCE CHARACTERISTICS:
(A) LENGTH: 37 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: IEF SSP 9306 rIII, Fig. 29

(xi) SEQUENCE DESCRIPTION: SEQ ID NO:169:

Ser His Ser Val Asp Ala His Thr Ala Glu Val Asn Cys Leu Ser Phe
1 5 10 15

Asn Pro Tyr Ser Glu Phe Ile Leu Ala Thr Gly Ser Ala Asp Lys Thr
20 25 30

Val Ala Leu Trp Asp
35

(2) INFORMATION FOR SEQ ID NO:170:

(i) SEQUENCE CHARACTERISTICS:
(A) LENGTH: 37 amino acids
(B) TYPE: amino acid
(D) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: IEF SSP 9306 rIV, Fig. 29

( x i ) SEQUENCE DESCRIPTION: SEQ ID NO:170:

Leu His Ser Phe Glu Ser His Lys Asp Glu Ile Phe Gln Val Gln Trp
1 5 10 15

Ser Pro His Asn Glu Thr Ile Leu Ala Ser Ser Gly Thr Asp Arg Arg
20 25 30

Leu Asn Val Trp Asp
35

( 2 ) INFORMATION FOR SEQ ID NO:171:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: IEF SSP 9306 rV, Fig. 29

( x i ) SEQUENCE DESCRIPTION: SEQ ID NO:171:

Ile Gly Glu Glu Gln Ser Pro Glu Asp Ala Glu Asp Gly Pro Pro Glu
1 5 10 15

Leu Leu Phe Ile His Gly Gly His Thr Ala Lys Ile Ser Asp Phe Ser
20 25 30

Trp Asn ( 2 ) INFORMATION FOR SEQ ID NO:172:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: HUMAN 12.3 rI, Fig. 30

( x i ) SEQUENCE DESCRIPTION: SEQ ID NO:172:

Gly His Asn Gly Trp Val Thr Gln Ile Ala Thr Thr Pro Gln Phe Pro
1 5 10 15

Asp Met Ile Leu Ser Ala Ser Arg Asp Lys Thr Ile Ile Met Trp Lys
20 25 30

( 2 ) INFORMATION FOR SEQ ID NO:173:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: HUMAN 12.3 rII, Fig. 30

( x i ) SEQUENCE DESCRIPTION: SEQ ID NO:173:

Gly His Ser His Phe Val Ser Asp Val Val Ile Ser Ser Asp Gly Gln
1 5 10 15

Phe Ala Leu Ser Gly Ser Trp Asp Gly Thr Leu Arg Leu Trp Asp
20 25 30

( 2 ) INFORMATION FOR SEQ ID NO:174:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: HUMAN 12.3 rIII, Fig. 30

( x i ) SEQUENCE DESCRIPTION: SEQ ID NO:174:

Gly His Thr Lys Asp Val Leu Ser Val Ala Phe Ser Ser Asp Asn Arg
1 5 10 15

Gln Ile Val Ser Gly Ser Arg Asp Lys Thr Ile Lys Leu Trp Asn
20 25 30

( 2 ) INFORMATION FOR SEQ ID NO:175:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: HUMAN 12.3 rIV, Fig. 30

( x i ) SEQUENCE DESCRIPTION: SEQ ID NO:175:

Ser His Ser Glu Trp Val Ser Cys Val Arg Phe Ser Pro Asn Ser Ser
1 5 10 15

Asn Pro Ile Ile Val Ser Cys Gly Trp Asp Lys Leu Val Lys Val Trp
20 25 30

Asn ( 2 ) INFORMATION FOR SEQ ID NO:176:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide (iii) HYPOTHETICAL: NO (iv) ANTI-SENSE: NO (vi) ORIGINAL SOURCE:
(C) INDIVIDUAL ISOLATE: HUMAN 12.3 rV, Fig. 30

(xi) SEQUENCE DESCRIPTION: SEQ ID NO:176:

Gly His Thr Gly Tyr Leu Asn Thr Val Thr Val Ser Pro Asp Gly Ser
1 5 10 15

Leu Cys Ala Ser Gly Gly Lys Asp Gly Gln Ala Met Leu Trp Asp
20 25 30

(2) INFORMATION FOR SEQ ID NO:177:

(i) SEQUENCE CHARACTERISTICS:
(A) LENGTH: 36 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: HUMAN 12.3 rVI, Fig. 30

(xi) SEQUENCE DESCRIPTION: SEQ ID NO:177:

Lys His Leu Tyr Thr Leu Asp Gly Gly Asp Ile Ile Asn Ala Leu Cys
1 5 10 15

Phe Ser Pro Asn Arg Tyr Trp Leu Cys Ala Ala Thr Gly Pro Ser Ile
20 25 30

Lys Ile Trp Asp
35

(2) INFORMATION FOR SEQ ID NO:178:

(i) SEQUENCE CHARACTERISTICS:
(A) LENGTH: 38 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: HUMAN 12.3 rVII, Fig. 30

(xi) SEQUENCE DESCRIPTION: SEQ ID NO:178:

Val Ile Ser Thr Ser Ser Lys Ala Glu Pro Pro Gln Cys Thr Ser Leu
1 5 10 15

Ala Trp Ser Ala Asp Gly Gln Thr Leu Phe Ala Gly Tyr Thr Asp Asn
20 25 30

Leu Val Arg Val Trp Gln
35

(2) INFORMATION FOR SEQ ID NO:179:

(i) SEQUENCE CHARACTERISTICS:
(A) LENGTH: 32 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: IEF-7442- human rI, Fig. 31

(xi) SEQUENCE DESCRIPTION: SEQ ID NO:179:

Gly His Gln Lys Glu Gly Tyr Gly Leu Ser Trp Asn Ser Asn Leu Ser
1 5 10 15

Gly His Leu Leu Ser Ala Ser Asp Asp His Thr Val Cys Leu Trp Asp
20 25 30

(2) INFORMATION FOR SEQ ID NO:180:

(i) SEQUENCE CHARACTERISTICS:
(A) LENGTH: 32 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: IEF-7442- human rII, Fig. 31

(xi) SEQUENCE DESCRIPTION: SEQ ID NO:180:

Gly His Ser Ala Val Val Glu Asp Val Ala Trp His Leu Leu His Glu
1 5 10 15

Ser Leu Phe Gly Ser Val Ala Asp Asp Gln Lys Leu Met Ile Trp Asp
20 25 30

(2) INFORMATION FOR SEQ ID NO:181:

(i) SEQUENCE CHARACTERISTICS:
(A) LENGTH: 32 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: IEF-7442- human rIII, Fig. 31

(xi) SEQUENCE DESCRIPTION: SEQ ID NO:181:

Ala His Thr Ala Glu Val Asn Cys Leu Ser Phe Asn Pro Tyr Ser Glu
1 5 10 15

Phe Ile Leu Ala Thr Gly Ser Ala Asp Lys Thr Val Ala Leu Trp Asp
20 25 30

(2) INFORMATION FOR SEQ ID NO:182:

(i) SEQUENCE CHARACTERISTICS:
(A) LENGTH: 24 amino acids
(B) TYPE: amino acid
(D) TOPOLOGY: unknown (ii) MOLECULE TYPE: peptide (iii) HYPOTHETICAL: NO (iv) ANTI-SENSE: NO ( v i ) ORIGINAL SOURCE:
( C ) INDIVIDUAL ISOLATE: IEF-7442- human rIV, Fig. 31

( x i ) SEQUENCE DESCRIPTION: SEQ ID NO:182:

Val His Trp Ser Pro His Asn Glu Thr Ile Leu Ala Ser Ser Gly Thr
1 5 10 15

Asp Arg Arg Leu Asn Val Trp Asp
20

( 2 ) INFORMATION FOR SEQ ID NO:183:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: IEF-7442- human rV, Fig. 31

( x i ) SEQUENCE DESCRIPTION: SEQ ID NO:183:

Gly His Thr Ala Lys Ile Ser Asp Phe Ser Trp Asn Pro Asn Glu Pro
1 5 10 15

Trp Val Ile Cys Ser Val Ser Glu Asp Asn Ile Met Gln Ile Trp Gln
20 25 30

( 2 ) INFORMATION FOR SEQ ID NO:184:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Insulin-like GF binding protein complex rI, Fig. 32

( x i ) SEQUENCE DESCRIPTION: SEQ ID NO:184:

Ala His Thr Pro Ala Leu Ala Ser Leu Gly Leu Ser Asn Asn Arg Leu
1 5 10 15

Ser Arg Leu Glu Asp Gly Leu Phe Glu Gly Leu Gly Ser Leu Trp Asp
20 25 30

( 2 ) INFORMATION FOR SEQ ID NO:185:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Insulin-like growth factor bind. pro. complex- rat rI, Fig. 33

( x i ) SEQUENCE DESCRIPTION: SEQ ID NO:185:

Thr His Thr Pro Ser Leu Ala Ser Leu Ser Leu Ser Ser Asn Leu Leu
1 5 10 15

Gly Arg Leu Glu Glu Gly Leu Phe Gln Gly Leu Ser His Leu Trp Asp
20 25 30

( 2 ) INFORMATION FOR SEQ ID NO:186:

( i ) SEQUENCE CHARACTERISTICS:
( A ) LENGTH: 47 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Insulin-like growth factor bind. pro. complex- rat rII, Fig. 33

( x i ) SEQUENCE DESCRIPTION: SEQ ID NO:186:

Asn His Leu Glu Thr Leu Ala Glu Gly Leu Phe Ser Ser Leu Gly Arg
1 5 10 15

Val Arg Tyr Leu Ser Leu Arg Asn Asn Ser Leu Gln Thr Phe Ser Pro
20 25 30

Gln Pro Gly Leu Glu Arg Leu Trp Leu Asp Ala Asn Pro Trp Asp
35 40 45

( 2 ) INFORMATION FOR SEQ ID NO:187:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rI, Fig. 34

( x i ) SEQUENCE DESCRIPTION: SEQ ID NO:187:

Gly His Arg Ser Pro Val Thr Arg Val Ile Phe His Pro Val Phe Ser
1 5 10 15

Val Met Val Ser Ala Ser Glu Asp Ala Thr Ile Lys Val Trp Asp
20 25 30

( 2 ) INFORMATION FOR SEQ ID NO:188:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rII, Fig. 34

( x i ) SEQUENCE DESCRIPTION: SEQ ID NO:188:

Gly His Thr Asp Ser Val Gln Asp Ile Ser Phe Asp His Ser Gly Lys
1 5 10 15

Leu Leu Ala Ser Cys Ser Ala Asp Met Thr Ile Lys Leu Trp Asp
20 25 30

( 2 ) INFORMATION FOR SEQ ID NO:189:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rIII, Fig. 34

( x i ) SEQUENCE DESCRIPTION: SEQ ID NO:189:

Gly His Asp His Asn Val Ser Ser Val Ala Ile Met Pro Asn Gly Asp
1 5 10 15

His Ile Val Ser Ala Ser Arg Asp Lys Thr Ile Lys Met Trp Glu
20 25 30

( 2 ) INFORMATION FOR SEQ ID NO:190:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rIV, Fig. 34

( x i ) SEQUENCE DESCRIPTION: SEQ ID NO:190:

Gly His Arg Glu Trp Val Arg Met Val Arg Pro Asn Gln Asp Gly Thr
1 5 10 15

Leu Ile Ala Ser Cys Ser Asn Asp Gln Thr Val Arg Val Trp Val
20 25 30

( 2 ) INFORMATION FOR SEQ ID NO:191:

( i ) SEQUENCE CHARACTERISTICS:
( A ) LENGTH: 26 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rV, Fig. 34

( x i ) SEQUENCE DESCRIPTION: SEQ ID NO:191:

Gly Ser Glu Thr Lys Lys Ser Gly Lys Pro Gly Pro Phe Leu Leu Ser
1 5 10 15

Gly Ser Arg Asp Lys Thr Lys Met Trp Asp 20 25

( 2 ) INFORMATION FOR SEQ ID NO:192:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rVI, Fig. 34

( x i ) SEQUENCE DESCRIPTION: SEQ ID NO:192:

Gly His Asp Asn Trp Val Arg Gly Val Leu Phe His Ser Gly Gly Lys
1 5 10 15

Phe Ile Leu Ser Cys Ala Asp Asp Lys Thr Leu Arg Val Trp Asp
20 25 30

( 2 ) INFORMATION FOR SEQ ID NO:193:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: LIS1 (human) rVII, Fig. 34

( x i ) SEQUENCE DESCRIPTION: SEQ ID NO:193:

Ala His Glu His Phe Val Thr Ser Leu Asp Phe His Lys Thr Ala Pro
1 5 10 15

Tyr Val Val Thr Gly Ser Val Asp Gln Thr Val Lys Val Trp Glu
20 25 30

( 2 ) INFORMATION FOR SEQ ID NO:194:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MD6 rI, Fig. 35

( x i ) SEQUENCE DESCRIPTION: SEQ ID NO:194:

Gly His Ser Ala Arg Val Tyr Ala Leu Tyr Tyr Lys Asp Gly Leu Leu
1 5 10 15

Cys Thr Gly Ser Asp Asp Leu Ser Ala Lys Leu Trp Asp
20 25

( 2 ) INFORMATION FOR SEQ ID NO:195:

( i ) SEQUENCE CHARACTERISTICS:
( A ) LENGTH: 27 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MD6 rII, Fig. 35

( x i ) SEQUENCE DESCRIPTION: SEQ ID NO:195:

```
Thr His Thr Cys Ala Ala Val Lys Phe Asp Glu Gln Lys Leu Val Thr
1               5                   10                  15

Gly Ser Phe Asp Asn Thr Val Ala Cys Trp Glu
            20                  25
```

( 2 ) INFORMATION FOR SEQ ID NO:196:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MD6 rIII, Fig. 35

( x i ) SEQUENCE DESCRIPTION: SEQ ID NO:196:

```
Gly His Thr Gly Ala Val Phe Ser Val Asp Tyr Ser Asp Glu Leu Asp
1               5                   10                  15

Ile Leu Val Ser Gly Ser Ala Asp Phe Ala Val Lys Val Trp Ala
            20                  25                  30
```

( 2 ) INFORMATION FOR SEQ ID NO:197:

( i ) SEQUENCE CHARACTERISTICS:
( A ) LENGTH: 40 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MD6 rIV, Fig. 35

( x i ) SEQUENCE DESCRIPTION: SEQ ID NO:197:

```
Gly His Thr Glu Trp Val Thr Lys Val Val Leu Gln Lys Cys Lys Val
1               5                   10                  15

Lys Ser Leu Leu His Ser Pro Gly Asp Tyr Ile Leu Leu Ser Ala Asp
            20                  25                  30

Lys Tyr Glu Ile Lys Ile Trp Pro
        35                  40
```

( 2 ) INFORMATION FOR SEQ ID NO:198:

( i ) SEQUENCE CHARACTERISTICS:
( A ) LENGTH: 32 amino acids ( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MSL1 rI, Fig. 36

( x i ) SEQUENCE DESCRIPTION: SEQ ID NO:198:

Lys His Asp Gly Gly Val Asn Ser Cys Arg Phe Asn Tyr Lys Asn Ser
1 5 10 15

Leu Ile Leu Ala Ser Ala Asp Ser Asn Gly Arg Leu Asn Leu Trp Asp
20 25 30

( 2 ) INFORMATION FOR SEQ ID NO:199:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MSL1 rII, Fig. 36

( x i ) SEQUENCE DESCRIPTION: SEQ ID NO:199:

Glu His Gly Thr Ser Val Ser Thr Leu Glu Trp Ser Pro Asn Phe Asp
1 5 10 15

Thr Val Leu Ala Thr Ala Gly Gln Glu Asp Gly Leu Val Lys Leu Trp
20 25 30

Asp ( 2 ) INFORMATION FOR SEQ ID NO:200:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MSL1 rIII, Fig. 36

( x i ) SEQUENCE DESCRIPTION: SEQ ID NO:200:

Gly His Met Leu Gly Val Asn Asp Ile Ser Trp Asp Ala His Asp Pro
1 5 10 15

Trp Leu Met Cys Ser Val Ala Asn Asp Asn Ser Val His Ile Trp Lys
20 25 30

( 2 ) INFORMATION FOR SEQ ID NO:201:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MUS MUSCULUS PROTEIN rI, Fig. 37

( x i ) SEQUENCE DESCRIPTION: SEQ ID NO:201:

Gly His Ser Gly Cys Val Asn Thr Val His Phe Asn Gln His Gly Thr
1 5 10 15

Leu Leu Ala Ser Gly Ser Asp Asp Leu Lys Val Ile Val Trp Asp
20 25 30

( 2 ) INFORMATION FOR SEQ ID NO:202:

( i ) SEQUENCE CHARACTERISTICS:
( A ) LENGTH: 50 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: MUS MUSCULUS PROTEIN rII, Fig. 37

( x i ) SEQUENCE DESCRIPTION: SEQ ID NO:202:

Gly His Ile Phe Ile Trp Glu Lys Ser Ser Cys Gln Ile Val Gln Phe
1 5 10 15

Leu Glu Ala Asp Glu Gly Gly Thr Ile Asn Cys Ile Asp Ser His Pro
20 25 30

Tyr Leu Pro Val Leu Ala Ser Ser Gly Leu Asp His Glu Val Lys Ile
35 40 45

Trp Ser
50

( 2 ) INFORMATION FOR SEQ ID NO:203:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: ORF RB1 rI, Fig. 38

( x i ) SEQUENCE DESCRIPTION: SEQ ID NO:203:

Lys His Asp Gly Gly Val Asn Ser Cys Arg Phe Asn Tyr Lys Asn Ser
1 5 10 15

Leu Ile Leu Ala Ser Ala Asp Ser Asn Gly Arg Leu Asn Leu Trp Asp
20 25 30

( 2 ) INFORMATION FOR SEQ ID NO:204:

( i ) SEQUENCE CHARACTERISTICS:
( A ) LENGTH: 33 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: ORF RB1 rII, Fig. 38

( x i ) SEQUENCE DESCRIPTION: SEQ ID NO:204:

Glu His Gly Thr Ser Val Ser Thr Leu Glu Trp Ser Pro Asn Phe Asp
1 5 10 15

Thr Val Leu Ala Thr Ala Gly Gln Glu Asp Gly Leu Val Lys Leu Trp
20 25 30

Asp ( 2 ) INFORMATION FOR SEQ ID NO:205:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: ORF RB1 rIII, Fig. 38

( x i ) SEQUENCE DESCRIPTION: SEQ ID NO:205:

Gly His Met Leu Gly Val Asn Asp Ile Ser Trp Asp Ala His Asp Pro
1 5 10 15

Trp Leu Met Cys Ser Val Ala Asn Asp Asn Ser Val His Ile Trp Lys
20 25 30

( 2 ) INFORMATION FOR SEQ ID NO:206:

( i ) SEQUENCE CHARACTERISTICS:
( A ) LENGTH: 37 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Periodic Trp prt rI, Fig. 39

( x i ) SEQUENCE DESCRIPTION: SEQ ID NO:206:

Gly His Ile Thr Thr His His Thr Asp Ala Val Leu Ser Met Ala His
1 5 10 15

Asn Lys Tyr Phe Arg Ser Val Leu Ala Ser Thr Ser Ala Asp His Thr
20 25 30

Val Lys Leu Trp Asp
35

( 2 ) INFORMATION FOR SEQ ID NO:207:

( i ) SEQUENCE CHARACTERISTICS:
( A ) LENGTH: 47 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Periodic Trp prt rII, Fig. 39

( x i ) SEQUENCE DESCRIPTION: SEQ ID NO:207:

```
Ile His Ser Asn Lys Asn Val Ser Ser Ser Glu Trp His Met Leu Asn
1               5                   10                  15

Gly Ser Ile Leu Leu Thr Gly Gly Tyr Asp Ser Arg Val Ala Leu Thr
            20                  25                  30

Asp Val Arg Ile Ser Asp Glu Ser Gln Met Ser Lys Tyr Trp Ser
        35                  40                  45
```

( 2 ) INFORMATION FOR SEQ ID NO:208:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: PLAP rI, Fig. 40

( x i ) SEQUENCE DESCRIPTION: SEQ ID NO:208:

```
Gly His Lys Asp Thr Val Cys Ser Leu Ser Ser Gly Lys Phe Gly Thr
1               5                   10                  15

Leu Leu Ser Gly Ser Trp Asp Thr Thr Ala Lys Val Trp Leu
            20                  25                  30
```

( 2 ) INFORMATION FOR SEQ ID NO:209:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: PLAP rII, Fig. 40

( x i ) SEQUENCE DESCRIPTION: SEQ ID NO:209:

```
Gly His Thr Ala Ala Val Trp Ala Val Lys Ile Leu Pro Glu Gln Gly
1               5                   10                  15

Leu Met Leu Thr Gly Ser Ala Asp Lys Thr Ile Lys Leu Trp Lys
            20                  25                  30
```

( 2 ) INFORMATION FOR SEQ ID NO:210:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: PLAP rIII, Fig. 40

( x i ) SEQUENCE DESCRIPTION: SEQ ID NO:210:

Gly His Glu Asp Cys Val Arg Gly Leu Ala Ile Leu Ser Glu Thr Glu
1 5 10 15

Phe Leu Ser Cys Ala Asn Asp Ala Ser Ile Arg Arg Trp Gln
20 25 30

( 2 ) INFORMATION FOR SEQ ID NO:211:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: PLAP rIV, Fig. 40

( x i ) SEQUENCE DESCRIPTION: SEQ ID NO:211:

Gly His Thr Asn Tyr Ile Tyr Ser Ile Ser Val Phe Pro Asn Ser Lys
1 5 10 15

Asp Phe Val Thr Thr Ala Glu Asp Arg Ser Leu Arg Ile Trp Lys
20 25 30

( 2 ) INFORMATION FOR SEQ ID NO:212:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RETINOBLASTOMA BINDING PROTEIN - HUMAN. rI, Fig. 41

( x i ) SEQUENCE DESCRIPTION: SEQ ID NO:212:

Gly His Gln Lys Glu Gly Tyr Gly Leu Ser Trp Asn Pro Asn Leu Ser
1 5 10 15

Gly His Leu Leu Ser Ala Ser Asp Asp His Thr Ile Cys Leu Trp Asp
20 25 30

( 2 ) INFORMATION FOR SEQ ID NO:213:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RETINOBLASTOMA BINDING PROTEIN - HUMAN rII, Fig. 41

( x i ) SEQUENCE DESCRIPTION: SEQ ID NO:213:

Gly His Thr Ala Val Val Glu Asp Val Ser Trp His Leu Leu His Glu
1 5 10 15

Ser Leu Phe Gly Ser Val Ala Asp Asp Gln Lys Leu Met Ile Trp Asp
20 25 30

( 2 ) INFORMATION FOR SEQ ID NO:214:

( i ) SEQUENCE CHARACTERISTICS:
( A ) LENGTH: 37 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RETINOBLASTOMA BINDING PROTEIN - HUMAN rIII, Fig. 41

( x i ) SEQUENCE DESCRIPTION: SEQ ID NO:214:

Ser His Ser Val Asp Ala His Thr Ala Glu Val Asn Cys Leu Ser Phe
1 5 10 15

Asn Pro Tyr Ser Glu Phe Ile Leu Ala Thr Gly Ser Ala Asp Lys Thr
20 25 30

Val Ala Leu Trp Asp
35

( 2 ) INFORMATION FOR SEQ ID NO:215:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RETINOBLASTOMA BINDING PROTEIN - HUMAN rIV, Fig. 41

( x i ) SEQUENCE DESCRIPTION: SEQ ID NO:215:

Ser His Lys Asp Glu Ile Phe Gln Val Gln Trp Ser Pro His Asn Glu
1 5 10 15

Thr Ile Leu Ala Ser Ser Gly Thr Asp Arg Arg Leu Asn Val Trp Asp
20 25 30

( 2 ) INFORMATION FOR SEQ ID NO:216:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: RETINOBLASTOMA BINDING PROTEIN - HUMAN rV, Fig. 41

( x i ) SEQUENCE DESCRIPTION: SEQ ID NO:216:

Gly His Thr Ala Lys Ile Ser Asp Phe Ser Trp Asn Pro Asn Glu Pro
1 5 10 15

Trp Val Ile Cys Ser Val Ser Glu Asp Asn Ile Met Gln Val Trp Gln
20 25 30

( 2 ) INFORMATION FOR SEQ ID NO:217:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: S253 PROTEIN rI, Fig. 42

( x i ) SEQUENCE DESCRIPTION: SEQ ID NO:217:

Glu His Ala Leu Asp Ile Leu Asp Ala Asn Trp Ser Lys Asn Gly Phe
1 5 10 15

Leu Ile Thr Ala Ser Met Asp Lys Thr Ala Lys Leu Trp His
20 25 30

( 2 ) INFORMATION FOR SEQ ID NO:218:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: S253 PROTEIN rII, Fig. 42

( x i ) SEQUENCE DESCRIPTION: SEQ ID NO:218:

Val His Pro Asp Phe Val Thr Ser Ala Ile Phe Phe Pro Asn Asp Asp
1 5 10 15

Arg Phe Ile Ile Thr Gly Cys Leu Asp His Arg Cys Arg Leu Trp Ser
20 25 30

( 2 ) INFORMATION FOR SEQ ID NO:219:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: SOF1 rI, Fig. 43

(xi) SEQUENCE DESCRIPTION: SEQ ID NO:219:

Gly His Arg Asp Gly Val Tyr Ala Ile Ala Lys Asn Tyr Gly Ser Leu
1 5 10 15

Asn Lys Leu Ala Thr Gly Ser Ala Asp Gly Val Ile Lys Tyr Trp
20 25 30

(2) INFORMATION FOR SEQ ID NO:220:

(i) SEQUENCE CHARACTERISTICS:
(A) LENGTH: 35 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: SOF1 rII, Fig. 43

(xi) SEQUENCE DESCRIPTION: SEQ ID NO:220:

Gly Leu Cys Val Thr Gln Pro Arg Phe His Asp Lys Lys Pro Asp Leu
1 5 10 15

Lys Ser Gln Asn Phe Met Leu Ser Cys Ser Asp Asp Lys Thr Val Lys
20 25 30

Leu Trp Ser
35

(2) INFORMATION FOR SEQ ID NO:221:

(i) SEQUENCE CHARACTERISTICS:
(A) LENGTH: 35 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: SOF1 rIII, Fig. 43

(xi) SEQUENCE DESCRIPTION: SEQ ID NO:221:

Gly Leu Ile Arg Thr Phe Asp Gly Glu Ser Ala Phe Gln Gly Ile Asp
1 5 10 15

Ser His Arg Glu Asn Ser Thr Phe Ala Thr Gly Gly Ala Lys Ile His
20 25 30

Leu Trp Asp
35

(2) INFORMATION FOR SEQ ID NO:222:

(i) SEQUENCE CHARACTERISTICS:
(A) LENGTH: 39 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:

( C ) INDIVIDUAL ISOLATE: SOF1 rIV, Fig. 43

( x i ) SEQUENCE DESCRIPTION: SEQ ID NO:222:

Gly His Ser Arg Glu Ile Tyr His Thr Lys Arg Met Gln His Val Phe
1 5 10 15

Val Lys Tyr Ser Met Asp Ser Lys Tyr Ile Ile Ser Gly Ser Asp Asp
20 25 30

Gly Asn Val Arg Leu Trp Arg
35

( 2 ) INFORMATION FOR SEQ ID NO:223:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: STE4-YEAST rI, Fig. 44

( x i ) SEQUENCE DESCRIPTION: SEQ ID NO:223:

Gly His Asn Asn Lys Ile Ser Asp Phe Arg Trp Ser Arg Asp Ser Lys
1 5 10 15

Arg Ile Leu Ser Ala Ser Gln Asp Gly Phe Met Leu Ile Trp Asp
20 25 30

( 2 ) INFORMATION FOR SEQ ID NO:224:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: STE4-YEAST rII, Fig. 44

( x i ) SEQUENCE DESCRIPTION: SEQ ID NO:224:

Gly His Thr Cys Tyr Ile Ser Asp Ile Glu Phe Thr Asp Asn Ala His
1 5 10 15

Ile Leu Thr Ala Ser Gly Asp Met Thr Cys Ala Leu Trp Asp
20 25 30

( 2 ) INFORMATION FOR SEQ ID NO:225:

( i ) SEQUENCE CHARACTERISTICS:
( A ) LENGTH: 37 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: STE4-YEAST rIII, Fig. 44

( x i ) SEQUENCE DESCRIPTION: SEQ ID NO:225:

Asp His Leu Gly Asp Val Leu Ala Leu Ala Ile Pro Glu Glu Pro Asn
1 5 10 15

Leu Glu Asn Ser Ser Asn Thr Phe Ala Ser Cys Gly Ser Asp Gly Tyr
20 25 30

Thr Tyr Ile Trp Asp
35

( 2 ) INFORMATION FOR SEQ ID NO:226:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: STE4-YEAST rIV, Fig. 44

( x i ) SEQUENCE DESCRIPTION: SEQ ID NO:226:

Leu Asp Asn Gln Gly Val Val Ser Leu Asp Phe Ser Ala Ser Gly Arg
1 5 10 15

Leu Met Tyr Ser Cys Tyr Thr Asp Ile Gly Cys Val Val Trp Asp
20 25 30

( 2 ) INFORMATION FOR SEQ ID NO:227:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: STE4-YEAST rV, Fig. 44

( x i ) SEQUENCE DESCRIPTION: SEQ ID NO:227:

Gly His Gly Gly Arg Val Thr Gly Val Arg Ser Ser Pro Asp Gly Leu
1 5 10 15

Ala Val Cys Thr Gly Ser Trp Asp Ser Thr Met Lys Ile Trp Ser
20 25 30

( 2 ) INFORMATION FOR SEQ ID NO:228:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TRNSCRPTION FCTR TIIF rI, Fig. 45

( x i ) SEQUENCE DESCRIPTION: SEQ ID NO:228:

Gly His Thr Gly Pro Val Tyr Arg Cys Ala Phe Ala Pro Glu Met Asn
1 5 10 15

Leu Leu Leu Ser Cys Ser Glu Asp Ser Thr Ile Arg Leu Trp Ser
20 25 30

( 2 ) INFORMATION FOR SEQ ID NO:229:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TRNSCRPTION FCTR TIIF rII, Fig. 45

( x i ) SEQUENCE DESCRIPTION: SEQ ID NO:229:

Gly His Val Tyr Pro Val Trp Asp Val Arg Phe Ala Pro His Gly Tyr
1 5 10 15

Tyr Phe Val Ser Cys Ser Tyr Asp Lys Thr Ala Arg Leu Trp Ala
20 25 30

( 2 ) INFORMATION FOR SEQ ID NO:230:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TRNSCRPTION FCTR TIIF rIII, Fig. 45

( x i ) SEQUENCE DESCRIPTION: SEQ ID NO:230:

Gly His Leu Ser Asp Val Asp Cys Val Gln Phe His Pro Asn Ser Asn
1 5 10 15

Tyr Val Ala Thr Gly Ser Ser Asp Arg Thr Val Arg Leu Trp Asp
20 25 30

( 2 ) INFORMATION FOR SEQ ID NO:231:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TRNSCRPTION FCTR TIIF rIV, Fig. 45

( x i ) SEQUENCE DESCRIPTION: SEQ ID NO:231:

Gly His Lys Gly Ser Val Ser Ser Leu Ala Phe Ser Ala Cys Gly Arg
1 5 10 15

Tyr Leu Ala Ser Gly Ser Val Asp His Asn Ile Ile Ile Trp Asp
20 25 30

(2) INFORMATION FOR SEQ ID NO:232:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: TRNSCRPTION FCTR TIIF rV, Fig. 45

(xi) SEQUENCE DESCRIPTION: SEQ ID NO:232:

```
Arg His Thr Ser Thr Val Thr Thr Ile Thr Phe Ser Arg Asp Gly Thr
1               5                   10                  15

Val Leu Ala Ala Ala Gly Leu Asp Asn Asn Leu Thr Leu Trp Asp
            20                  25                  30
```

(2) INFORMATION FOR SEQ ID NO:233:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: TUP1 rI, Fig. 46

(xi) SEQUENCE DESCRIPTION: SEQ ID NO:233:

```
Ser Ser Asp Leu Tyr Ile Arg Ser Val Cys Phe Ser Pro Asp Gly Lys
1               5                   10                  15

Phe Leu Ala Thr Gly Ala Glu Asp Arg Leu Ile Arg Ile Trp Asp
            20                  25                  30
```

(2) INFORMATION FOR SEQ ID NO:234:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: TUP1 rII, Fig. 46

(xi) SEQUENCE DESCRIPTION: SEQ ID NO:234:

```
Gly His Glu Gln Asp Ile Tyr Ser Leu Asp Tyr Phe Pro Ser Gly Asp
1               5                   10                  15

Lys Leu Val Ser Gly Ser Gly Asp Arg Thr Val Arg Ile Trp Asp
            20                  25                  30
```

(2) INFORMATION FOR SEQ ID NO:235:

(i) SEQUENCE CHARACTERISTICS:

( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 rIII, Fig. 46

( x i ) SEQUENCE DESCRIPTION: SEQ ID NO:235:

Ile Glu Asp Gly Val Thr Thr Val Ala Val Ser Pro Gly Asp Gly Lys
1 5 10 15

Tyr Ile Ala Ala Gly Ser Leu Asp Arg Ala Val Arg Val Trp Asp
20 25 30

( 2 ) INFORMATION FOR SEQ ID NO:236:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 rIV, Fig. 46

( x i ) SEQUENCE DESCRIPTION: SEQ ID NO:236:

Gly His Lys Asp Ser Val Tyr Ser Val Val Phe Thr Arg Asp Gly Gln
1 5 10 15

Ser Val Val Ser Gly Ser Leu Asp Arg Ser Val Lys Leu Trp Asn
20 25 30

( 2 ) INFORMATION FOR SEQ ID NO:237:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 rV, Fig. 46

( x i ) SEQUENCE DESCRIPTION: SEQ ID NO:237:

Gly His Lys Asp Phe Val Leu Ser Val Ala Thr Thr Gln Asn Asp Glu
1 5 10 15

Tyr Ile Leu Ser Gly Ser Lys Asp Arg Gly Val Leu Phe Trp Asp
20 25 30

( 2 ) INFORMATION FOR SEQ ID NO:238:

( i ) SEQUENCE CHARACTERISTICS:
( A ) LENGTH: 22 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG rI, Fig. 47

( x i ) SEQUENCE DESCRIPTION: SEQ ID NO:238:

Asp Phe Ser Asp Asp Cys Arg Ile Ala Ala Ala Gly Phe Gln Asp Ser
1 5 10 15

Tyr Ile Lys Ile Trp Ser
20

( 2 ) INFORMATION FOR SEQ ID NO:239:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG rII, Fig. 47

( x i ) SEQUENCE DESCRIPTION: SEQ ID NO:239:

Gly His Ser Gly Thr Val Tyr Ser Thr Ser Phe Ser Pro Asp Asn Lys
1 5 10 15

Tyr Leu Leu Ser Gly Ser Glu Asp Lys Thr Val Arg Leu Trp Ser
20 25 30

( 2 ) INFORMATION FOR SEQ ID NO:240:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG rIII, Fig. 47

( x i ) SEQUENCE DESCRIPTION: SEQ ID NO:240:

Gly His Asn His Pro Val Trp Asp Val Ser Phe Ser Pro Leu Gly His
1 5 10 15

Tyr Phe Ala Thr Ala Ser His Asp Gln Thr Ala Arg Leu Trp Ser
20 25 30

( 2 ) INFORMATION FOR SEQ ID NO:241:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG rIV, Fig. 47

( x i ) SEQUENCE DESCRIPTION: SEQ ID NO:241:

```
Gly His Leu Asn Asp Val Asp Cys Val Ser Phe His Pro Asn Gly Cys
1               5                   10                  15

Tyr Val Phe Thr Gly Ser Ser Asp Lys Thr Cys Arg Met Trp Asp
            20                  25                  30
```

( 2 ) INFORMATION FOR SEQ ID NO:242:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG rV, Fig. 47

( x i ) SEQUENCE DESCRIPTION: SEQ ID NO:242:

```
Gly His Thr Ala Pro Val Ile Ser Ile Ala Val Cys Pro Asp Gly Arg
1               5                   10                  15

Trp Leu Ser Thr Gly Ser Glu Asp Gly Ile Ile Asn Val Trp Asp
            20                  25                  30
```

( 2 ) INFORMATION FOR SEQ ID NO:243:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: TUP1 HOMOLOG rVI, Fig. 47

( x i ) SEQUENCE DESCRIPTION: SEQ ID NO:243:

```
Gly His Gly Lys Asn Ala Ile Tyr Ser Leu Ser Tyr Ser Lys Glu Gly
1               5                   10                  15

Asn Val Leu Ile Ser Gly Gly Ala Asp His Thr Val Arg Val Trp Asp
            20                  25                  30
```

( 2 ) INFORMATION FOR SEQ ID NO:244:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCU7 rI, Fig. 48

( x i ) SEQUENCE DESCRIPTION: SEQ ID NO:244:

Gly His Phe Asp Ser Thr Asn Ser Leu Ala Tyr Ser Pro Asp Gly Ser
1 5 10 15

Arg Val Val Thr Ala Ser Glu Asp Gly Lys Ile Lys Val Trp Asp
20 25 30

( 2 ) INFORMATION FOR SEQ ID NO:245:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCU7 rII, Fig. 48

( x i ) SEQUENCE DESCRIPTION: SEQ ID NO:245:

Glu His Thr Ser Ser Val Thr Ala Val Gln Phe Ala Lys Arg Gly Gln
1 5 10 15

Val Met Phe Ser Ser Ser Leu Asp Gly Thr Val Arg Ala Trp Asp
20 25 30

( 2 ) INFORMATION FOR SEQ ID NO:246:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCU7 rIII, Fig. 48

( x i ) SEQUENCE DESCRIPTION: SEQ ID NO:246:

Arg Ile Gln Phe Asn Cys Leu Ala Val Asp Pro Ser Gly Glu Val Val
1 5 10 15

Cys Ala Gly Ser Leu Asp Asn Phe Asp Ile His Val Trp Ser
20 25 30

( 2 ) INFORMATION FOR SEQ ID NO:247:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCU7 rIV, Fig. 48

( x i ) SEQUENCE DESCRIPTION: SEQ ID NO:247:

Gly His Glu Gly Pro Val Ser Cys Leu Ser Phe Ser Gln Glu Asn Ser
1 5 10 15

Val Leu Ala Ser Ala Ser Trp Asp Lys Thr Ile Arg Ile Trp Ser
20 25 30

( 2 ) INFORMATION FOR SEQ ID NO:248:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rI, Fig. 49

( x i ) SEQUENCE DESCRIPTION: SEQ ID NO:248:

Gly His Gly Ser Thr Ile Leu Cys Ser Ala Phe Ala Pro His Thr Ser
1 5 10 15

Ser Arg Met Val Thr Gly Ala Gly Asp Asn Thr Ala Arg Ile Trp Asp
20 25 30

( 2 ) INFORMATION FOR SEQ ID NO:249:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rII, Fig. 49

( x i ) SEQUENCE DESCRIPTION: SEQ ID NO:249:

Gly His Tyr Asn Trp Val Leu Cys Val Ser Trp Ser Pro Asp Gly Glu
1 5 10 15

Val Ile Ala Thr Gly Ser Met Asp Asn Thr Ile Arg Leu Trp Asp
20 25 30

( 2 ) INFORMATION FOR SEQ ID NO:250:

( i ) SEQUENCE CHARACTERISTICS:
( A ) LENGTH: 38 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rIII, Fig. 49

( x i ) SEQUENCE DESCRIPTION: SEQ ID NO:250:

Gly His Ser Lys Trp Ile Thr Ser Leu Ser Trp Glu Pro Ile His Leu
1 5 10 15

Val Lys Pro Gly Ser Lys Pro Arg Leu Ala Ser Ser Ser Lys Asp Gly
20 25 30

Thr Ile Lys Ile Trp Asp
35

( 2 ) INFORMATION FOR SEQ ID NO:251:

( i ) SEQUENCE CHARACTERISTICS:
( A ) LENGTH: 30 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rIV, Fig. 49

( x i ) SEQUENCE DESCRIPTION: SEQ ID NO:251:

Gly His Thr Asn Ser Val Ser Cys Val Lys Trp Gly Gly Gln Gly Leu
1 5 10 15

Leu Tyr Ser Gly Ser His Asp Arg Thr Val Arg Val Trp Asp
20 25 30

( 2 ) INFORMATION FOR SEQ ID NO:252:

( i ) SEQUENCE CHARACTERISTICS:
( A ) LENGTH: 26 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rV, Fig. 49

( x i ) SEQUENCE DESCRIPTION: SEQ ID NO:252:

Lys Ile Cys Lys Lys Asn Gly Asn Ser Glu Glu Met Met Val Thr Ala
1 5 10 15

Ser Asp Asp Tyr Thr Met Phe Leu Trp Asn
20 25

( 2 ) INFORMATION FOR SEQ ID NO:253:

( i ) SEQUENCE CHARACTERISTICS:
( A ) LENGTH: 25 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rVI, Fig. 49

( x i ) SEQUENCE DESCRIPTION: SEQ ID NO:253:

Asn His Val Ala Phe Ser Pro Asp Gly Arg Tyr Ile Val Ser Ala Ser
1 5 10 15

Phe Asp Asn Ser Ile Lys Leu Trp Asp
20 25

( 2 ) INFORMATION FOR SEQ ID NO:254:

( i ) SEQUENCE CHARACTERISTICS:
( A ) LENGTH: 31 amino acids
( B ) TYPE: amino acid ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rVII, Fig. 49

( x i ) SEQUENCE DESCRIPTION: SEQ ID NO:254:

Gly His Ile Ala Ser Val Tyr Gln Val Ala Trp Ser Ser Asp Cys Arg
1 5 10 15

Leu Leu Val Ser Cys Ser Lys Asp Thr Thr Leu Lys Val Trp Asp
20 25 30

( 2 ) INFORMATION FOR SEQ ID NO:255:

( i ) SEQUENCE CHARACTERISTICS:
( A ) LENGTH: 35 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YCW2 PROTEIN rVIII, Fig. 49

( x i ) SEQUENCE DESCRIPTION: SEQ ID NO:255:

Ser Val Asp Leu Pro Gly Ile Lys Thr Lys Leu Tyr Val Asp Trp Ser
1 5 10 15

Val Asp Gly Lys Arg Val Cys Ser Gly Gly Lys Asp Lys Met Val Arg
20 25 30

Leu Trp Thr
35

( 2 ) INFORMATION FOR SEQ ID NO:256:

( i ) SEQUENCE CHARACTERISTICS:
( A ) LENGTH: 29 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YKL525 rI, Fig. 50

( x i ) SEQUENCE DESCRIPTION: SEQ ID NO:256:

Leu His Leu Tyr Ala Pro Val Phe Tyr Ser Asp Val Phe Arg Val Phe
1 5 10 15

Met Glu His Ala Leu Asp Ile Leu Asp Ala Asn Trp Ser
20 25

( 2 ) INFORMATION FOR SEQ ID NO:257:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: YKL525 rII, Fig. 50

( x i ) SEQUENCE DESCRIPTION: SEQ ID NO:257:

Val His Pro Asp Phe Val Thr Ser Ala Ile Phe Phe Pro Asn Asp Asp
1 5 10 15

Arg Phe Ile Ile Thr Gly Cys Leu Asp His Arg Cys Arg Leu Trp Ser
20 25 30

( 2 ) INFORMATION FOR SEQ ID NO:258:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: yrb 1410 yeast rI, Fig. 51

( x i ) SEQUENCE DESCRIPTION: SEQ ID NO:258:

Gly His Asn His Pro Val Trp Asp Val Ser Phe Ser Pro Leu Gly His
1 5 10 15

Tyr Phe Ala Thr Ala Ser His Asp Gln Thr Ala Arg Leu Trp Ser
20 25 30

( 2 ) INFORMATION FOR SEQ ID NO:259:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: yrb 1410 yeast rII, Fig. 51

( x i ) SEQUENCE DESCRIPTION: SEQ ID NO:259:

Gly His Leu Asn Asp Val Asp Cys Val Ser Phe His Pro Asn Gly Cys
1 5 10 15

Tyr Val Phe Thr Gly Ser Ser Asp Lys Thr Cys Arg Met Trp Asp
20 25 30

( 2 ) INFORMATION FOR SEQ ID NO:260:

( i ) SEQUENCE CHARACTERISTICS:
( A ) LENGTH: 31 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: yrb 1410 yeast rIII, Fig. 51

( x i ) SEQUENCE DESCRIPTION: SEQ ID NO:260:

Gly His Thr Ala Pro Val Ile Ser Ile Ala Val Cys Pro Asp Gly Arg
1 5 10 15

Trp Leu Ser Thr Gly Ser Glu Asp Gly Ile Ile Asn Val Trp Asp
20 25 30

( 2 ) INFORMATION FOR SEQ ID NO:261:

( i ) SEQUENCE CHARACTERISTICS:
( A ) LENGTH: 32 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: yrb 1410 yeast rIV, Fig. 51

( x i ) SEQUENCE DESCRIPTION: SEQ ID NO:261:

Gly His Gly Lys Asn Ala Ile Tyr Ser Leu Ser Tyr Ser Lys Glu Gly
1 5 10 15

Asn Val Leu Ile Ser Gly Gly Ala Asp His Thr Val Arg Val Trp Asp
20 25 30

( 2 ) INFORMATION FOR SEQ ID NO:262:

( i ) SEQUENCE CHARACTERISTICS:
( A ) LENGTH: 34 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: WD40 Consensus Sequence ( x i ) SEQUENCE DESCRIPTION: SEQ ID NO:262:

Gly His Ser Ala Ala Leu Ala Ala Leu Ala Leu Ser Pro Asp Ala Ala
1 5 10 15

Ala Ala Ala Leu Ala Ser Gly Ala Arg Asp Ala Thr Leu Arg Leu Trp
20 25 30

Asp Leu ( 2 ) INFORMATION FOR SEQ ID NO:263:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:

-continued ( C ) INDIVIDUAL ISOLATE: WRTAA peptide ( x i ) SEQUENCE DESCRIPTION: SEQ ID NO:263:

Trp Arg Thr Ala Ala
1 5

( 2 ) INFORMATION FOR SEQ ID NO:264:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
( C ) INDIVIDUAL ISOLATE: WRTAV peptide ( x i ) SEQUENCE DESCRIPTION: SEQ ID NO:264:

Trp Arg Thr Ala Val
1 5

( 2 ) INFORMATION FOR SEQ ID NO:265:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
( C ) INDIVIDUAL ISOLATE: WRTA peptide ( x i ) SEQUENCE DESCRIPTION: SEQ ID NO:265:

Trp Arg Thr Ala
1